US012605467B2

(12) United States Patent
Tao et al.

(10) Patent No.: US 12,605,467 B2
(45) Date of Patent: Apr. 21, 2026

(54) RECOMBINANT AAV VECTORS FOR TREATING NEURODEGENERATIVE DISORDERS

(71) Applicant: SHANGHAI VITALGEN BIOPHARMA CO., LTD., Shanghai (CN)

(72) Inventors: Yezheng Tao, Shanghai (CN); Shin-Shay Tian, Shanghai (CN); Xiaoping Zhao, Shanghai (CN)

(73) Assignee: SHANGHAI VITALGEN BIOPHARMA CO., LTD., Shanghai (CN)

( * ) Notice: Subject to any disclaimer, the term of this patent is extended or adjusted under 35 U.S.C. 154(b) by 0 days.

(21) Appl. No.: 18/919,740

(22) Filed: Oct. 18, 2024

(65) Prior Publication Data

US 2025/0041456 A1 Feb. 6, 2025

Related U.S. Application Data

(63) Continuation of application No. PCT/CN2023/089291, filed on Apr. 19, 2023.

(30) Foreign Application Priority Data

Apr. 19, 2022 (WO) ................ PCT/CN2022/087771

(51) Int. Cl.
C07K 14/52 (2006.01)
A61K 48/00 (2006.01)
(Continued)

(52) U.S. Cl.
CPC .......... *A61K 48/0058* (2013.01); *C07K 14/52* (2013.01); *C12N 9/2402* (2013.01);
(Continued)

(58) Field of Classification Search
CPC ..... A61K 48/0058; C07K 14/52; C12N 15/86
See application file for complete search history.

(56) References Cited

U.S. PATENT DOCUMENTS

| | | | |
|---|---|---|---|
| 10,335,466 B2 * | 7/2019 | Kotin | ..................... A61P 25/14 |
| 11,027,000 B2 | 6/2021 | Kotin et al. | |

(Continued)

FOREIGN PATENT DOCUMENTS

| | | |
|---|---|---|
| CA | 3 136 117 A1 | 10/2020 |
| CN | 107106689 A | 8/2017 |

(Continued)

OTHER PUBLICATIONS

NCBI (Genbank: *Homo sapiens* glial cell derived neurotrophic factor, mRNA (cDNA clone MGC:95398 Image:7216973), complete cds (BC069119.1)). https://www.ncbi.nlm.nih.gov/nuccore/BC069119 (Year: 2006).*

(Continued)

*Primary Examiner* — James D Schultz
*Assistant Examiner* — Keenan A Bates
(74) *Attorney, Agent, or Firm* — Merchant & Gould P.C.; Daniel J. Pereira

(57) ABSTRACT

Provided is a recombinant adeno-associated viral (rAAV) vector comprising one or two of (a) to (c): (a) a nucleotide sequence encoding aromatic L-amino acid decarboxylase (AADC), (b) a nucleotide sequence encoding glucocerebrosidase (GBA1); and (c) a nucleotide sequence encoding a neurotrophic factor (NTF), such as cerebral dopamine neurotrophic factor (CDNF) or glial cell derived neurotrophic factor (GDNF), for treating neurodegenerative disorders, particularly Parkinson's disease (PD), Multiple system atrophy (MSA), Gaucher's disease (GD), and other proteinopathies. Also provided herein are viral particles comprising the (Continued)

rAAV vector, a pharmaceutical composition comprising the viral particles, and uses thereof.

14 Claims, 33 Drawing Sheets

Specification includes a Sequence Listing.

(51) Int. Cl.
    *C12N 9/24*          (2006.01)
    *C12N 9/88*          (2006.01)
    *C12N 15/86*        (2006.01)
(52) U.S. Cl.
    CPC .............. *C12N 9/88* (2013.01); *C12N 15/86* (2013.01); *C12Y 302/01045* (2013.01); *C12Y 401/01028* (2013.01); *C12N 2750/14143* (2013.01)

(56) References Cited

U.S. PATENT DOCUMENTS

| | | | |
|---|---|---|---|
| 11,078,247 B2 * | 8/2021 | Fotin-Mleczek | .... C12N 15/113 |
| 2013/0224836 A1 | 8/2013 | Muramatsu | |
| 2017/0096683 A1 * | 4/2017 | Scaria | .................. C12N 15/113 |
| 2018/0142260 A1 * | 5/2018 | Logan | .................... C12N 15/86 |
| 2020/0332265 A1 | 10/2020 | Abeliovich et al. | |
| 2020/0397919 A1 * | 12/2020 | Wu | .................... A61K 48/0058 |
| 2025/0051750 A1 * | 2/2025 | Jiang | ............. C12Y 401/01015 |

FOREIGN PATENT DOCUMENTS

| | | | | |
|---|---|---|---|---|
| CN | 107523581 | A | 12/2017 | |
| CN | 107828820 | A | 3/2018 | |
| CN | 108841868 | A | 11/2018 | |
| CN | 109069496 | A | 12/2018 | |
| CN | 109266648 | A * | 1/2019 | ........ A61K 31/7088 |
| CN | 111492061 | A | 8/2020 | |
| CN | 112481269 | A | 3/2021 | |
| CN | 112553229 | A | 3/2021 | |
| CN | 113005123 | A | 6/2021 | |
| CN | 113423434 | A | 9/2021 | |
| CN | 114317610 | A * | 4/2022 | |
| WO | 03/018821 | A2 | 3/2003 | |
| WO | 2019/068854 | A1 | 4/2019 | |
| WO | 2019/227595 | A1 | 12/2019 | |
| WO | WO-2021138350 | A1 * | 7/2021 | .............. A61F 11/00 |
| WO | 2022/032153 | A1 | 2/2022 | |
| WO | 2023/093905 | A1 | 6/2023 | |

OTHER PUBLICATIONS

NCBI (Genbank: *Homo sapiens* dopa decarboxylase (DDC), transcript variant 2, mRNA (NM_000790.4)) https://www.ncbi.nlm.nih.gov/nuccore/NM_000790.4 (Year: 2019).*
Furler et al. Recombinant AAV vectors containing the foot and mouth disease virus 2A sequence confer efficient bicistronic gene expression in cultured cells and rat substantia nigra neurons. Gene Therapy 8: 864-873. (Year: 2001).*
Wang et al. Codon Usage in Signal Sequences Affects Protein Expression and Secretion Using Baculovirus/Insect Cell Expression System. PLoS One 10: 1-15. (Year: 2015).*
Mead et al. Novel Focused Ultrasound Gene Therapy Approach Noninvasively Restores Dopaminergic Neuron Function in a Rat Parkinson's Disease Model. Nano Lett. 17: 3533-3542. (Year: 2017).*
Kim et al. AAV-Mediated Combination Gene Therapy for Neuropathic Pain: GAD65, GDNF, and IL-10. Molecular Therapy: Methods & Clinical Development 18: 473-483. (Year: 2020).*

International Search Report issued Aug. 28, 2023, in International Patent Application No. PCT/CN2023/089291 (8 pages).
Aristide Merola, et al., "Gene Therapy in Movement Disorders: A Systematic Review of Ongoing and Completed Clinical Trials," Frontiers in Neurology, vol. 12, Article 648532, Apr. 6, 2021, pp. 1-21.
Office Action issued Feb. 9, 2026, in Chinese Patent Application No. 202511079772.3 (with attached English Translation).
S. Furler, et al., "Recombinant AAV vectors containing the foot and mouth disease virus 2A sequence confer efficient bicistronic gene expression in cultured cells and rat substantia nigra neurons," Gene Therapy (2011) 8, 864-873.
Yalan Wang, et al., "Codon Usage in Signal Sequences Affects Protein Expression and Secretion Using Baculovirus/ Insect Cell Expression System," PLOS ONE, vol. 10 (12), pp. 1-15, Dec. 23, 2015.
Brian P. Mead, et al., "Novel Focused Ultrasound Gene Therapy Approach Noninvasively Restores Dopaminergic Neuron Function in a Rat Parkinson's Disease Model," Nano Letters, 17 (6), Jun. 14, 2017, pp. 3533-3542.
Search Report issued Feb. 9, 2026, in Chinese Patent Application No. 202511079772.3 (with attached English Translation).
Yao Yao, et al., "The Research Advancement of Virus Vector in the Gene Therapy of Parkinson's Disease" West China Medical Journal (2005), vol. 20, No. 4, pp. 797-798 (with attached English translation).
Office Action issued Jan. 22, 2026, in Chinese Patent Application No. 202511079819.6(with attached English Translation).
Search Report issued Jan. 22, 2026, in Chinese Patent Application No. 202511079819.6(with attached English Translation).
Mpekoulis G., NCBI Reference Sequence, "*Homo sapiens* dopa decarboxylase (DDC), transcript variant 2, mRNA", (Sep. 19, 2021).
Strausberg, R.L., *Homo sapiens* glial cell derived neurotrophic factor, mRNA (cDNA clone MGC:95398 Image: 7216973), Jul. 15, 2006.
He Tianqi et al., "Application of Adeno-associated virus in Parkinson's Disease," Chin J. Clinicians (Electronic Edition), vol. 14, No. 8, Aug. 15, 2020, pp. 643-647 (with attached English Translation).
Supplementary Partial European Search Report issued in the corresponding European Application No. 23 79 1291, Dec. 3, 2025.
Chadwick W. Christine, et al., "Safety of AADC Gene Therapy for Moderately Advanced Parkinson Disease," Neurology, vol. 98, No. 1, Jan. 4, 2022, pp. e40-e50.
Adrian P. Kells, et al., "Glial-derived Neurotrophic Factor Gene Transfer for Parkinson's Disease: Anterograde Distribution of AAV2 Vectors in the Primate Brain," Neurobiology of Disease, vol. 48, No. 2, Nov. 1, 2012, pp. 228-235.
Leila Haery et al., "Adeno-Associated Virus Technologies and Methods for Targeted Neuronal Manipulation," Frontiers in Neuroanatomy, vol. 13, Article 93, Nov. 2019, p. 1-16.
Search Report issued Dec. 24, 2025, in Chinese Patent Application No. 2025110448525 (with attached English translation).
Office Action issued Dec. 24, 2025, in Chinese Patent Application No. 2025110448525 (with attached English translation).
Supplementary European Search Report issued Feb. 17, 2026, in corresponding European Patent Application No. 23 79 1291.0.
Search Report issued Mar. 4, 2026, in corresponding Chinese Patent Application 202511044894.9 (with attached English translation).
Office Action issued Mar. 6, 2026, in corresponding Chinese Patent Application No. 202511044894.9 (with attached English translation).
Second Office Action issued Mar. 11, 2026, in corresponding Chinese Patent Application No. 202511044852.5 (with attached English translation).
A.M. Fletcher, et al., "Transgene Expression in the Striatum Following Intracerebral Injections of DNA Nanoparticles Encoding for Human Glial Cell Line-Derived Neurotrophic Factor," Neuroscience 194 (2011) pp. 220-226.

* cited by examiner

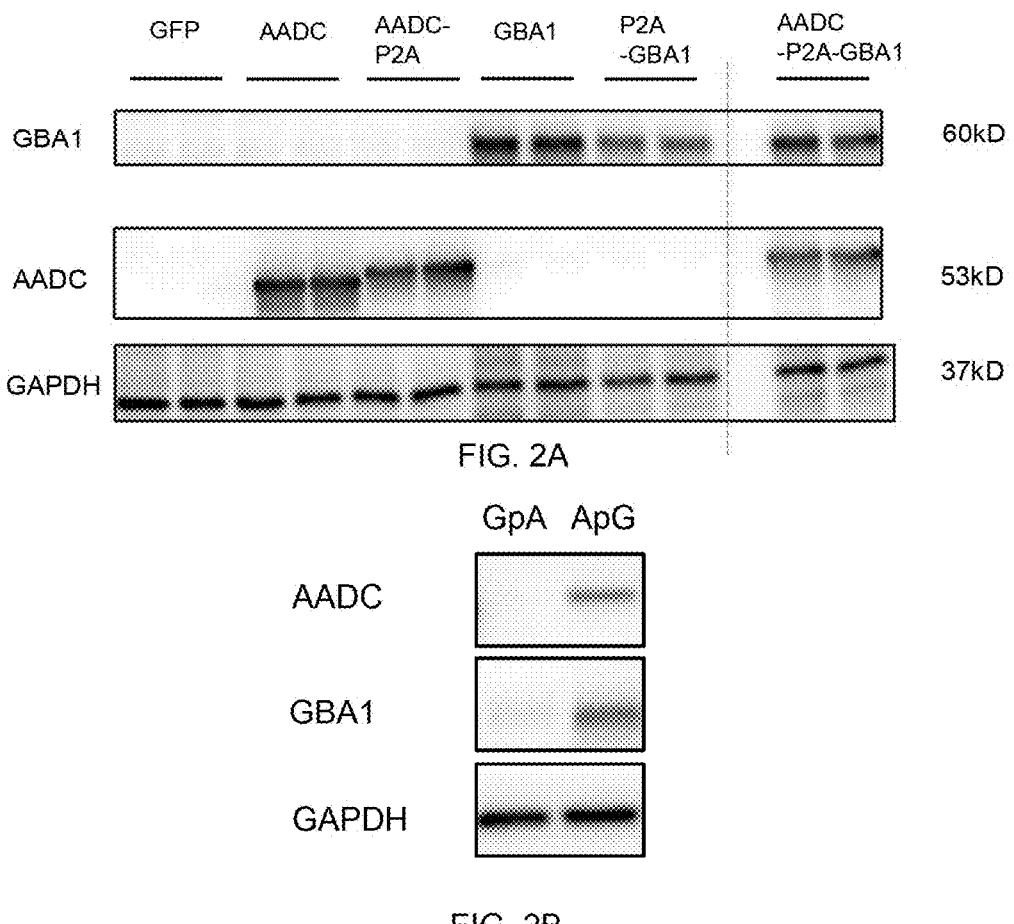
FIG. 2A
FIG. 2B
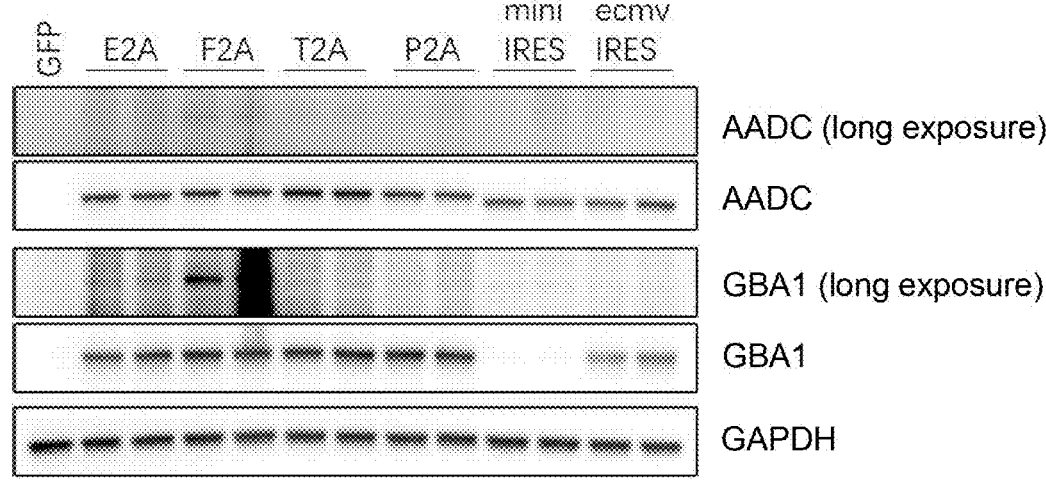
FIG. 3

A0G3   A0G4   A0G5   A0G6   A0G8   A0G9 A0G10 A0G0   G0    GFP

GBA1

GAPDH

1.5 mM MPP⁺

40 nM Rotenone

Cell lysate

Supernatant

GDNF-WT    GDNF-GS    GDNF-SA    GDNF-MN    GDNF-alone    GFP

GDNF

AADC

Tubulin

GDNF

AADC 293 72h cell lysate                 293 72h supernatant

1.5 mM MPP⁺

293 72h cell lysate        293 72h cell lysate

SEQUENCE LISTING

```
Sequence total quantity: 60
SEQ ID NO: 1              moltype = DNA   length = 1443
FEATURE                   Location/Qualifiers
misc_feature              1..1443
                          note = Codon-optimized coding sequence
source                    1..1443
                          mol_type = other DNA
                          organism = synthetic construct
SEQUENCE: 1
atgaacgcca gcgagtttag aaggagaggc aaggagatgg tggattacat ggccaattat   60
atggagggca tcgaaggcag acaggtgtat cctgacgtgg aacctggata tctgagacct  120
ctgattcctg ccgctgcccc tcaggaacct gacacattcg aggacatcat taatgacgtg  180
gagaagatca tcatgcctgg cgtgacccac tggcacagcc cttacttctt cgcctacttt  240
cccaccgcca gcagctatcc cgccatgctg gccgacatgc tgtgcggcgc catcggctgc  300
atcggcttca gctgggccgc cagccccgcc tgcaccgagc tggagaccgt gatgatggac  360
tggctgggca agatgctgga gctgcccaag gcctttctga cgagaaggc cggcgagggc  420
ggcggagtga ttcagggatc cgctagcgaa gccacactgg tggctctgct ggctgccaga  480
acaaaggtga ttcacagact gcaggccgct tctcccgagc tgacccaggc cgccatcatg  540
gagaaggtgg tggcctatag cagcgatcag gcccacagca gcgtggagag agccggcctg  600
atcggcggcg tgaagctgaa ggccatccct agcgacggca acttcgccat gcgcgccagc  660
gccctgcagg aggccctgga gcgcgacaag gccgccggcc tgatcccttt cttcatggtg  720
gccaccctgg gcacaaccac ctgctgcagc ttcgacaacc tgctggaggt gggacccatc  780
tgcaacaagg aggacatctg gctgacacgtg gacgccgcct acgccggcag cgccttcatc  840
tgccccgagt tcaggcacct gctgaacggc gtggagttcg ccgatagctt taacttcaat  900
ccccacaagt ggctgctggt gaattttgac tgcagcgcca tgtgggtgaa gaagaggacc  960
gacctgaccg gcgccttcag gctggatccc acctacctga gcacagcca ccaggacagc 1020
ggcctgatca ccgactacag gcactggcag atcccccctgg gcaggagatt ccgcagcctg 1080
aagatgtggt tcgtgttcag aatgtacggc gtgaagggcc tgcaggccta catcagaaag 1140
cacgtgcagc tgagccacga gtttgaaagc ctggtgagac aggatcctag atttgaaatc 1200
tgtgtggagg tgatcctggg cctggtgtgt tttagactga agggaagcaa taaagtgaac 1260
gaagccctgc tgcagaggat caatagcgcc aagaagattc acctggtgcc ttgtcacctg 1320
agagacaagt ttgtgctgag attcgccatt tgttctagaa ccgtggagag cgcccacgtg 1380
cagagagcct gggagcacat caaggagctg gccgccgacg tgctgagagc cgagagggag 1440
tga                                                                1443

SEQ ID NO: 2              moltype = DNA   length = 1443
FEATURE                   Location/Qualifiers
misc_feature              1..1443
                          note = CDS
source                    1..1443
                          mol_type = other DNA
                          organism = synthetic construct
SEQUENCE: 2
atgaacgcca gcgagttccg cagacggggc aaggagatgg tggactacat ggccaactac   60
atggagggca ttgagggcag acaggtgtac cccgacgtgg agcccggcta cctgagacca  120
ctcatccctg ccgccgcccc tcaggagccc gacaccttcg aggacatcat taacgacgtg  180
gagaagatta ttatgcccgg cgtgacccac tggcactccc cttacttctt cgcctacttc  240
ccaacagctc ctagctaccc agccatgctc gccgacatgc tgtgcggcgc cattggctgc  300
atcggcttct cttgggccgc ctccccagcc tgcacagagt tagaaacagt gatgatggac  360
tggctgggca agatgttgga actcccaaag gccttcctga cgagaaaggc cggcgagggc  420
ggcggcgtga tccagggctc tgccagcgag gccacactcg tggccctcct cgccgcccgc  480
acaaaggtga tccacagact gcaggccgcc agcctgagc tgacacagc cgccattatg  540
gagaagctgg tggcctactc tagcgaccag gcccactctt ctgtggagag agccggcctc  600
attggcggcg tgaagctcaa ggccatccct agcgacggca acttcgccat gagagccagc  660
gccctccagg aggcccttga acgggacaag gccgccggcc tgattccttt cttcatggtg  720
gccacactgg gcacaaccac atgctgctct ttcgacaacc tcctagaagt gggccctatt  780
tgcaacaagg aggacatttg gctgacagtg gacgccgcct acgccggctc tgccttcatt  840
tgccccgagt tcagacacct cctgaacggc gtggagttcg ccgactcttt caacttcaac  900
ccacacaagt ggtcctggt gaacttcgac tgcagcgcca tgtgggtgaa gaagcgcacc  960
gacctgaccg gcgccttcag actggaccca acatacctga gcactctca ccaggactcc 1020
ggcctgatca ccgactacag acactggcag attccaggt gcagacggtt ccggtctctc 1080
aagatgtggt tcgtgttccg gatgtacggc gtgaagggcc tccaggccta cattagaaag 1140
cacgtgcagc tgtctcacga gttcgagtct ctggtgcggc aggaccctag attcgagatt 1200
tgcgtggagg tgattctcgg cctcgtgtgc ttcagactca agggctctaa caaggtgaac 1260
gaggccctgc tgcagcggat taactctgcc aagaagattc acctggtgcc ttgccacctc 1320
cgggacaagt tcgtgctgcg gttcgccatt tgctcaagga cagtggagtc tgcccacgtg 1380
cagagagcct gggagcacat taaggaactc gccgccgacg tgctgagagc cgagcgcgag 1440
tga                                                                1443

SEQ ID NO: 3              moltype = DNA   length = 1443
FEATURE                   Location/Qualifiers
misc_feature              1..1443
                          note = CDS
source                    1..1443
                          mol_type = other DNA
                          organism = synthetic construct
SEQUENCE: 3
atgaacgcca gcgagtttag aagacggggc aaagagatgg tcgactacat ggccaattac   60
```

```
atggaaggca tcgagggcag gcaggtgtac cctgatgtgg aacccggata tctgagacct   120
ctgattcccg ctgcagcccc tcaggagcct gacacattcg aggatatcat caacgacgtg   180
gaaaaaatca tcatgcctgg cgtcacccac tggcactctc cttacttctt tgcctatttc   240
cctacagcca gcagctaccc cgccatgctg gccgacatgc tgtgtggcgc catcggctgc   300
atcggcttca gctgggccgc ctccccagcc tgcaccgagc tggaaaccgt gatgatggac   360
tggctgggaa agatgctgga actgcctaag gcctttctga atgagaaggc tggcgagggc   420
ggaggagtga tccagggctc cgcttctgag gccaccctgg ttgctctgct tgccgccaga   480
accaaggtga tccacagact gcaggccgct tctccagagc tgacccaggc cgccatcatg   540
gaaaagctgg tggcttacag cagcgaccag gcccattcca gcgtggaacg ggccggcctg   600
atcggcggcg tgaagctcaa agccatccct agcgacggaa atttcgccat gcgggcctcc   660
gccctgcaag aggccctgga aagagataag gccgccggac tcatcccgtt cttcatggtg   720
gccacactgg gtacaactac atgctgctct tttgacaacc tgctggaagt gggccctatc   780
tgcaacaaag aggacatctg gctgcacgtg gacgccgcct acgccggctc tgccttcatc   840
tgtcctgagt tcagacatct gctgaacggc gtggagttcg ctgatagctt caacttcaac   900
ccccacaagt ggctgctggt caacttcgac tgcagcgcta tgtgggtgaa aaagcgcacc   960
gacctgaccg gcgcttttag actggacccc acctacctga aacacagcca ccaggatagc   1020
ggcctgatca ccgattacag acactggcag attcccctgg gcagacggtt ccggagcctg   1080
aagatgtggt tcgtttttcag aatgtacggc gtgaaggggcc tgcaagccta catcagaaag   1140
cacgttcagc tgagccacga gttcgagagc ctggtgcggc aggaccctag atttgagatc   1200
tgcgtggaag tgatcctggg cctcgtgtgc ttccgcctga agggcagcaa caaggtgaac   1260
gaggctctgc tgcagcggat caacagcgcc aagaagatcc acctggtgcc ttgtcacctg   1320
cgggacaagt tcgtgctgag attcgcaatt tgtagcagaa ccgtgaaaag cgcccacgtg   1380
cagagagcct gggagcacat caaggaactg gccgctgatg tgctgagagc cgagcgggaa   1440
tga                                                                  1443
```

```
SEQ ID NO: 4             moltype = DNA   length = 1443
FEATURE                  Location/Qualifiers
misc_feature             1..1443
                         note = CDS
source                   1..1443
                         mol_type = other DNA
                         organism = synthetic construct
SEQUENCE: 4
atgaacgcta gcgagttcag acggagaggc aaggagatgg tggactacat ggccaactac   60
atggagggca tcgagggcag acaagtgtac cccgacgtgg agcccgggta cctgagaccc   120
ctgattcccg ccgctgcccc ccaagagccc gacaccttcg aggacatcat caacgacgtg   180
gagaagatca tcatgcccgg cgtgacccac tggcacagcc cctacttctt cgcctacttc   240
cccaccgcta gcagctaccc cgccatgctg gccgacatgc tgtgcggggc catcggctgc   300
atcggcttca gctgggccgc tagccccgcc tgcaccgagc tggagaccgt gatgatggac   360
tggctgggca gatgctgga gctgcccaag gccttcctga cgaaaaggc tggcgaaggc   420
ggggggggtga tccaaggcag cgctagcgag gctacactgg tggccctgct ggccgctaga   480
accaaggtga tccacagact gcaagccgct tcccctgagc tgacccaagc cgccatcatg   540
gagaagctgg tggcctacag cagcgaccaa gcccacagca gcgtggagag agccggcctg   600
atcggcgggg tgaagctgaa ggccatccct agcgacggca acttcgccat gagagctagc   660
gccctgcaag aggccctgga gagagacaag gccgccggcc tgatcccctt cttcatggtg   720
gccaccctgg gcaccacaac ctgctgcagc ttcgacaacc tgctggaggt gggcccccatc   780
tgcaacaagg aggacatctg gctgcacgtg gacgccgcct acgccggcag cgccttcatc   840
tgccccgagt tcagacacct gctgaacggc gtggagttcg ccgacagctt caacttcaac   900
ccccacaagt ggctgctggt gaacttcgac tgcagcgcca tgtgggtgaa gaagagaacc   960
gacctgaccg gcgccttcag actggacccc acctacctga gcacagcca ccaagacagc   1020
ggcctgatca ccgactacag acactggcag atcccctgg gcagaagatt cagaagcctg   1080
aagatgtggt tcgtgttcag aatgtacggc gtgaagggcc tgcaagccta catcagaaag   1140
cacgtgcagc tgagccacga gttcgagagc ctggtgagac aagaccctag attcgagatc   1200
tgcgtggagg tgatcctggg cctggtgtgc ttcagactga agggcagcaa caaggtgaac   1260
gaggccctgc tgcagagaat caacagcgcc aagaagatcc acctggtgcc ctgccacctg   1320
agagacaagt tcgtgctgag attcgccatc tgcagcagaa ccgtggagag cgcccacgag   1380
cagagagcct gggagcacat caaggagctg gccgccgacg tgctgagagc cgagagagag   1440
tga                                                                  1443
```

```
SEQ ID NO: 5             moltype = DNA   length = 1443
FEATURE                  Location/Qualifiers
misc_feature             1..1443
                         note = CDS
source                   1..1443
                         mol_type = other DNA
                         organism = synthetic construct
SEQUENCE: 5
atgaatgcct cagaattccg caggagggggt aaggagatgg tggactacat ggccaattat   60
atggaaggca tcgaaggtcg gcaggtgtat cctgacgtgg agcccggcta cttgagaccc   120
ctgattcccg ccgcagcccc ccaggaaccg gacacatttg aggatatcat caatgacgtc   180
gagaagatca tcatgccggg agtgactcat tggcactcac cgtacttttt tgcctatttt   240
ccgactgcct cctcctatcc tgccatgctt gcggacatgt tgtgtggagc gatcggctgc   300
atcggcttct cttgggcagc atcccccgcc tgtaccgagc tggaaaccgt catgatggat   360
tggcttggaa agatgcttga gctgcccaag gcttttctga tgaaaaaggc tggcgaggggg   420
ggcggcgtga tccaggggttc tgcaagtgaa gccactctgg tcgcattgct ggctgcccgg   480
acaaaagtta ttcacagact gcaggccgct tcacctgaac tgacgcaagc agccatcatg   540
gaaaagctgg tggcctattc ttccgaccag gcccatagct ctgttgagcg ggctgggctt   600
ataggaggtg tgaaacttaa agctatccct tcagacggta attttgccat gcgcgcttcc   660
gccctgcagg aggctctgga acgcgataaa gctgccggcc tcattccttt cttcatggtt   720
```

-continued

```
gccaccctcg gtactactac ctgttgcagc tttgataacc tgctggaggt ggggccctatt    780
tgcaacaaag aggatatctg gctgcacgtg gacgcagcat acgctgggtc tgccttcatc    840
tgcccggagt ttcggcatct ccttaatgga gttgagttcg cagacagttt caattttaat    900
cctcacaagt ggttgcttgt gaacttcgac tgttctgcaa tgtgggtgaa gaaaaggact    960
gacctgactg gcgccttccg gctcgaccca acttacctga aacattctca ccaagactca   1020
ggactgatta cagactatag acattggcag attcctctcg gcagaaggtt caggagtctg   1080
aaaatgtggt tcgtctttcg gatgtacgga gtgaaaggtc tgcaggccta tatccgcaag   1140
cacgtgcaac tttcccatga gttcgagtct ctcgttcggc aggatcctcg ctttgagatc   1200
tgtgtggagg tcattctggg gctggtgtgc ttcaggctga agggcagcaa caaagtgaat   1260
gaggctttgc ttcagaggat caactctgcc aaaaagatcc acttggtgcc ctgccatctg   1320
agggacaagt tcgtcctgag attcgctatt tgttccagaa ctgttgaaag tgcacacgtg   1380
caacgggcgt gggagcacat caaagaactg gccgcagacg tgctgagggc cgagagggag   1440
tga                                                                  1443
```

```
SEQ ID NO: 6              moltype = DNA   length = 1443
FEATURE                   Location/Qualifiers
misc_feature              1..1443
                          note = CDS
source                    1..1443
                          mol_type = other DNA
                          organism = synthetic construct
SEQUENCE: 6
atgaacgcca gcgagtttag aaggaggggga aaggagatgg tggattacat ggctaactac     60
atggagggga tcgagggcag acaggtctac cctgatgtgg agcctggcta cctgaggccc    120
ctgatccctg ccgccgcccc acaggaacca gatactttg aggatattat taacgatgtc     180
gagaagatta ttatgccagg agtgacacac tggcatacc cctacttctt tgcttatttt     240
cccacagcta gctcttaccc tgcaatgttg gctgatatgc tgtgcggcgc cattggatgc    300
attggctttta gttgggctgc cagtcctgcc tgcacagaat tggagacagt gatgatggat    360
tggctggaa agatgctgga gctgcctaag gcctttctga cgagaaggc cggcgagggg     420
ggcggcgtga tccaggggga gcgccagcgag gccaccctgc tcgccctgct ggccgcccgg    480
accaaggtca ttcacaggct gcaggccgcc agccccgagc tgacacaggc cgccatcatg    540
gagaagctgg tggcctacag ctccgaccag gcccacagct ccgtggagcg ggccggcctg    600
atcggcggc tgaagctgaa ggccattccc tcagacggga acttcgccat gcgggccagc    660
gccctccagg aggccttgga gagggataag gccgccggcc tgatcccctt ctttatggtg    720
gctaccctgg ggacaaccac atgctgctcc ttcgataacc tgctggaggt ggggcccatc    780
tgcaacaagg aggacatctg gctgcacgtg gatgccgcct acgccgggtc cgccttcatt    840
tgcccccgagt ccggcacct gctgaacggc gtggagttcg ccgatagctt caacttcaac    900
ccccacaagt ggctgctggt gaacttcgac tgcagcgcca tgtgggtgaa gaagaggacc    960
gacctgaccg gcgcctttag gctcgacccc acatacctga agcacagcca ccaggactcc   1020
gggctgatca cagattacag gcactggcag atcccctcg gcaggcggtt ccggtccctg   1080
aagatgtggt tcgtgttccg gatgtacggg gtgaaggggc tgcaggccta catcaggaag   1140
cacgtccagc tcagccacga gttcgagagc ctggtgaggc aggaccccg gttcgagatc   1200
tgcgtggagg tcatcctggg gctggtgtgt ttccggctca agggctccaa caaggtgaac   1260
gaggccctcc tccagcggat taactccgcc aagaagatcc acctggtccc ctgccacctg   1320
agggataagt tcgtgctgcg gttcgccatt tgcagcagga cagtggagag cgcccacgtg   1380
cagcgggcct gggagcacat taaggagctg gccgccgatg tgctgagggc cgagagggag   1440
tga                                                                  1443
```

```
SEQ ID NO: 7              moltype = DNA   length = 1443
FEATURE                   Location/Qualifiers
misc_feature              1..1443
                          note = CDS
source                    1..1443
                          mol_type = other DNA
                          organism = synthetic construct
SEQUENCE: 7
atgaacgcca gcgagttcag acgcaggggc aaggagatgg tggactacat ggccaactac     60
atggagggca ttgagggcag acaggtgtac cccgacgtgg agcccggcta cctcagacca    120
ctcatcccag ccgccgcccc tcaggagccc gacacattcg aggacatttat taacgacgtg    180
gagaagatta ttatgcccgg cgtgacccac tggcactccc cttacttctt cgcctacttc    240
ccaacagcct ctagctaccc agccatgctc gccgacatgc tgtgcggcgc catcggctgc    300
attggcttct cttgggccgc ctccccagcc tgcaccgagt tagagacagt gatgatggac    360
tggctgggca gatgcttga gctacctaag gccttcctga cgagaaggc cggcgagggc    420
ggcggcgtga tccagggctc tgccagcgag gccacactgc tggccctcct gccgccccgg    480
acaaaggtga tccacagact ccaggccgcc tccccagagc tgacacaggc cgccatcatg    540
gagaagctgg tggcctactc tagcgaccag gcccactctt ctgtggagag agccggcctg    600
attggcggc tgaagctgaa ggccattcca tctgacggca acttcgccat gagagccagc    660
gccctccagg aggccttga acgggacaag gccgccggcc tgattccttt cttcatggtg    720
gccacactgg gcaccacaac atgctgctct ttcgataacc tcctggaggt gggggcccaatt    780
tgcaacaagg aggacatttg gctgcacgtg gacgccgcct acgccgggctc tgccttcatt    840
tgccctgagt tcagacacct cctgaacggc gtggagttcg ccgactcttt caacttcaac    900
ccacacaagt ggtcctggt gaacttcgac tgctctgcca tgtgggtgaa gaagcgcacc    960
gacctgaccg gcgccttcag actggaccca acatacctca gcactctca ccaggactcc   1020
ggcctcatca cagactacag acactggcag attcctctcg gcagaaggtt ccggagtctg   1080
aagatgtggt tcgtgttccg gatgtacggc gtgaaggggcc tccaggccta cattagaaag   1140
cacgtgcagc tgtctcacga gttcgagtct ctcgtgagac aggaccctag gttcgagatt   1200
tgcgtggagg tgattctcgg cctggtgtgc ttcagactca agggctctaa caaggtgaac   1260
gaggccctcc ttcagcggat taactctgcc aagaagatcc acctcgtgcc ttgccacctg   1320
cgggacaagt tcgtgctgcg gttcgccatt tgctcccgta cagtggagtc tgcccacgtg   1380
```

```
cagcgcgcct gggagcacat taaggaactc gccgccgacg tgctgagagc cgagcgcgag  1440
tga                                                                  1443

SEQ ID NO: 8           moltype = DNA  length = 1443
FEATURE                Location/Qualifiers
misc_feature           1..1443
                       note = CDS
source                 1..1443
                       mol_type = other DNA
                       organism = synthetic construct
SEQUENCE: 8
atgaacgcca gcgagttccg gagaagggg aaggagatgg tggactacat ggccaactac  60
atggagggga tcgaggggag acaggtgtac cccgacgtgg agcccgggta cctgagaccc  120
ctgattcccg ccgctgctcc ccaggaacca gacaccttcg aggacatcat taacgacgtg  180
gagaagatca ttatgccagg cgtgacccac tggcatagcc cctacttctt tgcctacttc  240
cccacagcct cctcataccc cgccatgctg gccgacatgc tgtgcggcgc cattggctgc  300
atcggcttca gctgggctgc ttctcccgct tgcaccgagc tggagaccgt gatgatggac  360
tggctgggca agatgctgga gctgcccaag gccttcctga cgagaaaggc cggcgagggc  420
ggaggcgtga tccagggatc cgccagcgag gccaccctgg tggctctgct ggccgctagg  480
accaaggtga tccacagact gcaggccgcc agtcccgagc tgacccaggc tgctatcatg  540
gagaagctgg tggcctactc ctccgaccag gcccacagct ccgtggagag agccggactg  600
atcggcggcg tgaaactgaa ggccattccc tccgacggca acttcgctat gccggccagc  660
gccctgcagg aggctctgga aagggacaag gccgccggcc tgattcccct tcttcatggtg  720
gctacactgg gcaccaccac ctgctgctcc tttgataacc tgctggaggt gggacccatt  780
tgcaacaagg aagacatttg gctgcacgtg gatgctgcct acgccggcag cgcctttatt  840
tgcccgagt tcagacacct gctgaatggc gtggagttcg ctgactcctt caacttcaac  900
ccccacaagt ggctgctggt gaacttcgat tgttctgcca tgtgggtgaa gaagaggacc  960
gacctgaccg gagccttccg gctggaccct acctacctga aacactccca ccaggactcc  1020
ggcctgatta ccgactacag acactggcag atccccctgg gcagaagatt cagaagcctg  1080
aaaatgtggt ttgtgttcag aatgtacggc gtgaaaggcc tgcaggccta catcaggaag  1140
cacgtgcagc tgagccacga attcgagagc ctggtgagac aggacccag atttgaaatc  1200
tgcgtggagg tgattctggg cctggtgtgt ttcagactga agggaagcaa caaggtgaac  1260
gaggccctgc tgcagaggat caactcagcc aagaagatcc acctggtgcc ctgtcacctg  1320
agagacaagt tcgtgctgag attcgccatc tgctctagaa cagtggagag cgcccacgtg  1380
cagagagcct gggagcacat caaggagctg ccgccgacg tgctgagagc cgaaagagag  1440
tga                                                                  1443

SEQ ID NO: 9           moltype = DNA  length = 1443
FEATURE                Location/Qualifiers
misc_feature           1..1443
                       note = CDS
source                 1..1443
                       mol_type = other DNA
                       organism = synthetic construct
SEQUENCE: 9
atgaacgcca gcgagtttcg gcggagaggc aaagaaatgg tggactacat ggccaactac  60
atggaaggca tcgagggcag acaggtgtac cccgatgtgg aacctggcta cctgaggcct  120
ctgattcctg ccgctgctcc ccaagagcct gacaccttcg aggacatcat caacgacgtg  180
gaaaagatca tcatgcccgg cgtgacccac tggcacagcc cctacttttt cgcctacttt  240
cccaccgcca gcagctaccc tgctatgctg gctgatatgc tgtgtggcgc catcggctgc  300
atcggctttt cttgggctgc ctctcctgcc tgcaccgagc tggaaaccgt gatgatggat  360
tggctgggca agatgctgga actgcccaag gccttcctga cgagaaaagc tggcgaaggc  420
ggcggagtga ttcagggatc tgcctctgaa gccacactgg tggctctgct ggccgccaga  480
acaaaagtga tccacagact gcaggccgcc tctccagaac tgacacaggc cgccatcatg  540
gaaaagctga tggcctacag cagcgatcag gcccacagct ctgtggaaag agccggactg  600
attggcggcg tgaagctgaa ggccattcct agcgacggca acttcgccat gagagcctct  660
gctctgcaag aggccctgga aagagataag gccgctggac tgatcccctt cttcatggtg  720
gctaccctgg gcaccaccac ctgttgcagc ttcgacaacc tgctggaagt gggccccatc  780
tgcaacaaag aggacatctg gctgcacgtg gacgccgcct atgccggctc tgcctttatc  840
tgcccccgagt tcagacatct gctgaacggc gtggaattcg ccgacagctt caacttcaac  900
cctcacaagt ggctgctggt caacttcgac tgcagcgcta tgtgggtcaa gaagcggacc  960
gatctgaccg gcgccttcag actggatccc acctacctga gcactccca ccaggatagc  1020
ggcctgatca ccgactaccg gcactggcag attcctctgg gcagaagatt tcggagcctg  1080
aagatgtggt tcgtgttccg gatgtatggc gtgaaaggcc tccaggccta catcaggaag  1140
catgtgcagc tgagccacga gttcgagagc cttgtcagac aggaccccag attcgagatc  1200
tgcgtggaag tgatcctggg cctcgtgtgc tttagactga agggcagcaa caaagtgaac  1260
gaggccctgc tgcagcggat caacagcgcc aaaaagatcc acctggtgcc ttgccacctg  1320
agagacaagt tcgtgctgag attcgccatc tgcagccgga cagtggaaag cgcccatgtg  1380
cagagagcct gggagcacat caaagaactg gccgccgatg tgctgagggc cgagagagaa  1440
tga                                                                  1443

SEQ ID NO: 10          moltype = DNA  length = 1443
FEATURE                Location/Qualifiers
misc_feature           1..1443
                       note = CDS
source                 1..1443
                       mol_type = other DNA
                       organism = synthetic construct
SEQUENCE: 10
```

```
atgaacgcaa gtgaattccg aaggagaggg aaggagatgg tggattacgt ggccaactac    60
atggaaggca ttgagggacg ccaggtctac cctgacgtgg agcccgggta cctgcggccg    120
ctgatccctg ccgctgcccc tcaggagcca gacacgtttg aggacatcat caacgacgtt    180
gagaagataa tcatgcctgg ggtgacgcac tggcacagcc cctacttctt cgcctacttc    240
cccactgcca gctcgtaccc ggccatgctt gcggacatgc tgtgcggggc cattggctgc    300
atcggcttct cctgggcggc aagcccagca tgcacagagc tggagactgt gatgatggac    360
tggctcggga agatgctgga actaccaaag gcatttttga atgagaaagc tggagaaggg    420
ggaggagtga tccagggaag tgccagtgaa gccaccctgg tggccctgct ggccgctcgg    480
accaaagtga tccatcggct gcaggcagcg tccccagagc tcacacaggc cgctatcatg    540
gagaagctgg tggcttactc atccgatcag gcacactcct cagtggaaag agctgggtta    600
attggtggag tgaaattaaa agccatcccc tcagatggca acttcgccat gcgtgcgtct    660
gccctgcagg aagccctgga gagagacaaa gcggctggcc tgattccttt ctttatggtt    720
gccaccctgg ggaccacaac atgctgctcc tttgacaatc tcttagaagt cggtcctatc    780
tgcaacaagg aagacatatg gctgcacgtt gatgcagcct acgcaggcag tgcattcatc    840
tgccctgagt tccggcacct tctgaatgga gtggagtttg cagattcatt caactttaat    900
ccccacaaat ggctattggt gaattttgac tgttctgcca tgtgggtgaa aaagagaaca    960
gacttaacgg gagcctttag actggacccc acttacctga agcacagcca tcaggattca    1020
gggcttatca ctgactaccg gcattggcag ataccactgg gcagaagatt tcgctctttg    1080
aaaatgtggt ttgtatttag gatgtatgga gtcaaaggac tgcaggctta tatccgcaag    1140
catgtccagc tgtcccatga gtttgagtca ctggtgcgcc aggatccccg ctttgaaatc    1200
tgtgtggaag tcattctggg gcttgtctgc tttcggctaa agggttccaa caaagtgaat    1260
gaagctcttc tgcaaagaat aaacagtgcc aaaaaaatcc acttggttcc atgtcacctc    1320
agggacaagt ttgtcctgcg ctttgccatc tgttctcgca cggtggaatc tgcccatgtg    1380
cagcgggcct gggaacacat caaagagctg gcggccgacg tgctgcgagc agagagggag    1440
tag                                                                  1443
```

SEQ ID NO: 11          moltype = DNA   length = 1443
FEATURE                Location/Qualifiers
source                 1..1443
                       mol_type = genomic DNA
                       organism = Homo sapiens
SEQUENCE: 11

```
atgaacgcaa gtgaattccg aaggagaggg aaggagatgg tggattacat ggccaactac    60
atggaaggca ttgagggacg ccaggtctac cctgacgtgg agcccgggta cctgcggccg    120
ctgatccctg ccgctgcccc tcaggagcca gacacgtttg aggacatcat caacgacgtt    180
gagaagataa tcatgcctgg ggtgacgcac tggcacagcc cctacttctt cgcctacttc    240
cccactgcca gctcgtaccc ggccatgctt gcggacatgc tgtgcggggc cattggctgc    300
atcggcttct cctgggcggc aagcccagca tgcacagagc tggagactgt gatgatggac    360
tggctcggga agatgctgga actaccaaag gcatttttga atgagaaagc tggagaaggg    420
ggaggagtga tccagggaag tgccagtgaa gccaccctgg tggccctgct ggccgctcgg    480
accaaagtga tccatcggct gcaggcagcg tccccagagc tcacacaggc cgctatcatg    540
gagaagctgg tggcttactc atccgatcag gcacactcct cagtggaaag agctgggtta    600
attggtggag tgaaattaaa agccatcccc tcagatggca acttcgccat gcgtgcgtct    660
gccctgcagg aagccctgga gagagacaaa gcggctggcc tgattccttt ctttatggtt    720
gccaccctgg ggaccacaac atgctgctcc tttgacaatc tcttagaagt cggtcctatc    780
tgcaacaagg aagacatatg gctgcacgtt gatgcagcct acgcaggcag tgcattcatc    840
tgccctgagt tccggcacct tctgaatgga gtggagtttg cagattcatt caactttaat    900
ccccacaaat ggctattggt gaattttgac tgttctgcca tgtgggtgaa aaagagaaca    960
gacttaacgg gagcctttag actggacccc acttacctga agcacagcca tcaggattca    1020
gggcttatca ctgactaccg gcattggcag ataccactgg gcagaagatt tcgctctttg    1080
aaaatgtggt ttgtatttag gatgtatgga gtcaaaggac tgcaggctta tatccgcaag    1140
catgtccagc tgtcccatga gtttgagtca ctggtgcgcc aggatccccg ctttgaaatc    1200
tgtgtggaag tcattctggg gcttgtctgc tttcggctaa agggttccaa caaagtgaat    1260
gaagctcttc tgcaaagaat aaacagtgcc aaaaaaatcc acttggttcc atgtcacctc    1320
agggacaagt ttgtcctgcg ctttgccatc tgttctcgca cggtggaatc tgcccatgtg    1380
cagcgggcct gggaacacat caaagagctg gcggccgacg tgctgcgagc agagagggag    1440
tag                                                                  1443
```

SEQ ID NO: 12          moltype = DNA   length = 1611
FEATURE                Location/Qualifiers
misc_feature           1..1611
                       note = CDS
source                 1..1611
                       mol_type = other DNA
                       organism = synthetic construct
SEQUENCE: 12

```
atggagttca gctctcccag cagagaagaa tgtcctaagc ctctgagcag ggtgtccatc    60
atggccggca gcctgaccgg actcctgctc ctgcaggccg tgagctgggc cagcggcgcc    120
aggccttgca ttcccaagag cttcggctac agcagcgtgg tgtgcgtgtg caacgccacc    180
tactgcgaca gcttcgatcc tcctaccttt cctgccctgg gaacattctc ccgctacgag    240
agcaccagga gcgagccgga aatggagctg agcatgggac ccatccaggc caaccacaca    300
ggaacaggcc tcctgctcac cctgcagcct gagcaaaaat ttcagaaggt gaagggcttc    360
ggcggcgcca tgaccgacgc tgccgctctg aacatcctgg ccctgagccc tcctgcccag    420
aacctcctga tcaagagcta cttcagcgag gagggcatcg gctacaacat catcagagtg    480
cccatggcca gctgcgactt tagcattagg acatatacct acgccgatac acctgatgac    540
ttccagctgc ataactttag cctgcctgag gaggatacca agctgaaaat ccctctgatc    600
catcgcgccc tgcagctggc ccagagacct gtgtccctgc tggccagccc ttggacaagc    660
cctacatggc tgaagaccaa cggcgctgtg aatggcaaag cagcctgaa aggacagcct    720
ggcgatatct atcaccagac ctgggccagg tattttgtga aatttctgga tgcctacgcc    780
```

```
gagcacaagc tgcagttctg ggccgtgacc gctgagaatg aaccttctgc cggactgttg    840
agcggctatc cctttcagtg tctgggattc acccctgagc accagcgcga cttcatcgcc    900
cgcgacctgg gccctaccct ggccaacagc acccaccaca acgtgcgcct gctgatgctg    960
gacgatcaga gactgctgct gccccactgg gccaaggtgg tgctgaccga ccctgaggcc    1020
gccaagtacg tgcacggcat cgccgtgcac tggtacctgg acttcctggc tcctgccaag    1080
gccaccctgg gcgagaccca caggctgttc cctaacacca tgctgttcgc cagcgaggcc    1140
tgcgtgggct ccaagttctg ggagcagtcc gtgaggctgg gaagctggga caggggcatg    1200
cagtacagcc acagcatcat caccaacctg ctgtaccacg tggtgggctg gaccgactgg    1260
aacctggccc tgaaccctga gggcggccca aactgggtgc gcaacttcgt ggacagccct    1320
atcatcgtgg acatcaccaa ggacaccttc tacaagcagc ccatgttcta ccacctgggc    1380
cacttcagca gtttattcc tgagggcagc caaaggtgg gactggtggc cagccagaaa    1440
aatgacctga cgccgtggc tctgatgcat cctgatggca gcgccgtcgt ggttgtcctg    1500
aaccgcagca gcaaggacgt gcccctgacc atcaaggatc ctgccgtggg cttcctggag    1560
accatcagcc ctggctacag catccacacc tacctgtgga gggagacagtg a            1611
```

SEQ ID NO: 13          moltype = DNA   length = 1611
FEATURE                Location/Qualifiers
misc_feature           1..1611
                       note = CDS
source                 1..1611
                       mol_type = other DNA
                       organism = synthetic construct
SEQUENCE: 13

```
atggagttca gctccccatc tagggaggag tgccctaagc cactgagtcg cgtgtctatt    60
atggccggct ctctgacagg cctcctgctc ctgcaggccg tgtcttgggc ctctggcgcc    120
agaccttgca tcccaaagtc tttcggctac tctagcgtgg tgtgcgtgtg caacgccaca    180
tactgcgact ctttcgaccc accaaccttc cccgccctcg gcaccttctc ccggtacgag    240
tctacacggt ccggcaggcg gatggagctg tccatgggcc caattcaggc caaccacaca    300
ggcacaggc tgctcctgac actgcagcca gagcagaagt ccagaaggt gaagggcttc    360
ggcggcgcca tgaccgacgc cgccgccctc aacattctcg ccctgtcccc acccgcccag    420
aacctgctgc tcaagtctta cttcagcgag gagggcattg gctacaacat catccgggtg    480
cctatggcct cttgcgactt cagcattaga acatacacat acgccgacac acctgacgac    540
ttccagctgc acaacttcag cctccccgag gaggacacaa agctcaagat tccactgatt    600
caccgcgcc tgcagctggc ccagagacca gtgtctctgc tcgcctcccc ttggacatct    660
ccaacatggc tgaagacaaa cggcgccgtg aacggcaagg gctctctgaa gggccagcca    720
ggcgacattt accaccagac atgggccggg tacttcgtga agttcctcga cgcctacgcc    780
gagcacaagc tgcagttctg ggccgtgaca gccgagaacg agcctagcgc cggcctgctg    840
tccggctacc ctttccagtg cctcggcttc acccctgagc accagcggga cttcattgcc    900
cgggacctcg gccctacact cgccaactct ccccaccaca acgtgagact cctgatgctg    960
gacgaccaga gactgctgct ccctcactgg gccaaggtgg tgctcaccga ccccgaggcc    1020
gccaagtacg tgcacggcat tgccgtgcac tggtacctcg acttcctcgc cccagccaag    1080
gccacactcg gcgagaccca cagactgttc cctaacacca tgctgttcgc ctctgaggcc    1140
tgcgtgggca gcaagttctg ggagcagtct gtgagactgg gccgcggcat cagtactctc    1200
actccattat tacaaacctg ctgtaccacg tggtgggctg gaccgactgg    1260
aacctcgccc tgaaccccga gggcggccct aactgggtgc ggaacttcgt ggactctcct    1320
atcattgtgg acattacaaa ggacacattc tacaagcagc ctatgttcta ccacctcggc    1380
cacttctcta gttcatccc cgagggctct cagagagag gcctggtggc cagccagaag    1440
aacgacctgg acgccgtggc cctgatgcac cccgacggca gcgccgtggt ggtggtgctc    1500
aacagatcga gcaaggacgt gccactgaca attaaggacc cagccgtggg cttccttgaa    1560
acaatttctc caggctactc tattcacaca tacctgtggc gggagacagtg a            1611
```

SEQ ID NO: 14          moltype = DNA   length = 1611
FEATURE                Location/Qualifiers
misc_feature           1..1611
                       note = CDS
source                 1..1611
                       mol_type = other DNA
                       organism = synthetic construct
SEQUENCE: 14

```
atggagttca gcagccccag ccgggaagag tgccctaagc ctctgagcag agtgtccatc    60
atggccggtt ccctgaccgg cctgctgctt ctgcaagccg tgtcttgggc cagcggagcc    120
agacctgca tcccaaagtc cttcggctac agctctgtgg tctgcgtgtg caacgccacc    180
tactgcgaca gcttcgaccc tccaaccttc cctgccttgg gaaccttcag cagatatgag    240
agcacaagaa gcggcaggaag aatggaactg agcatgggcc ctattcaggc caatcacaca    300
ggcaccggct tactgctgac actgcagcct gagcagaagt ccagaaagt gaaaggcttc    360
ggcggcgcca tgaccgacgc cgctgctctg aatatcctgg ctctgagccc acctgctcag    420
aacctgctgc tgaaaagcta cttttctgag gaaggcatcg gatacaacat catcagagtg    480
cctatggcct cttgtgactt cagcatccgg acctacacct atgccgacac acctgatgac    540
tttcagctgc acaatttcag cctgcccgag gaagatacaa agctgaagat ccccctgatc    600
caccgggccc tgcagctggc ccagagacct gtgtccctgc tggcttctcc ttggaccagc    660
cctacctggc tcaaaacaaa cggcgccgtg aacggcaagg gctctctgaa gggccagcct    720
ggagatatct accaccaaac atgggccaga tacttcgtga agttcctgga cgcctacgcc    780
gaacacaagc tgcagttctg ggcagtgacc gccgagaacg agcttctgc cggactgctg    840
agcggctacc ccttccaatg tctgggcttt acccctgagc accagcgcga cttcatcgcc    900
agagatctgg ccctacact ggccaacagc acccaccaca acgtgcgcct gctcatgctg    960
gacgaccaga gactgctgct tcctcactgg gccaaggtgg tcctgaccga ccctgaagcc    1020
gctaagtacg tgcacggcat cgccgttcac tggtacctgg attttctggc ccctgccaag    1080
gccacgctgc gcgagacaca cagactgttt ccaaatacca tgctgttcgc cagcgaggca    1140
tgcgtgggga gcaaattctg ggagcagagc gtgcggctgg gctcctggga cagaggcatg    1200
```

-continued

```
caatacagcc actctatcat caccaacctg ctgtaccatg tggtgggctg gacagactgg   1260
aacctggccc tgaaccccga gggaggcccc aactgggtca ggaacttcgt ggatagcccc   1320
atcatcgttg acatcaccaa ggacaccttc tacaagcagc ccatgttcta ccatctggga   1380
cacttctcca agtttatccc tgagggctcc cagcgggtgg gcctggtggc cagccagaag   1440
aacgacctgg atgccgtggc tctgatgcac cctgacggca ggctgtgtgt ggtggtgctg   1500
aacagatcct ccaaggatgt gcccctgact atcaaggacc ccgccgtggg attcctggaa   1560
accatcagcc ctggctatag cattcacacc tacctgtggc ggagacagtg a             1611
```

```
SEQ ID NO: 15             moltype = DNA  length = 1611
FEATURE                   Location/Qualifiers
misc_feature              1..1611
                          note = CDS
source                    1..1611
                          mol_type = other DNA
                          organism = synthetic construct
SEQUENCE: 15
atggagttca gctcccctag cagagaggag tgccccaagc ccctgagcag agtgtccatt   60
atggctggca gcctgaccgg cctgctgctc ctgcaagccg tgagctgggc tagcggcgct   120
agaccctgca tccccaagag cttcggctac agcagcgtgg tgtgcgtgtg caacgccacc   180
tactgcgaca gcttcgaccc ccccaccttc cccgccctgg gcaccttcag cagatacgag   240
agcacaagaa gcggcagaag aatggagctg agcatgggcc ccatccaagc caaccacacc   300
ggcaccggcc tgctcctgac actgcagccc gagcagaagt ttcagaaggt gaagggcttt   360
ggggcgcca tgaccgacgc cgctgccctg aatatcctgg ccctgagccc ccccgctcag   420
aacctgctcc tgaagagcta cttcagcgag gagggcatcg gctacaacat catcagagtg   480
cccatggcta gctgcgactt cagcatcaga acctacacct acgccgacac ccccgacgac   540
tttcagctgc acaacttcag cctgcccgag gaggacacca agctgaagat ccccctgatc   600
cacagagccc tgcagctggc tcagagaccc gtgagcctgc tggctagccc ctggacaagc   660
cccacctggc tgaagaccaa cggcgccgtg aacggcaagg gcagcctgaa ggggcagccc   720
ggcgacatct accatcagac ctgggctaga tacttcgtga agttcctgga cgcctacgcc   780
gagcacaagc tgcagtgttttg ggctgtgacc gccgagaacg agcctagcgc cggcctgctg   840
agcggctacc cctttcagtg cctgggcttc accccccgagc atcagagaga cttcatcgct   900
agagacctgg gccccaccct ggccaacagc acccaccaca acgtgagact gctgatgctg   960
gacgatcaga gactgctcct gccccactgg gccaaggtgg tgctgaccga ccccgagggc   1020
gccaagtacg tgcacggcat cgccgtgcac tggtacctgg acttcctggc ccccgccaag   1080
gccaccctgg gcgagaccca cagactgttc cccaacacca tgctgttcgc tagcgaggcc   1140
tgcgtgggca gcaagttctg gggagcagagc gtgagactgg gcagctggga cagaggcatg   1200
cagtacagcc acagcatcat caccaacctg ctgtaccacg tggtgggctg gaccgactgg   1260
aacctggccc tgaaccccga gggcggcccc aactgggtga gaaacttcgt ggacagcccc   1320
atcatcgtgg acatcaccaa ggacaccttc tacaagcagc ccatgttcta ccacctgggc   1380
cacttcagca gttcatccc cgagggcagc caaagagtgg gcctggtggc tagccaaaag   1440
aacgacctgg acgccgtggc cctgatgcac cccgacggca gcgccgtggt cgtggtgctg   1500
aacagaagca gcaaggacgt gcccctgacc atcaaggacc ccgccgtggg cttcctggag   1560
accatcagcc ccggctacag catccacacc tacctgtgga gaagacagtg a              1611
```

```
SEQ ID NO: 16             moltype = DNA  length = 1611
FEATURE                   Location/Qualifiers
misc_feature              1..1611
                          note = CDS
source                    1..1611
                          mol_type = other DNA
                          organism = synthetic construct
SEQUENCE: 16
atggaattta gctcacctag ccgggaggaa tgcccaaaac ccctctcccg ggtgtccatt   60
atggctggaa gcctcacagg ccttctgctc ttgcaagccg tcagctgggc ctctggggcc   120
cggccatgta ttcaaaatc cttcggttac tcatctgtgg tctgtgtgtg taatgcaacg   180
tactgcgact cattcgatcc ccccacattc ccagccctgg ggacgttttc ccgctacgaa   240
agcactcggt ctggcaggcg gatggaactg tccatgggtc ccatccaggc taaccacact   300
ggaactggac tgctgctgac gctgcagccc gaacagaagt ttcagaaggt taagggtttc   360
ggcggcgcca tgactgacgc cgcggctctg aatatcctgg cgctgagccc acctgcacag   420
aatctgctgc tgaaaagcta cttcagtgag gaagggatcg gatacaatat tatcagggta   480
cctatggcaa gctgtgattt ttctatccgg acatacacgt acgctgacac tccagatgat   540
ttccagctgc ataactttc tctccccgag gaggatacaa agctgaagat ccctctgatc   600
catcgcgccc tccagctggc ccagcgcccc gtatctcttc ttgcgagccc ttggacaagt   660
cctacatggc tgaagactaa tggtgccgtt aatggaaagg gcagtttgaa aggccagcca   720
ggtgacatct atcaccagac atgggcccgg tactttgtaa agttcctcga tgcgtatgcc   780
gaacacaagc tgcagtttttg ggccgtgacg gcagaaaatg agccctctgc tggcctgctt   840
tctggttacc ctttccagtg ccttggtttc acaccggagc accagcggga tttcatcgct   900
agagatctgg gacccacgct ggccaactcc acccatcaca acgtgcgcct cttgatgctg   960
gatgaccaga gactcctcct cccacactgg gctaaggttg ttcttactga tccagaagcc   1020
gccaaatacg ttcacggaat tgccgtccac tggtatttgg acttcctcgc ccccgctaaa   1080
gctacactgg gcgaaacgca cagactgttt cccaacacca tgctctttgc tagtgaagcg   1140
tgcgtcggtt ctaagttctg ggaacagagc gtacgcctgg gctcatggga cagggggatg   1200
caatattccc acagcataat caccaacctg ctgtatcatg tggtcgggtg gacagactgg   1260
aacttggcct tgaaccccga gggcggcccc aactgggtga gaaacttttgt ggacagtcca   1320
attatcgtcg atattactaa ggatacattc tataagcaac ctatgttcta tcacctcggc   1380
catttctcta gtttatccc tgaaggcagc cagcgagtcg gactggtggc aagtcaaaag   1440
aacgatctcg atgcggtggc attgatgcac cccgacggaa gtgcagttgt tgtggtcctg   1500
aataggagct caaaggatgt tccactgacc ataaaggacc ctgccgtggg cttcttggaa   1560
accatttccc cagggtacag cattcacacc tacctgtggc gacggcagtg a              1611
```

-continued

```
SEQ ID NO: 17          moltype = DNA  length = 1611
FEATURE                Location/Qualifiers
misc_feature           1..1611
                       note = CDS
source                 1..1611
                       mol_type = other DNA
                       organism = synthetic construct
SEQUENCE: 17
atggagttta gctcccctag cagagaggag tgccctaagc ccctgagtag agtgagcatt   60
atggccggct ccctgacagg gctgctcctt ctgcaggccg tgagctgggc cagcggggcc  120
cggccctgca tccctaaatc cttcgggtac tcctcggtgg tgtgtgtgtg caatgctacc  180
tactgtgatt cctttgaccc cccaacattt cccgccctgg gcacctttag caggtacgag  240
tccacacggt ccgggaggag gatggagctg agcatgggcc ccattcaggc caaccacacc  300
ggcaccggcc tcctgctgac tctgcagccc gagcagaagt tccagaaggt gaagggcttt  360
ggcggcgcca tgactgacgc cgccgccctg aacatcctgg ccctgagccc ccccgcccaa  420
aacctgctgc tgaagtccta ctttagtgag gaggggatcg gctacaacat tattcggggtg  480
cctatggcca gctgcgactt ctccatccgg acatacacct acgctgatac acccgatgac  540
ttccagctcc acaactttag cctgcctgag gaggatacta agctgaagat tcccctgatc  600
cacagggccc tccagcttgc ccagagaccc gtgagcctcc tggccagccc ctggacaagc  660
cccacctggc tcaagaccaa cggggccgtg aacgggaagg ggtccctgaa ggggcagcca  720
ggcgacatct accaccagac ctgggcccgg tacttcgtga agttcctgag tgcctacgcc  780
gagcacaagc tgcagttttg ggccgtgacc gccgagaacg agcccagcgc cggcctgctg  840
agcgggtacc ccttccagtg cctggggttt acaccagagc accagcggga ctttattgct  900
cgggacctcg gccccaccct ggccaacagc acacaccaca acgtgaggct gctgatgctg  960
gatgatcagc ggctcctgct gccccactgg gctaaggtgg tcctgactga ccctgaggcc 1020
gccaagtacg tgcacggcat cgccgtgcat tggtacctgg atttcctggc ccccgccaag 1080
gccaccctgg gggagacaca ccggctgttc cctaacacaa tgctgtttgc cagcgaggcc 1140
tgcgtgggct ccaagttctg ggagcagagc gtgcggctgg ggagctggga tcgggggatg 1200
cagtacagcc acagcattat caccaacctg ctctaccacg tggtggggtg gaccgactgg 1260
aacctggccc tgaaccccga gggcggcccc aactgggtca ggaacttcgt cgatagcccc 1320
ataatcgtgg atatcacaaa ggatacctttt tacaagcagc ccatgttcta ccacctcggg 1380
cacttctcca agttcatccc cgagggctcc cagcgggtgg gcctggtcgc cagccagaag 1440
aacgatctgg acgccgtggc cctgatgcac cctgacggga gcgccgtcgt ggtggtgctg 1500
aaccggtcca gcaaggacgt ccccctgaca atcaaggacc ccgccgtcgg gttcctggag 1560
accatcagcc aggctacag cattcacaca tacctgtggc ggcggcagtg a           1611

SEQ ID NO: 18          moltype = DNA  length = 1611
FEATURE                Location/Qualifiers
misc_feature           1..1611
                       note = CDS
source                 1..1611
                       mol_type = other DNA
                       organism = synthetic construct
SEQUENCE: 18
atggagttca gctctccatc tagggaggag tgccctaagc cactgtctcg tgtgtccatc   60
atggccggca gcctgacagg cctcctgctg ctgcaagccg tgtcttgggc ctccggcgcc  120
agaccttgca tccctaagtc tttcggctac tctagcgtgg tgtgcgtgtg caacgccaca  180
tactgcgact ctttcgaccc accaaccttc cccgccctcg gcaccttctc ccggtacgag  240
tctacacggt ccggcaggcg gatggagctg tcgatgggcc caattcaggc caaccacaca  300
ggcacagcc tgctgctcac actccaaccc gagcagaagt tccagaaggt gaagggcctc  360
ggcggcgcca tgaccgacgc cgccgccctc aacattctcg ccctgtcccc acccgcccag  420
aacctgctcc tgaagtctta cttcagcgag gagggcattg gctacaacat tatccgggtg  480
cctatggcct cttgcgactt ctctattaga acatacacat acgccgacac ccccgacgac  540
ttccagctgc acaacttcag cctcccagag gaggacacaa agctcaagat tccactgatt  600
caccgcgcct tgcaactcgc ccagagacca gtgtctctgc tcgcctcccc ttggacatct  660
cctacatggc tcaagacaaa cggcgccgtg aacggcaagg gctctctgaa gggccagcca  720
ggcgacattt accaccagac atgggcccgg tacttcgtga agttcctcga cgcctacgcc  780
gagcacaagt tacaattctg ggccgtgaca gccgagaacg agcccatctgc cggcctcctg  840
tctggctacc cttttccagtg cctcggcttc accccgagc accagcggga cttcattgca  900
cgcgacctcg gcccaaacact cgccaactct acccaccaca acgtgagact gctgatgctc  960
gacgaccaga gactgctgct ccctcactgg gccaaggtgg tgctgaccga ccctgaggcc 1020
gccaagtacg tgcacggcat tgccgtgcac tggtatctgg acttcctggc cccagccaag 1080
gccacactcg gcgagaccca cagactgttc ccaaacacaa tgctgtttgc caggaggcc 1140
tgcgtgggca gcaagttctg ggagcagtct gtgagactcg gctcttggga ccgcggaatg 1200
cagtactctc actctatcat tacaaacctc ctgtaccacg tggtgggctg gaccgactgg 1260
aacctcgccc tcaaccccga gggcggccct aactgggtgc ggaacttcgt ggactctcct 1320
attattgtgg acattacaaa ggacacattc tacaagcagc ctatgttcta ccacctcggc 1380
cacttcagca gttcatccc tgagggctct cagagacggg gcctggtcgc cctctcagaag 1440
aacgacctgg acgccgtggc cctgatgcac cccgacggca gcgccgtggt ggtggtgctg 1500
aacaggtcga gcaaggacgt gccactgaca attaaggacc ccgccgtggg cttccttgag 1560
acaatttctc aggctactc tattcacaca tacctgtggc ggagacagtg a            1611

SEQ ID NO: 19          moltype = DNA  length = 1611
FEATURE                Location/Qualifiers
misc_feature           1..1611
                       note = CDS
source                 1..1611
                       mol_type = other DNA
```

-continued

```
                        organism = synthetic construct
SEQUENCE: 19
atggagttca gcagccccag cagggaagag tgccccaagc ccctgagcag ggtgagcatc   60
atggccggaa gcctgaccgg gctgctgctg ctgcaggccg tgagctgggc cagcggagct  120
aggccttgca tccccaaaag cttcggctac agctccgtcg tgtgcgtgtg taacgccacc  180
tattgtgact ctttcgaccc ccccaccttt cccgccctgg gcactttcag cagatatgag  240
tccacccgca gcggcagacg gatggagctg agcatgggac ccattcaggc caaccacacc  300
ggcaccggcc tgctgctgac cctgcagcct gaacagaaat tccagaaagt gaagggcttc  360
ggcggcgcca tgaccgacgc cgctgctctg aacatcctgc ccctgtcccc ccccgcccag  420
aacctgctgc tgaagagcta cttcagcgag gaaggcatcg gctacaatat catccgcgtg  480
cctatggcca gctgcgactt ttctatcagg acctacacct acgccgacac ccccgacgac  540
tttcagctgc acaacttcag cctgccagag gaagacacca aactgaagat cccccctgatc  600
cacagagccc tgcagctggc ccagagaccc gtgagcctgc tggccagccc ctggacatcc  660
cccacctggc tgaagaccaa cggcgccgtg aacggcaaag gcagcctgaa aggccagccc  720
ggagatattt accaccagac ctgggccaga tactttgtga aattcctgga cgcctacgcc  780
gaacacaagc tgcagttctg ggccgtgaca gccgagaatg agcccagcgc tggcctgctg  840
agcggctacc ctttccagtg tctgggcttc accccccgagc accagagaga tttcatcgcc  900
cgcgacctgg gccccaccct ggctaatagc acccaccaca acgtgagact gctgatgctg  960
gacgaccaga ggctgctgct gccccactgg gctaaagtgg tgctgaccga ccccgaagcc 1020
gccaaatacg tgcacggcat cgccgtgcac tggtacctgg atttcctggc ccccgccaag 1080
gccaccctgg agaaaccca cagactgttt cccaatacca tgctgttcgc cagcgaagcc 1140
tgcgtggggca gcaagttctg ggagcagagc gtgcgcctgg gcagctggga cagaggaatg 1200
cagtacagcc acagcatcat caccaacctg ctgtaccacg tggtgggatg gacagattgc 1260
aacctggccc tgaaccccga gggcggaccc aactgggtga gaaactttgt ggacagcccc 1320
atcatcgtgg acatcaccaa ggacaccttc tacaaacagc ctatgttcta ccacctgggc 1380
cacttctcca agttcattcc cgagggcagc cagagagtgg gcctggtggc cagccagaag 1440
aacgatctgg acgccgtggc cctgatgcac cccgacggaa gcgccgtggt ggtggtgctg 1500
aacagaagca gtaaggatgt gccccctgacc atcaaggatc ccgctgtggg attcctggaa 1560
accatcagcc ctggctactc catccacacc tacctgtgga gaagacagtg a            1611
```

```
SEQ ID NO: 20               moltype = DNA  length = 1611
FEATURE                     Location/Qualifiers
misc_feature               1..1611
                            note = CDS
source                     1..1611
                            mol_type = other DNA
                            organism = synthetic construct
SEQUENCE: 20
atggaattca gcagccccag cagagaggaa tgccccaagc ctctgagccg ggtgtcaatc   60
atggccggat ctctgacagg actgctgctg cttcaggccg tgtcttgggc ttctggcgct  120
agaccttgca tccccaagag cttcggctac agcagcgtcg tgtgcgtgtg caatgccacc  180
tactgcgaca gcttcgaccc tcctaccttt cctgctctgg gcaccttcag cagatacgag  240
agcaccagat ccggcagacg gatggaactg agcatgggac ccatccaggc caatcacaca  300
ggcactggcc tgctgctgac actgcagcct gagcagaaat tccagaaagt gaaaggcttc  360
ggcggagcca tgacagatgc cgccgctctg aatatcctgg ctctgtctcc accagctcag  420
aacctgctgc tcaagagcta cttcagcgag gaaggcatcg gctacaacat catcagagtg  480
cccatggcca gctgcgactt cagcatcagg acctacacct acgccgacac acccgacgat  540
ttccagctgc acaacttcag cctgcctgaa gaggacacca agctgaagat ccctctgatc  600
cacagagccc tgcagctggc acaaagaccc gtgtcactgc tggcctctcc atggacatct  660
cccacctggc tgaaaacaaa tggcgccgtg aatggcaagg gcagcctgaa aggccaacct  720
ggcgatatct accaccagac ctgggccaga tacttcgtga gttcctgga cgcctatgcc  780
gagcacaagc tgcagttttg ggccgtgaca gccgagaacg aaccttctgc tggactgctg  840
agcggctacc cctttcagtg cctgggcttt acacccgagc accagcggga ctttatcgcc  900
agagatctgg gacccacact ggccaatagc acccaccata atgtgcggct gctgatgctg  960
gacgaccaga gactgcttct gccccactgg gctaaagtgg tgctgacaga tcctgaggcc 1020
gccaaatacg tgcacggaat cgccgtgcac tggtatctgg actttctggc ccctgccaag 1080
gccacactgg agagacaca cagactgttc cccaacacca tgctgttcgc cagcgaagcc 1140
tgtgtgggca gcaagttttg ggaacagagc gtgcggctcg gcagctggga tagaggcatg 1200
cagtacagcc acagcatcat caccaacctg ctgtaccacg tcgtcggctg gaccgactgg 1260
aatctggccc tgaatcctga aggcggccct aactgggtcc gaaacttcgt ggacagcccc 1320
atcatcgtgg acatcaccaa ggacaccttc tacaagcagc ccatgttcta ccacctggga 1380
cacttcagca agttcatccc cgagggctct cagcgcgttg gactggtggc ttcccagaag 1440
aacgatctgg acgccgtggc tctgatgcac cctgatggat ctgctgtggt ggtggtcctg 1500
aaccggtcca gcaaagatgt gccccctgacc atcaaggatc ccgccgtggg attcctggaa 1560
acaatcagcc ctggctactc catccacacc tacctgtggc ggagacagtg a            1611
```

```
SEQ ID NO: 21               moltype = DNA  length = 1611
FEATURE                     Location/Qualifiers
misc_feature               1..1611
                            note = CDS
source                     1..1611
                            mol_type = other DNA
                            organism = synthetic construct
SEQUENCE: 21
atggaattca gcagccccag cagagaggaa tgccccaagc ctctgagccg ggtgtcaatc   60
atggccggat ctctgacagg actgctgctg cttcaggccg tgtcttgggc ttctggcgct  120
agaccttgca tccccaagag cttcggctac agcagcgtcg tgtgcgtgtg caatgccacc  180
tactgcgaca gcttcgaccc tcctaccttt cctgctctgg gcaccttcag cagatacgag  240
agcaccagat ccggcagacg gatggaactg agcatgggac ccatccaggc caatcacaca  300
```

-continued

```
ggcactggcc tgctgctgac actgcagcct gagcagaaat tccagaaagt gaaaggcttc  360
ggcggagcca tgacagatgc cgccgctctg aatatcctgg ctctgtctcc accagctcag  420
aacctgctgc tcaagagcta cttcagcgag gaaggcatcg gctacaacat catcagagtg  480
cccatggcca gctgcgactt cagcatcagg acctacacct acgccgacac acccgacgat  540
ttccagctgc acaacttcag cctgcctgaa gaggacacca agctgaagat ccctctgatc  600
cacagagccc tgcagctggc acaaagaccc gtgtcactgc tggcctctcc atggacatct  660
cccacctggc tgaaaacaaa tggcgccgtg aatggcaagg gcagcctgaa aggccaacct  720
ggcgacatct accaccagac ctgggccaga tacttcgtga agttcctgga cgcctatgcc  780
gagcacaagc tgcagttttg ggccgtgaca gccgagaacg aaccttctgc tggactgctg  840
agcggctacc cctttcagtg cctgggcttt acacccgagc accagcggga ctttatcgcc  900
cgtgatctgg gacccacact ggccaatagc acccaccata atgtgcggct gctgatgctg  960
gacgaccaga gactgcttct gccccactgg gctaaagtgg tgctgacaga tcctgaggcc 1020
gccaaatacg tgcacggaat cgccgtgcac tggtatctgg actttctggc cctgccaag  1080
gccacactgg gagagacaca cagactgttc cccaacacca tgctgttcgc cagcgaagcc 1140
tgtgtgggca gcaagttttg ggaacagagc gtgcggctcg gcagctggga tagaggcatg 1200
cagtacagcc acagcatcat caccaacctg ctgtaccacg tcgtcggctg gaccgactgg 1260
aatctggccc tgaatcctga aggcggccct aactgggtcc gaaacttcgt ggacagcccc 1320
atcatccgtg acatcaccaa ggacaccttc tacaagcagc ccatgttcta ccacctggga 1380
cacttcagca agttcatccc cgagggctct cagcgcgttg gactggtggc ttcccagaag 1440
aacgatctgg acgccgtggc tctgatgcac cctgatggat ctgctgtggt ggtggtcctg 1500
aaccgcagca gcaaagatgt gccccctgacc atcaaggatc ccgccgtggg attcctggaa 1560
acaatcagcc ctggctactc catccacacc tacctgtggc gtagacagtg a          1611
```

```
SEQ ID NO: 22            moltype = DNA   length = 1611
FEATURE                  Location/Qualifiers
source                   1..1611
                         mol_type = genomic DNA
                         organism = Homo sapiens
SEQUENCE: 22
atggagtttt caagtccttc cagagaggaa tgtcccaagc ctttgagtag ggtaagcatc  60
atggctggca gcctcacagg attgcttcta cttcaggcag tgtcgtgggc atcaggtgcc  120
cgccctgca tccctaaaag cttcggctac agctcggtgg tgtgtgtctg caatgccaca  180
tactgtgact ccttgaccc cccgacctt cctgcccttg gtaccttcag ccgctatgag  240
agtacacagc gtgggcgacg gatggagctg agtatggggc ccatccaggc taatcacacg  300
ggcacaggcc tgctactgac cctgcagcca gaacagaagt tccagaaagt gaagggattt  360
ggaggggcca tgacagatgc tgctgctctc aacatccttg ccctgtcacc ccctgcccaa  420
aatttgctac ttaaatcgta cttctctgaa gaaggaatcg gatataacat catccgggta  480
cccatggcca gctgtgactt ctccatccgc acctacacct atgcagacac ccctgatgat  540
ttccagttgc acaacttcag cctcccagag gaagatacca agctcaagat acccctgatt  600
caccgagccc tgcagttggc ccagcgtccc gtttcactcc ttgccagccc ctggacatca  660
cccacttggc tcaagaccaa tggagcggtg aatgggaagg ggtcactcaa gggacagccc  720
ggagacatct accaccagac ctgggccaga tactttgtga agttcctgga tgcctatgct  780
gagcacaagt tacagttctg ggcagtgaca gctgaaaatg aaccttctgc tgggctgttg  840
agtggatacc ccttccagtg cctgggcttt acccctgaac atcagcgaga cttcattgcc  900
cgtgacctag gtcctacct cgccaacagt actcaccaca atgtccgcct actcatgctg  960
gatgaccaac gcttgctgct gccccactgg gcaaaggtgg tactgacaga cccagaagca 1020
gctaaatatg ttcatggcat tgctgtacat tggtacctgg actttctggc tccagccaaa 1080
gccaccctag gggagacaca ccgcctgttc cccaacacca tgctctttgc ctcagaggcc 1140
tgtgtgggct ccaagttctg ggagcagagt gtgcggctag ctcctggga tcgagggatg 1200
cagtacagcc acagcatcat cacgaacctc ctgtaccatg tggtcggctg gaccgactgg 1260
aaccttgccc tgaaccccga aggaggaccc aattgggtgc gtaactttgt cgacagtccc 1320
atcattgtag acatcaccaa ggacacgttt tacaaacagc ccatgttcta ccaccttggc 1380
cacttcagca agttcattcc tgagggctct cagagagtgg ggctggttgc cagtcagaag 1440
aacgacctgg acgcagtggc actgatgcat cccgatggct ctgctgttgt ggtcgtgcta 1500
aaccgctcct ctaaggatgt gcctcttacc atcaaggatc ctgctgtggg cttcctggag 1560
acaatctcac ctggctactc cattcacacc tacctgtggc gtcgccagtg a          1611
```

```
SEQ ID NO: 23            moltype = DNA   length = 564
FEATURE                  Location/Qualifiers
misc_feature             1..564
                         note = CDS
source                   1..564
                         mol_type = other DNA
                         organism = synthetic construct
SEQUENCE: 23
atgtggtgcg cgagcccagt tgctgtggtg gccttttgcg ccgggctttt ggtctctcac  60
ccggtgctga cgcaaggcca ggaggccggc ggaagacctg gtgctgattg cgaggtgtgc  120
aaggaattcc tgaaccggtt ttataagtcc ctgatcgaca gaggcgtgaa cttcagcctg  180
gataccatcg agaaagaact catctccttc tgcctggaca ccaagggcaa ggaaaaccgg  240
ctgtgctact acctgggcgc cacaaaggac gccgctacaa agatcctgag cgaggtgacc  300
agaccaatga gcgtgcacat gcctgccatg aaaatctgtg aaaaactgaa aaagctggac  360
agccagatct gcgagctgaa gtacgagaag accctggatc tggcttctgt cgacctgaga  420
aagatgcggg tggccgaact gaagcagatc ctgcacagct ggggcgagga atgtagagcc  480
tgcgccgaga agaccgacta cgtgaatctg attcaggagc tggcccctaa gtacgccgcc  540
acccacccca agacagagct gtga                                        564
```

```
SEQ ID NO: 24            moltype = DNA   length = 564
FEATURE                  Location/Qualifiers
misc_feature             1..564
```

-continued

```
                            note = CDS
source                      1..564
                            mol_type = other DNA
                            organism = synthetic construct
SEQUENCE: 24
atgtggtgcg cgagcccagt tgctgtggtg gcctttttgcg ccgggctttt ggtctctcac   60
ccggtgctga cgcagggcca ggaggccggg gggcggcccg gcgccgactg cgaggtgtgt  120
aaggagtttc tgaaccggtt ctacaagtcc ctgatcgatc ggggcgtcaa cttcagcctg  180
gatactatcg agaaggagct gatcagcttc tgcctggata caaaggggaa ggagaaccgg  240
ctgtgctact acctggggc caccaaggac gccgccacca agatcctgtc cgaggtgacc  300
cggcccatga gcgtgcacat gcccgccatg aagatctgcg agaagctgaa gaagctggat  360
agccagatct gcgagctgaa gtacgagaaa acactggacc tggccagcgt ggacctgagg  420
aagatgaggg tggccgagct gaagcagatt ctgcacagct ggggagagga atgcagggcc  480
tgcgctgaaa agactgatta cgtcaacctg atccaggagc tggcccccaaa gtacgctgcc  540
acacacccca agacagagct gtga                                         564

SEQ ID NO: 25            moltype = DNA   length = 564
FEATURE                  Location/Qualifiers
misc_feature             1..564
                            note = CDS
source                   1..564
                            mol_type = other DNA
                            organism = synthetic construct
SEQUENCE: 25
atgtggtgcg cgagcccagt tgctgtggtg gcctttttgcg ccgggctttt ggtctctcac   60
ccggtgctga cgcagggcca ggaggctgga ggcagacctg gcgctgactg cgaggtgtgc  120
aaggagttcc tgaacaggtt ctacaagagc ctgatcgaca ggggagtgaa cttcagcctg  180
gacaccattg agaaggagct gatcagcttc tgcctggaca ccaagggcaa ggagaacagg  240
ctgtgctact acctgggagc caccaaggac gctgccacca agatcctgtc tgaggtgacc  300
agacccatga gtgtgcatat gcctgccatg aagatctgtg agaagctgaa gaagctggac  360
agccagatct gtgagctgaa gtatgagaag accctggacc tggcctctgt ggacctgagg  420
aagatgagag tggccgagct gaagcagatc ctgcacagct ggggagagga gtgcagagcc  480
tgcgccgaga agaccgacta cgtgaacctg atccaggagc tggctcctaa gtacgccgcc  540
acccatccca agaccgagct gtga                                         564

SEQ ID NO: 26            moltype = DNA   length = 564
FEATURE                  Location/Qualifiers
source                   1..564
                            mol_type = genomic DNA
                            organism = Homo sapiens
SEQUENCE: 26
atgtggtgcg cgagcccagt tgctgtggtg gcctttttgcg ccgggctttt ggtctctcac   60
ccggtgctga cgcagggcca ggaggccggg gggcggccag gggccgactg tgaagtatgt  120
aaagaattct tgaaccgatt ctacaagtca ctgatagaca gaggagttaa cttttcgctg  180
gacactatag agaaagaatt gatcagtttt tgcttggaca ccaaaggaaa agaaaaccgc  240
ctgtgctatt atctaggagc cacaaaagac gcagccacaa agatcctaag tgaagtcact  300
cgcccaatga gtgtgcatat gcctgcaatg aagatttgtg agaagctgaa gaagttggat  360
agccagatct gtgagctgaa atatgaaaaa acactggact tggcatcagt tgacctgcgg  420
aagatgagag tggcagagct gaagcagatc ctgcatagct gggggggagga gtgcagggcc  480
tgtgcagaaa aaactgacta tgtgaatctc attcaagagc tggccccaa gtatgcagcg  540
acacacccca aaacagagct ctga                                         564

SEQ ID NO: 27            moltype = DNA   length = 636
FEATURE                  Location/Qualifiers
misc_feature             1..636
                            note = CDS
source                   1..636
                            mol_type = other DNA
                            organism = synthetic construct
SEQUENCE: 27
atgaagttat gggatgtcgt ggctgtctgc ctggtgctgc tccacaccgc gtccgccttt   60
ccactgcctg ccggcaagcg gcccccccgag gccctgctg aagatagaag cctgggcaga  120
cggcgggccc ctttcgccct gtctagcgac agcaacatgc ctgaggacta ccccgatcag  180
ttcgacgacg tgatggactt catccaggct acaatcaaga gactgaagcg gagccctgac  240
aaacagatgg ccgtgctgcc aagacgcgag agaaatagac aggccgccgc tgctaatcct  300
gagaacagca gaggcaaagg cagaagggggc cagagaggca agaacagagg atgtgtgctg  360
accgccattc acctgaacgt gacagacctg ggactgggat atgagaccaa ggaagagctg  420
atcttcagat actgcagcgg ctcttgcgac gccgccgaaa ccacctacga caagatcctg  480
aaaaacctct ccagaaaccg gcggctggtg tccgataagg tgggccaagc ctgctgcaga  540
cctatcgcct ttgacgatga tctgagcttc ctggatgaca acctggtcta ccacatcctg  600
agaaagcaca cgcgccaagcg gtgcggctgt atctga                           636

SEQ ID NO: 28            moltype = DNA   length = 636
FEATURE                  Location/Qualifiers
misc_feature             1..636
                            note = CDS
source                   1..636
                            mol_type = other DNA
                            organism = synthetic construct
```

```
SEQUENCE: 28
atgaagttat gggatgtcgt ggctgtctgc ctggtgctgc tccacaccgc gtccgccttc    60
ccgctgcccg ccggtaagag gcctcccgag gcgcccgccg aagaccgctc cctcggccgc   120
cgccgcgcgc ccttcgcgct gagcagtgac tcaaatatgc cagaggatta tcctgatcag   180
ttcgatgatg tcatggattt tattcaagcc accattaagc gactgaagcg gtctcccgat   240
aagcagatgg ccgtgttgcc ccggcgggag cggaacaggc aggccgccgc cgccaacccc   300
gagaacagca gggggaaggg caggcggggg cagcggggca agaacagggg ctgcgtgctg   360
accgccatcc acctgaacgt gacagacctg gggctgcggt acgagacaaa ggaggagctg   420
atcttcaggt actgcagcgg gagctgcgac gctgccgaga ccacatacga taagatccgt   480
aagaacctga gcaggaacag gaggctggtg agcgacaagt ggggcaggc ctgttgcagg   540
cccattgcct ttgatgatga tctgagcttt cttgatgata acctggtgta ccatattctg   600
agaaagcact ccgccaagag atgcggatgc atttga                            636

SEQ ID NO: 29          moltype = DNA   length = 636
FEATURE                Location/Qualifiers
misc_feature           1..636
                       note = CDS
source                 1..636
                       mol_type = other DNA
                       organism = synthetic construct
SEQUENCE: 29
atgaagttat gggatgtcgt ggctgtctgc ctggtgctgc tccacaccgc gtccgccttc    60
cctctgcctg ctggcaagag gcctcccgag gctcctgccg aggacagaag cctcggcaga   120
aggagagctc cttttgccct gagcagcgac agcaacatgc ctgaggacta ccccgaccag   180
tttgatgacg tgatggactt catccaggcc accatcaaaa gactgaaaag gtcacctgac   240
aagcagatgg ctgtgctgcc taaaagggag aggaacaggc aggccgccgc tgccaatcct   300
gagaatagca gaggcaaggg caggagagga cagagaggca agaacagagg ctgtgtgctg   360
acagccatcc acctgaatgt gacagacctg ggactgggct atgagaccaa agaggagctg   420
atctttagat actgctctgg cagctgtgat gccgctgaga ccacctacga caagatcctg   480
aagaacctga gcagaaacag gagactggtg agcgacaagt gggccaggc ctgctgcagg   540
cccatcgcct tcgacgacga cctgagcttc ctggacgaca acctggtgta ccacatcctg   600
agaaagcaca cgccaagag gtgcggctgc atctga                            636

SEQ ID NO: 30          moltype = DNA   length = 636
FEATURE                Location/Qualifiers
source                 1..636
                       mol_type = genomic DNA
                       organism = Homo sapiens
SEQUENCE: 30
atgaagttat gggatgtcgt ggctgtctgc ctggtgctgc tccacaccgc gtccgccttc    60
ccgctgcccg ccggtaagag gcctcccgag gcgcccgccg aagaccgctc cctcggccgc   120
cgccgcgcgc ccttcgcgct gagcagtgac tcaaatatgc cagaggatta tcctgatcag   180
ttcgatgatg tcatggattt tattcaagcc accattaagc gactgaaaag gtcaccagat   240
aaacaaatgg cagtgcttcc tagaagagag cggaatcggc aggctgcagc tgccaaccca   300
gagaattcca gaggaaaagg tcggagaggc cagaggggca aaaaccgggg ttgtgtctta   360
actgcaatac atttaaatgt cactgacttg ggtctgggct atgaaaccaa ggaggaactg   420
attttaggt actgcagcgg ctcttgcgat gcagctgaca gaacgtacga caaaatattg   480
aaaaacttat ccagaaatag aaggctggtg agtgacaaag tagggcaggc atgttgcaga   540
cccatcgcct tgatgatga cctgtcgttt ttagatgata acctggttta ccatattcta   600
agaaagcatt ccgctaaaag gtgtggatgt atctga                            636

SEQ ID NO: 31          moltype = AA   length = 480
FEATURE                Location/Qualifiers
source                 1..480
                       mol_type = protein
                       organism = Homo sapiens
SEQUENCE: 31
MNASEFRRRG KEMVDYMANY MEGIEGRQVY PDVEPGYLRP LIPAAAPQEP DTFEDIINDV    60
EKIIMPGVTH WHSPYFFAYF PTASSYPAML ADMLCGAIGC IGFSWAASPA CTELETVMMD   120
WLGKMLELPK AFLNEKAGEG GGVIQGSASE ATLVALLAAR TKVIHRLQAA SPELTQAAIM   180
EKLVAYSSDQ AHSSVERAGL IGGVKLKAIP SDGNFAMRAS ALQEALERDK AAGLIPFFMV   240
ATLGTTTCCS FDNLLEVGPI CNKEDIWLHV DAAYAGSAFI CPEFRHLLNG VEFADSFNFN   300
PHKWLLVNFD CSAMWVKKRT DLTGAFRLDP TYLKHSHQDS GLITDYRHWQ IPLGRRFRSL   360
KMWFVFRMYG VKGLQAYIRK HVQLSHEFES LVRQDPRFEI CVEVILGLVC FRLKGSNKVN   420
EALLQRINSA KKIHLVPCHL RDKFVLRFAI CSRTVESAHV QRAWEHIKEL AADVLRAERE   480

SEQ ID NO: 32          moltype = AA   length = 536
FEATURE                Location/Qualifiers
source                 1..536
                       mol_type = protein
                       organism = Homo sapiens
SEQUENCE: 32
MEFSSPSREE CPKPLSRVSI MAGSLTGLLL LQAVSWASGA RPCIPKSFGY SSVVCVCNAT    60
YCDSFDPPTF PALGTFSRYE STRSGRRMEL SMGPIQANHT GTGLLLTLQP EQKFQKVKGF   120
GGAMTDAAAL NILALSPPAQ NLLLKSYFSE EGIGYNIIRV PMASCDFSIR TYTYADTPDD   180
FQLHNFSLPE EDTKLKIPLI HRALQLAQRP VSLLASPWTS PTWLKTNGAV NGKGSLKGQP   240
GDIYHQTWAR YFVKFLDAYA EHKLQFWAVT AENEPSAGLL SGYPFQCLGF TPEHQRDFIA   300
RDLGPTLANS THHNVRLLML DDQRLLLPHW AKVVLTDPEA AKYVHGIAVH WYLDFLAPAK   360
ATLGETHRLF PNTMLFASEA CVGSKFWEQS VRLGSWDRGM QYSHSIITNL LYHVVGWTDW   420
```

-continued

```
NLALNPEGGP NWVRNFVDSP IIVDITKDTF YKQPMFYHLG HFSKFIPEGS QRVGLVASQK    480
NDLDAVALMH PDGSAVVVVL NRSSKDVPLT IKDPAVGFLE TISPGYSIHT YLWRRQ         536

SEQ ID NO: 33              moltype = AA  length = 187
FEATURE                    Location/Qualifiers
source                     1..187
                           mol_type = protein
                           organism = Homo sapiens
SEQUENCE: 33
MWCASPVAVV AFCAGLLVSH PVLTQGQEAG GRPGADCEVC KEFLNRFYKS LIDRGVNFSL    60
DTIEKELISF CLDTKGKENR LCYYLGATKD AATKILSEVT RPMSVHMPAM KICEKLKKLD    120
SQICELKYEK TLDLASVDLR KMRVAELKQI LHSWGEECRA CAEKTDYVNL IQELAPKYAA    180
THPKTEL                                                              187

SEQ ID NO: 34              moltype = AA  length = 211
FEATURE                    Location/Qualifiers
source                     1..211
                           mol_type = protein
                           organism = Homo sapiens
SEQUENCE: 34
MKLWDVVAVC LVLLHTASAF PLPAGKRPPE APAEDRSLGR RRAPFALSSD SNMPEDYPDQ    60
FDDVMDFIQA TIKRLKRSPD KQMAVLPRRE RNRQAAAANP ENSRGKGRRG QRGKNRGCVL    120
TAIHLNVTDL GLGYETKEEL IFRYCSGSCD AAETTYDKIL KNLSRNRRLV SDKVGQACCR    180
PIAFDDDLSF LDDNLVYHIL RKHSAKRCGC I                                   211

SEQ ID NO: 35              moltype = DNA  length = 69
FEATURE                    Location/Qualifiers
misc_feature               1..69
                           note = CDS
source                     1..69
                           mol_type = other DNA
                           organism = synthetic construct
SEQUENCE: 35
ggaagcggac agtgtactaa ttatgctctc ttgaaattgg ctggagatgt tgagagcaac    60
cctggacct                                                            69

SEQ ID NO: 36              moltype = AA  length = 23
FEATURE                    Location/Qualifiers
source                     1..23
                           mol_type = protein
                           organism = equine rhinitis a virus
SEQUENCE: 36
GSGQCTNYAL LKLAGDVESN PGP                                            23

SEQ ID NO: 37              moltype = DNA  length = 75
FEATURE                    Location/Qualifiers
misc_feature               1..75
                           note = CDS
source                     1..75
                           mol_type = other DNA
                           organism = synthetic construct
SEQUENCE: 37
ggaagcggag tgaaacagac tttgaatttt gaccttctca agttggcggg agacgtggag    60
tccaaccctg gacct                                                     75

SEQ ID NO: 38              moltype = AA  length = 25
FEATURE                    Location/Qualifiers
source                     1..25
                           mol_type = protein
                           organism = foot-and-mouth disease virus
SEQUENCE: 38
GSGVKQTLNF DLLKLAGDVE SNPGP                                          25

SEQ ID NO: 39              moltype = DNA  length = 63
FEATURE                    Location/Qualifiers
misc_feature               1..63
                           note = CDS
source                     1..63
                           mol_type = other DNA
                           organism = synthetic construct
SEQUENCE: 39
ggaagcggag agggcagagg aagtctgcta acatgcggtg acgtcgagga gaatcctgga    60
cct                                                                  63

SEQ ID NO: 40              moltype = AA  length = 21
FEATURE                    Location/Qualifiers
source                     1..21
                           mol_type = protein
                           organism = thoseaasigna virus
```

-continued

```
SEQUENCE: 40
GSGEGRGSLL TCGDVEENPG P                                             21

SEQ ID NO: 41            moltype = DNA  length = 66
FEATURE                  Location/Qualifiers
misc_feature             1..66
                         note = CDS
source                   1..66
                         mol_type = other DNA
                         organism = synthetic construct
SEQUENCE: 41
ggaagcggag ctactaactt cagcctgctg aagcaggctg agacgtgga ggagaaccct   60
ggacct                                                              66

SEQ ID NO: 42            moltype = AA  length = 22
FEATURE                  Location/Qualifiers
source                   1..22
                         mol_type = protein
                         organism = porcine teschovirus-1
SEQUENCE: 42
GSGATNFSLL KQAGDVEENP GP                                            22

SEQ ID NO: 43            moltype = DNA  length = 22
FEATURE                  Location/Qualifiers
misc_feature             1..22
                         note = CDS
source                   1..22
                         mol_type = other DNA
                         organism = synthetic construct
SEQUENCE: 43
tttataattt cttcttccag aa                                            22

SEQ ID NO: 44            moltype = DNA  length = 552
FEATURE                  Location/Qualifiers
misc_feature             1..552
                         note = CDS
source                   1..552
                         mol_type = other DNA
                         organism = synthetic construct
SEQUENCE: 44
acgttactgg ccgaagcgct tggaataagg ccggtgtgcg tttgtctata tgttattttc   60
caccatattg ccgtcttttg gcaatgtgag ggcccggaaa cctggccctg tcttcttgac  120
gagcattcct aggggtcttt ccctctcgc caaaggaatg caaggtctgt tgaatgtcgt   180
gaaggaagca gttcctctgg aagcttcttg aagacaaaca acgtctgtag cgacccttg   240
caggcagcgg aaccccccac ctggcgacag gtgcctctgc ggccaaaagc cacgtgtata  300
agatacacct gcaaaggcgg cacaacccca gtgccacgtt gtgagttgga tagttgtgga  360
aagagtcaaa tggctctcct caagcgtatt caacaagggg ctgaaggatg cccagaaggt  420
accccattgt atgggatctg atctgggccc tcggtgcaca tgctttacat gtgtttagtc  480
gaggttaaaa aaacgtctag gccccccgaa ccacgggac gtggttttcc tttgaaaaac   540
acgatgataa ta                                                      552

SEQ ID NO: 45            moltype = DNA  length = 1611
FEATURE                  Location/Qualifiers
misc_feature             1..1611
                         note = CDS
source                   1..1611
                         mol_type = other DNA
                         organism = synthetic construct
SEQUENCE: 45
atggagttca gctctcccag cagagaagaa tgtcctaagc ctctgagcag ggtgtccatc   60
atggctggca gcctgacagg actcctgctc ctgcaggctg tgagctgggc ctctggagcc  120
aggccttgca ttcccaagag cttcggctac agcagcgtgg tgtgcgtgtg caacgccacc  180
tactgcgaca gctttgaccc tcctacctt cctgccctgg gaacattcag cagatatgag   240
agcaccagga gcggccggag aatggagctg agcatggcac ccatccaggc caaccacaca  300
ggaacaggcc tcctgctcac cctgcagcct gagcagaagt tcagaaggt gaagggcttc   360
ggaggagcca tgacagatgc tgccgctctg aacatcctgg ccctgagccc tcctgcccag  420
aacctcctgc tcaagagcta cttcagcgaa gaaggaatcg gctacaacat catcagagtg  480
cccatggcca gctgcgcatt tagcattagg acatatacct acgccgatac acctgatgac  540
ttccagctgc ataactttag cctgcctgag gaggatacca agctgaaaat ccctctgatc  600
catcgcgccc tgcagctggc ccagagacct gtgtccctgc tggccagccc ttggacaagc  660
cctacatggc tgaagaccaa tggcgctgtg aatggcaaag gcagcctgaa gggccagcct  720
ggagatatct atcaccagac ctgggccagg tactttgtga agttcctgga tgcctatgcc  780
gagcacaagc tgcagttctg ggctgtgacc gctgagaatg aaccctctgc cggactgttg  840
agcggctatc cctttcagtg tctgggattc accctgacc accagaggga cttcattgag   900
cgcgacctgg ccctaccct ggccaacagc actcaccaca atgtgcgcct gctgatgctg   960
gacgatcaga gactgctgct gccccactgg gccaaggtgg tgctgaccga ccctgaggcc  1020
gccaagtacg tgcacggcat cgccgtgcac tggacctgg acttcctggc tcctgccaag  1080
gccaccctgg cgagaccca caggctgttc cctaacacca tgctgttcgc cagcgaggcc  1140
tgcgtgggct ccaagttctg ggagcagtcc gtgaggctgg aagctgggga caggggcatg  1200
```

```
cagtacagcc acagcatcat caccaacctg ctgtaccacg tggtgggctg gaccgactgg   1260
aacctggccc tgaaccctga gggcggccca aactgggtgc gcaacttcgt ggacagccct   1320
atcatcgtgg acatcaccaa ggacaccttc tacaagcagc ccatgttcta ccacctgggc   1380
cacttcagca gtttattcc tgagggcagc caaagggtgg gactggtggc cagccagaaa   1440
aatgacctgg acgccgtggc tctgatgcat cctgatgcat cctgatgcag cgccgtcgt ggttgtcctg   1500
aaccgcagca gcaaggacgt gcccctgacc atcaaggatc ctgctgtggg cttcctggag   1560
accatcagcc ctggctacag catccacacc tacctgtgga ggagacagtg a           1611
```

```
SEQ ID NO: 46          moltype = DNA  length = 1443
FEATURE                Location/Qualifiers
misc_feature           1..1443
                       note = CDS
source                 1..1443
                       mol_type = other DNA
                       organism = synthetic construct
SEQUENCE: 46
atgaatgcca gcgagtttag aagaaggggc aaagagatgg ttgactacat ggccaattac   60
atggaaggca tcgagggcag gcaggtgtac cctgatgtgg aacctggata tctgagacct   120
ctgattcctg ctgcagctcc tcaggagcct gacacattcg aggatatcat caacgacgtg   180
gagaaaatca tcatgcctgg cgtcacccac tggcactctc cttacttctt tgcctatttc   240
cctacagcca gcagctaccc tgccatgctg gctgacatgc tgtgtggagc catcggctgc   300
atcggcttca gctgggcggc aagcccagcc tgcaccgagc tggaaacagt gatgatggac   360
tggctgggaa agatgctgga actgcctaag gcctttctga atgagaaggc tggcgaggga   420
ggaggagtga tccagggctc tgcttctgag gccaccctgg ttgctctgct tgctgccaga   480
accaaggtga tccacagact gcaggctgcc tctcctgagc tgacccaggc agccatcatg   540
gaaaagctgg tggcttacag ctctgaccag gcccattcca gcgtggaaag gggcggcctg   600
attggcggag tgaagctcaa ggctatccct agcgatggca actttgccat gagagcctct   660
gccctgcaag aggccctgga aagagataag gccgctggac tcatcccgtt cttcatggtg   720
gccacactgg gcacaacaac atgctgcagc tttgacaacc tgctggaagt gggccctatc   780
tgcaacaaag aggacatctg gctgcatgtg gatgctgcct acgctggctc tgccttcatc   840
tgtcctgagt tcagacatct gctgaacggc gtggagtttg ctgatagctt caacttcaac   900
cctcacaagt ggctgctggt caactttgac tgctctgcta tgtgggtgaa gaagagaacc   960
gacctgacag gagctttcag actggatccc acctacctga aacacagcca ccaggattct   1020
ggcctgatca ccgattacag acactggcag attcctctgg gcagaaggtt cagaagcctg   1080
aagatgtggt ttgtgttcag aatgtatggc gtgaagggcc tgcaagccta catcagaaag   1140
catgtgcagc tgagccatga gttcgagagc ctggtgaggc aggaccctag atttgagatc   1200
tgtgtggagg tgatcctggg cctggtgtgc ttcaggctga agggcagcaa caaggtgaac   1260
gaggctctgc tgcagaggat caacagcgcc aagaagatcc acctggtgcc ttgccacctg   1320
agagacaagt ttgtgctgag atttgctatt tgtagcagaa ccgtgaaag cgcccacgtg   1380
cagagagcct gggagcacat caaggaactg gccgctgatg tgctgagagc cgagcgggaa   1440
tga                                                               1443
```

```
SEQ ID NO: 47          moltype = DNA  length = 1611
FEATURE                Location/Qualifiers
misc_feature           1..1611
                       note = CDS
source                 1..1611
                       mol_type = other DNA
                       organism = synthetic construct
SEQUENCE: 47
atggagtttt caagtccttc cagagaggaa tgtcccaagc ctttgagtag ggtaagcatc   60
atggctggca gcctcacagg attgcttcta cttcaggcag tgtcgtgggc atcaggtgcc   120
cgcccctgca ttcccaagag ctttggctac agcagcgtgg tgtgcgtgtg caacgccacc   180
tactgtgaca gctttgaccc tcctaccttt cctgctctgg gaacattcag cagatatgag   240
agcaccaggt ctggccggag aatggagctg agcatggcac ccatccaggc caaccacaca   300
ggaacaggac tcctgctcac cctgcagcct gagcagaagt ttcagaaggt gaagggcttc   360
ggaggagcca tgcagatgc tgccgctctg aacatcctgg ccctgagccc tcctgcccag   420
aacctcctgc tcaagagcta cttcagcgaa gaaggaatcg gctacaacat catcagagtg   480
cccatggcca gctgcgactt tagcattagg acatatacct acgccgatac acctgatgac   540
ttccagctgc ataactttag cctgcctgag gaggatacca agctgaaaat ccctctgatc   600
catcgcgccc tgcagctggc ccagagacct gtgtccctgc tggccagccc cttggacaagc   660
cctacatggc tgaagaccaa tggcgctgtg aatggcaaag gcagcctgaa gggccagcct   720
ggagatatct atcaccagac ctgggccagg tactttgtga agttcctgga tgcctatgcc   780
gagcacaagc tgcagttctg ggctgtgacc gctgagaatg aaccctctgc tggactgttg   840
tctggctatc cctttcagtg tctgggattc acacctgagc accagaggga cttcattgcc   900
agagacctgg gacctaccct ggccaacagc actcaccaca atgtgagact gctgatgctg   960
gatgatcaga gactgctgct gcctcattgg gccaaggtgg tgctgacaga tcctgaggca   1020
gccaagtatg tgcacggcat tgccgtgcac tggtacctgg acttcctggc tcctgccaag   1080
gccacccctgg gagagaccca caggctgttc cctaacacca tgctgttcgc ctctgaagcc   1140
tgcgtgggct ccaagttctg gggagcagag ctgaggctgg aagctggga caggggcatg   1200
cagtacagcc acagcatcat caccaacctg ctgtaccatg tggtgggctg gaccgactgg   1260
aacctggccc tgaaccctga gggaggccca aactgggtgc gcaacttcgt ggacagccct   1320
atcattgtgg acatcaccaa ggacaccttc tacaagcagc ccatgttcta ccacctgggc   1380
cacttcagca gtttattcc tgagggcagc caaagggtgg gactggtggc cagccagaaa   1440
aatgacctgg acgccgtggc tctgatgcat cctgatggct ctgctgtggt ggttgtcctg   1500
aacagaagca gcaaggatgt gccactgacc atcaaggatc ctgctgtggg cttcctggag   1560
accatcagcc ctggctacag catccacacc tacctgtgga ggagacagtg a           1611
```

```
SEQ ID NO: 48          moltype = DNA  length = 3103
```

-continued

```
FEATURE              Location/Qualifiers
misc_feature         1..3103
                     note = CDS
source               1..3103
                     mol_type = other DNA
                     organism = synthetic construct
SEQUENCE: 48
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccacccca ttgacgtcaa tgggagtttg ttttggcacc aaaatcaacg   420
ggactttcca aaatgtcgta acaactccgc cccattgacg caaatgggcg gtaggcgtgt   480
acggtgggag gtctatataa gcagagctcg tttagtgaac cgtcagatcg cctggagacg   540
ccatccacgc tgttttgacc tccatagaag acaccgggac cgatccagcc tccgcggatt   600
cgaatcccgg ccgggaacgg tgcattggaa cgcggattcc ccgtgccaag agtgacgtaa   660
gtaccgccta tagagtctat aggcccacaa aaaatgcttt cttcttttaa tatacttttt   720
tgtttatctt atttctaata cttttcccta tctctttctt tcagggcaat aatgatacaa   780
tgtatcatgc ctctttgcac cattctaaag aataacagtg ataatttctg ggttaaggca   840
atagcaatat ttctgcatat aaatatttct gcatataaat tgtaactgat gtaagaggtt   900
tcatattgct aatagcagct acaatccagc taccattctg cttttatttt atggttggga   960
taaggctgga ttattctgag tccaagctag gcccttttgc taatcatgtt catacctctt  1020
atcttcctcc cacagctcct gggcaacgtg ctggtctgtg tgctggccca tcactttggc  1080
aaagaattgg gattcgaaca tcgattgaat tccccgtggga tccaccatga acgcaagtga  1140
attccgaagg agaggggaagg agatggtgga ttacgtggcc aactacatgg aaggcattga  1200
gggacgccag gtctaccctg acgtggagcc cgggtacctg cggccgctga tccctgccgc  1260
tgcccctcag gagccagaca cgtttgagga catcatcaac gacgttgaga agataatcat  1320
gcctgggggtg acgcactggc acagcccca cttcttcgcc tacttcccca ctgccagctc  1380
gtacccggcc atgcttgcgc acatgctgtg cgggggccatt ggctgcatcg gcttctcctg  1440
ggcggcaagc ccagcatgca cagagctgga gactgtgatg atggactggc tcgggaagat  1500
gctggaacta ccaaaggcat ttttgaatga gaaagctgga gaagggggag gagtgatcca  1560
gggaagtgcc agtgaagcca ccctggtggc cctgctggcc gctcggacca aagtgatcca  1620
tcggctgcag gcagcgtccc cagagctcac acaggccgct atcatggaga agctggtggc  1680
ttactcatcc gatcaggcac actcctcagt ggaaagagct gggttaattg gtggagtgaa  1740
attaaaagcc atccctcag atggcaactt cgccatgcgt gcgtctgccc tgcaggaagc  1800
cctggagaga gacaaagcgg ctggcctgat tcctttcttt atggttgcca ccctgggggac  1860
cacaacagtc tgctcctttg acaatctctt agaagtcggt cctatctgca acaaggaaga  1920
catatggctg cacgttgatg cagcctacgc aggcagtgca ttcatctgcc ctgagttccg  1980
gcaccttctg aatggagtgg agtttgcaga ttcattcaac tttaatcccc acaaatggct  2040
attggtgaat tttgactgtt ctgccatgtg ggtgaaaaag agaacagact taacgggagc  2100
ctttagactg gaccccactt acctgaagca cagccatcag gattcagggc ttatcactga  2160
ctaccggcat tggcagatac cactgggcag aagatttcgc tctttgaaaa tgtggtttgt  2220
atttaggatg tatggagtca aaggactgca ggcttatatc cgcaagcatg tccagctgtc  2280
ccatgagttt gagtcactgg tgcgccagga tccccgcttt gaaatctgtg tggaagtcat  2340
tctggggctt gtctgctttc ggctaaaggg ttccaacaaa gtgaatgagg ctcttctgca  2400
aagaataaac agtgccaaaa aaatccactt ggttccatgt cacctcaggg acaagtttgt  2460
cctgcgcttt gccatctgtt ctcgcacggt ggaatctgcc catgtgcagc gggcctggga  2520
acacatcaaa gagctggcgg ccgacgtgct gcgagcagag agggagtagg agtgaagcca  2580
ggacctgcag aagcttgcct cgagcagcgc tgctcgaagg atctacgggt ggcatccctg  2640
tgacccctcc ccagtgcctc tcctggccct ggaagttgcc actccagtgc ccaccagcct  2700
tgtcctaata aaattaagtt gcatcatttt gtctgactag gtgtccttct ataatattat  2760
gggggtgagg ggggtggtat ggagcaaggg gcaagttggg aagacaacct gtagggcctg  2820
cggggtctat tgggaaccaa gctggagtgc agtggcacaa tcttggctca ctgcaatctc  2880
cgcctcctgg gttcaagcga ttctcctgcc tcagcctccc gagttgttgg gattccaggc  2940
atgcatgacc aggctcagct aatttttgtt tttttggtag agacggggtt tcaccatatt  3000
ggccaggctg gtctccaact cctaatctca ggtgatctac ccaccttggc ctcccaaatt  3060
gctgggatta caggcgtgaa ccactgctcc cttccctgtc ctt                    3103

SEQ ID NO: 49       moltype = DNA   length = 3597
FEATURE              Location/Qualifiers
misc_feature        1..3597
                    note = CDS
source              1..3597
                    mol_type = other DNA
                    organism = synthetic construct
SEQUENCE: 49
accggtgacg tctcccatgg tgaagcttgg atctgaattc ggtacccctag ttattaatag    60
taatcaatta cggggtcatt agttcatagc ccatatatgg agttccgcgt tacataactt   120
acggtaaatg gcccgcctgg ctgaccgccc aacgacccccc gcccattgac gtcaataatg   180
acgtatgttc ccatagtaac gccaataggg actttccatt gacgtcaatg ggtggactat   240
ttacggtaaa ctgcccactt ggcagtacat caagtgtatc atatgccaag tacgccccct   300
attgacgtca atgacggtaa atggcccgcc tggcattatg cccagtaccc ttatggatgt   360
gactttccta cttggcagta catctacgta ttagtcatcg ctattaccat ggtcgaggtg   420
agccccacgt tctgcttcac tctccccatc tcccccccct ccccacccccc aattttgtat   480
ttatttattt tttaattatt ttgtgcagcg atgggggcgg gggggggggg ggggcgcgcg   540
ccaggcgggg cggggcgggg cgaggggcgg ggcggggcga ggcggagagg tgcggcggca   600
gccaatcaga gcggcgcgct ccgaaagttt ccttttatgg cgaggcggcg gcggcggcgg   660
```

```
ccctataaaa agcgaagcgc gcggcgggcg ggagtcgctg cgacgctgcc ttcgccccgt   720
gccccgctcc gccgccgcct cgcgccgccc gccccggctc tgactgaccg cgttactccc   780
acaggtgagc gggcgggacg gcccttctcc tccgggctgt aattagcgct tggtttaatg   840
acggcttgtt ttctgtggct gcgtgaaagc cttgaggggc tccgggagct agagcctctg   900
ctaaccatgt tcatgccttc ttctttttcc tacagctcct gggcaacgtg ctggttattg   960
tgctgtctca tcattttggc aaagaattcc tcgaagatcc gaagggaaag tcttccacga  1020
ctgtgggatc cgttcgaaga tatcaccggt tgagccacca tggaattcag cagccccagc  1080
agagaggaat gccccaagcc tctgagccgg gtgtcaatca tggccggatc tctgacagga  1140
ctgctgctgc ttcaggccgt gtcttgggct tctggcgcta gaccttgcat ccccaagagc  1200
ttcggctaca gcagcgtcgt gtgcgtgtgc aatgccacct actgcgacag cttcgaccct  1260
cctacctttc ctgctctggg caccttcagc agatacgaga gcaccagatc cggcagacgg  1320
atggaactga gcatgggacc catccaggcc aatcacacag gcactggcct gctgctgaca  1380
ctgcagcctg agcagaaatt ccagaaagtg aaaggcttcg gcggagccat gacagatgcc  1440
gccgctctga atatcctggc tctgtctcca ccagctcaga acctgctgct caagagctac  1500
ttcagcgagg aaggcatcgg ctacaacatc atcagagtgc ccatggccag ctgcgacttc  1560
agcatcagga cctacacctt cgccgacaca cccgacgatt tccagctgca caacttcagc  1620
ctgcctgaag aggacaccaa gctgaagatc cctctgatcc acagagccct gcagctggca  1680
caaagacccg tgtcactgct ggcctctcca tggacatctc ccacctggcc gaaaacaaat  1740
ggcgccgtga atggcaaggg cagcctgaaa ggccaacctg gcgacatcta ccaccagacc  1800
tgggccagat acttcgtgaa gttcctggac gcctatgccg agcacaagct gcagttttgg  1860
gccgtgacag ccgagaacga accttctgct ggactgctga gcggctaccc ctttcagtgc  1920
ctgggcttta caccgagca ccagcgggac tttatcgccc gtgatctgga acccacactg  1980
gccaatagca cccaccataa tgtgcggctg ctgatgctgg acgaccagag actgcttctg  2040
ccccactggg ctaaagtggt gctgacagat cctgaggccg ccaaatacgt gcacggaatc  2100
gccgtgcact ggtatctgga ctttctggcc cctgccaagg ccacactggg agagacacac  2160
agactgttcc ccaacaccat gctgttcgcc agcgaagcct gtgtgggcag caagtttttgg  2220
gaacagagcg tgcggctcgg cagctgggat agaggcatgc agtacagcca cagcatcatc  2280
accaacctgc tgtaccacgt cgtcggctgg accgactgga atctggccct gaatcctgaa  2340
ggcggcccta actgggtccg aaacttcgtg gacagcccca tcatcgtgga catcaccaag  2400
gacaccttct acaagcagcc catgttctac cacctggacg acttcagcaa gttcatcccc  2460
gagggctctc agcgcgttgg actggtggct ctccagaaga acgatctgga cgccgtggct  2520
ctgatgcacc ctgatggatc tgctgtggtg gtggtcctga accgcagcag caaagatgtg  2580
cccctgacca tcaaggatcc cgccgtggga ttcctggaaa caatcagccc tggctactcc  2640
atccacacct accgtggcg tagacagtga caattgttaa ttaagtttaa accctcgagg  2700
ccgcaagctt atcgataatc aacctctgga ttacaaaatt tgtgaaagat tgactggtat  2760
tcttaactat gttgctcctt ttacgctatg tggatacgct gctttaatgc ctttgtatca  2820
tgctattgct tcccgtatgg ctttcatttt ctcctccttg tataaatcct ggttgctgtc  2880
tctttatgag gagttgtggc ccgttgtcag gcaacgtggc gtggtgtgca ctgtgtttgc  2940
tgacgcaacc cccactggtt ggggcattgc caccacctgt cagctccttt ccgggacttt  3000
cgctttcccc ctccctattg ccacggcgga actcatcgcc gcctgccttg cccgctgctg  3060
gacaggggct cggctgttgg gcactgacaa ttccgtggtg ttgtcgggga atcatcgtc  3120
ctttccttgg ctgctcgcct gtgttgccac ctggattctg cgcgggacgt ccttctgcta  3180
cgtcccttcg gccctcaatc cagcggacct tccttcccgc ggcctgctgc cggctctgcg  3240
gcctcttccg cgtcttcgcc ttcgccctca gacgagtcgg atctcccttt gggccgcctc  3300
cccgcatcga taccgtcgac tagagctcgc tgatcagcct cgactgtgcc ttctagttgc  3360
cagccatctg ttgtttgccc ctcccccgtg ccttccttga ccctggaagg tgccactccc  3420
actgtccttt cctaataaaa tgaggaaatt gcatcgcatt gtctgagtag gtgtcattct  3480
attctggggg gtggggtggg gcaggacagc aaggggagg attggaaga caatagcagg  3540
catgctgggg agagatccac gataacaaac agctttttg gggtgaacat attgact     3597
```

```
SEQ ID NO: 50           moltype = DNA  length = 630
FEATURE                 Location/Qualifiers
misc_feature            1..630
                        note = CDS
source                  1..630
                        mol_type = other DNA
                        organism = synthetic construct
SEQUENCE: 50
tctagagtgc ccgtcagtgg gcagagcgca catcgcccac agtccccgag aagttggggg    60
gaggggtcgg caattgaacc ggtgcctaga aaggtggcg cggggtaaac tgggaaagtg    120
atgtcgtgta ctggctccgc cttttttccg agggtgggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
cttccacctg gctgcagtac gtgattcttg atcccgagct tcgggttcgg agtgggtgg  360
agagttcgag gccttgcgct taaggagccc cttcgcctcg tgcttgagtt gaggcctggc   420
ctgggcgctg gggccgccgc gtgcgaatct ggtggcacct tcgcgcctgt ctcgctgctt   480
tcgataagtc tctagccatt taaaattttt gatgacctgc tgcgacgctt ttttctggc   540
aagatagtct tgtaaatgcg ggccaagatc tgcacactgg tatttcggtt tttggggccg   600
cggggcggcga cggggcccgt gcgtcccagc                                      630
```

```
SEQ ID NO: 51           moltype = DNA  length = 580
FEATURE                 Location/Qualifiers
misc_feature            1..580
                        note = CDS
source                  1..580
                        mol_type = other DNA
                        organism = synthetic construct
SEQUENCE: 51
tctagagtgc ccgtcagtgg gcagagcgca catcgcccac agtccccgag aagttggggg    60
```

```
gaggggtcgg caattgaacc ggtgcctaga gaaggtggcg cggggtaaac tgggaaagtg   120
atgtcgtgta ctggctccgc ctttttcccg agggtggggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
cttccacctg gctgcagtac gtgattcttg atcccgagct cgggttgga agtgggtggg   360
agagttcgag gccttgcgct taaggagccc cttcgcctcg tgcttgagtt gaggcctggc   420
ctgggcgctg gggccgccgc gtgcgaatct ggtggcacct tcgcgcctgt ctcgctgctt   480
tcgataagtc tctagccatt taaaattttt gatgacctgc tgcgacgctt ttttctggc   540
aagatagtct tgtaaatgcg ggccaagatc tgcacactgg                        580

SEQ ID NO: 52             moltype = DNA   length = 530
FEATURE                   Location/Qualifiers
misc_feature             1..530
                          note = CDS
source                    1..530
                          mol_type = other DNA
                          organism = synthetic construct
SEQUENCE: 52
tctagagtgc ccgtcagtgg gcagagcgca catcgcccac agtccccgag aagttggggg   60
gaggggtcgg caattgaacc ggtgcctaga gaaggtggcg cggggtaaac tgggaaagtg   120
atgtcgtgta ctggctccgc ctttttcccg agggtggggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
cttccacctg gctgcagtac gtgattcttg atcccgagct cgggttgga agtgggtggg   360
agagttcgag gccttgcgct taaggagccc cttcgcctcg tgcttgagtt gaggcctggc   420
ctgggcgctg gggccgccgc gtgcgaatct ggtggcacct tcgcgcctgt ctcgctgctt   480
tcgataagtc tctagccatt taaaattttt gatgacctgc tgcgacgctt               530

SEQ ID NO: 53             moltype = DNA   length = 480
FEATURE                   Location/Qualifiers
misc_feature             1..480
                          note = CDS
source                    1..480
                          mol_type = other DNA
                          organism = synthetic construct
SEQUENCE: 53
tctagagtgc ccgtcagtgg gcagagcgca catcgcccac agtccccgag aagttggggg   60
gaggggtcgg caattgaacc ggtgcctaga gaaggtggcg cggggtaaac tgggaaagtg   120
atgtcgtgta ctggctccgc ctttttcccg agggtggggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
cttccacctg gctgcagtac gtgattcttg atcccgagct cgggttgga agtgggtggg   360
agagttcgag gccttgcgct taaggagccc cttcgcctcg tgcttgagtt gaggcctggc   420
ctgggcgctg gggccgccgc gtgcgaatct ggtggcacct tcgcgcctgt ctcgctgctt   480

SEQ ID NO: 54             moltype = DNA   length = 430
FEATURE                   Location/Qualifiers
misc_feature             1..430
                          note = CDS
source                    1..430
                          mol_type = other DNA
                          organism = synthetic construct
SEQUENCE: 54
tctagagtgc ccgtcagtgg gcagagcgca catcgcccac agtccccgag aagttggggg   60
gaggggtcgg caattgaacc ggtgcctaga gaaggtggcg cggggtaaac tgggaaagtg   120
atgtcgtgta ctggctccgc ctttttcccg agggtggggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
cttccacctg gctgcagtac gtgattcttg atcccgagct cgggttgga agtgggtggg   360
agagttcgag gccttgcgct taaggagccc cttcgcctcg tgcttgagtt gaggcctggc   420
ctgggcgctg                                                          430

SEQ ID NO: 55             moltype = DNA   length = 380
FEATURE                   Location/Qualifiers
misc_feature             1..380
                          note = CDS
source                    1..380
                          mol_type = other DNA
                          organism = synthetic construct
SEQUENCE: 55
tctagagtgc ccgtcagtgg gcagagcgca catcgcccac agtccccgag aagttggggg   60
gaggggtcgg caattgaacc ggtgcctaga gaaggtggcg cggggtaaac tgggaaagtg   120
atgtcgtgta ctggctccgc ctttttcccg agggtggggg agaaccgtat ataagtgcag   180
tagtcgccgt gaacgttctt tttcgcaacg ggtttgccgc cagaacacag gtaagtgccg   240
tgtgtggttc ccgcgggcct ggcctcttta cgggttatgg cccttgcgtg ccttgaatta   300
cttccacctg gctgcagtac gtgattcttg atcccgagct cgggttgga agtgggtggg   360
agagttcgag gccttgcgct                                               380

SEQ ID NO: 56             moltype = DNA   length = 330
```

-continued

```
FEATURE             Location/Qualifiers
misc_feature        1..330
                    note = CDS
source              1..330
                    mol_type = other DNA
                    organism = synthetic construct
SEQUENCE: 56
tctagagtgc ccgtcagtgg gcagagcgca catcgcccac agtccccgag aagttggggg   60
gaggggtcgg caattgaacc ggtgcctaga gaaggtggcg cggggtaaac tgggaaagtg  120
atgtcgtgta ctggctccgc cttttccccg agggtggggg agaaccgtat ataagtgcag  180
tagtcgccgt gaacgttctt tttcgcaacg ggtttgccgc cagaacacag gtaagtgccg  240
tgtgtggttc ccgcgggcct ggcctcttta cgggttatgg cccttgcgtg ccttgaatta  300
cttccacctg gctgcagtac gtgattcttg                                   330

SEQ ID NO: 57      moltype = DNA   length = 1184
FEATURE             Location/Qualifiers
misc_feature        1..1184
                    note = CDS
source              1..1184
                    mol_type = other DNA
                    organism = synthetic construct
SEQUENCE: 57
tctagagtgc ccgtcagtgg gcagagcgca catcgcccac agtccccgag aagttggggg   60
gaggggtcgg caattgaacc ggtgcctaga gaaggtggcg cggggtaaac tgggaaagtg  120
atgtcgtgta ctggctccgc cttttccccg agggtggggg agaaccgtat ataagtgcag  180
tagtcgccgt gaacgttctt tttcgcaacg ggtttgccgc cagaacacag gtaagtgccg  240
tgtgtggttc ccgcgggcct ggcctcttta cgggttatgg cccttgcgtg ccttgaatta  300
cttccacctg gctgcagtac gtgattcttg atcccgagct tcgggttgga agtgggtggg  360
agagttcgag gccttgcgct taaggagccc cttcgcctcg tgcttgagtt gaggcctggc  420
ctgggcgctg gggccgcccgc gtgcgaatct ggtggcacct tcgcgcctgt ctcgctgctt  480
tcgataagtc tctagccatt taaaattttt gatgacctgc tgcgacgctt tttttctggc  540
aagatagtct tgtaaatgcg ggccaagatc tgcacactgg tatttcggtt tttggggccg  600
cgggcggcga cggggcccgt gcgtcccagc gcacatgttc ggcgaggcgg ggcctgcgag  660
cgcggccacc gagaatcgga cgggggtagt ctcaagctgg ccggcctgct ctggtgcctg  720
gcctcgcgcc gccgtgtatc gcccccgccct gggcggcaag gctggcccgg tcggcaccag  780
ttgcgtgagc ggaaagatgg ccgcttcccg gccctgctgc agggagctca aaatggagga  840
cgcggcgctc gggagagcgg gcgggtgagt cacccacaca aaggaaaagg gcctttccgt  900
cctcagccgt cgcttcatgt gactccacgg agtaccgggc gccgtccagg cacctcgatt  960
agttctcgag ctttttgggagt acgtcgtctt taggttgggg ggagggggttt tatgcgatgg 1020
agtttcccca cactgagtgg gtggagactg aagttaggcc agcttggcac ttgatgtaat 1080
tctccttgga atttgccctt tttgagtttg gatcttggtt cattctcaag cctcagacag 1140
tggttcaaag ttttttttctt ccatttcagg tgtcgtgaac gcgt                   1184

SEQ ID NO: 58      moltype = DNA   length = 1718
FEATURE             Location/Qualifiers
misc_feature        1..1718
                    note = CDS
source              1..1718
                    mol_type = other DNA
                    organism = synthetic construct
SEQUENCE: 58
gacattgatt attgactagt tattaatagt aatcaattac ggggtcatta gttcatagcc   60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggactatt tacggtaaac tgcccacttg gcagtacatc  240
aagtgtatca tatgccaagt acgccccta ttgacgtcaa tgacggtaaa tggcccgcct  300
ggcattatgc ccagtacatg accttatggg actttcctac ttggcagtac atctacgtat  360
tagtcatcgc tattaccatg gtcgaggtg agccccacgt tctgcttcac tctccccatc  420
tccccccct cccacccc aatttttgtat ttatttattt tttaattatt ttgtgcagcg  480
atggggcgg ggggggggggg gcgcgcgcca ggcggggcgg ggcggggcga gggcgggggc  540
ggggcgaggc ggagaggtgc ggcggcagcc aatcagagcg gcgcgctccg aaagtttcct  600
tttatgcgcga ggcggcggcg gcgcgggccc tataaaaagc gaagcgcgcg gcgggcggga  660
gtcgctgcgt tgccttcgcc ccgtgcccg ctccgcgccg cctcgcgccg cccgccccg   720
ctctgactga ccgcgttact cccacaggtg agcgggcggg acggcccttc tcctccgggc  780
tgtaattagc gcttggttta atgacggctc gtttctttttc tgtggctgcg tgaaagcctt  840
aaagggctcc gggagggccc tttgtgcggg gggagcggc tcgggggggtg cgtgcgtgtg  900
tgtgtgcgtg gggagcgccg cgtgcggccc gcgctgcccg gcggctgtga gcgctgcggg  960
cgcggcgcgg ggctttgtgc gctccgcgtg tgcgcgaggg gagcgcggcc ggggggcggtg 1020
ccccgcggtg cggggggggct gcgagggaaa caaaggctgc gtgcggggtg tgtgcgtggg 1080
ggggtgagca ggggggtgtgg gcgcggcggt cgggctgtaa ccccccctg cacccccctc 1140
cccgagttgc tgagcacggc ccggcttcgg gtgcggggct ccgtacgggg cgtgcgcgg  1200
ggctcgccgt gccgggcggg gggtggcggc aggtgggggt gccgggcggg gcggggccgc 1260
ctcgggccgg ggagggctcg gggggggagggc gcggcggccc ccggagcgcc ggcggctgtc 1320
gaggcggc gagccgcagc cattgccttt tatggtaatc gtgcgagagg gcgcagggac 1380
ttcctttgtc ccaaatctgt gcggagccga aatctgggag gcgccgcgc acccctcta 1440
gcggcgcgg ggcgaagcgg tgcggcgccg gcaggaagga aatgggcggg gagggcttc  1500
gtgcgtcgcc gcgccgccgt ccccttctcc atctccagcc tcggggctgt ccgcaggggg 1560
acggctgcct tcgggggga cggggcaggg cggggttcgg cttctggcgt gtgaccggcg 1620
gctctagcgc ctctgctaac catgttcatg ccttcttctt tttcctacag ctcctgggca 1680
```

-continued

```
acgtgctggt tattgtgctg tctcatcatt ttggcaaa                              1718

SEQ ID NO: 59        moltype = DNA   length = 1366
FEATURE              Location/Qualifiers
misc_feature         1..1366
                     note = CDS
source               1..1366
                     mol_type = other DNA
                     organism = synthetic construct
SEQUENCE: 59
aagctttgag agaaaggga ccagatctta ttcctcaccg tggctttaac acttagagaa    60
aatgcatccc ctctaatcaa taagtcatcg acagtgggta gatggaggaa cggcagtgcg   120
tagtaggatg cgtgctaagc atagtctcgt gcatgggtgc atagatcgct gggcaggtgg   180
acaaggtggg ggtggataaa gaagtgggta gatgattgat gttaggtaaa tatcactggg   240
tggacagatg ggtggtaggt ggatggatgg ttagaatagt cagaagaggg atggattgat   300
aaggtgaaca gatgataaat gggtgataga ctggaagggt tgtcaaaaga ggataaggga   360
agtgtgagct agccgtattt ctaaggtcag taatagagtt gggagaagag gttaagttac   420
atccatttaa acctcacacg aagctgagtg ggaatggact tgctgccgtt ggtgaggaaa   480
gcgttgcatt tcccgtgtgc ttggttgtgg aagtgctcag gtcccacatg aagcagtcag   540
gttactgcgg cttacagagg agccagatcc aaatgccccg agtaagcacg tccccgagcc   600
agaggcctcc agcggaatcc gggagaggga ttgctcagtg ccctgcttcc ctggactgta   660
agctgcagaa agatgtggga agtcctgttc tccactgaga acactaaaag caccttttgt   720
caaacgaccg cttcacatct ggggcttgtg cactggtggc cttttaaacc agagacaacc   780
cacaagatac ctaacctgcg gggctctctg gtacagtgag caactcagga aatgctttgg   840
cttgattgct gtgggctctc aggccatcgc cctctggagt ggttctttta atgagaacct   900
gaagattggc ccctgagcca tgtataccaa gcaagctcaa tccaggttag ctccctctgg   960
ttggggcaag ctaacgtgct ccttgggccc cgcgcgtaac tgtgcgtttt ataggagaca  1020
gctagttcaa gaccccagga agaaagcggc tttgtccccc tctaggcctc gtacaggccc  1080
acattcatat ctcattgttg ttgcagggga ggcagatgcg atccagaaca atgggacctc  1140
ggctgaggac acggcggtga cagactccaa gcacacagca gacccaaaga ataactggca  1200
aggcgcccac ccagctgacc cagggaaccg cccccacttg atccgcctct tttcccgaga  1260
tgccccggga agggaggaca acaccttcaa agacaggccc tcagagtccg acgagcttca  1320
gaccatccaa gaagacccca cagcagcttc cggaggcctg gatgtg                  1366

SEQ ID NO: 60        moltype = DNA   length = 812
FEATURE              Location/Qualifiers
misc_feature         1..812
                     note = CDS
source               1..812
                     mol_type = other DNA
                     organism = synthetic construct
SEQUENCE: 60
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtcgag gtgagcccca cgttctgctt cactctcccc atctccccc cctcccccacc   360
cccaattttg tatttattta tttttaatt attttgtgca gcgatggggg cggggggggg   420
ggggggcgc gcgccaggcg gggcggggcg gggcgagggg cggggcgggg cgaggcggag   480
aggtgcggcg gcagccaatc agagcggcgc gctccgaaag tttccttta tggcgaggcg   540
gcggcggcgc cggccctata aaaagcgaag cgcgcggcgg gcgggagtcg ctgcgacgct   600
gccttcgccc cgtgccccgc tccgccgccg cctcgccgcc cccgcccgg ctctgactga   660
ccgcgttact cccacaggtg agcgggcggg acggcccttc tcctccgggc tgtaattagc   720
tgagcaagag gtaaggtttt aagggatggt tggttggtgg ggtattaatg tttaattacc   780
tggagcacct gcctgaaatc actttttttc ag                                 812
```

RECOMBINANT AAV VECTORS FOR TREATING NEURODEGENERATIVE DISORDERS

CROSS-REFERENCE TO RELATED APPLICATION

The present application is a Continuation Applications of PCT International Application No. PCT/CN2023/089291 filed on Apr. 19, 2023, which claims priority to Chinese Patent Application No. PCT/CN2022/087771, filed Apr. 19, 2022, the disclosure of which all is incorporated herein by reference in its entirety.

REFERENCE TO SEQUENCE LISTING

In accordance with 37 CFR § 1.52(e)(5) and with 37 CFR § 1.831, the specification makes reference to a Sequence Listing submitted electronically as a .xml file named 19684.0088FPWO Sequence Listing.xml copy, created and filed herewith is 128,000 bytes in size. The entire contents of the Sequence Listing are hereby incorporated by reference.

FIELD OF THE INVENTION

The present disclosure relates to the technical field of gene therapy. Specifically, the present disclosure provides a recombinant adeno-associated viral (rAAV) vector comprising one or two of (a) to (c): (a) a nucleotide sequence encoding aromatic L-amino acid decarboxylase (AADC), (b) a nucleotide sequence encoding glucocerebrosidase (GBA1); and (c) a nucleotide sequence encoding a neurotrophic factor (NTF), such as cerebral dopamine neurotrophic factor (CDNF) or glial cell derived neurotrophic factor (GDNF), for treating neurodegenerative disorders, particularly Parkinson's disease (PD), Multiple system atrophy (MSA), Gaucher's disease (GD), AADC deficiency (AADCD), and other proteinopathies. Also provided herein are viral particles comprising the rAAV vector, a pharmaceutical composition comprising the viral particles, and uses thereof.

BACKGROUND

Neurodegenerative diseases (NDs) occur when nerve cells in the brain or peripheral nervous system progressively lose function and ultimately die, resulting in loss of mobility, coordination, strength, sensation, and cognition. Due to their slow and progressive nature and lack of suitable treatments to slow the disease progression or cure, NDs are associated with large socioeconomic and personal costs and sufferings. Aging is the primary risk factor for most NDs. With people living longer, it means more people will be afflicted with NDs in the coming decades to place huge financial burden on our society and bring immense global public health challenges.

Parkinson's disease (PD), caused by the degeneration of midbrain dopaminergic transmission and characterized by both motor symptoms (e.g., tremor and rigidity) and non-motor symptoms (e.g., mental retardation and depression), affects almost 0.3% of the general population and ~1% of the population over the age of 60 (de Lau, L. M. and M. M. Breteler, Epidemiology of Parkinson's disease. Lancet Neurol, 2006. 5(6): p. 525-35).

Most PD cases are sporadic and caused by unknown factors. Only a minority of cases has family history. Currently, six specific human genome loci have been identified to contain genes whose mutations may lead to the onset of rare familial forms of PD (Klein, C. and A. Westenberger, Genetics of Parkinson's disease. Cold Spring Harb Perspect Med, 2012. 2(1): p. a008888). It is widely accepted that the etiology of PD results from an elaborate interplay of intrinsic factors like genetics with extrinsic environmental factors. The pathological changes and their relation to PD symptoms are well-established (Kouli, A., K. M. Torsney, and W. L. Kuan, Parkinson's Disease: Etiology, Neuropathology, and Pathogenesis, in Parkinson's Disease: Pathogenesis and Clinical Aspects, T. B. Stoker and J. C. Greenland, Editors. 2018: Brisbane (AU)). PD is pathologically characterized by the degeneration and loss of dopaminergic neurons in the substantia nigra pars compacta (SNc) and the loss of dopaminergic pathway from SNc to striatum (Putamen and caudate nuclei), leading to a reduced levels of dopamine in the striatum that results in impaired motor function. Based on this knowledge, several drugs have been developed by different approaches to restore the dopamine levels.

Another pathological hallmark of PD is the formation of Lewy bodies (LBs) in patient's brain, or the so-called "Lewy pathology". The alpha-synuclein (α-syn)-containing LBs or Lewy neurites induce cellular toxicity within DA neurons and other neuron subtypes, and is one of the main PD pathogenesis (Teil, M., et al., Targeting alpha-synuclein for PD Therapeutics: A Pursuit on All Fronts. Biomolecules, 2020. 10(3)). Multiple strategies targeting the Lewy pathology are currently under investigation, including stabilization of the α-syn physiological conformation, decrease of α-syn expression, inhibition of α-syn aggregation, and increase of α-syn clearance. Moreover, Lewy pathology is not restricted to the dopaminergic circuitry but extends to other brain regions via cell-to-cell propagation of α-syn aggregates, which might be one of the mechanisms underlying the non-motor PD symptoms. So theoretically, therapeutic treatments tackling α-syn aggregation may benefit both motor and non-motor functions of the PD patients.

Among the currently available treatments, L-DOPA (levodopa) is effective at treating motor symptoms of some of the PD patients. But L-DOPA has limited effects on treating non-motor symptoms or late stage PD patients. Moreover, it was shown that L-DOPA could cause severe side effects when taken at high doses (Zahoor, I., A. Shafi, and E. Haq, Pharmacological Treatment of Parkinson's Disease, in Parkinson's Disease: Pathogenesis and Clinical Aspects, T. B. Stoker and J. C. Greenland, Editors. 2018: Brisbane (AU)). Other treatments such as deep brain stimulation only ameliorate symptoms but do not stop the progression of disease (Dallapiazza, R. F., et al., Considerations for Patient and Target Selection in Deep Brain Stimulation Surgery for Parkinson's Disease, in Parkinson's Disease: Pathogenesis and Clinical Aspects, T. B. Stoker and J. C. Greenland, Editors. 2018: Brisbane (AU)). Therefore, better treatments for PD are urgently needed.

Current biologic PD treatments under investigation can be categorized into three types. 1) By modulating neuronal signaling to restore neurotransmitter imbalances. For example, gene therapies delivering AADC, an enzyme involved in dopamine synthesis, by viral vectors, e.g., AAV2-AADC (CN107106689A, relevant clinical trials@https://clinicaltrials.gov/ct2/show/ NCT03065192?term=AADC&cond=PD&draw=2&rank=8) and a lentivirus-based gene therapy (ProSavin) have shown promising results in early stage clinical trials with mild improvements in the motor function of patients. 2) By expression of neurotrophic and regenerative factors to improve neuronal survival. For example, neurotrophic factor (GDNF) (clinical trial@https://clinicaltrials.gov/ct2/show/NCT04167540?term=GDNF&cond=PD&draw=2&rank=1) and Neurturin (NRTN) (clinical trial@https://clinicaltrials.gov/ct2/show/NCT00985517?term=Neurturin&draw=2&rank=1) are beneficial in the survival of neurons in the dopaminergic midbrain. 3) By targeting disease-associated genes or gene mutations, e.g., alpha synaptic nuclear protein (SNCA), glucocerebrosidase (GBA1) (clinical trial@https://clinical-trials.gov/ct2/show/NCTO4127578?term=GBA1&cond=Parkinson+Disease&draw=2&rank=1), and the leucine-rich repeat kinase 2 (LRRK2). Several antisense oligonucleotides (ASOs)-, CRISPR-, and AAV-based gene therapies aiming to edit gene and/or regulate gene expression are currently in early-stage clinical trials.

Accordingly, there remains an unmet need for a treatment for PD, which can restore dopamine level in the striatum, clear α-syn, and preserve the dopaminergic transmission in the patient brain.

AAV-mediated gene replacement therapies may also have potential in treating other neurodegenerative disorders or neurodevelopmental diseases including, but not limited to multiple system atrophy (MSA), Lewy body dementia (LBD), Alzheimer's disease with Amygdalar restricted Lewy body (AD/ALB), Gaucher disease, AADC deficiency, and so on.

MSA is a rapidly progressive sporadic adult-onset neurodegenerative disorder. Clinical symptoms of MSA include parkinsonism (bradykinesia, rigidity, and postural instability which are similar to Parkinson's disease); cerebellar syndrome, and autonomic failure which is caused by brain stem nuclei degeneration. Two clinical subtypes are defined, MSA-P (Parkinsonism) and MSA-C(Cerebellar syndrome) based on the predominant symptomatology (Monzio Compagnoni, G. and A. Di Fonzo, Understanding the pathogenesis of multiple system atrophy: state of the art and future perspectives. Acta Neuropathol Commun, 2019. 7(1): p. 113). Main pathological features of MSA are the widespread neuronal and oligodendrocyte loss and gliosis in multiple brain regions.

The cause of MSA is still unclear, while the main pathogenic mechanism of MSA is the presence of argyrophilic filamentous glial cytoplasmic inclusions (GCIs), predominantly in oligodendrocytes. The GCIs are primarily composed of loosely packed filaments of α-synuclein protein that is phosphorylated at residue Ser129 and ubiquitinated. Based on its pathology and symptoms, currently available MSA treatments and therapies being developed are designed to target the loss of dopamine transmission, neuronal loss, and aggregation of α-synuclein, which are quite similar to approaches for treating PD.

Epidemiologic studies of MSA have shown a prevalence in the range of 3.4 to 4.9 per 100,000 people, increasing to 7.8 per 100,000 among people older than 40 years of age. Currently available treatments only alleviate symptoms. For example, dopamine derivatives (e.g., Medopa or Duopa) are used to reduce PD-like symptoms. However, these drugs are not as effective in treating MSA-P patients as they are in treating PD patients. In addition, some MSA-P patients only respond to these drugs at higher doses and they usually become less effective over time. Therefore, enhancement of dopamine production via delivery of AADC may not benefit MSA patients as much as shown for PD patients. Additional disease modifying therapies which could delay the disease progression are needed. Such therapies could potentially target three aspects of the MSA pathogenesis: (1) α-synuclein aggregation, (2) cellular dysfunction and loss, and (3) neuroinflammation. There are several active clinical-stage candidates, including an immunogenic peptide of α-synuclein (PD01 and PD03, NCT02270489), an α-synuclein aggregation inhibitor (Anle138b, NCT04208152; ATH434, NCT05109091), an antisense oligonucleotide (ASO) against α-synuclein (BIIB101, NCT04165486), and a neuroprotective factor like GDNF delivered by AAV (AAV2-GDNF, NCT04680065). All of the above-mentioned therapies that are under development target a single pathology or symptom. For a complex ND like MSA, simultaneously targeting multiple disease-causing pathologies could potentially provide better therapeutic effects or even disease modifying effects not only to alleviate its symptoms, but to slow the disease progression.

Gaucher disease (GD) is an autosomal recessive disorder mainly caused by the loss-of-function mutation of the GBA1 gene. GD has been classified into three types based on the absence (type 1), or presence and severity of the central nervous system (CNS) impairments (nGD, type 2 and type 3) (Bennett, L. L. and C. Fellner, Pharmacotherapy of Gaucher Disease: Current and Future Options. P T, 2018. 43(5): p. 274-309). Enzyme replacement therapy has been developed that is only effective for treating type 1 GD since the recombinant enzyme could not cross the blood-brain barrier (BBB). CNS-tropism AAV expressing GBA1 would be a promising approach to treat nGD. An active clinical trial (NCT04411654) sponsored by Prevail Therapeutics delivers codon-optimized GBA1 transgene via intra-cisterna *magna* (ICM) injection of rAAV9.

AADC deficiency (AADCD) is a rare, autosomal recessive disorder mainly caused by the loss-of-function mutation of the AADC gene. The abnormality of AADC protein leads to a severe deficiency of some of the most critical neurotransmitters for brain function, like serotonin, dopamine, norepinephrine and epinephrine. rAAV9 expressing functional wild-type AADC was developed to treat this disease by PTC therapeutics, called Upstaza™ (eladocagene exuparvovec) which has been approved by the EMEA (European Agency for the Evaluation of Medicinal Products) and UK for treating patients at an age of 18 months or older.

Taken together of the above evidence, NDs are complex, multifaceted and debilitating diseases that have huge impact on global public health. Development of innovated treatments that are disease modifying to slow the disease progression and alleviate patient sufferings is urgently needed.

SUMMARY OF THE INVENTION

To develop better therapies for treating various NDs, the present inventors have modified the nucleotide sequences encoding for AADC, GBA1, and NTF such as CDNF and GDNF to optimize their expression when delivered into the human brain via rAAV vectors. In addition, the present inventors have developed rAAV vectors that express two genes of interest (GOI) in tandem to develop therapies targeting multiple disease pathologies synergistically to achieve greater therapeutic effects.

Therefore, in a first aspect, the present application provides a nucleotide sequence encoding one of the above listed GOIs, specifically AADC, GBA1, CDNF and GDNF, wherein the nucleotide sequence is a codon-optimized sequence as compared to the wild-type sequence of the GOI.

In a second aspect, the present application provides a nucleic acid construct comprising the nucleotide sequence of the first aspect operatively linked to a promoter.

In a third aspect, the present application provides a nucleic acid construct comprising two nucleotide sequences operatively linked to a promoter, wherein the first nucleotide sequence and the second nucleotide sequence encodes for two of (a), (b) and (c), respectively: (a) AADC, (b) GBA1, and (c) GDNF or CDNF. In a preferred embodiment, the nucleotide sequence encoding AADC is a codon-optimized sequence. In a specific embodiment, the nucleotide encoding for AADC is a nucleotide sequence of the first aspect. In another preferred embodiment, the nucleotide sequence encoding for GBA1 is a codon-optimized sequence. In a specific embodiment, the nucleotide encoding for GBA1 is a nucleotide sequence of the first aspect. In another preferred embodiment, the nucleotide sequence encoding for CDNF or GDNF is a partially codon-optimized sequence with the nucleotide region coding for the signal peptide unchanged. In a further embodiment, the nucleotide sequence encoding for CDNF or GDNF has a reduced number of CpG sites as compared to the wild-type coding sequence. In a further embodiment, the nucleotide sequence encoding for CDNF or GDNF does not contain any CpG island. In a specific embodiment, the nucleotide sequence encoding for CDNF or GDNF is a nucleotide sequence of the first aspect.

In a preferred embodiment, the nucleic acid construct of the third aspect comprises a linker sequence between the GOIs of first nucleotide sequence and the second nucleotide sequence. In a specific embodiment, the linker sequence is a 2A peptide. In a specific embodiment, the linker sequence is IRES.

In a fourth aspect, the present application relates to a rAAV vector comprising the nucleotide sequence of the first aspect, or the nucleic acid construct of the second or third aspect. In a preferred embodiment, the AAV vector is AAV9.

In a fifth aspect, the present application relates to a composition, e.g., a pharmaceutical composition, comprising the rAAV vector of the fourth aspect and a pharmaceutically acceptable excipient.

In a sixth aspect, the present application relates to a viral particle comprising the rAAV vector of the fourth aspect.

In a seventh aspect, the present application relates to a method of treating or preventing neurodegenerative disorders (NDs), e.g., Parkinson's disease (PD), Multiple system atrophy (MSA), Gaucher's disease (GD), AADC deficiency (AADCD), and other proteiopathies, in a subject in need thereof, comprising administering the rAAV vector of the fourth aspect to the subject.

In an eighth aspect, the present application relates to the use of the rAAV vector of the fourth aspect in treating or preventing neurodegenerative disorders, or in the manufacture of a medicament for treating or preventing neurodegenerative disorders, wherein the neurodegenerative disorders are particularly Parkinson's disease (PD), Multiple system atrophy (MSA), Gaucher's disease (GD), AADC deficiency (AADCD), and other proteinopathies.

The nucleic acid constructs of the present application comprise a combination of a promoter, a linker, and one or two therapeutic protein coding sequences specially optimized for rAAV vector so as to provide desirable levels of expression of the therapeutic proteins, e.g., one or two of AADC, GBA1, and CDNF/GDNF. Especially for the rAAV vector comprising two GOIs, such rAAV vector of the present invention can achieve co-expression of both therapeutic proteins at the desirable levels that in combination, they will work synergistically as novel therapies to treat the intended neurodegenerative diseases more effectively to achieve better therapeutic outcomes.

BRIEF DESCRIPTION OF THE DRAWINGS

FIG. 2A and FIG. 2B show representative images of the Western blot (WB) results of AADC and GBA1 protein expression, alone or in combination in HEK293 cells. (FIG. 2A) Cells were transfected with constructs comprising coding sequence of AADC, GBA1, or AADC-P2A-GBA1 (AADC coding sequence linked to the GBA1 coding sequence with a P2A linker). (FIG. 2B) Cells were transfected with constructs comprising AADC and GBA1 coding sequences in different orders. GpA: GBA1-P2A-AADC; ApG: AADC-P2A-GBA1.

FIG. 3 shows representative images of the WB showing evaluation of the cleavage efficiency of different linkers used when expressing both AADC and GBA in the same construct.

(FIG. 18A) WB images; (FIG. 18B) normalized data.

(FIG. 19A) WB images; (FIG. 19B) normalized data.

Pre: data collected before MPTP modeling; Post MPTP/P: data collected after induction by MPTP/P and before AAV treatment; Post AAV: data collected post AAV treatment.

Figure 35:
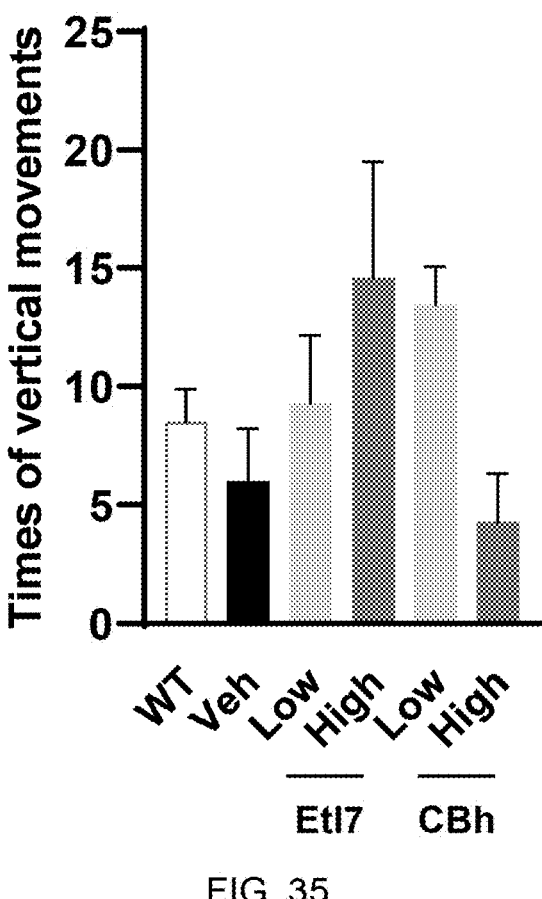

FIG. 35 shows the rearing behavior (standing by hindlimbs) taken from the study subjects of an α-synuclein A53T transgenic mouse model of PD after dosing of EtI7-A11G11 (EtI7) and CBh-A11G11 (CBh) rAAVs. Low: 4E+9 vg, High: 4E+10 vg.

Figure 36:
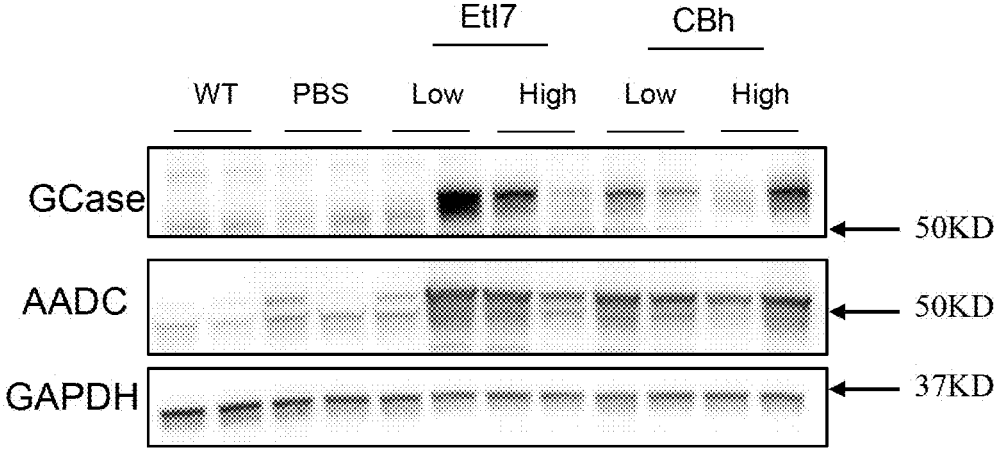

FIG. 36 shows representative images of the WB showing the expression of AADC and GCase in the tissue samples collected from the study subjects of the α-synuclein A53T transgenic mouse model of PD after dosing of EtI7-A11G11 and CBh-A11G11 rAAVs. Low: 4E+9 vg, High: 4E+10 vg.

Figures 37A, 37B:
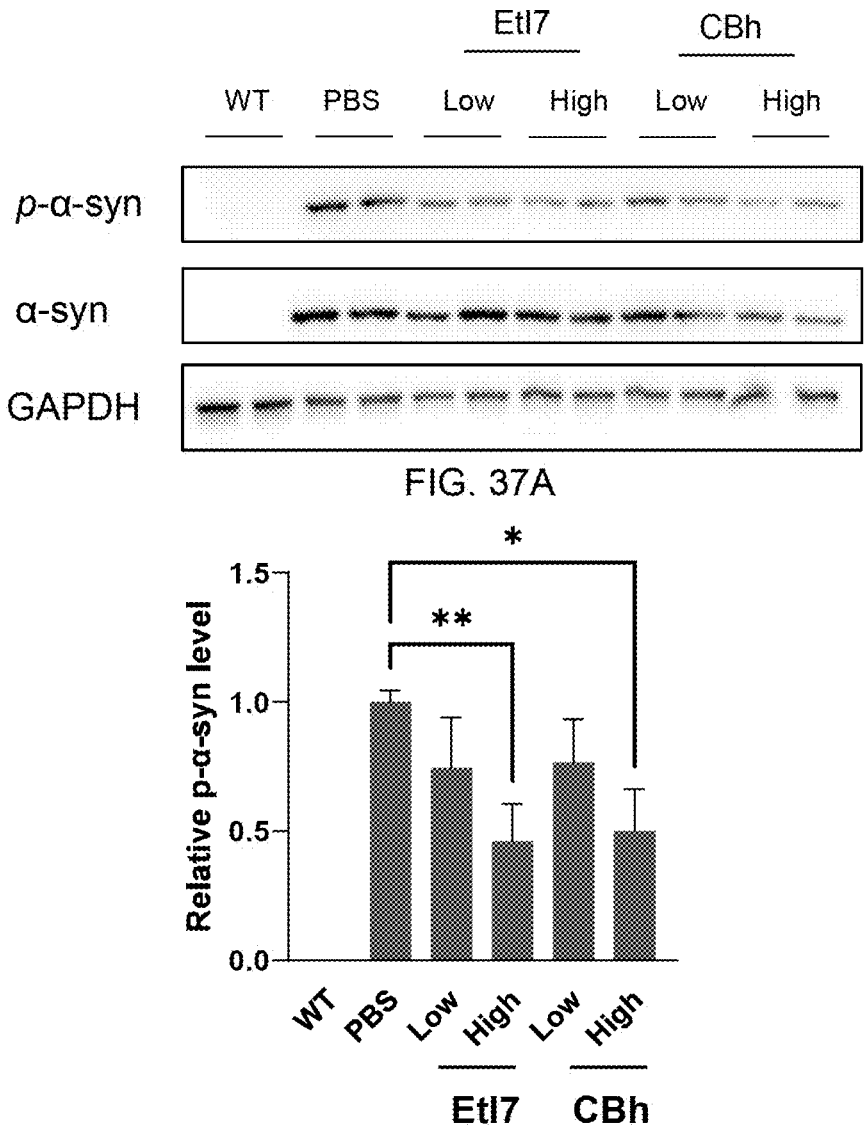

FIG. 37A and FIG. 37B show representative images of the WB (FIG. 37A) and the normalized data (FIG. 37B) showing the levels of phosphorylated and total α-synuclein in the tissue samples collected from the α-synuclein A53T transgenic mouse model of PD after dosing of EtI7-A11G11 and CBh-A11G11 rAAVs. Low: 4E+9 vg, High: 4E+10 vg.

Figures 38A, 38B:
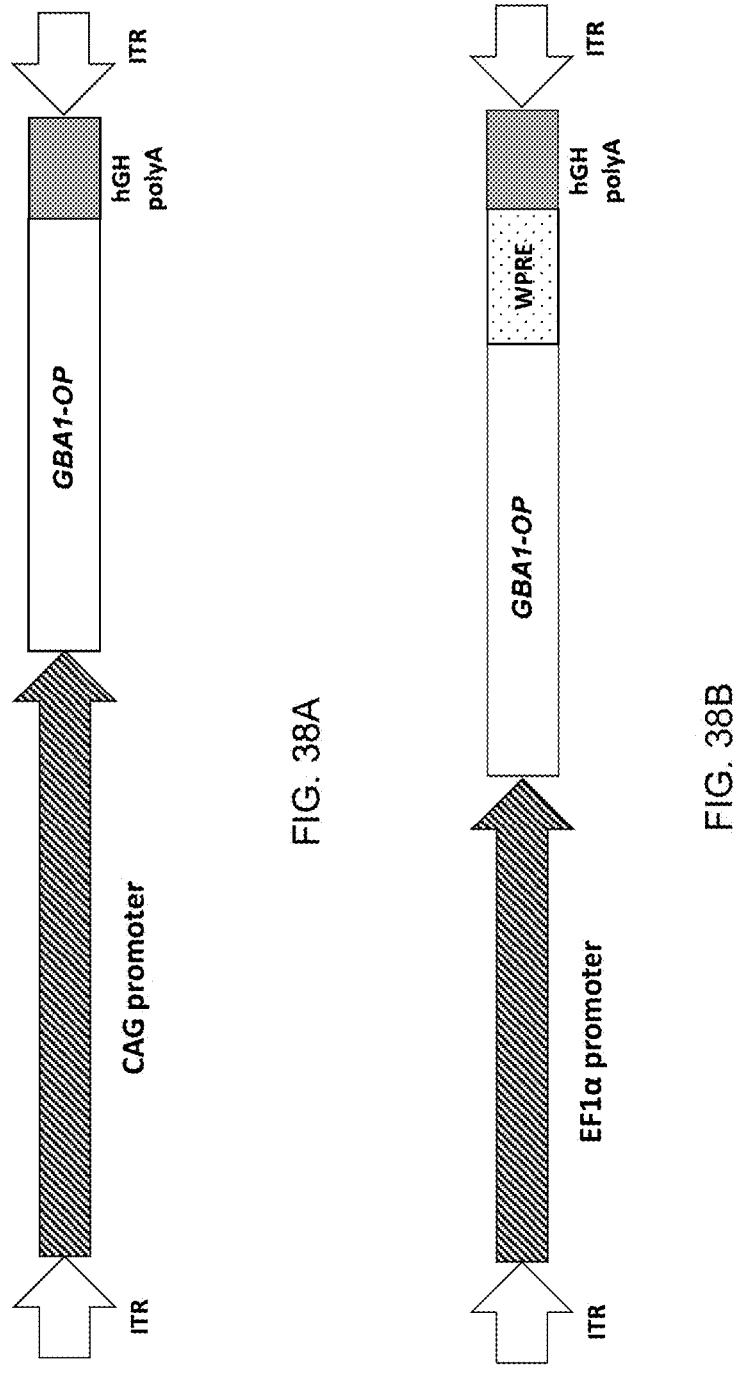

FIG. 38A and FIG. 38B show the schematic of constructs comprising different promotors and the codon optimized GBA1.

Figure 39:
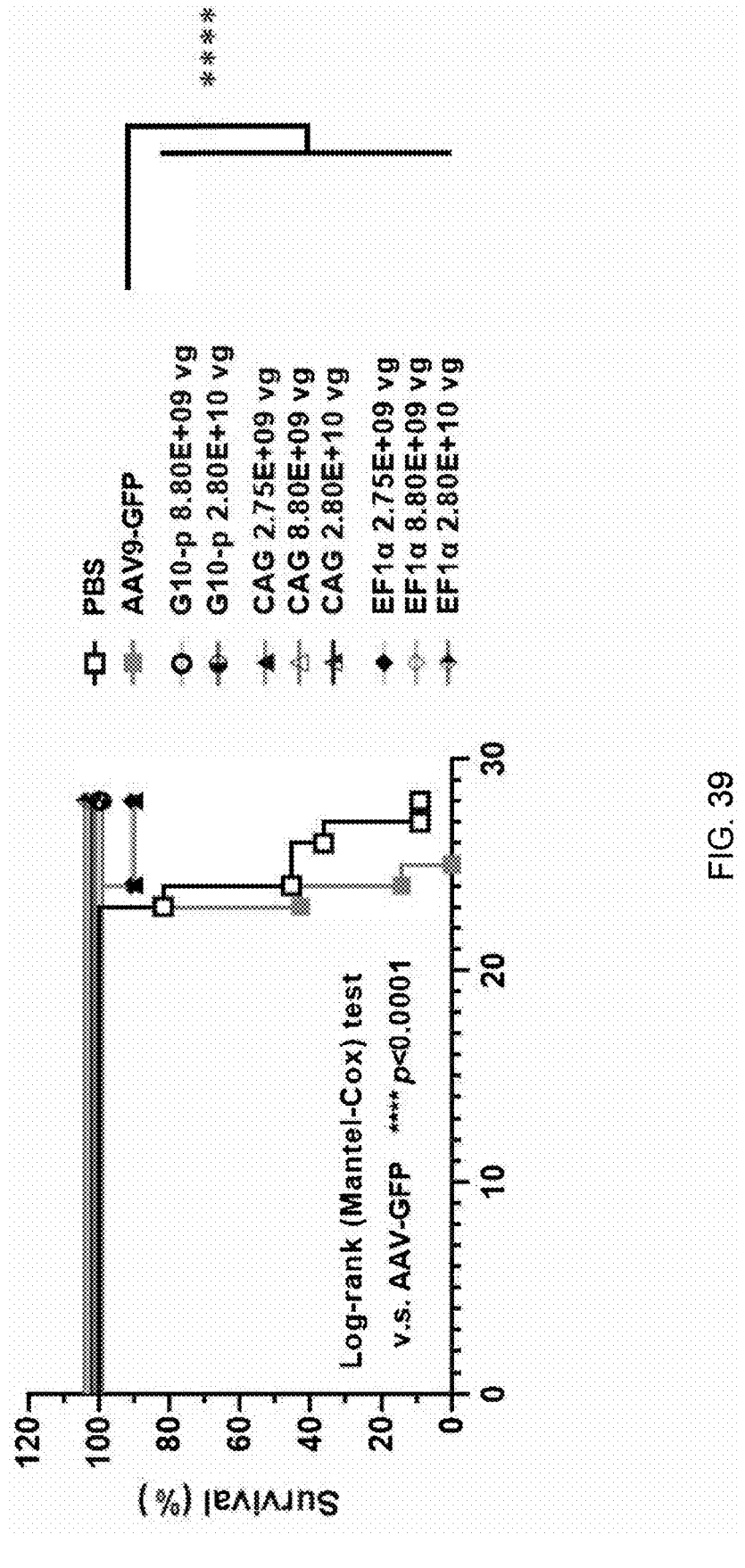

FIG. 39 shows the survival curve (viability) of the CBE induced GD mice after the administration of G10-p, CAG-G11 and EF1α-G11 rAAVs, respectively.

Figures 40A, 40B:
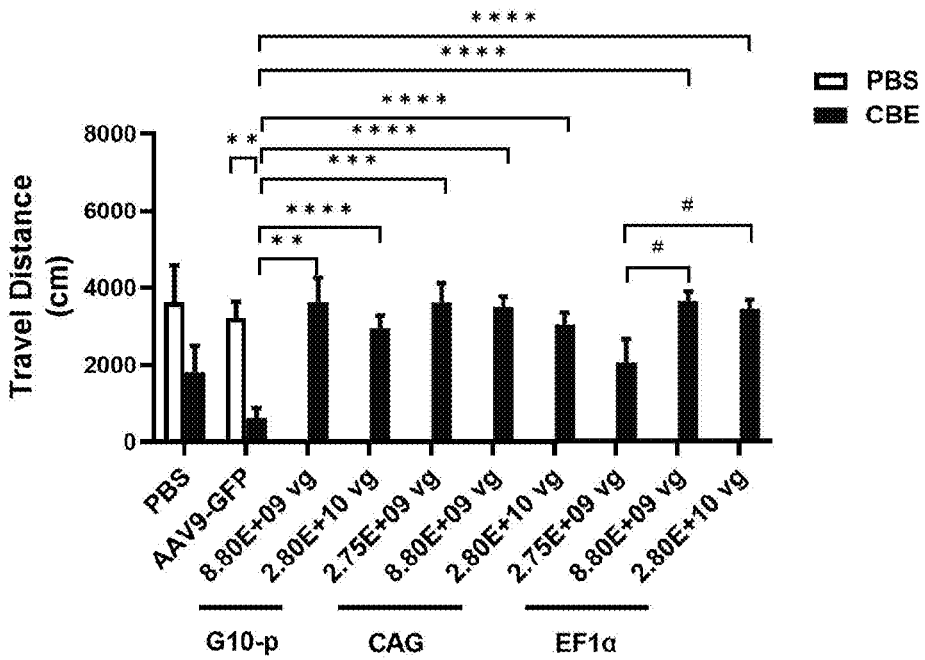

FIG. 40A and FIG. 40B show the moving distance in open field test (FIG. 40A) and latency to fall in rotarod test (FIG. 40B) of CBE induced GD mice after the administration of G10-p, CAG-G11, and EF1α-G11 rAAVs, respectively, in different doses.

Figure 41:
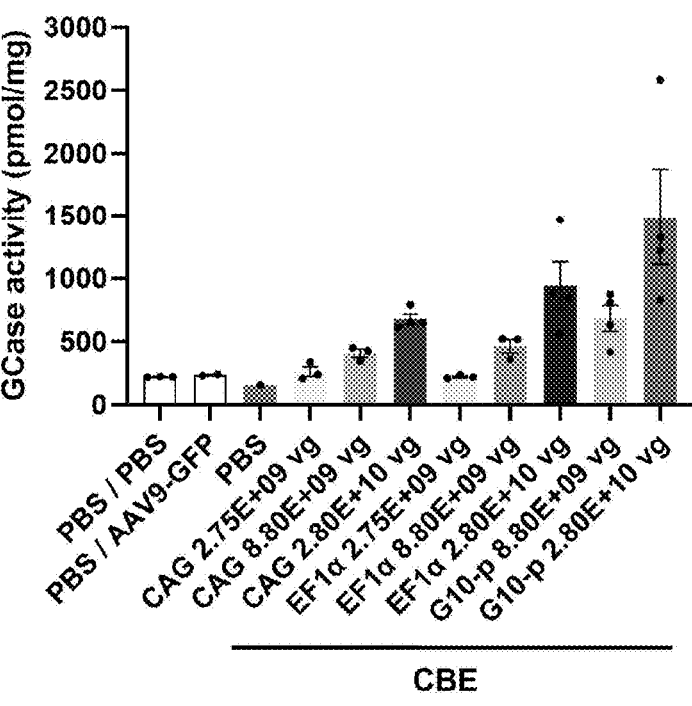

FIG. 41 shows the GCase activity in the striatum samples collected from the CBE induced GD mice after the administration of G10-p, CAG-G11, and EF1α-G11 rAAVs, respectively, in different doses.

Figure 42:
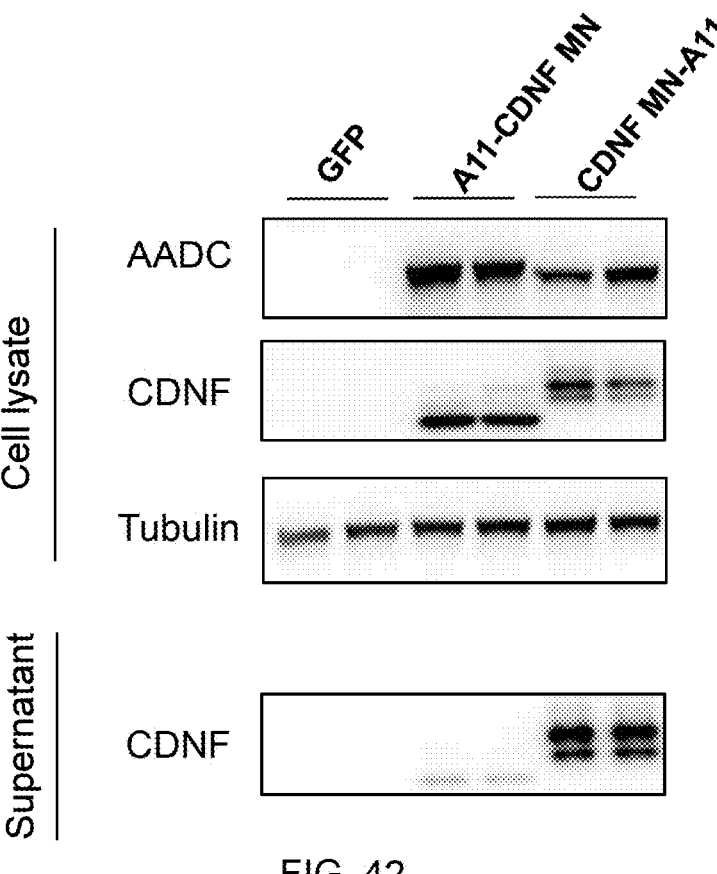

FIG. 42 shows the representative WB images showing the protein expression of AADC and CDNF in cell lysates and CDNF protein levels in the supernatants of the HEK293 cells transfected with the indicated candidate constructs.

Figure 43:
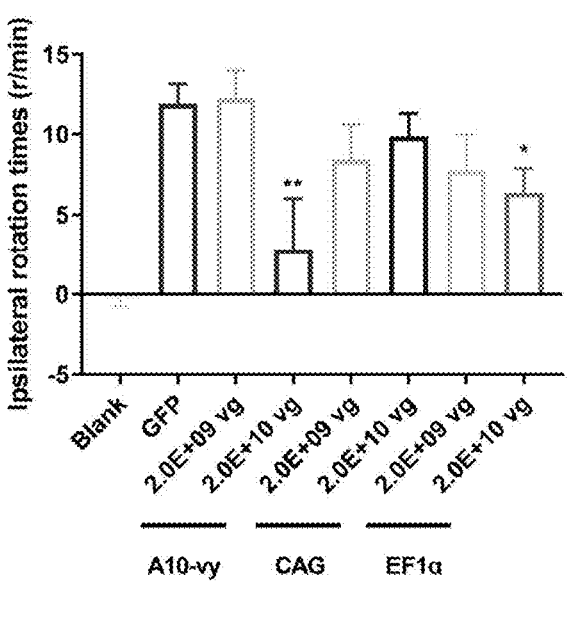

FIG. 43 shows the net rotation numbers (amphetamine induced ipsilateral rotation) of 6-OHDA induced PD model mice after dosing with the indicated doses of CAG-A11-GDNF MN, EF1α-A11-GDNF MN, and benchmark A10-vy rAAVs.

Figure 44A:
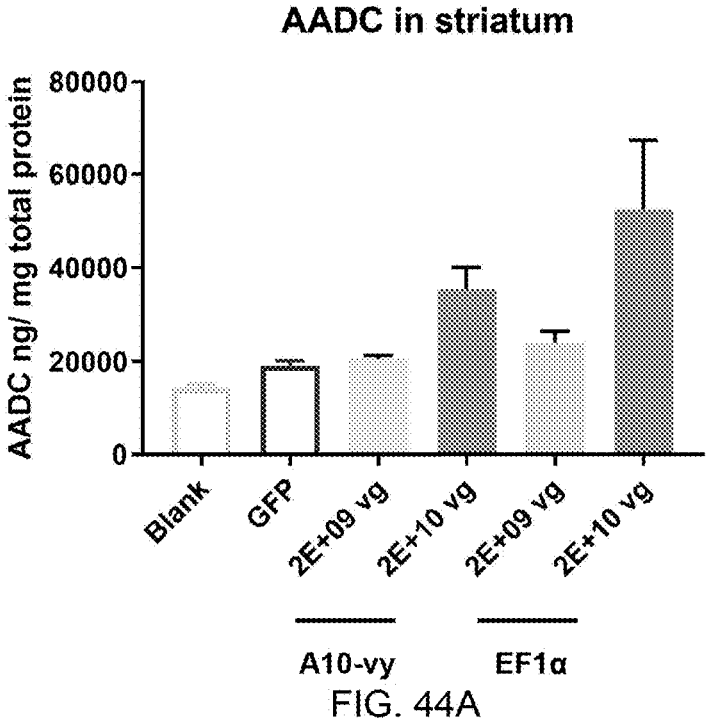
Figure 44B:
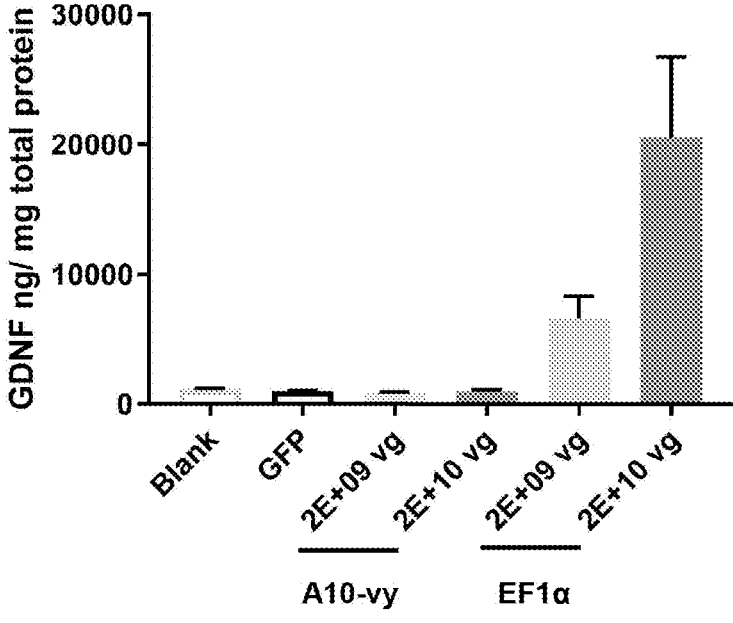

FIG. 44A and FIG. 44B show the AADC (FIG. 44A) and GDNF (FIG. 44B) protein expression levels in striatum samples collected from 6-OHDA induced PD model mice after dosing with the indicated amounts of EF1α-A11-GDNF MN and benchmark A10-vy rAAVs, as determined by ELISA.

Figure 45:
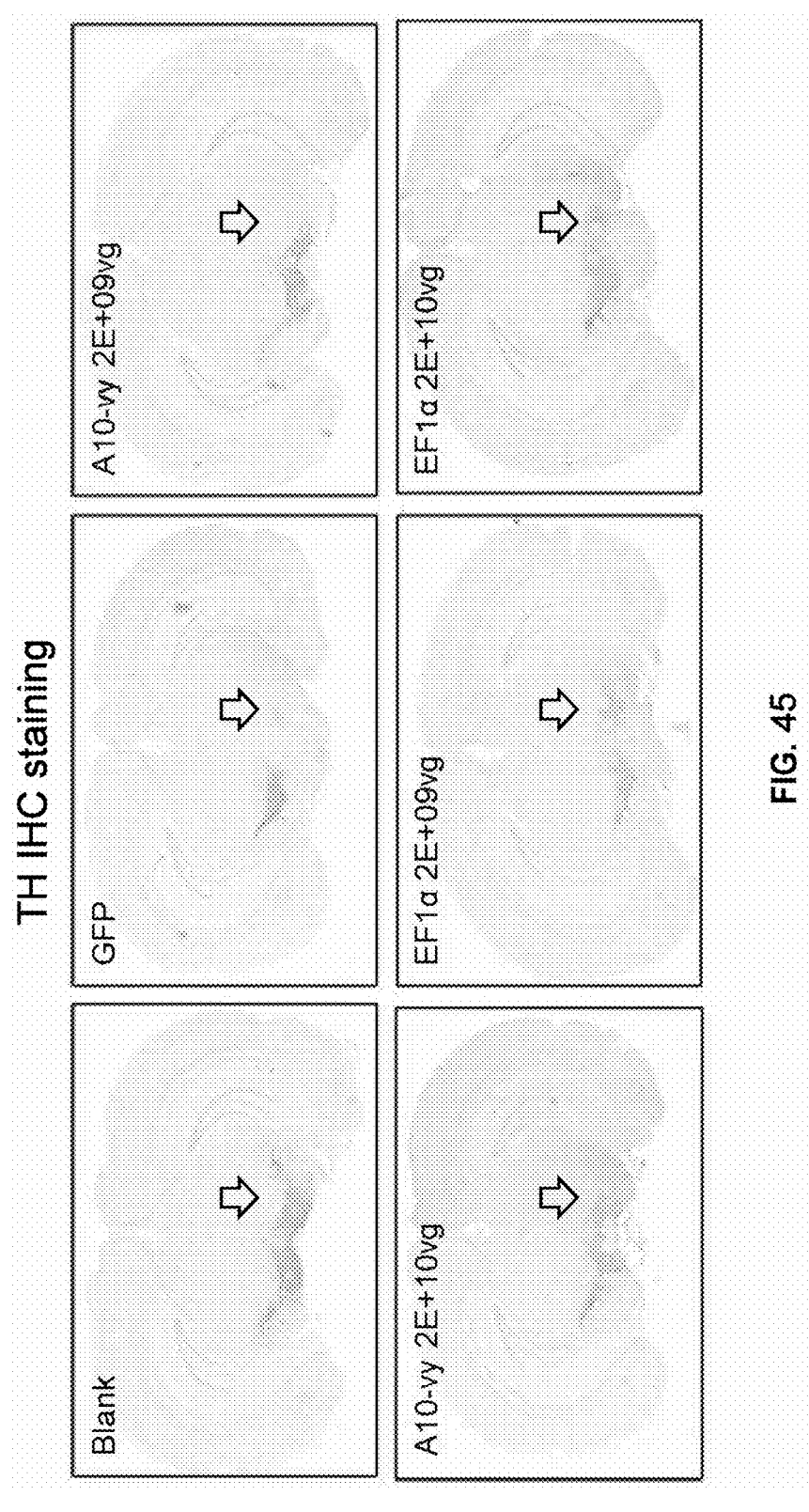

FIG. 45 shows the representative images showing the tyrosine hydroxylase (TH) levels in the nigra samples collected from the 6-OHDA induced PD model mice after dosing with the indicated amounts of EF1α-A11-GDNF MN and benchmark A10-vy rAAVs, as determined by immunohistochemistry (IHC). Blank: healthy control.

Figure 46:
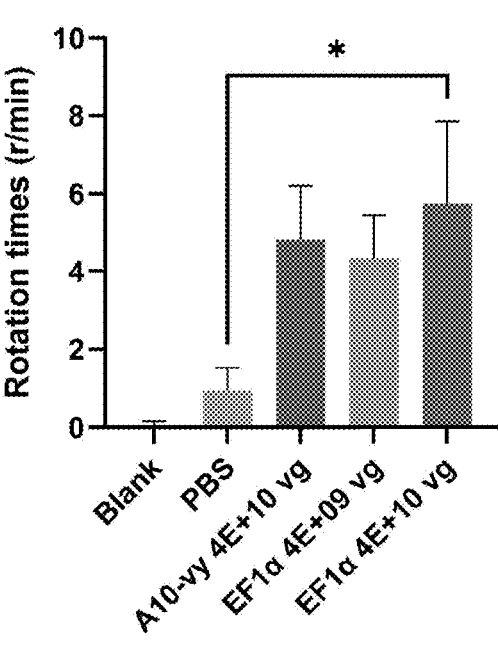

FIG. 46 shows the A rotation numbers (L-DOPA induced contralateral rotation) taken from the 6-OHDA induced PD model rats after dosing with the indicated doses of EF1α-A11-GDNF MN and benchmark A10-vy rAAVs. Blank represents healthy control.

Figure 47:
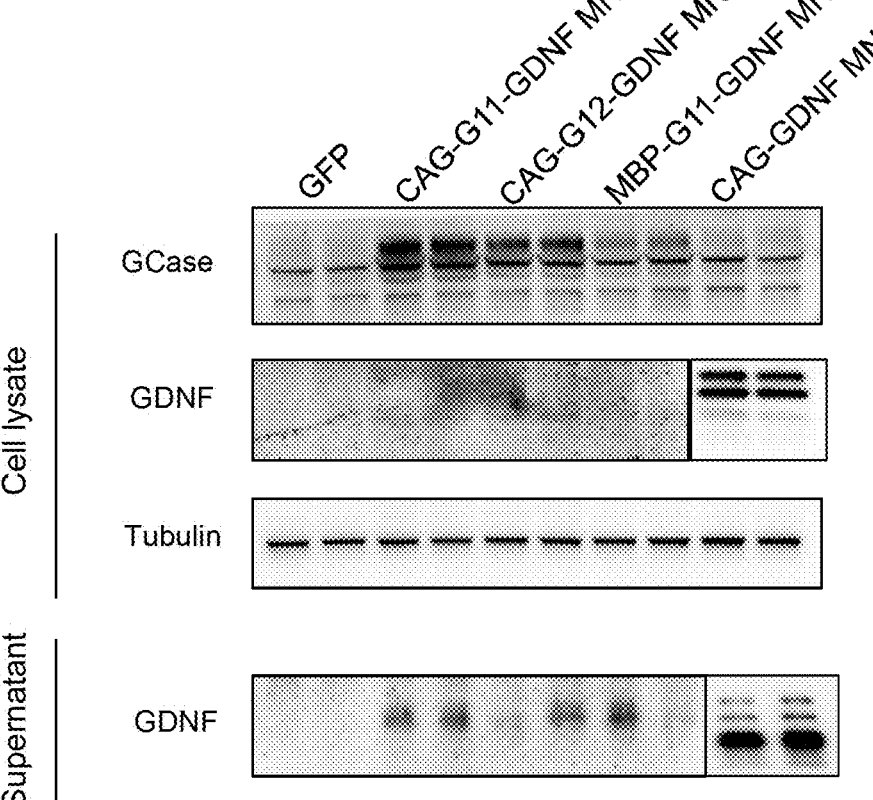

FIG. 47 shows the representative WB images showing the protein expression of GCase and GDNF in cell lysates and GDNF protein levels in the supernatants of the U87-MG-AAVR cells treated with different candidate rAAV vectors.

Figure 48:
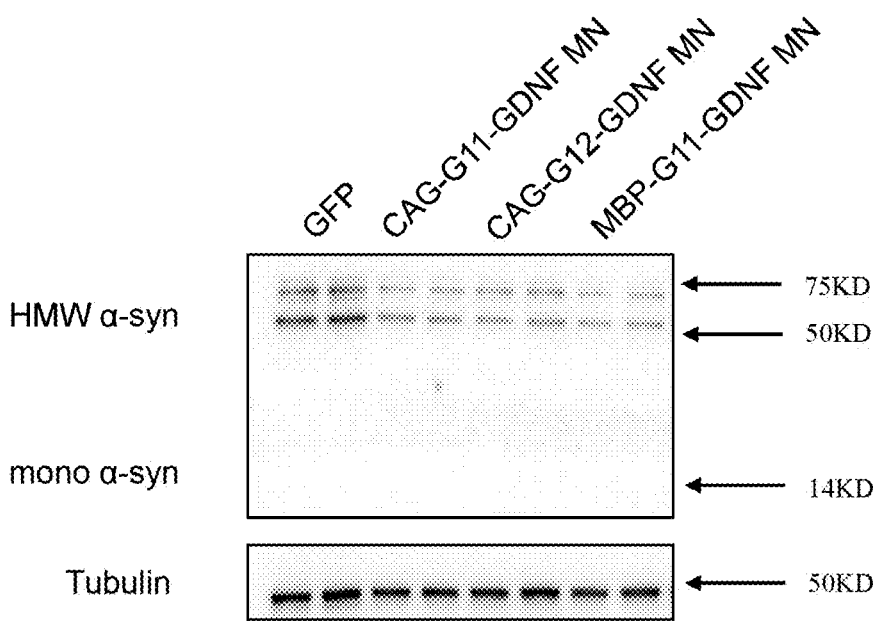

FIG. 48 shows the representative WB images showing the protein levels of the high molecular weight α-syn (HMW) of the SH-SY5Y-AAVR-A53T cells treated with different candidate rAAV vectors.

Figure 49:
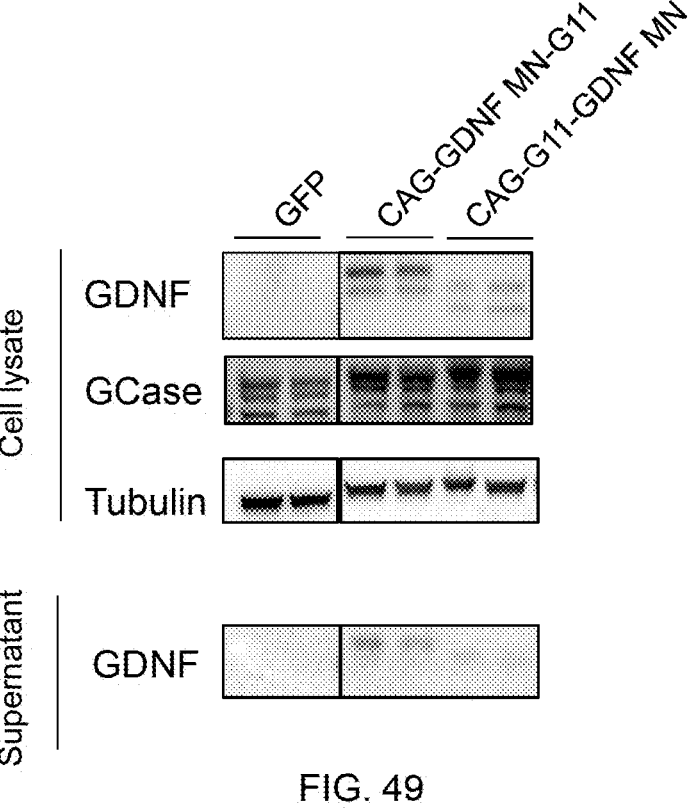

FIG. 49 shows the representative WB images showing the protein expression of GCase and GDNF in cell lysates and GDNF protein levels in the supernatants of the HEK293 cells transfected with different candidate constructs.

DETAILED DESCRIPTION OF THE INVENTION

Unless specifically defined elsewhere in this document, all of the technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

In the context of the present disclosure, unless being otherwise indicated, the wording "comprise", and variations thereof such as "comprises" and "comprising" will be understood to imply the inclusion of a stated element, e.g. an amino acid sequence, a nucleotide sequence, a property, a step or a group thereof, but not the exclusion of any other elements, e.g. amino acid sequences, nucleotide sequences, properties and steps. When used herein the term "comprise" or any variation thereof can be substituted with the term "contain", "include" or sometimes "have" or equivalent variation thereof. In certain embodiments, the wording "comprise" also include the scenario of "consisting of".

The term "gene" as used herein refers to a nucleic acid (such as DNA, e.g., genomic DNA or cDNA) and its corresponding nucleotide sequence encoding an RNA transcript. As used herein, terms with reference to genomic DNA can include intervening non-coding regions as well as regulatory regions, and may include both 5' and 3' terminus. In some instances, the term includes transcribed sequences, including 5' and 3' untranslated regions (5'-UTR and 3'-UTR), exons and introns. In some genes, the transcribed regions will contain an "open reading frame" encoding the polypeptide. In some instances, a "gene" comprises only the coding sequence (e.g., an "open reading frame" or "coding region") necessary to encode a polypeptide. In some instances, the term "gene" includes not only transcribed sequences, but also non-transcribed regions, including upstream and downstream regulatory regions, enhancers, and promoters. A gene may refer to an "endogenous gene" or a native gene. A gene may refer to a "foreign gene" or a non-native gene. A non-native gene can refer to a gene not normally found in the host organism but introduced into the host organism by gene transfer. A non-native gene can also refer to a gene that is not in its natural location in the genome of an organism. A non-native gene can also refer to a naturally occurring nucleic acid that contains mutations, insertions and/or deletions (e.g., non-native sequences), e.g., a codon-optimized nucleotide sequence. In the context of the present application, by "GOI" it specifically refers to CDS region, namely the sequences coding for amino acids in a protein, unless being otherwise indicated.

The terms "polynucleotide", "oligonucleotide" and "nucleic acid" are used interchangeably herein and refer to a polymeric form of nucleotides of any length. A polynucleotide can be exogenous or endogenous to a cell. A polynucleotide can exist in a cell-free environment. A polynucleotide can be a gene or a fragment thereof. A polynucleotide can be DNA. A polynucleotide can be RNA. A polynucleotide can have any three-dimensional structure and can perform any function, known or unknown. A polynucleotide may contain one or more analogs (e.g., altered backbones, sugars or nucleobases).

"Cassette" or "expression cassette" as described herein refers to a DNA component included in a vector (e.g., a plasmid vector or viral vector), and consisted of one or more genes under the control of regulatory sequences to be expressed in a host cell transduced by the vector.

"Operatively linked" as described herein is used to describe that two or more components, particularly nucleotide sequences, are connected in a way that each of the components can perform their designated functions.

"AAV" refers to adeno-associated virus.

"AADC" refers to aromatic L-amino acid decarboxylase. AADC is also known as DOPA decarboxylase (DDC).

"GBA1" refers to glucocerebrosidase that cleaves the beta-glucosidic linkage of glucocerebroside. In some cases, "GBA1" can be interchangeably referred as "GBA", "GCB" or "GLUC".

"NTF" refers to neurotrophic factor, which is a group of supportive proteins facilitating the development and maintenance of neurons. Both CDNF and GDNF belong to neurotrophic factors.

"CpG island" refers to a region in the genome rich in CpG sites. "CpG site" refers to two consecutive nucleotides consisting of a cytosine (C) and a guanine (G) in a 5' to 3' direction.

"2A peptide" refers to a group of short (18-22 amino acids) self-cleaving peptides derived from viruses. 2A peptides create ribosome skipping during translation, leading to separation between the end of the 2A sequence and downstream protein.

"IRES" refers to internal ribosome entry site.

"Proteinopathy" refers to a neurodegenerative disorder with accumulation of structurally abnormal protein, for example, α-synuclein, leading to formation of aggregates or inclusions in axons of neurons or oligodendrocytes.

In the context of the present application, "subject" refers to an animal, preferably a mammal, such as a primate, such as a cynomolgus monkey, preferably a higher primate, such as a human. Unless otherwise stated, the term "subject" is interchangeable with the term "patient" or "individual" in the context of this application.

AADC

The present disclosure provides rAAV vectors which deliver aromatic L-amino acid decarboxylase (AADC) gene alone, or in combination with another gene of interest, e.g., GBA1, CDNF or GDNF. The rAAV vectors delivering AADC can be used to treat NDs, such as PD or AADCD.

The biosynthetic pathway of dopamine requires both tyrosine hydroxylase (TH), which converts tyrosine to 1-3, 4-hydroxyphenylalanine (L-Dopa), and aromatic L-amino acid decarboxylase (AADC), which decarboxylates L-Dopa to generate dopamine.

It is known that AADC levels decline as PD progresses, and that L-DOPA taken by patients cannot be efficiently converted to dopamine in the axonal terminals within striatum. This makes more frequent and increased doses of L-DOPA necessary in order to achieve sufficient clinical responses. However, increasing the dose of L-DOPA could bring unwanted side effects, such as L-Dopa-induced dyskinesias (LID).

The potential of intra-putaminal AADC delivery by AAV in treating PD has been reported and evaluated clinically (Bankiewicz, K. S., et al., Long-term clinical improvement in MPTP-lesioned primates after gene therapy with AAV-hAADC. Mol Ther, 2006. 14(4): p. 564-70; Christine, C. W., et al., Magnetic resonance imaging-guided phase 1 trial of putaminal AADC gene therapy for Parkinson's disease. Ann Neurol, 2019. 85(5): p. 704-714). Considering that restoring AADC levels will "rescue" and boost the L-DOPA therapeutic effect, and dopamine levels are the most critical factor for the recovery of motor function, AADC is included in the candidate constructs to restore the dopamine levels, which would be especially beneficial for AADC deficient patients.

AADC deficiency is caused by loss-of-function mutation of the AADC gene. The rAAV of the present application comprising AADC as the sole GOI or in combination with another GOI, so as to compensate the molecular defects leading to the disease.

In a preferred embodiment, the nucleotide sequence encoding AADC can be optimized for expression in a rAAV construct. The optimization can be codon optimization.

In one embodiment, the rAAV of the present application comprises a nucleotide sequence encoding AADC, which comprises or consists of the nucleotide sequence as shown by any one of SEQ ID Nos: 1-9, 11 and 46, preferably as shown by any one of SEQ ID Nos: 1-9 and 46 (optimized sequence), more preferably as shown by SEQ ID NO: 3, SEQ ID NO: 9 or SEQ ID NO: 46. In some embodiments, the rAAV comprising a nucleotide sequence encoding AADC as the sole GOI can be used to treat PD or AADCD.

In some embodiments, the rAAV of the present application comprises a combination construct comprising both AADC and GBA1, e.g., for use in the treatment of PD. In one embodiment, the combination construct comprising a coding sequence of AADC and a coding sequence of GBA1. In some embodiments, the coding sequence of GBA1 is arranged at 5' upstream of the coding sequence of AADC. In more preferred embodiments, the coding sequence of AADC is arranged at 5' upstream of the coding sequence of GBA1. Preferably, the two coding sequences are arranged in frame and under the control of the same promoter. Preferably, the nucleotide sequence encoding GBA1 comprises or consists of the nucleotide sequence as shown by any one of SEQ ID Nos: 12-20, 45 or 47. Preferably, the nucleotide sequence encoding AADC comprises or consists of the nucleotide sequence as shown by any one of SEQ ID Nos: 1-9 and 46.

In one specific embodiment, the combination construct of AADC and GBA1 comprises a coding sequence of AADC as shown in SEQ ID NO: 46, and a coding sequence of GBA1 as shown in SEQ ID NO: 45. In one specific embodiment, the combination construct of AADC and GBA1 comprises from 5' to 3': a promoter sequence which is a truncated variant of EF1α promoter, e.g. the one as shown in SEQ ID NO: 56 (EFIt7); a coding sequence of AADC as shown in SEQ ID NO: 46; a coding sequence of GBA1 as shown in SEQ ID NO: 45; and a polyA sequence such as a hGH poly A sequence. In one specific embodiment, the combination construct of AADC and GBA1 comprises from 5' to 3' a promoter sequence as shown in SEQ ID NO: 60 (CBh promoter); a coding sequence of AADC as shown in SEQ ID NO: 46; a coding sequence of GBA1 as shown in SEQ ID NO: 45; and a polyA sequence such as a hGH poly A sequence.

In some embodiments, the rAAV of the present application comprises a combination construct comprising both AADC and a NTF selected from GDNF or CDNF, e.g., for use in the treatment of AADCD. In one embodiment, the combination construct comprising a coding sequence of AADC and a coding sequence of either GDNF or CDNF. In some embodiments, the coding sequence of GDNF or CDNF is arranged at 5' upstream of the coding sequence of AADC. In more preferred embodiments, the coding sequence of AADC is arranged at 5' upstream of the coding sequence of GDNF or CDNF. Preferably, the two coding sequences are arranged in frame and under the control of the same promoter. Preferably, the nucleotide sequence encoding AADC comprises or consists of the nucleotide sequence as shown by any one of SEQ ID Nos: 1-9 and 46. Preferably, the nucleotide sequence encoding GDNF comprises or consists of the nucleotide sequence as shown by any one of SEQ ID Nos: 27-29. Preferably, the nucleotide sequence encoding CDNF comprises or consists of the nucleotide sequence as shown by any one of SEQ ID Nos: 23-25.

In some embodiments, the rAAV of the present application comprises a combination construct comprising a coding sequence of AADC and a coding sequence of CDNF, e.g., for use in the treatment of AADCD. In one specific embodiment, the combination construct of AADC and CDNF comprises a coding sequence of AADC as shown in SEQ ID NO: 3 or SEQ ID NO: 46, and a coding sequence of CDNF as shown in SEQ ID NO: 25 (CDNF-MN). In one specific embodiment, the combination construct of AADC and CDNF comprises from 5' to 3': a CAG promoter sequence as shown in SEQ ID NO: 58 (CAG); a coding sequence of AADC as shown in SEQ ID NO: 3; and a coding sequence of CDNF as shown in SEQ ID NO: 25 (CDNF-MN). In one specific embodiment, the combination construct of AADC and CDNF comprises from 5' to 3': an EF1α promoter sequence as shown in SEQ ID NO: 57 (EF1α); a coding sequence of AADC as shown in SEQ ID NO: 46; and a coding sequence of CDNF as shown in SEQ ID NO: 25 (CDNF-MN). In one specific embodiment, the combination construct of AADC and CDNF comprises from 5' to 3': an EF1α promoter sequence as shown in SEQ ID NO: 57 (EF1α); a coding sequence of CDNF as shown in SEQ ID NO: 25 (CDNF-MN); and a coding sequence of AADC as shown in SEQ ID NO: 46.

In some preferred embodiments, the rAAV of the present application comprises a combination construct comprising a coding sequence of AADC and a coding sequence of GDNF, e.g., for use in the treatment of AADCD. In one specific embodiment, the combination construct of AADC and GDNF comprises a coding sequence of AADC as shown in SEQ ID NO: 46, and a coding sequence of GDNF as shown in SEQ ID NO: 29 (GDNF-MN). In one specific embodiment, the combination construct of AADC and GDNF comprises from 5' to 3': a EF1α promoter sequence as shown in SEQ ID NO: 57 (EF1α); a coding sequence of AADC as shown in SEQ ID NO: 46; and a coding sequence of GDNF as shown in SEQ ID NO: 29 (GDNF-MN).

GBA1

The present disclosure provides rAAV vectors which deliver glucocerebrosidase 1 (GBA1) gene alone, or in combination with another gene, e.g., AADC, CDNF or GDNF. The rAAV vector delivering GBA1 can be used for treating NDs, including Gaucher disease (GD), Parkinson's disease (PD) and Multiple system atrophy (MSA). For example, the rAAV vector delivering GBA1 alone can be used to treat type 2 and type 3 Gaucher disease (GD) or PD. For example, the rAAV vector delivering both GBA1 and NTF, such as GDNF can be used to treat MSA.

In a preferred embodiment, the nucleotide sequence encoding GBA1 can be optimized for expression by a rAAV construct. The optimization can be codon optimization.

In one embodiment, the rAAV of the present application comprises a nucleotide sequence encoding GBA1, which comprises or consists of the nucleotide sequence as shown by any one of SEQ ID Nos: 12-20, 22, 45, and 47, preferably as shown by any one of SEQ ID Nos: 12-20, 45 or 47 (codon-optimized sequence), more preferably as shown by SEQ ID NO: 15, SEQ ID NO: 16, SEQ ID NO: 20, SEQ ID NO: 45 or SEQ ID NO:47.

In some embodiments, the rAAV of the present application comprises a nucleotide sequence encoding GBA1, e.g., for use in the treatment of GD or PD. Preferably, the nucleotide sequence encoding GBA1 comprises or consists of the nucleotide sequence as shown by any one of SEQ ID Nos: 12-20, 45 or 47. In one specific embodiment, the rAAV comprises a coding sequence of GBA1 as shown in SEQ ID NO: 45. In one specific embodiment, the rAAV comprising a construct that comprises from 5' to 3': a CAG promoter sequence as shown in SEQ ID NO: 58 (CAG); a coding sequence of GBA1 as shown in SEQ ID NO: 45; and a polyA sequence such as a hGH poly A sequence. In one specific embodiment, the rAAV comprising a construct that comprises from 5' to 3': a EF1α promoter sequence as shown in SEQ ID NO: 57 (EF1α); a coding sequence of GBA1 as shown in SEQ ID NO: 45; optionally WPRE; and a polyA sequence such as a hGH poly A sequence.

In some embodiments, the rAAV of the present application comprises a combination construct comprising both GBA1 and a NTF selected from GDNF or CDNF, e.g., for use in the treatment of MSA. In some embodiments, the coding sequence of GBA1 is arranged at 5' upstream of the coding sequence of NTF. In some embodiments, the coding sequence of NTF is arranged at 5' upstream of the coding sequence of GBA1. Preferably, the two coding sequences are arranged in frame and under the control of the same promoter.

In some embodiments, the rAAV of the present application comprises a combination construct comprising both GBA1 and GDNF, e.g., for use in the treatment of MSA. Preferably, the nucleotide sequence encoding GBA1 comprises or consists of the nucleotide sequence as shown by any one of SEQ ID Nos: 12-20, 45 or 47. Preferably, the nucleotide sequence encoding GDNF comprises or consists of the nucleotide sequence as shown by any one of SEQ ID Nos: 27-29. In specific embodiments, the combination construct of both GBA1 and GDNF comprises a coding sequence of GBA1 as shown in SEQ ID NO: 45 or SEQ ID NO: 47, and a coding sequence of GDNF as shown in any one of SEQ ID NOs: 27-29. In one specific embodiment, the combination construct of GBA1 and GDNF comprises from 5' to 3': a CAG promoter sequence as shown in SEQ ID NO: 58 (CAG) or a MBP promoter sequence as shown in SEQ ID NO: 59 (MBP); a coding sequence of GBA1 as shown in SEQ ID NO: 45 or SEQ ID NO: 47; a coding sequence of GDNF as shown in SEQ ID NO: 29 (GDNF-MN); an optionally WPRE; and a polyA sequence such as a SV40 polyA or a bGH poly A. In one specific embodiment, the combination construct of GBA1 and GDNF comprises from 5' to 3': a CAG promoter sequence as shown in SEQ ID NO: 58 (CAG) or a MBP promoter sequence as shown in SEQ ID NO: 59 (MBP); a coding sequence of GDNF as shown in SEQ ID NO: 29 (GDNF-MN); a coding sequence of GBA1 as shown in SEQ ID NO: 45 or SEQ ID NO: 47; an optionally WPRE; and a polyA sequence such as a SV40 polyA or a bGH poly A.

Neurotrophic Factors: CDNF and GDNF

The present disclosure provides rAAV vectors which deliver a neurotrophic factor, specifically CDNF or GDNF, alone, or in combination with another gene, e.g., AADC or GBA1. The rAAV vector delivering a neurotrophic factor can be used for treating NDs.

The neuronal protective role of neurotrophic factors has been well-established. Both CDNF and GDNF proteins have been studied in the framework of PD (Nasrolahi, A., et al., Neurotrophic factors hold promise for the future of Parkinson's disease treatment: is there a light at the end of the tunnel?Rev Neurosci, 2018. 29(5): p. 475-489).

In one embodiment, AADC is co-expressed with CDNF or GDNF, respectively, by a rAAV vector. This is the first example that AADC and a neurotrophic factor are co-expressed in the same AAV vector and show significant efficacy in a mouse PD model.

In another embodiment, GBA1 is co-expressed with GDNF or CDNF by a rAAV vector.

In a preferred embodiment, the nucleotide sequence encoding CDNF or GDNF can be optimized for expression by a rAAV construct. The optimization can be codon optimization. The codon optimization can be limited to the coding region of the mature protein of GDNF or CDNF, without changing the nucleotide sequence corresponding to the signal peptide of CDNF or GDNF, or the nucleotide sequence corresponding to the pre-peptide GDNF. In a preferred embodiment, the codon-optimized CDNF or GDNF coding sequence has reduced numbers of CpG islands as compared to the wild-type coding sequence.

In one embodiment, the rAAV of the present application comprises a nucleotide sequence encoding CDNF, which comprises or consists of the nucleotide sequence as shown by any one of SEQ ID Nos: 23-25.

In one embodiment, the rAAV of the present application comprises a nucleotide sequence encoding GDNF, which comprises or consists of the nucleotide sequence as shown by any one of SEQ ID Nos: 27-29.

Expression Cassette

The term "expression cassette" herein refers to a DNA component included in a vector (e.g., rAAV vector) and consisted of one or more, specifically one or two GOIs selected from AADC, GBA1, and NTF (CDNF or GDNF) gene under the control of regulatory sequences to be expressed in a host cell transduced by the vector.

The term "combination construct" in the context of the present application refers to a construct comprising two GOIs, specifically two GOIs selected from AADC, GBA1, and a NTF (CDNF or GDNF) gene. In preferred embodiments, the two gene coding sequences in a combination construct is under the control of the same promoter.

In one embodiment, the expression cassette of the present application is characterized by expression of one GOI, preferably expression of a codon-optimized sequence of GOI, in particular those as recited in the present disclosure.

In one embodiment, the expression cassette of the present application is characterized by co-expression of two GOIs spaced by a linker sequence. In a further embodiment, one or two of the GOIs is expressed via a codon-optimized sequence, in particular those as recited in the present disclosure. For example, the two GOIs can be selected from the following combinations: AADC+GBA1, AADC+CDNF, AADC+GDNF, GBA1+GDNF, and GBA1+CDNF.

By optimizing cDNA sequence (codon) of the AADC gene, the GBA1 gene, the CDNF gene and the GDNF gene, their regulatory sequences, and optionally the linker, the expression cassette of the present disclosure inserted into an AAV vector can achieve higher and more consistent protein expression or co-expression in neuronal cells in vitro or in vivo. For example, the expression cassette of the present disclosure shows better performance in expression of GOI(s) in human cell lines with neuronal identity, such as U87-MG or SH-SY5Y. For example, the expression cassette of the present disclosure shows better performance in expression of GOI(s) in vivo in neuronal cells at Striatum, Substantial nigra, or other CNS regions.

In one embodiment, as an essential part of the expression cassette, the present disclosure first provides a group of wild-type or codon-optimized nucleotide sequences encoding for AADC protein, and a second protein which is selected from a group consisting of GBA1 protein, CDNF protein and GDNF protein, specifically, the human AADC protein having an amino acid sequence as shown in SEQ ID NO: 31, the human GBA1 protein having an amino acid sequence as shown in SEQ ID NO: 32, the human CDNF protein having an amino acid sequence as shown in SEQ ID NO: 33, the human GDNF protein having an amino acid sequence as shown in SEQ ID NO: 34.

In one embodiment, as an essential part of the expression cassette, the present disclosure first provides a group of wild-type or codon-optimized nucleotide sequences encoding for GBA1 protein, and a second protein which is selected from a group consisting of CDNF protein and GDNF protein, specifically, the human GBA1 protein having an amino acid sequence as shown in SEQ ID NO: 32, the human CDNF protein having an amino acid sequence as shown in SEQ ID NO: 33, the human GDNF protein having an amino acid sequence as shown in SEQ ID NO: 34.

By "isolated nucleic acid", it means a DNA or RNA which is removed from all or a portion of a polynucleotide in which the isolated polynucleotide is found in nature, or is linked to a polynucleotide to which it is not linked in nature. An isolated nucleic acid molecule "comprising" a specific nucleotide sequence may include, in addition to the specified sequence, operably linked regulatory sequences that control expression of the coding region of the recited nucleic acid sequences. Due to the codon degeneracy, one skilled in the art understands that any specific amino acid sequence can be coded by several different nucleotide sequences.

"Codon-optimized coding sequence" herein refers to a nucleotide sequence coding for a protein, such as AADC protein, GBA1 protein, CDNF protein or GDNF protein modified from their wild-type coding sequence accommodating codon bias. Optimization may be achieved by reducing sequence complexity, adjusting GC content, adjusting codon usage and/or avoiding rare codons. The coding sequence which has been codon optimized usually shows an increased translational efficiency of the gene of interest (GOI), leading to a higher protein expression. Tools (e.g., JCat) with embedded algorithm to design codon optimized coding sequence are readily accessible to those skilled in the art. In a preferred embodiment, the codon of the AADC coding sequence of the present application has a Codon Adaptation Index (CAI) greater than 0.8. CAI is a measure of codon bias. One skilled in the art would understand that the actual efficiency of any sequence generated by running an algorithm still needs to be verified by experiments.

In the preferred embodiments, the codon-optimized coding sequence for human AADC protein comprises or consists of a nucleotide sequence selected from SEQ ID No: 1-10 and 46, the codon-optimized coding sequence for human GBA1 protein comprises or consists of a nucleotide sequence of SEQ ID No: 12-21, 45, and 47, the codon-optimized coding sequence for human CDNF protein comprises or consists of a nucleotide sequence of SEQ ID No: 23-25, the codon-optimized coding sequence for human GDNF protein comprises or consists of a nucleotide sequence of SEQ ID No: 27-29.

Further, an expression cassette can comprise one or more regulatory sequences in addition to coding sequence. Regulatory sequence can be selected from one or more of promoter, enhancer, polyadenylation sequence, and translation termination signal. A certain combination of regulatory sequences of the present disclosure can achieve unexpected effect in improving the expression efficiency of the coding sequence.

"Promoter" refers to a DNA sequence enables initiation of transcription of a downstream gene under the control of said promoter. Promoters include but not limited to constitutive promoters, cell type-specific promoters, tissue-specific promoters, development stage-specific promoters. Promoter can be a naturally occurring promoter of a gene, a modified version of a naturally occurring promoter or a synthetic promoter.

In the preferred embodiments, the promoter of the present disclosure can be a constitutive promoter. In the preferred embodiments, the promoter can be a CBh promoter, an EFIIa promoter, a CAG promoter, an MBP promoter (myelin basic protein promoter) or a promoter derived therefrom.

"Enhancer" is a regulatory DNA sequence which can enhance the transcription of the GOI in rAAV together with the promoter. In a preferred embodiment, the expression cassette of the present application comprises of an enhancer. More preferably, the enhancer can be a CMV enhancer, e.g., in a CBh promoter.

In some embodiments, intron sequences functioning as enhancers can be included. For example, an intron sequence originated from the intron of GOI can be included in the expression cassette.

In some cases, a promoter together with an enhancer and/or an intron sequence are collectively referred to as "promoter" or "promoter element". In a preferred embodiment, the promoter is the CBh promoter. In another preferred embodiment, the promoter is consisted of the EFS promoter and an intron sequence.

Preferably, the intron sequence has a total length of about or less than 200 bp, about or less than 250 bp, about or less than 300 bp, about or less than 350 bp, about or less than 400 bp.

For example, the intron sequence of the present disclosure is derived from the gene of interest. For example, the intron sequence is consisted of one or more fragments derived from one or more intronic regions of the gene of interest.

In a preferred embodiment, the promoter or promoter/intron element has a length of no more than 1000 bp, no more than 900 bp, no more than 850 bp, no more than 800 bp, no more than 700 bp, no more than 600 bp, no more than 500 bp, or no more than 400 bp, due to the limited packaging capacity of AAV.

In some cases, when the intron sequence is derived from an intronic region of the gene of interest, it can be inserted into the coding sequence (e.g., codon-optimized coding sequence) at a position corresponding to the position where it locates in the gene in nature, e.g., between two exons, instead of locating at a position 5'-upstream of the coding sequence and constituting a promoter/intron element.

The Kozak consensus sequence (Kozak sequence), named after the scientist who discovered it, is a nucleic acid sequence motif present in most eukaryotic mRNA transcripts that functions as the protein translation initiation site. Kozak sequence ensures the protein is accurately and efficiently translated.

In one specific embodiment, the expression cassette comprises an CMV enhancer, a chicken β-actin promoter, the first coding sequence of the first GOI, a linker, the second coding sequence of the second GOI, and SV40 polyA, wherein the first coding sequence and the second coding sequence is independently selected from those disclosed herein and encode any of the following combinations of two GOIs: AADC+GBA1, AADC+CDNF, AADC+GDNF, GBA1+GDNF, and GBA1+CDNF.

Linker Sequence

In one aspect, the present application provides a linker sequence that produces high efficiency and fidelity when the linker sequence is used to connect two coding sequences of the present application to be co-expressed by one rAAV vector of the present application.

As an example of linker sequence, a sequence coding for 2A peptide (such as P2A, F2A, or E2A) or IRES (full-length version referred as "ECMV IRES" herein, and a shorter truncated version referred as "mini IRES" herein) can be used to connect the two coding sequences of the present application. The position of GOI(s) relative to linker sequence can be adjusted so as to achieve desirable performance in protein expression and function. In preferred embodiments, a P2A linker sequence is used in a rAAV between the two GOIs.

In specific embodiments, the linker sequence of the present application comprises or consists of a nucleotide sequence as shown in SEQ ID NOs: 35, 37, 39, 41, 43 or 44.

Promoter

The rAAV vector of the present application may comprise a promoter conventionally used in rAAV vectors, including naturally occurring promoters, variants or hybrids thereof.

In some embodiments, the promoter can be a truncated variant of the wild-type promoter. For example, the promoter can be a truncated version of EF1α promoter as shown in Table 2 of Example 6, having a nucleotide sequence as shown in any one of SEQ ID NOs: 50-56.

In some embodiments, the promoter of the present application may also be used together with an enhancer, which can be native to said promoter or not. For example, a CBh promoter is a hybrid of CMV enhancer and chicken β-actin (CBA) promoter. In this case, reference to a promoter implies the inclusion of an enhancer, which can be understood by one skilled in the art. In one embodiment, the rAAV vector of the present application comprises a CBh promoter, e.g. a CBh promoter having a nucleotide sequence as shown in SEQ ID NO: 60.

In another embodiment, to drive the co-expression of AADC and CDNF, or the co-expression of AADC and GDNF, an EF1α promoter is used, e.g. an EF1α promoter having a nucleotide sequence as shown in SEQ ID NO: 57. In another embodiment, to drive the co-expression of AADC and GBA1, a truncated EF1α promoter is used, e.g. a truncated EF1α promoter having a nucleotide sequence as shown in any one of SEQ ID NOs: 50-56. In another aspect, to drive the co-expression of GBA1 and GDNF, a CAG promoter having a nucleotide sequence as shown in SEQ ID NO: 58 or a MBP promoter having a nucleotide sequence as shown in SEQ ID NO: 59 (or its truncation) is used.

Poly A Signal

The rAAV vector of the present application also contains a polyadenylation signal (Poly A).

For example, the Poly A sequence can be used in the present application includes SV40 polyA, human growth hormone (hGH) polyA, bovine growth hormone (bGH) polyA.

In one embodiment, the expression cassette of the present disclosure comprises a hGH poly A. In one embodiment, the expression cassette of the present disclosure comprises a hGH poly A when the promoter is an EF1α promoter or a variant thereof.

In some embodiments, a woodchuck hepatitis virus post-transcriptional regulatory element (WPRE) is placed downstream of the GOI and proximal to the polyadenylation signal.

AAV Vector Serotype

In one preferred embodiment, the rAAV of the present application is AAV9 vector.

Based on a previous report, intra-parenchymal injected AAV9 showed better dispersion in the target site than other serotypes including AAV1, AAV2, AAV5, and AAV8 (Watakabe, A., et al., Comparative analyses of adeno-associated viral vector serotypes 1, 2, 5, 8 and 9 in marmoset, mouse and macaque cerebral cortex. Neurosci Res, 2015. 93: p. 144-57). Since human striatum is a relatively large brain region, to achieve broader coverage of genes delivered by AAV, molecular engineering of the wild-type AAV capsid is necessary.

The inventors have identified novel AAV serotypes with significantly improved tissue tropism than the currently known AAVs for the putamen, the intended target region for AAV-based gene therapy in treating PD. Therefore, in another preferred embodiment, the rAAV of the present application uses the novel AAV capsids.

Exemplary Constructs

In one embodiment, the present application provides an expression cassette which comprises from 5' to 3':

(a) 5' ITR;

(b) a promoter;

(c) optionally an intron sequence;

(d) a coding sequence of a GOI;

(e) a polyA, and (f) 3' ITR, wherein the GOI is selected from AADC, GBA1, CDNF or GDNF, and the coding sequence is a codon-optimized sequence.

In another embodiment, the present application provides an expression cassette which comprises from 5' to 3':

(g) 5' ITR;

(h) a promoter;

(i) optionally an intron sequence;

(j) a coding sequence of the first GOI;

(k) a linker sequence;

(l) a coding sequence of the second GOI;

(m) a polyA, and (n) 3' ITR, wherein the first coding sequence and the second coding sequence are independently selected from wild-type coding sequences or codon-optimized sequences, e.g., those as recited in the present disclosure, and encode any of the following combinations of two GOIs: AADC+GBA1, AADC+CDNF, AADC+GDNF, GBA1+GDNF, and GBA1+CDNF, in which the two GOIs can be arranged in any order.

In the constructs indicated in the two above paragraphs, each of the element can be independently selected from those described in the present disclosure. For example, the first nucleotide sequence can be an AADC coding sequence as shown in any one of SEQ ID NOs: 1-9, 11, and 46; a GBA1 coding sequence as shown in any one of SEQ ID NOs: 12-20, 22, 45, and 47; or a CDNF or GDNF coding sequence as shown in any one of SEQ ID NOs: 23-30. For example, the second nucleotide sequence can be an AADC coding sequence as shown in any one of SEQ ID NOs: 1-9, 11, and 46; an GBA1 coding sequence as shown in any one of SEQ ID NO: 12-20, 22, 45, and 47; or a CDNF or GDNF coding sequence as shown in any one of SEQ ID NOs: 23-30. Preferably, the first nucleotide sequence can be an AADC coding sequence as shown in SEQ ID NO: 3 or 46; or a GBA1 coding sequence as shown in any one of SEQ ID NOs: 16, 45, and 47. Additionally or alternatively in a preferred embodiment, the second nucleotide sequence can be a CDNF coding sequence as shown in SEQ ID NO:25 or a GDNF coding sequence as shown in SEQ ID NO: 29. In some embodiments, the first nucleotide sequence and the second nucleotide sequence are linked by a P2A linker sequence.

Pharmaceutical Composition

The term "pharmaceutical composition" refers to a composition suitable for delivering to a subject. The pharmaceutical composition of the present disclosure comprises the isolated nucleic acid, the rAAV vector or the viral particle of the present disclosure and a pharmaceutically acceptable excipient. Conventional pharmaceutically acceptable excipients are known in the art and can be solid or liquid excipients. In one embodiment, the pharmaceutical composition can be a liquid for injection.

Delivery Methods

The terms "administration", "administering", "treating" and "treatment" as used herein, when applied to a subject, e.g., an animal, including human, or to cell, tissue, organ, or biological fluid, means contact of an exogenous pharmaceutical, therapeutic, diagnostic agent, or composition with the subject, cell, tissue, organ, or biological fluid. Treatment of a cell encompasses contact of a reagent with the cell, as well as contact of a reagent with a fluid, where the fluid is in contact with the cell. The term "administration" and "treatment" also include in vitro and ex vivo treatments, e.g., of a cell, by a reagent, diagnostic, binding compound, or by another cell.

In preferred embodiments, the rAAV vector of the present application can be delivered via intravenous, intra cerebroventricular, intrathecal or intra-striatum administration. In a specific embodiment, the rAAV vector is delivered via intra-striatum route. In another specific embodiment, the rAAV vector is delivered via intra-cerebroventricular route. In the most preferred embodiment, the treatment or administration is carried out intra-cerebroventricularly (ICV), such as by ICV injection.

The rAAV vector can be administered via a single dose or multiple doses. In a specific embodiment, the rAAV vector is administered via a single injection.

The dosage of the rAAV vector injection can be varied based on the administration route. For example, intra-parenchymal/intra-striatum injection, usually needs the delivery of a specific volume of rAAV to cover striatum as much as possible to achieve sufficient therapeutic effects, given that the loss of dopaminergic transmission in the striatum results in the movement problems of the PD patients. The dosage can also be varied based on the body weight of the subject. Therefore, the dose range can be within a broad scope which covers $1.5 \times 10^{10}$-$1.5 \times 10^{14}$ vg/kg.

Therapeutic Uses

The term "treat", "treating" or "treatment" includes to cure or at least to alleviate the symptoms of a neurodegenerative disorder, such as PD, MSA, GD, AADCD or other proteinopathies.

A subject having any of these neurodegenerative disorders can be diagnosed by a well-trained neurologist based on the genetic background, medical history, symptoms and signs, as well as the results of neurological and physical examinations, according to the Clinical Diagnostic Criteria (Postuma, R. B., et al., MDS clinical diagnostic criteria for Parkinson's disease. Mov Disord, 2015. 30(12): p. 1591-

601; Palma, J. A., L. Norcliffe-Kaufmann, and H. Kaufmann, Diagnosis of multiple system atrophy. Auton Neurosci, 2018. 211: p. 15-25).

The viral vector expressing one aforementioned gene or co-expressing two aforementioned genes can be used to treat a subject who has aforementioned neurodegenerative disorder. The subject can be a clinically diagnosed early-stage PD patient, with one or more mutations in the AADC gene, GBA1 gene or other PD genetic risk genes like SNCA. The subject can also be a clinically diagnosed late-stage PD patient, without or with one or more mutations in AADC gene, GBA1 gene or other PD genetic risk genes as aforementioned. The subject can be one who has previously been treated or is being treated with dopamine derivatives, like Medopa, with or without L-DOPA induced dyskinesia. The subject can also be one resistant to currently available treatments.

The subject can be a clinically diagnosed GD patient classified as type 2 or type 3, or classified as type 1 with central nervous system symptoms. The subject can also be a clinically diagnosed MSA patient, who have shown parkinsonism (bradykinesia with rigidity tremor or postural instability), cerebellar syndrome (gait ataxia with cerebellar dysarthria limb ataxia or cerebellar oculomotor dysfunction) or at least one feature suggesting autonomic dysfunction, with or without GBA1 gene mutations or reduced activity of GBA1 protein.

The subject can also be a clinically diagnosed MSA patient resistant to currently available treatments, like dopamine derivatives.

EXAMPLES

To facilitate the understanding and utilization of the present invention, the merits of the present invention will be described in more details with reference to examples and appended drawings. However, it should be understood that the following examples only intend to exemplify the present invention without any intention in limiting the scope of the present invention. The scope of the present invention should be defined by the claims.

Example 1. Determination of the Optimal Linker to Connect the Coding Sequences of AADC and GBA1

In this example, the performance of different linker sequences, specifically E2A (SEQ ID NO: 35), F2A (SEQ ID NO: 37), T2A (SEQ ID NO: 39), P2A (SEQ ID NO: 41), mini IRES (SEQ ID NO: 43), and ECMV TRES (SEQ ID NO: 44) was tested in the construct comprising the wild-type coding sequences of both AADC and GBA1.

Figure 1:
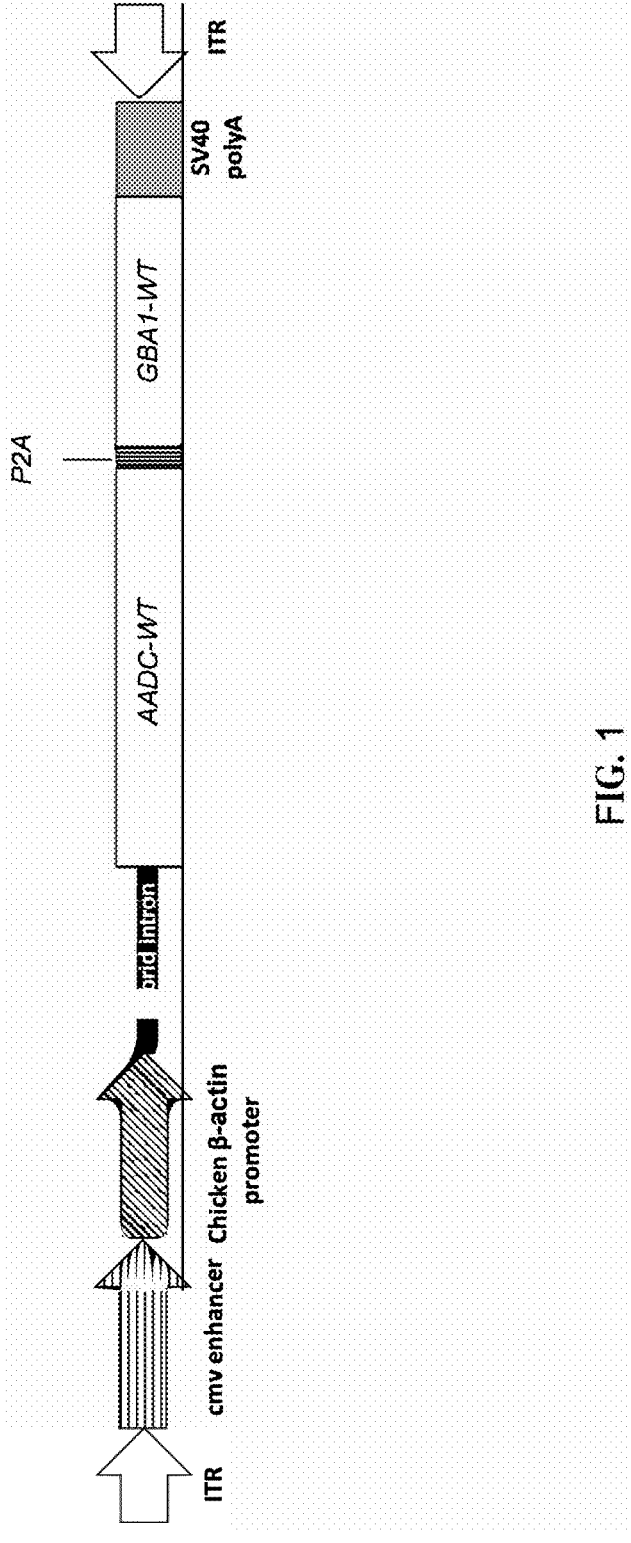
FIG. 1 shows the schematic of an exemplary construct containing the AADC wild-type coding sequence and GBA1 wild-type coding sequence linked by P2A peptide.

To construct an AAV vector containing both AADC and GBA1, the wild-type coding sequences of AADC (SEQ ID No:11) and GBA1 (SEQ ID No: 22) were connected by a self-cleaving P2A sequence in the order of AADC sequence followed by P2A then GBA1 sequence placed under the control of a CBh promoter (SEQ ID NO: 60) (FIG. 1). Also prepared is another construct with GBA1 coding sequence located upstream of the AADC coding sequence. Both constructs were introduced into a plasmid. The resulting plasmids are designated as CBh-AADC-P2A-GBA1-WPRE-SV40 pA ("AADC-P2A-GBA" or "ApG") and CBh-GBA1-P2A-AADC-WPRE-SV40 pA ("GBA-P2A-AADC" or "GpA"), which were transfected into HEK293 cells (Procell, CL-0001). Plasmids containing the coding sequence of AADC or GBA1, alone ("AADC", "GBA") or together with the coding sequence of P2A ("AADC-P2A", "P2A-GBA"), were also constructed and transfected into the same cells for comparison. Plasmid expressing GFP was used as a control.

Western blot was performed to detect the expression of AADC and GBA1 by each construct. Specifically, cells were collected in the lysis buffer (RIPA buffer, Thermo fisher 89901) 72 hours after transfection, denatured in 5×SDS-PAGE Sample Loading Buffer (Beyotime, P0015L) for 15 min at 95° C., separated in 10% SDS-PAGE gel (Sangon, #C631100), and blotted onto 0.22 μm PVDF membrane (Merck Millipore). The protein expression levels of AADC-WT, GBA1-WT, and the housekeeping gene GAPDH were detected by antibodies against the human AADC (Millipore, #AB1569), GBA1 (Sigma, #G4171), and GAPDH (CST, #2118), respectively. Long exposure and normal exposure were performed with the WBs.

As shown in FIG. 2A, GBA1 protein expressed by the plasmid AADC-P2A-GBA1 (ApG) had almost the same molecular weight as GBA1 expressed by the plasmid comprising GBA1 alone, while the AADC derived from ApG was slightly larger than AADC expressed from the plasmid comprising AADC alone due to the P2A fragment attached thereto. This result indicates that self-cleaving 2A peptide is functional in this setting.

Unexpectedly, when the GBA1 gene was placed before (5' upstream of) AADC gene, the expression of both genes was significantly decreased after transfection into the HEK293 cells (see FIG. 2B).

Additional linkers, including E2A, F2A, T2A, P2A, mini IRES, and ECMV IRES were evaluated in the same experiment setting as P2A. The results showed that except mini IRES, all the linkers evaluated produced both AADC and GBA1 proteins with the expected molecular sizes.

Additional tests were conducted by extending the exposure time to find out whether any fusion protein (AADC+GBA1) existed due to incomplete cleavage. Clear positive bands were detected with both AADC and GBA1 antibodies in the E2A and F2A constructs (see FIG. 3). The cleavage efficiency of the different linkers, ranking from high to low was ECMV RES, P2A, T2A, E2A, and then F2A. Using the full-length ECMV RES as a linker will result in a construct which would exceed the packaging capacity of a rAAV. Therefore, P2A was selected as the linker to use for our invention.

Example 2. Codon Optimization to Improve the Protein Expressions of AADC and GBA1

In this example, nine sequences containing higher frequency codons were generated for AADC (referred as A1-A9, SEQ ID Nos: 1~9) and GBA1 (referred as G1-G9, SEQ ID Nos: 12-20), respectively. All of these sequences have Codon Adaptation Index (CAI) greater than 0.85 as calculated by an online tool (https://www.genscript.com/tools/rare-codon-analysis). An AADC coding sequence and a GBA1 coding sequence disclosed in previous patent application publications were synthesized and used as references and named as A10 (SEQ IDNo: 10, disclosed in CN107106689A, Voyager Therapeutics Inc.) and G10 (SEQ ID No: 21, disclosed in WO2020210698A1, Prevail Therapeutics, Inc.), respectively. A10 encodes an M17V mutated AADC protein.

Figure 4:
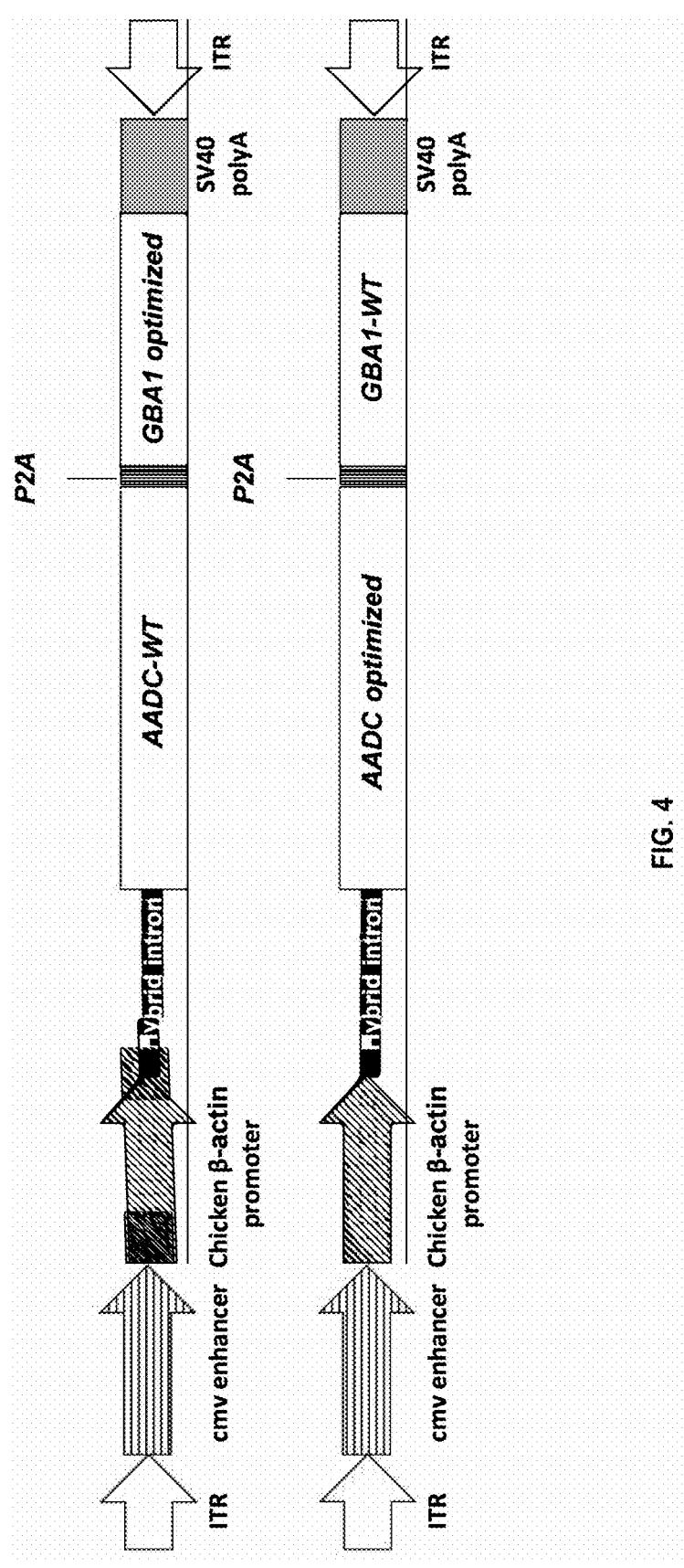
FIG. 4 shows the schematic of constructs containing the wild-type AADC (AADC-WT) and the optimized GBA1 via a P2A linker, or the optimized AADC and the wild-type GBA1 (GBA1-WT) via a P2A linker under the control of a CBh hybrid promoter which consisted of a CMV enhancer, a chicken-3-actin promoter, and a hybrid intron.

Twenty candidate constructs with configuration as shown in FIG. 4 were generated, by combining one of the codon-optimized AADC coding sequences (A1-A10) with the GBA1-WT (G0) sequence, or by combining the AADC-WT (A0) sequence with one of the codon-optimized GBA1 coding sequences (G1-G10) (see Table 1), with P2A used as the linker between the two coding sequences. Vectors containing G0 (wild-type GBA1 alone), A0 (wild-type AADC alone), and G0A0 were used as controls.

TABLE 1

| | Candidate recombinant constructs | | | |
|---|---|---|---|---|
| Group No. | Type of the combination | AADC | 2A | GBA |
| 1 | A0G0 | WT | P2A | WT |
| 2 | A1G0 | JCat | P2A | WT |
| 3 | A2G0 | BS | P2A | WT |
| 4 | A3G0 | GS | P2A | WT |
| 5 | A4G0 | GW1 | P2A | WT |
| 6 | A5G0 | NP | P2A | WT |
| 7 | A6G0 | SG | P2A | WT |
| 8 | A7G0 | SN | P2A | WT |
| 9 | A8G0 | TK | P2A | WT |
| 10 | A9G0 | TY | P2A | WT |
| 11 | A10G0 | Voyager | P2A | WT |
| 12 | A0 | WT | P2A | — |
| 13 | A0G1 | WT | P2A | JCat |
| 14 | A0G2 | WT | P2A | BS |
| 15 | A0G3 | WT | P2A | GS |
| 16 | A0G4 | WT | P2A | GW1 |
| 17 | A0G5 | WT | P2A | NP |
| 18 | A0G6 | WT | P2A | SG |
| 19 | A0G7 | WT | P2A | SN |
| 20 | A0G8 | WT | P2A | TK |
| 21 | A0G9 | WT | P2A | TY |
| 22 | A0G10 | WT | P2A | Prevail |
| 23 | G0 | — | P2A | WT |
| 24 | A0-P2A | WT | P2A | — |
| 25 | A10-vy | Voyager | — | — |
| 26 | G10-p | Prevail | — | — |

The vectors were transfected into HEK293 cells using Lipofectamine 3000 Transfection Reagent (Invitrogen, #L3000008) following the manufacturer's instructions. 48 hours after the transfection, cells were washed once with 1×PBS and harvested in the RIPA buffer (Thermo, 89901). The protein levels of AADC and GBA1 in the cell lysate were determined by a sandwich ELISA as described below ELISA to Detect AADC and GBA1 Protein Levels 1. On Day 1, 96-well plates were coated with the following capture antibodies in 100 μL coating buffer overnight at 4° C.: human DOPA Decarboxylase (DDC) monoclonal antibody (Sinobiological, 10560-R003, 2 μg/mL) for AADC samples, and GBA1 antibody (Abcam, ab55080, 1 μg/mL) for GBA1 samples.

2. The next day, the sample wells were washed with washing buffer 3 times. 300 μL blocking buffer (containing 2% BSA) was added and left for approximately 2 hrs at room temperature followed by 3 additional washing steps.

3. 100 μL assay buffer containing the following detection antibodies was added to each well: anti-DDC monoclonal antibody (tRP) (Sinobiological, 10560-R040, 1:1000 dilution) for AADC protein detection, and polyclonal anti-GBA antibody (Abcam, ab96246) for GBA1 protein detection. After incubation for approximately 1 hr at room temperature, the sample wells were washed for 3 times with washing buffer.

4. To detect GBA1 protein expression, an RP-conjugated antibody (Goat Anti-Rabbit IgG-Fc Secondary Antibody (HRP) (SinoBiological, SSA003) was applied, followed by washing steps.

5. The sample wells were then incubated with 100 μL TMB solution (Solarbio, #PR1200) for approximately 20 min, then the reactions terminated by adding 100 μL stop solution (Solarbio, #C1058).

6. The absorbance (at an excitation wavelength of 450 nm and emission at 630 nm) of each sample was detected by a fluorimeter (SPECTRAmax Gemini XPS, Molecular Devices, San Jose, CA, USA) and the results are shown in FIG. 5 and FIG. 6.

Figure 5:
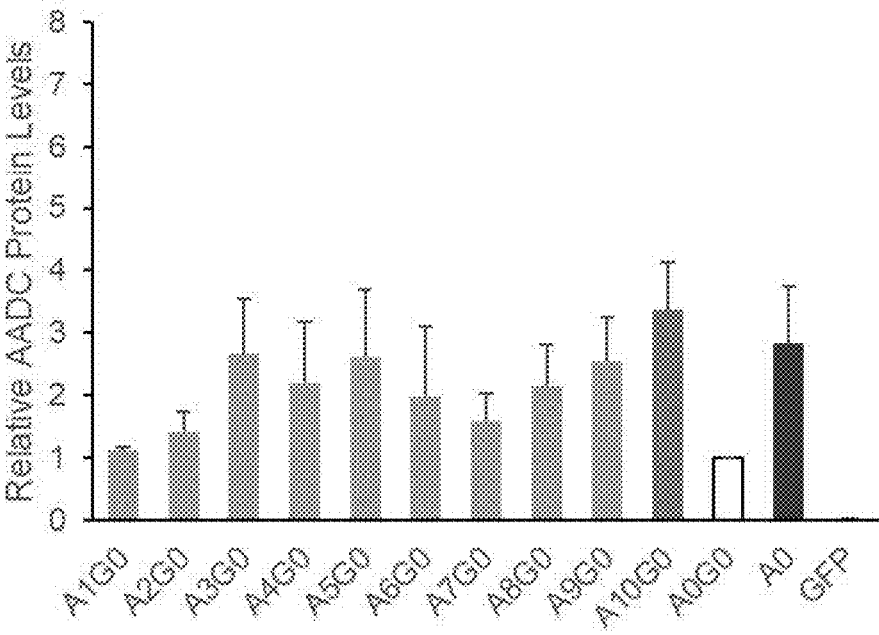
FIG. 5 shows the AADC protein expression levels of different candidate constructs in the HEK293 cells, as determined by ELISA.
Figure 6:
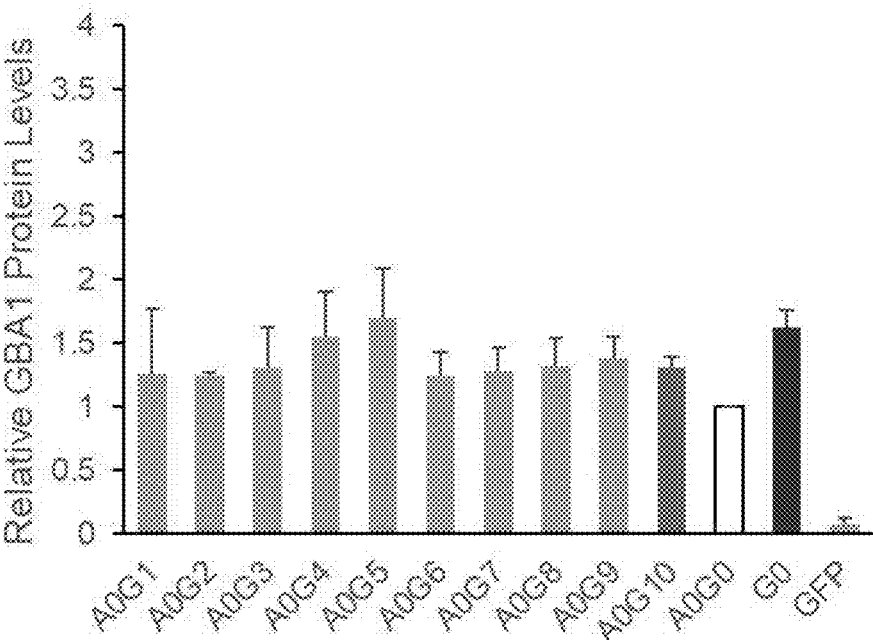
FIG. 6 shows the GBA1 protein expression levels of different candidate constructs in the HEK293 cells, as determined by ELISA.

As shown in FIG. 5, A3 and A9 were the top 2 candidates among the AADC coding sequences evaluated. A10 showed the highest AADC protein expression levels since it expressed an AADC mutant protein. As shown in FIG. 6, G4 and G5 were the top 2 candidates among the GBA1 coding sequences evaluated. In addition, both A0G4 and A0G5 expressed relatively higher GBA1 protein levels than the reference A0G10 construct containing a prior art reference GBA1 coding sequence G10.

Western Blot

Western blot (WB) assays were also conducted to detect protein expression. Again, the candidate vectors (except G1, G2, G7, A1, A2, and A7) were transfected into HEK293 cells with Lipofectamine 3000 Transfection Reagent (Invitrogen, #L3000008).

48 hours after transfection, cells were harvested in RIPA buffer (Thermo, 89901), diluted and boiled (denatured) in 5×loading buffer (Beyotime, P0015L). All WB samples were separated on SDS polyacrylamide gels (BioRad, 1703932) and transferred onto a 0.22 m PVDF membrane (BIO-RAD, 1620177).

The membrane was incubated with anti-AADC (Millipore, #AB1569) or anti-GBA1(Sigma, #G4171) antibody, or antibody against the housekeeping gene GAPDH (CST, #2118) overnight at 4° C., followed by 2 hour incubation with HRP-linked secondary antibody at room temperature the next day.

Figure 7:
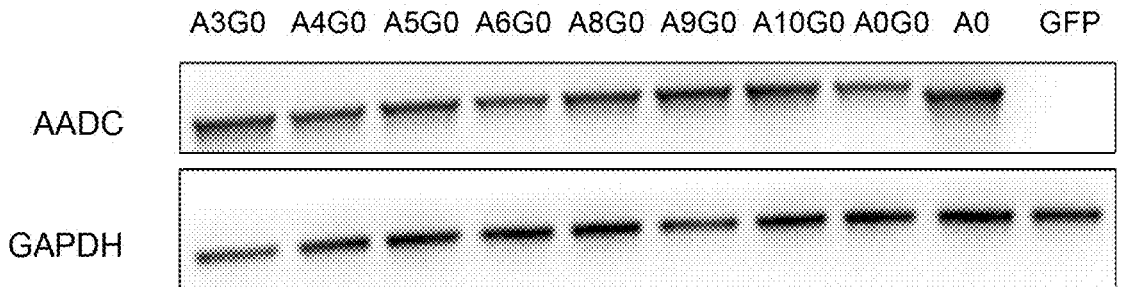
FIG. 7 shows the AADC protein expression levels of different candidate constructs in the HEK293 cells, as determined by WB.
Figure 8:
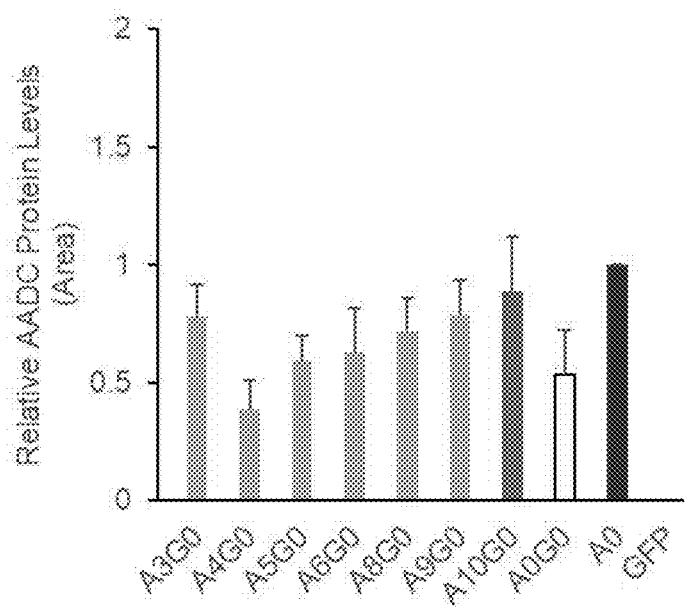
FIG. 8 shows the normalized AADC protein expression levels as shown in FIG. 7, presented as mean±S.E.M from three independent WB experiments.
Figure 9:
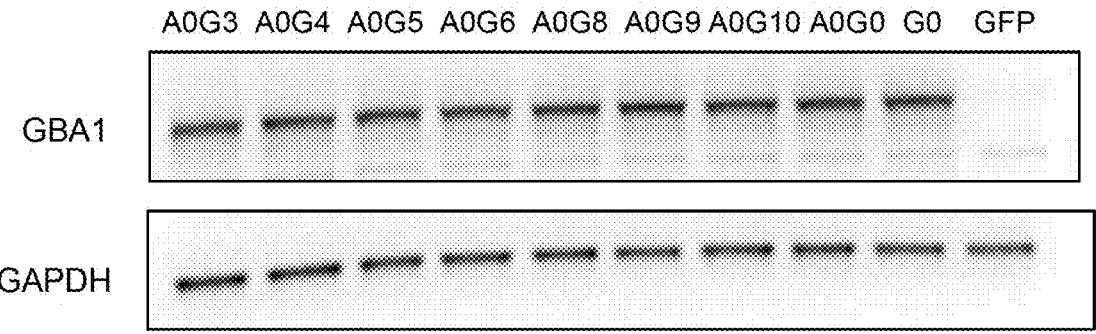
FIG. 9 shows the GBA1 protein expression levels in the HEK293 cells expressed by different candidate constructs, as determined by WB.

BeyoECL Moon kit (Beyotime, P0018F) was then applied to the membrane. Exposure and image capture were performed with a Tannon 5600 system, and the results are shown in FIGS. 7 and 9. The areas of the bands of AADC protein or GBA1 protein were determined by ImageJ 1.53 (NIH) and normalized to GAPDH levels. The GADPH normalized values were then normalized to that of A0 for the AADC group or G0 for the GBA1 group. The normalized data from three independent experiments were presented in FIGS. 8 and 10.

As shown by the WB results in FIGS. 7-10, it was found that A3G0 and A9G0 had the highest AADC protein expression among the codon optimized AADC candidates, and A0G4 and A0G5 were the best ones among the GBA1 candidates, consistent with results from the ELISA assays. A3, A9 (for AADC), and G4, G5 (for GBA1) were chosen as the codon-optimized sequences for further combination expression construct optimization.

Example 3. Catalytic Activities of the Co-Expressed AADC and GBA1 Proteins

This example aims to determine whether the exogenously expressed AADC protein and GBA1 protein are catalytically active, indicating normal functions. Moreover, the catalytic activity could also be used as an additional evaluation criterion for the candidate sequences. The methods for examining AADC and GBA1 activities in the cell lysates are described as following.

AADC Catalytic Activity (HPLC Analysis)

The AADC protein expressing cultures (A3G0, A9G0, A10G0, A0G0, A0) and the GFP protein expressing control sample were exposed to 100 M L-DOPA for 24 hrs. 100 μL of homogenization buffer (50 mM phosphate buffer, pH 7.4, containing 0.2 mM pyridoxyl phosphate and 0.2 mM pargyline) was added to each well, and cells were scraped from the bottom.

The cell homogenates were centrifuged for 10 min at 13,000 g, and 30 μL of each sample was used for the HPLC assay. Samples were subjected to HPLC/ECD to detect dopamine levels generated from catalytically active AADC protein expressed by different constructs. A standard curve of dopamine was used to calculate the relative AADC activities, as shown by the amount of dopamine transferred from L-DOPA in each sample.

GBA1 Activity

The GBA1 protein-expressing cultures (A0G4, A0G5, A0G10, A0G0, G0) and the GFP protein-expressing control sample were tested for GBA1 protein activities. Recombinant human GBA (rhGBA) was used as a positive control.

1. rhGBA (Catalog #7410-GHB) was diluted to 0.2 ng/μL in Assay Buffer (50 mM Sodium Citrate, 25 mM Sodium Cholate, 5 mM DTT, pH 6.0).

2. The Substrate (4-Methylumbelliferyl-beta-D-glucopyranoside, Sigma, Catalog #M3633, 10 mM in DMSO) was diluted to 6 mM in the Assay Buffer.

3. 25 μL of cell lysate (total protein 100 ng/μL) or 0.2 ng/μL rhGBA was loaded into the wells of a 96-well plate. The reaction was started by adding 25 μL of 6 mM Substrate. 25 μL of the assay buffer was loaded to the standard curve well.

4. The plate was sealed and incubated at 37° C. for 3 hours.

5. After incubation, reaction was stopped by adding 50 μL of Stop Solution (0.5 M Glycine, 0.3 M NaOH (~pH 10)) to each well.

6. Readings were recorded at excitation and emission wavelengths of 365 nm and 445 nm (top read), respectively, in an endpoint mode.

Figure 10:
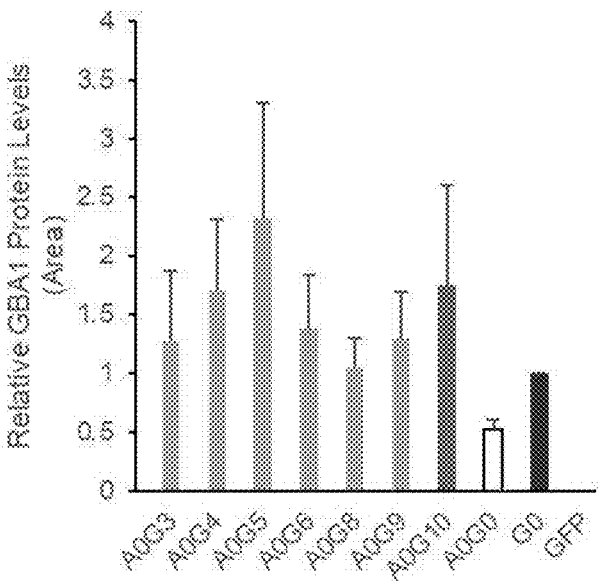
FIG. 10 shows the normalized GBA1 protein expression levels as shown in FIG. 9, presented as mean±S.E.M from three independent WB experiments.

7. The specific activity was calculated as: (Adjusted Fluorescence*25)/(180 min*0.0025 mg. The results are shown in FIGS. 9 and 10.

Figure 11:
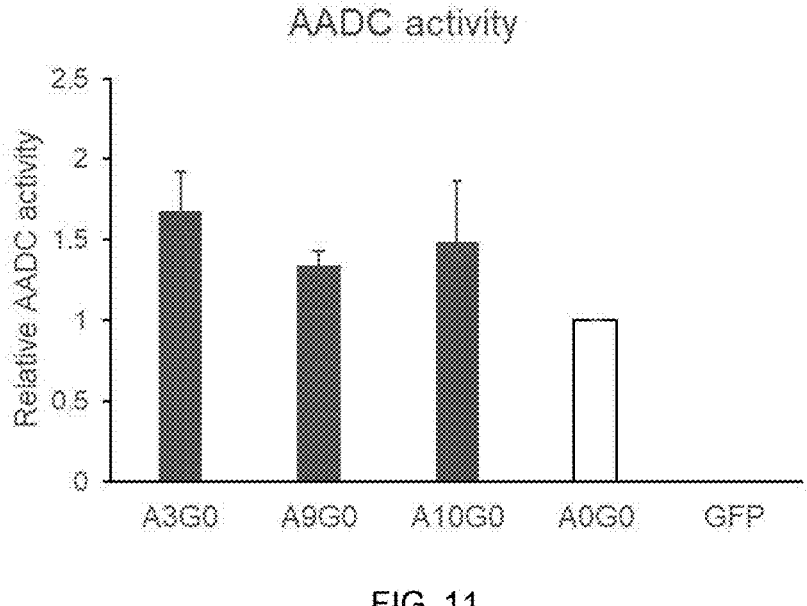
FIG. 11 shows the catalytic activity of AADC in HEK293 cells transfected with different candidate constructs.
Figure 12:
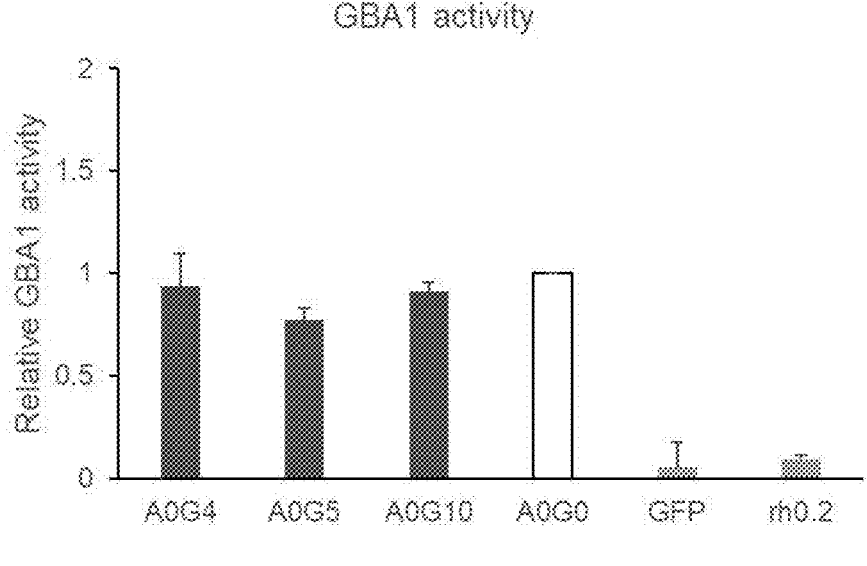
FIG. 12 shows the catalytic activity of GBA1 protein expressed in the HEK293 cells transfected with different candidate constructs.

As shown in FIG. 11, the AADC protein expressed by construct A3G0 exhibited the highest catalytic activity among all the constructs evaluated. As shown in FIG. 12, the GBA1 protein expressed by construct A0G4 exhibited the highest catalytic activity.

Example 4. Identification of Optimal Combination of Codon Optimized AADC and GBA1 Sequences To identify the best combinations of codon optimized AADC and GBA1 sequences, the coding sequences of AADC and GBA1 with better performance as shown above were paired together and used to construct recombinant AAV vectors. Specifically, constructs A3G4, A9G4, A3G5 and A9G5 were generated. In addition, construct A11G11 was generated, which was based on codons of A3 and G4 with further optimization to completely remove the CpG islands from the AADC and GBA1 coding sequences. Two benchmark vectors were also constructed, A10-vy (SEQ ID NO: 48, codon A10 containing the promoter and other regulatory elements described in the same patent) and G10-p (SEQ ID NO: 49, codon G10 containing the promoter and other regulatory elements described in the same patent).

Figure 13:
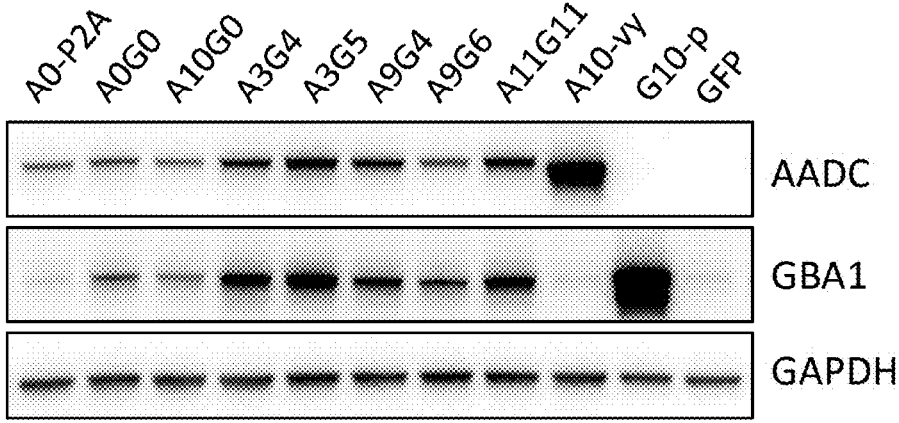
FIG. 13 shows the expression levels of both AADC and GBA1 proteins in the HEK293 cells transfected with different combination constructs.
Figure 14:
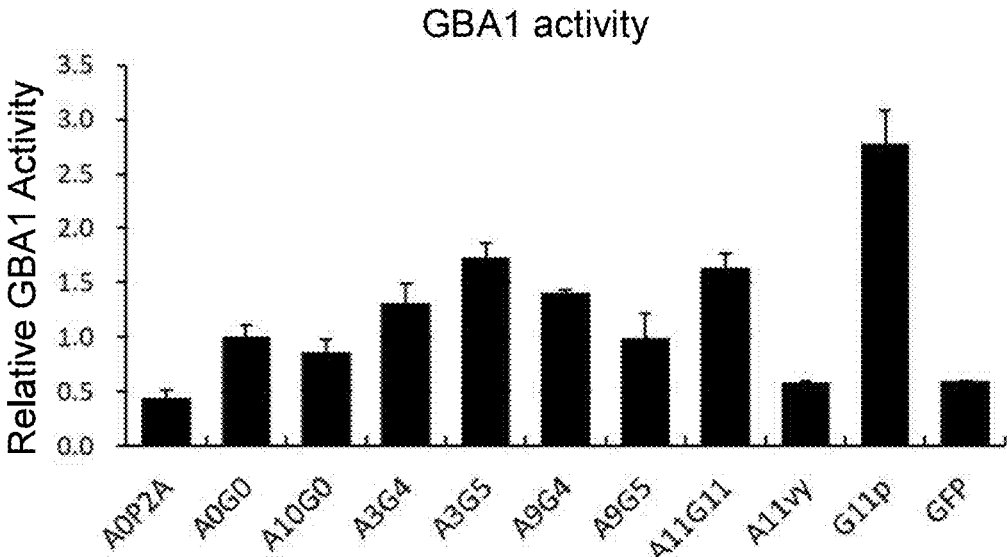
FIG. 14 shows the relative activity of GBA1 protein in the HEK293 cells transfected with different combination constructs.

The above described vectors together with A0-P2A, A0G0, A10G0, A10-vy, and G10-p were transfected into HEK293 cells. The AADC and GBA1 protein expression and the catalytic activity of GBA were determined. It was found that among the combination constructs evaluated, A11G11, A3G5, and A9G4 expressed the highest levels of AADC protein as determined by WB analysis (FIG. 13). For GBA1 protein expression, constructs A3G5 and A11G11 expressed the highest levels of proteins that were also the most active, followed by construct A9G4 (FIG. 14).

Figure 15:
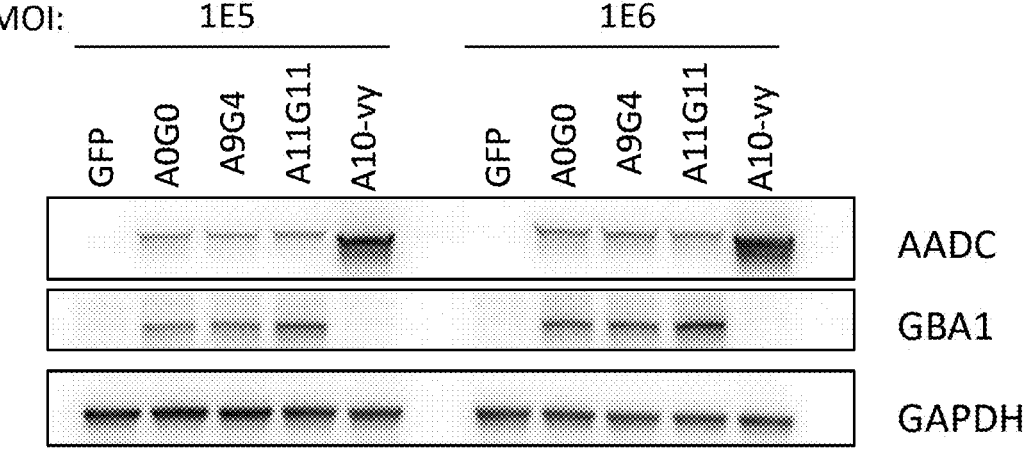
FIG. 15 shows the expression of AADC and GBA1 proteins in the HEK293 cells transduced with different candidate rAAV vectors.

Example 5. Evaluation of AADC and GBA1 Protein Expression of the AAV9 Packaged Combination Constructs Constructs A0G0, A9G4, A11G11, and A10-vy were packaged into AAV in which serotype AAV9 was used. AAV9-A0G0, A9G4, and A11G11 together with a control AAV which only expressed GFP were administrated @MOI 1e5 and 1e6 into the U-87 MG cells which stably express AAV receptor to increase the transduction efficiency. Five days post infection, the AADC and GBA1 protein expression levels in these cell samples were determined by WB analysis. As shown in FIG. 15, cells transduced with the A11G11 AAV virus expressed higher levels of AADC and GBA1 proteins than the A9G4 packaged AAV virus. It was observed that the AADC protein expression was significantly higher in the A10-vy AAV virus transduced cells, most likely due to the stronger promoter used in the A10-vy construct.

Example 6. Optimization of the Regulatory Elements Used in the Combination Expression Constructs To further improve the protein expression of the combination constructs, the promoter and poly A sequences used were also optimized. The CBh promoter in A11G11 was replaced with the EF1α promoter (SEQ ID NO: 57), and the SV40 polyA tail was replaced with either bovine growth hormone poly A (bGH) or human growth hormone poly (hGH) shown in Table 2. Since EF1α-A11G11-hGH exceeded the packaging capacity of AAV, its length was reduced by truncating part of the EF1α promoter, resulting in seven different truncations (Nos. 5-11) as shown in Table 2.

Figure 16:
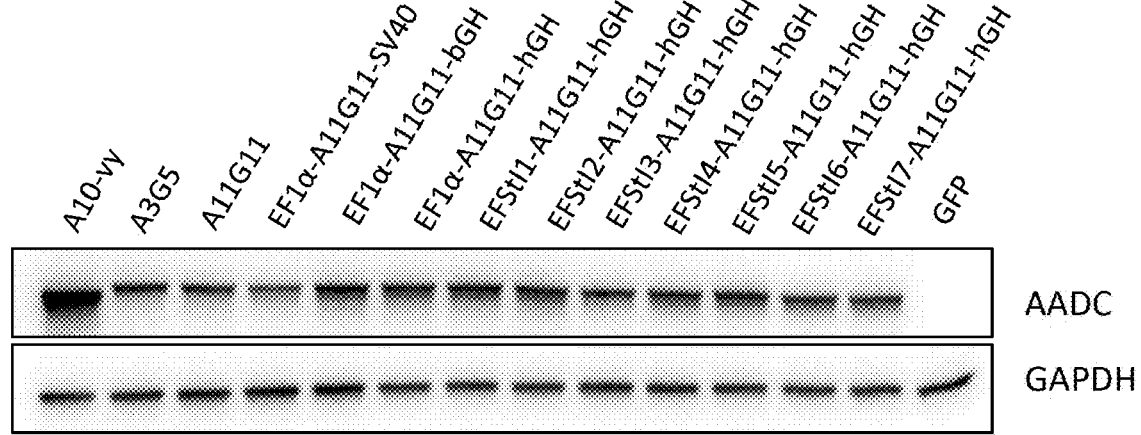
FIG. 16 shows the representative WB images illustrating the AADC protein expression levels in the HEK293 cells transfected with different candidate constructs.

The constructs in Table 2 together with A3G5, A10-vy, and GFP were transfected into the HEK293 cells. The AADC protein expression levels were determined by WB analysis. Among the first group of constructs evaluated, EF1α-A11G11-hGH expressed the highest levels of AADC protein. Among the constructs with truncated EF1α promoter (EFSlt1-7, SEQ NO: 50-56), construct EFSlt2 expressed the highest levels of AADC protein (FIG. 16).

TABLE 2

The combination constructs with EF1a and truncated EF1a promoter.

| No. | Vector | Promoter | PolyA | Length |
|---|---|---|---|---|
| 1 | CBh-A11G11-SV40 | CBh | SV40 | 4381 |
| 2 | EF1a-A11G11-SV40 | EF1a | SV40 | 4735 |
| 3 | EF1a-A11G11-bGH | EF1a | Bovine GH | 4812 |
| 4 | EF1a-A11G11-hGH | EF1a | Human GH | 5081 |
| 5 | EFStI1-A11G11-hGH | Truncated version 1 | Human GH | 4942 |
| 6 | EFStI2-A11G11-hGH | Truncated version 2 | Human GH | 4842 |
| 7 | EFStI3-A11G11-hGH | Truncated version 3 | Human GH | 4742 |
| 8 | EFStI4-A11G11-hGH | Truncated version 4 | Human GH | 4642 |
| 9 | EFStI5-A11G11-hGH | Truncated version 5 | Human GH | 4542 |
| 10 | EFStI6-A11G11-hGH | Truncated version 6 | Human GH | 4442 |
| 11 | EFStI7-A11G11-hGH | Truncated version 7 | Human GH | 4342 |

Example 7. In Vivo Efficacy of AAV Candidates Expressing Optimized AADC and GBA1 Sequences in PD Mouse Models The therapeutic effects of the AAVs expressing optimized AADC and GBA1 were evaluated in PD mouse models so as to determine if the candidate AAV can rescue the motor deficiency of PD animals.

First, a widely used chemical-induced PD mouse model was used. The mice were treated by MPTP/probenecid. Candidate rAAV vector CBh-A11G11 was administrated at a higher dose of 2E+10 vg/per animal and a lower dose of 2E+09 vg/per animal into the striatum of the PD mouse model ("CBh-A11G11 low" and "CBh-A11G11 high", respectively) once. rAAV vector A10-vy (2E+09 vg/per animal) was injected in a similar way as benchmark control ("A10-vy"), and rAAV vector expressing GFP was used as negative control ("GFP"). The motor function of the mice was evaluated by measuring the moving velocity and travelling distance before PD modeling (before induction with MPTP/P; "Pre"), as well as before and after administration of respective rAAV vectors ("Post MPTP/P" and "Post AAV", respectively). The "Pre" behavioral tests took 6 days followed by the daily MPTP/probenecid administration for 35 days. After 3-day environmental habituation, the subjects underwent the same behavioral tests ("Post MPTP/P") followed by rAAV injection. 21 days post rAAV injection, "Post AAV" behavioral tests were performed. The results are shown in FIG. 34.

Figure 34:
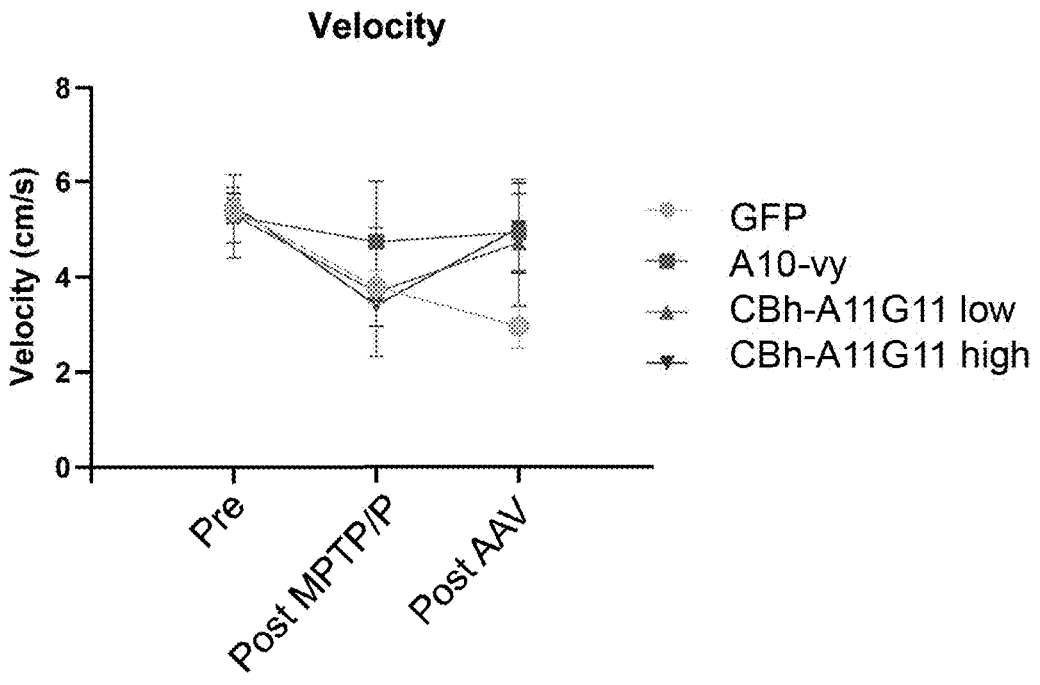
FIG. 34 shows the moving velocity and distance measurements of the 1-methyl-4-phenyl-1,2,3,6-tetrahydropyridine/probenecid (MPTP/P) induced PD mice after dosing of CBh-A11G11 and benchmark A10-vy rAAV, respectively.
Figure 34:
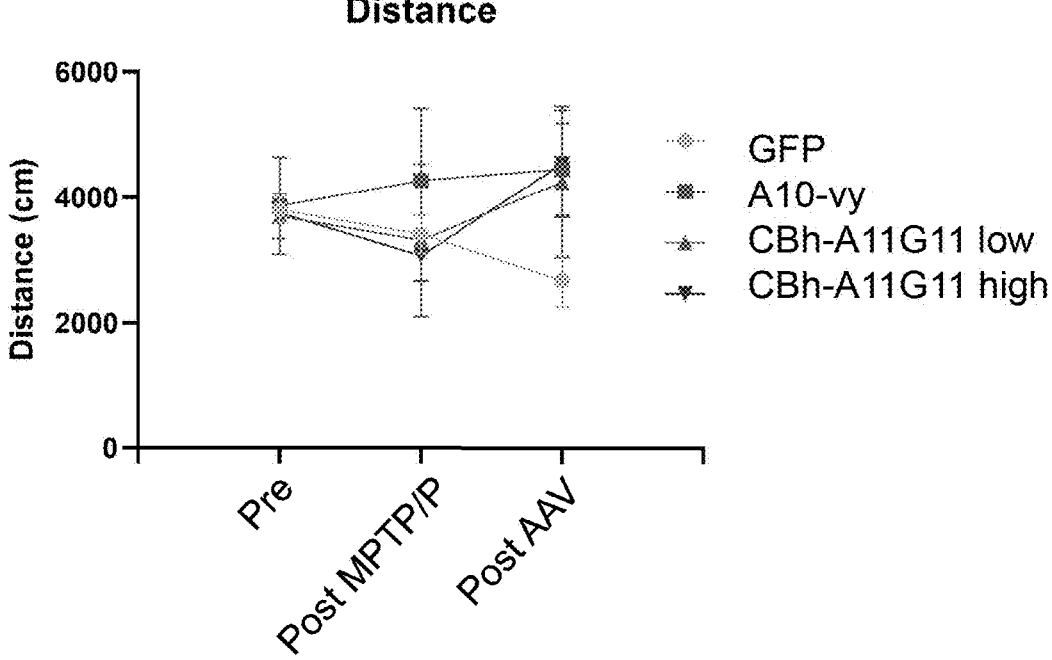

As shown in FIG. 34, the moving velocity of the mice decreased after using MPTP/probenecid. The mice to be treated with A10-vy (N=3) showed less severe loss in speed as compared to other mice. All mice, expect for those to be treated with A10-vy, showed shortened moving distance. After treatment with corresponding rAAV, the motor function of the mouse as negative control (N=5) showed persistent decline, representing by continuously reducing moving velocity and distance. On the contrary, mice treated with both low (N=5) and high dose (N=7) of CBh-A11G11-SV40 showed restoration of moving velocity and distance, with the higher dose showing a slightly better result than the lower dose. These results suggested that CBh-A11G11-SV40 achieved significant effect in rescuing the deficiency in moving velocity and travelling distance in a PD mouse model induced by MPTP/probenecid. Given the damage to the moving capacity of the mouse treated with A10-vy was less severe as compared to other mice, it seemed that CBh-A11G11-SV40 achieved a better effect in rescuing the deficiency in moving velocity and travelling distance in a PD mouse model induced by MPTP/probenecid as compared to the benchmark.

Then a transgenic PD mouse model was used to verify the results. The mice were genetically engineered to overexpress mutated α-synuclein (point mutation A53T) to recapitulate the PD pathology. Two rAAVs, EFSlt7-A11G11-hGH (EtI7) and CBh-A11G11-SV40 (CBh), were generated based on the construct A11G11 by using different promoters and polyA tails. The rAAVs were administered to the mice by intra-striatal injection, at a low dose of 4E+9 vg and a high dose of 4E+10 vg. Wild-type mouse without any treatment and A53T mouse treated with vehicle (PBS) were included as controls. The motor function was determined by measuring the times of vertical movements (rearing by the hindlimbs) and the results are shown in FIG. 35.

As shown in FIG. 35, the mice treated with vehicle (N=6) showed less times of vertical movements as compared to the WT mouse (N=8), indicating damage in motor function.

Mice treated with both high (N=7) and low doses (N=7) of EFSIt7-A11G11-hGH (EtI7) showed better performance than Veh, with the high dose showing a significantly increased result. Mice treated with low dose of CBh-A11G11-SV40 (CBh) (N=7) also showed increased times of vertical movements as compared to both WT and vehicle A11G11-based rAAVs. The increased times of vertical movements indicated the recovery of motor function.

The brain tissue samples of A53T mice were collected for determining the protein expression. The expression of AADC and GCase proteins in the striatum was determined by WB. As shown in FIG. 36, all the treated groups showed expression of AADC and GCase. Additionally, the level of phosphorylated α-synuclein and total α-synuclein in the striatum were measured. The level of phosphorylated α-synuclein was thought to be the biomarker for PD pathology. As shown in FIGS. 37A and 37B, both candidate rAAV vectors decreased the phosphorylated α-synuclein level in a dose-dependent manner, indicating amelioration of PD pathology. The exemplary bands in FIG. 37A were from 2 representative subjects in each group. The relative phosphorylated α-synuclein level as shown in FIG. 37B was the mean value of all the subjects in the indicated group.

Example 8. In Vivo Therapeutic Efficacy of AAV Candidates Expressing Optimized GBA1 Sequence in GD Mouse Model The therapeutic effects of the AAVs expressing optimized GBA1 were tested in GD mouse models.

Two candidate vectors which expressed optimized GBA1 (G11) were constructed as shown in FIG. 38. The first one was designed to comprise the CAG promoter, G11 codon, and hGH polyA ("CAG"). The second one was designed to comprise the EF1α promoter, G11 codon, WPRE, and hGH polyA ("EF1α"). Both vectors were packaged into AAV9 as rAAV The candidate rAAV vectors were injected into the lateral ventricle of a chemical-induced GD mouse model and a genetically engineered GD mouse model to evaluate their effects.

The chemical-induced mouse model was CBE-induced GD mouse model. The GCase activity was inhibited by conduritol B epoxide (CBE), a specific irreversible GCase inhibitor to mimic the loss-of-function mutation in GBA1 gene. At postnatal Day 2 (P2), the mice were treated with either PBS, AAV9-GFP (negative control) or three different doses of candidate rAAV vectors (Low, 2.75E+09 vg; Medium, 8.8E+09 vg; High, 2.8E+10 vg, per animal) via ICV injection. G10-p was used as the reference. To leave sufficient time for the gene to express, disease modeling was initiated at P8. 37.5 mg/kg of CBE was injected into the mice via IP injection once a day. The in-life assessment was performed until P28.

FIG. 39 shows the viability of GD mice until P28. As seen, the percentage survival of PBS group and negative control group dropped rapidly after P22. The negative control group has no animal survive at P25. On the contrary, both candidate vectors as well as the reference G10-p significantly improved the viability of GD mice.

FIG. 40 shows the change in motor function of the study animals. Both candidate vectors rescued the locomotor deficiency and motor incoordination induced by chronic CBE administration. As shown in FIGS. 40A and 40B, CAG increased the moving distance in open field test at all doses and enhanced the motor coordination in Rotarod at medium and high doses, while EF1α increased the moving distance at medium and high doses, but improve the motor coordination only at high dose.

At postnatal day 30, the brains samples were collected for determining the protein activity. The brain samples were homogenized in the lysis buffer (N-PER Neuronal Protein Extraction Reagent, Thermo Scientific #87792) containing Protease inhibitor (Roche #11697498001) to generate lysate samples. The GCase activity in these lysate samples was determined by the GBA1 activity assay as mentioned above. It was found that the GCase activity was increased dose-dependently in all of the candidate vector-treated groups (FIG. 41).

Example 9. Codon-Optimized Human CDNF Sequences for AADC Combination Constructs In this Example, AAV vectors were designed to co-express AADC and a gene encoding NTF, specifically CDNF. P2A was used as the linker sequence between the two coding sequences.

To determine the optimal coding sequence of CDNF, the wild-type AADC coding sequence (AADC WT) was linked via P2A with different codon-optimized CDNF sequences. Codon optimization was conducted based on different algorithm.

Two codon-optimized CDNF sequences with high CAI (>0.85) were obtained and named as CDNF GS and CDNF SA, respectively. Both sequences were subjected to codon optimization except for the sequence fragment coding for the signal peptide (Nucleotide positions 1-72 of the nucleotide sequence as shown in SEQ ID NO: 26). In CDNF SA, the 9 nucleotides encoding for three amino acids immediately after the signal peptide (nucleotide positions 73-81) were left unchanged.

Meanwhile, another candidate CDNF sequence named as CDNF manual (CDNF MN) was obtained based on the sequence of CDNF SA by manually identifying and reducing the "CG" components in the mature protein coding sequence (nucleotide positions 82-561). As a result, all of the CpG islands were intentionally removed from CDNF MN sequence.

For this study, an AAV backbone vector, containing from 5' to 3', 5' ITR, a CBh promoter, AADC WT coding sequence, a P2A sequence, a SV40 poly A, and a 3' ITR was prepared.

Figures 17A, 17B:
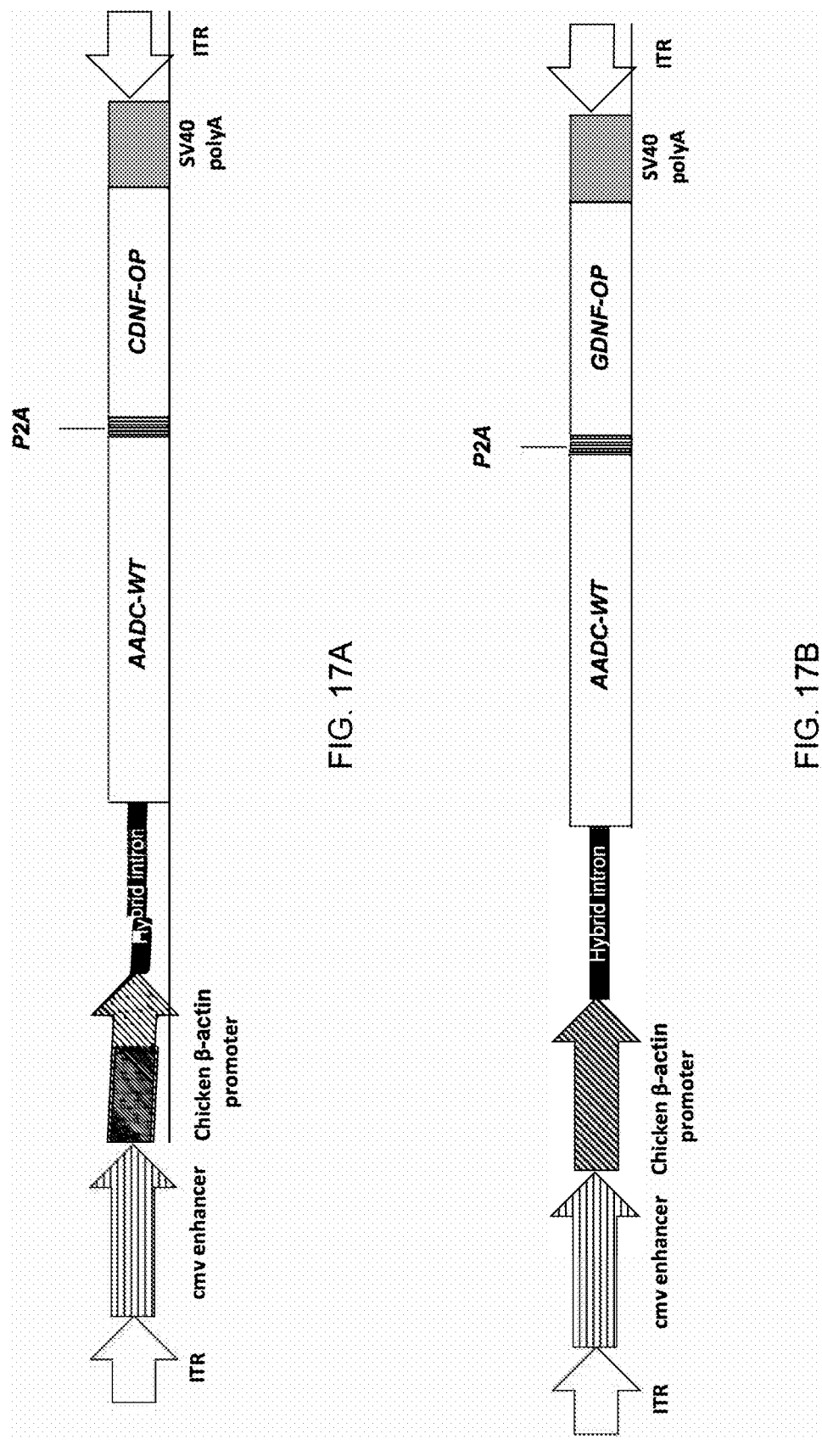
FIG. 17A and FIG. 17B show the schematic of constructs containing the wild-type AADC (AADC-WT) linked to an optimized CDNF (FIG. 17A) or GDNF (FIG. 17B) via a P2A linker under the control of a CBh promoter.

Sequences of CDNF GS, CDNF SA, CDNF MN and CDNF wild type (CDNF WT) were inserted into the aforementioned backbone vector respectively 3' of the P2A linker sequence (FIGS. 17A and B). The vectors obtained were named ApC-GS, ApC-SA, ApC-MN, and ApC-WT. A reference vector comprising CDNF WT Alone (no AADC) was also constructed.

The 5 plasmids described above and one negative control plasmid only expressing GFP were transfected into HEK293 cells using Lipofectamine 3000 Transfection Reagent (Invitrogen, #L3000008). 72 hours after transfection, the supernatant was centrifuged at 2,000 rpm for 10 minutes to remove debris in the medium, 40 μL of supernatant and 10 μL 5× loading buffer (Beyotime, P0015L) were then transferred into a new 1.5 mL tube and incubated for 5 min at 95° C. Cells were washed once with 1×PBS and harvested in the RIPA buffer (Thermo, 89901).

Figure 18A:
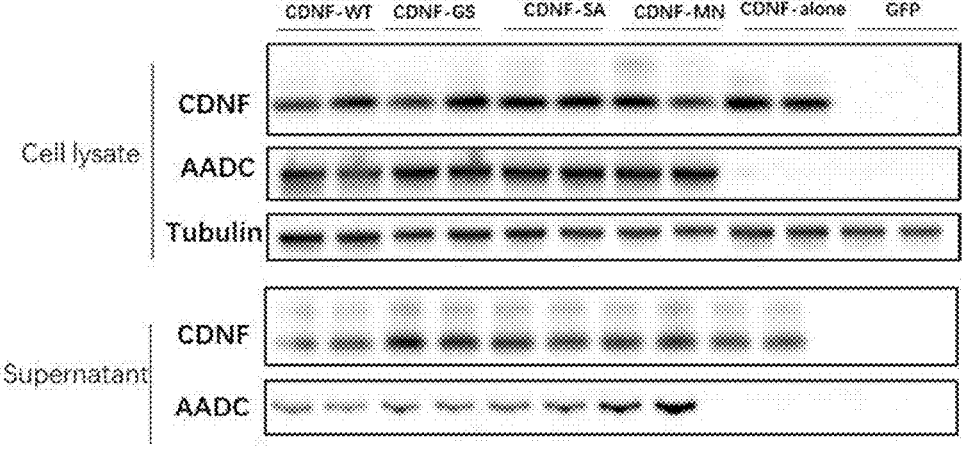
FIG. 18A and FIG. 18B show the CDNF protein expression levels in cell lysates and supernatants of the HEK293 cells transfected with different candidate constructs, as determined by WB.
Figure 18B:
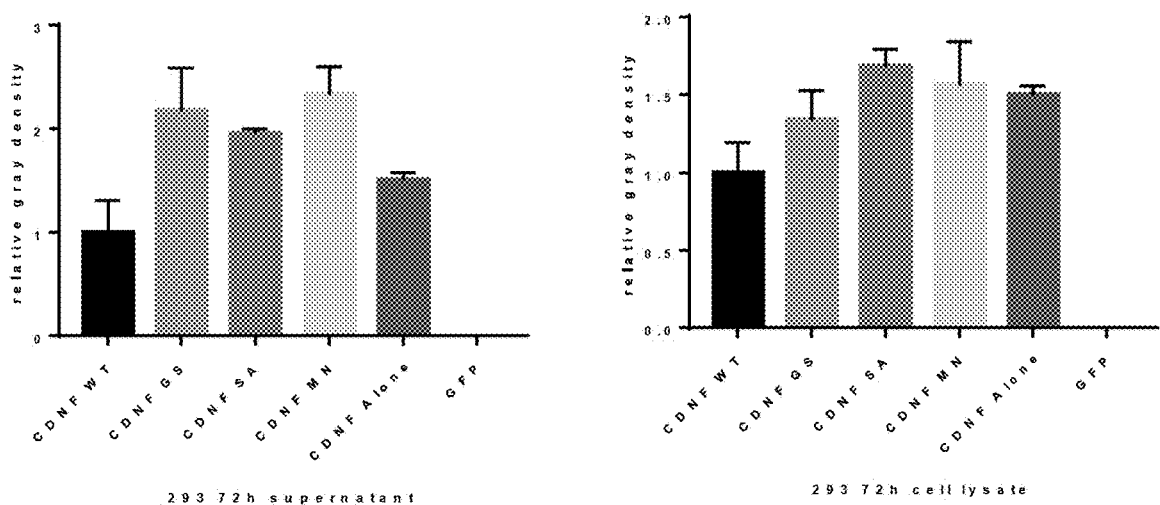
Figure 19A:
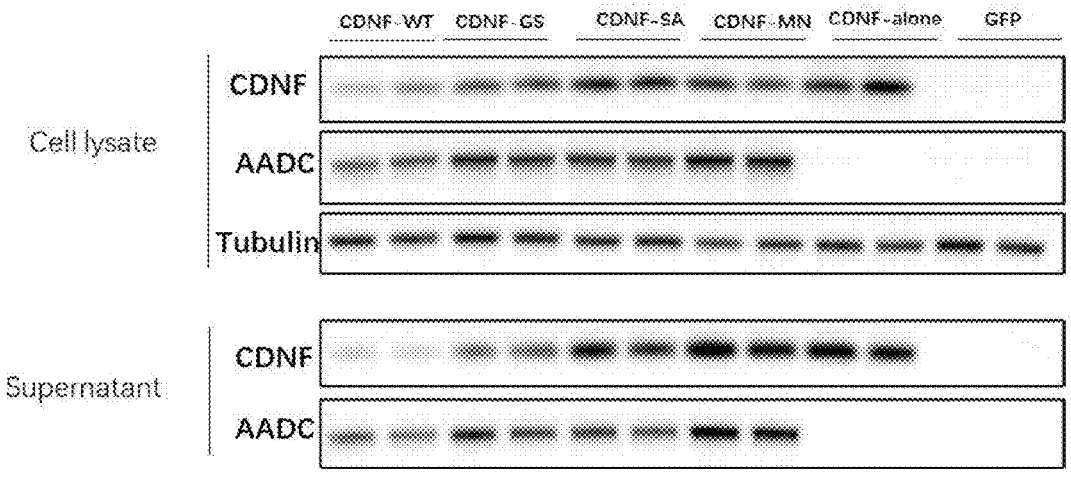
FIG. 19A and FIG. 19B show the CDNF protein expression levels in cell lysates and supernatants of the U87 cells transfected with different candidate constructs, as determined by WB.
Figure 19B:
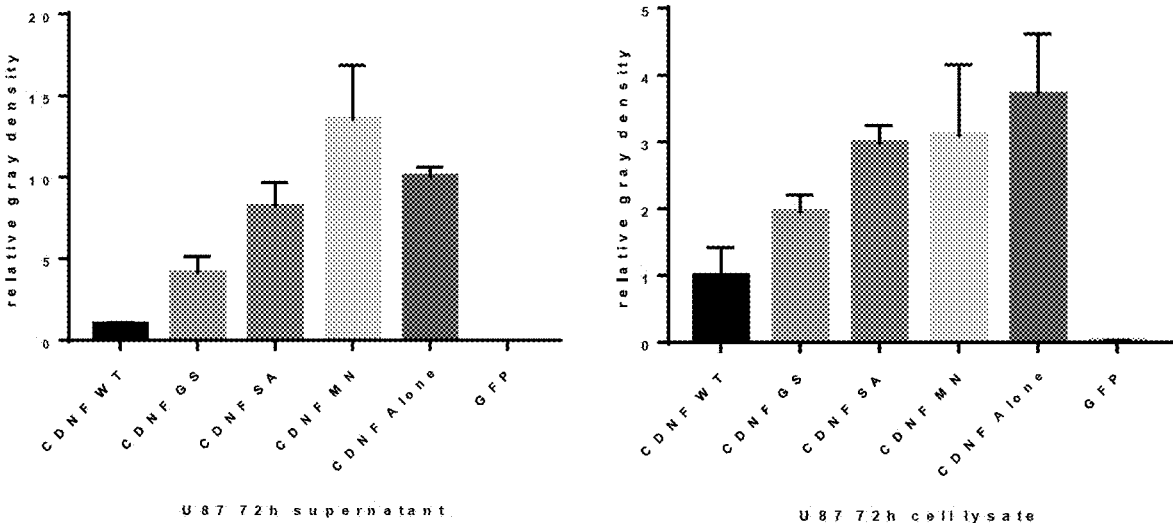

To conduct WB analysis, the samples were diluted and boiled in 5× loading buffer (Beyotime, P0015L), separated on SDS polyacrylamide gel (BIO-RAD, 1703932) and transferred onto a 0.22 μm PVDF membrane (BIO-RAD, 1620177). The membrane was incubated with antibodies for CDNF protein (Sigma, HPA044587), AADC protein (Merck Millipore, AB1569), and β-Tubulin protein (Tubulin, Proteintech, 66240-1-Ig) overnight at 4° C., followed by 2 hours incubation with HRP-linked secondary antibody at room temperature the next day. BeyoECL Moon kit (Beyotime, P0018F) was then applied to the membrane (FIG. 18A). Exposure and image capture were performed with a Tannon 5600 system. The intensities of the CDNF bands were calculated and normalized to construct ApC-WT and the results are shown in FIG. 18B. As shown in FIG. 18B, among all of the constructs evaluated, cells transfected with construct ApC-MN showed the highest levels of CDNF protein secreted into the supernatant, which was confirmed in U-87 MG cells transfected with the same set of plasmids (FIG. 19A-B).

The levels of secreted CDNF protein in the supernatants were further determined by a sandwich ELISA method. Briefly, 96-well microplates (Costar, 42592) were coated with a CDNF mouse Mab (SinoBiological, 15691-MM1) antibody as a capture antibody at 4° C. overnight. The next day, the plates were washed 3 times with PBST (Phosphate Buffered Saline with Tween), then blocked with 5% Nonfat-Dried Milk (Solarbio, D8340) at room temperature for 2 hours. After an additional wash step, CDNF protein standard (SinoBiological, 15691-H08H) or protein samples were added to the plates in duplicates. The samples were incubated with the detection antibody (SinoBiological, 15691-R104) for 2 hours at room temperature, followed by a wash step. Then the samples were incubated with HRP-conjugated goat anti-rabbit antibody (SinoBiological, HO14SE1801) for 1 hour, followed by one more wash step. The bound HRP conjugates were detected by addition of TMB (Solarbio, PR1200), and the reaction was terminated by the stop solution (Solarbio, C1058). The absorbance of each sample (at an excitation wavelength of 450 nm and emission @630 nm) was detected by a fluorimeter (SPEC-TRAmax Gemini XPS, Molecular Devices, San Jose, CA, USA) and the results are shown in FIG. 20A-B.

Figure 20A:
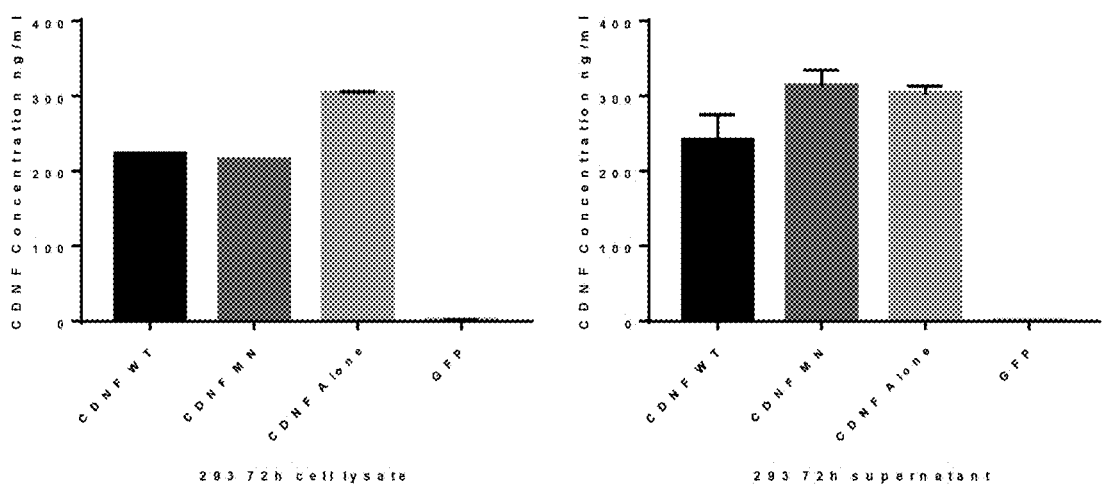
FIG. 20A and FIG. 20B show the CDNF protein expression levels in cell lysates and supernatants of the HEK293 cells (FIG. 20A) or U87 cells (FIG. 20B) transfected with different candidate constructs, as determined by ELISA.
Figure 20B:
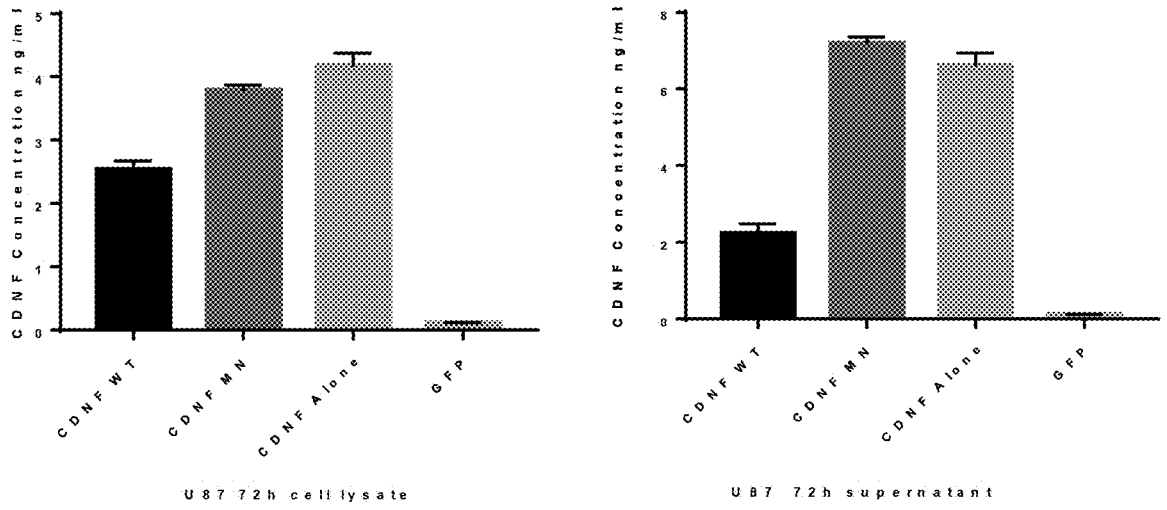

As shown in FIG. 20A-B, both HEK293 and U-87 MG cells transfected with construct ApC-MN expressed significantly higher levels of CDNF protein as shown in the high levels of secreted CDNF in the supernatants. As a result, ApC-MN was selected for further evaluation.

Example 10. Codon Optimized CDNF Expressed Protein Showed Significant Cytoprotective Effects In this Example, the cytoprotective effect of CDNF protein expressed and secreted by cells transfected with the plasmid AADC-CDNF MN (ApC-MN) was investigated. Two cell-based assays, LDH cytotoxicity assay and CCK-8 cell viability assay of cells treated with MPP+ or Rotenone were used to examine the CDNF cytoprotective effect.

In the LDH assay, a 96-well assay plate containing SH-SY5Y cells (National Collection of Authenticated Cell Cultures, SCSP-5014) was pre-treated with or without supernatant containing secreted CDNF protein collected from the previous experiments. Several wells were left without cells as the blank control to determine the background luminescence levels. Cells were then treated with MPP+ or Rotenone or DMSO vehicle control. When the plate was incubated at 37° C., LDH Detection Reagent (CytoTox 96® Non-Radioactive Cytotoxicity Assay, Promega) was prepared by mixing 12 mL of Assay Buffer with a bottle of Substrate Mix. $\frac{1}{10}^{th}$ volume of 10× Lysis Solution was added to the positive control (Maximum LDH Release Control) wells 45 minutes before adding the CytoTox 96® Reagent. Before plate reading, 50 μL of the CytoTox 96® Reagent was added to each well. The plate was covered with foil to protect from light exposure and incubated for 30 min at room temperature. Then, 50 μL of Stop Solution was added to each well to stop the reaction. One hour after adding the Stop Solution, the absorbance at 490 nm was recorded by a plate reader. Percent cytotoxicity=100×Experimental LDH Release (OD490)/Maximum LDH Release (OD490).

In the CCK-8 assay, the SH-SY5Y cells in logarithmic growth phase were plated in 96 well plates at a density of 5×10³/mL and cultured in high glucose/DMEM cell culture medium containing 10% fetal bovine serum (FBS) and 1% penicillin-streptomycin solution and maintained in a cell incubator with 5% $CO_2$ and 95% air at 37° C. for 12 hrs. Cells were then treated with or without supernatant containing secreted CDNF collected from the previous experiments. MPP+ or Rotenone containing serum-free media at a final concentration from 0 to 2 mM were used to induce cell apoptosis. 24 hrs later, cell viability was assessed by adding 10 μL of CCK-8 (Cell Counting Kit-8, Dojindo) to the culture and after incubation for 2 hrs, relative cell viability was determined by a spectrometry @450 nm wavelength.

Figures 21, 22:
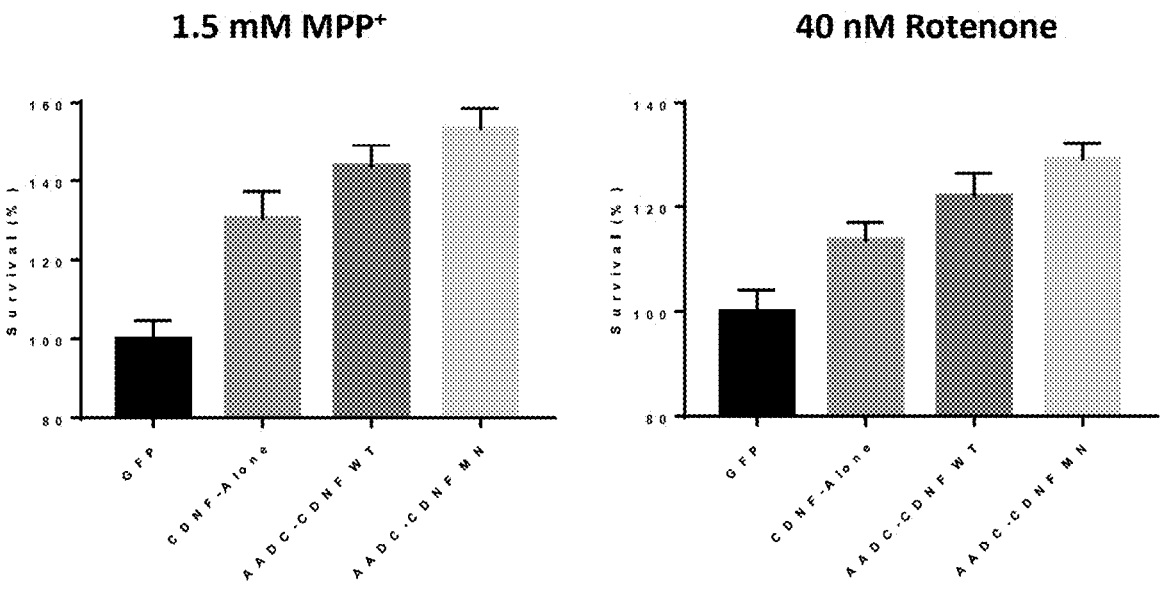
FIG. 21 shows the protective effects of CDNF protein in the supernatants of the HEK293 cells transfected with different candidate constructs treated with either 1.5 mM MPP+ or 40 nM Rotenone, as determined by CCK-8 assay.
FIG. 22 shows the GDNF protein expression levels in cell lysates and supernatants of the HEK293 cells transfected with different candidate constructs, as determined by WB.

As shown in FIG. 21, in the presence of MPP+(1.5 mM) or Rotenone (40 nM), SH-SY5Y cells treated with supernatants from construct ApC-MN transfected cells had a higher survival rate than those treated with supernatants from construct ApC-WT transfected cells, indicating that in comparison to construct ApC-WT, construct ApC-MN expressed and secreted higher levels of CDNF protein to the supernatants to exert its stronger cytoprotective effect.

Example 11. Codon-Optimized Human GDNF Sequences for AADC Combination Constructs In this example, the mature protein coding sequence of human GDNF was optimized by codon optimization process as performed in Example 9 (FIG. 17B), obtaining GDNF-GS sequence (SEQ ID No: 27), GDNF-SA sequence (SEQ ID No:28) and GDNF-MN sequence (SEQ ID No:29).

Figure 23:
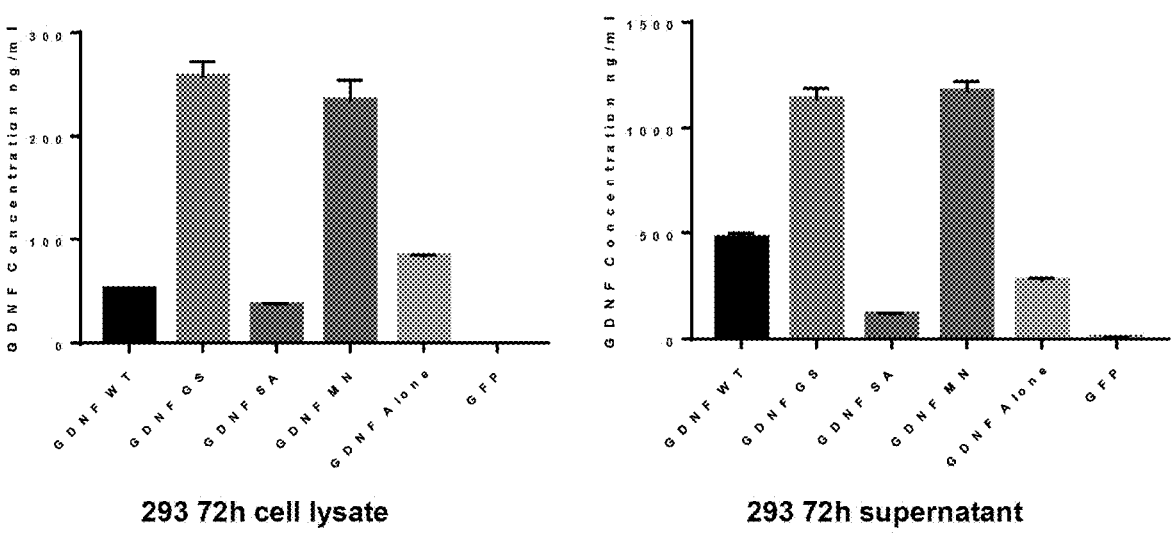
FIG. 23 shows the GDNF protein expression levels in cell lysates and supernatants of the HEK293 cells transfected with different candidate constructs, as determined by ELISA.
Figure 24:
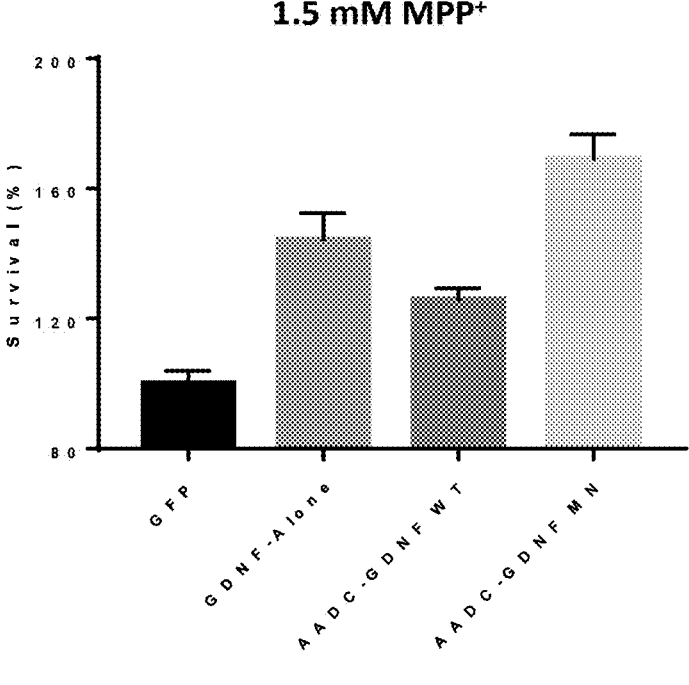
FIG. 24 shows the protective effects of GDNF protein in the supernatants of the HEK293 cells transfected with different candidate constructs treated with 1.5 mM MPP+, as determined by CCK-8 assay.

The same in vitro cellular experiments as described in Example 10 were performed in HEK293 cells transfected with constructs containing GDNF GS, GDNF SA and GDNF MN (FIGS. 22-24). Based on the results, the GDNF MN sequence with no CpG island had the best GDNF expression and protection potential among all the codon-optimized GDNF sequences evaluated.

Therefore, the GDNF MN sequence was chosen as the GDNF coding sequence for AADC combination construct for further evaluation.

Example 12. Determination of the Optimal Promoters to Use in the AADC and CDNF/GDNF Combination Constructs To determine the best promoter elements to use in the combination construct of AADC with either CDNF or GDNF, eight new combination constructs were made, specifically as shown in the Table 3 below. The four constructs containing CDNF are CAG-A3-P2A-CDNF MN, CAG-A11-P2A-CDNF MN, EF1α-A3-P2A-CDNF MN, and EF1α-A11-P2A-CDNF MN; and the four constructs containing GDNF are CAG-A3-P2A-GDNF MN, CAG-A11-P2A-GDNF MN, EF1α-A3-P2A-GDNF MN, and EF1α-A11-P2A-GDNF MN. Constructs CBh-AADC WT-P2A-

CDNF WT and CBh-AADC WT-P2A-GDNF WT were generated and used as controls.

TABLE 3

Constructs of CDNF/GDNF and AADC in combination with different regulatory sequences

| No. | Vector | Promoter | AADC | NTF | Results |
|---|---|---|---|---|---|
| | | CDNF groups | | | |
| 1 | CAG-A3-P2A-CDNF MN | CAG | A3 | CDNF MN | Lower |
| 2 | CAG-A11-P2A-CDNF MN | CAG | A11 | CDNF MN | ND* |
| 3 | EF1α-A3-P2A-CDNF MN | EF1α | A3 | CDNF MN | ND* |
| 4 | EF1α-A11-P2A-CDNF MN | EF1α | A11 | CDNF MN | Higher |
| | | GDNF groups | | | |
| 5 | CAG-A3-P2A-GDNF MN | CAG | A3 | GDNF MN | |
| 6 | CAG-A11-P2A-GDNF MN | CAG | A11 | GDNF MN | |
| 7 | EF1α-A3-P2A-GDNF MN | EF1α | A3 | GDNF MN | ND* |
| 8 | EF1α-A11-P2A-GDNF MN | EF1α | A11 | GDNF MN | Highest |

*N.D.: Non-detectable

Aforementioned constructs were transfected into HEK293 cells. Both the cell lysates and supernatants of these samples were collected. The secreted protein levels of CDNF or GDNF were determined by ELISA. The results showed that EF1α-A11-P2A-CDNF MN expressed higher levels of CDNF protein than that of CAG-A3-CDNF MN, while the other two constructs expressed undetectable levels of CDNF protein (FIG. 25).

Figure 25:
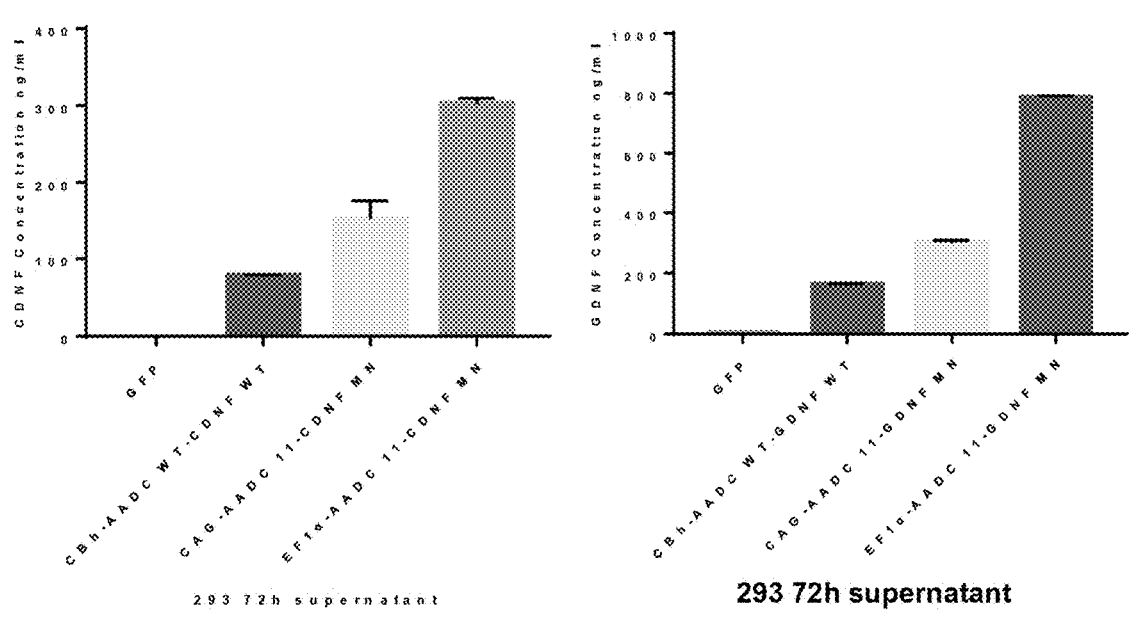
FIG. 25 shows the CDNF (left panel) or GDNF (right panel) protein expression levels in the supernatants of the HEK293 cells transfected with the indicated constructs.

For GDNF containing constructs, EF1α-A11-GDNF MN expressed and secreted the highest levels of GDNF (FIG. 25).

Figure 26:
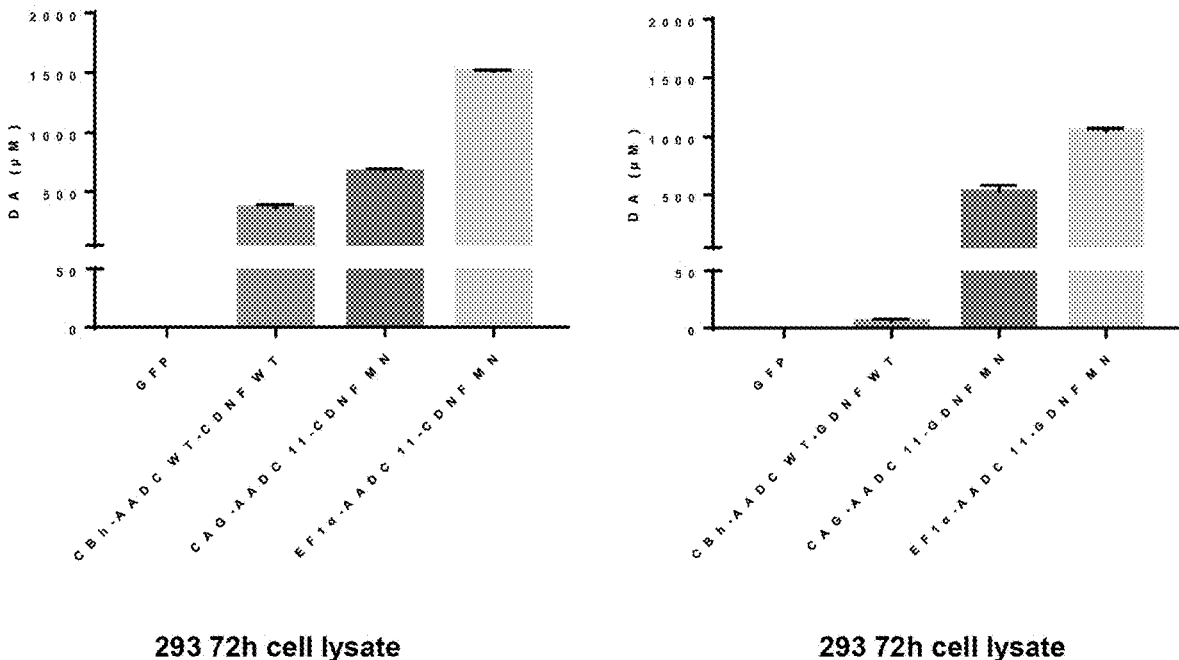
FIG. 26 shows the AADC protein activity in the cell lysates of the HEK293 cells transfected with the indicated candidate constructs.

The catalytic activities of AADC protein expressed by these combination constructs were also determined by HPLC assay of the cell lysates as described in the previous example. Shown in FIG. 26, the relative AADC activities of EF1α-A11-CDNF MN and EF1α-A11-GDNF MN were much higher than all of the other candidate constructs.

The construct EF1α-CDNF MN-A11 was generated by placing the CDNF codon before the AADC codon and linked by P2A.

Both EF1α-CDNF MN-A11 (CDNF MN-A11) and EF1α-A11-CDNF MN (A11-CDNF MN) were transfected into HEK293 cells by Lipofectamine 3000. 72 hours after transfection, the supernatant and cell lysate were collected. The protein level of AADC and CDNF in the cell lysate and CDNF level in the supernatant (secreted CDNF) were determined by WB. It was interesting to find that the protein level of secreted CDNF was much higher in the CDNF MN-A11 group than in A11-CDNF MN (FIG. 42).

Figure 27:
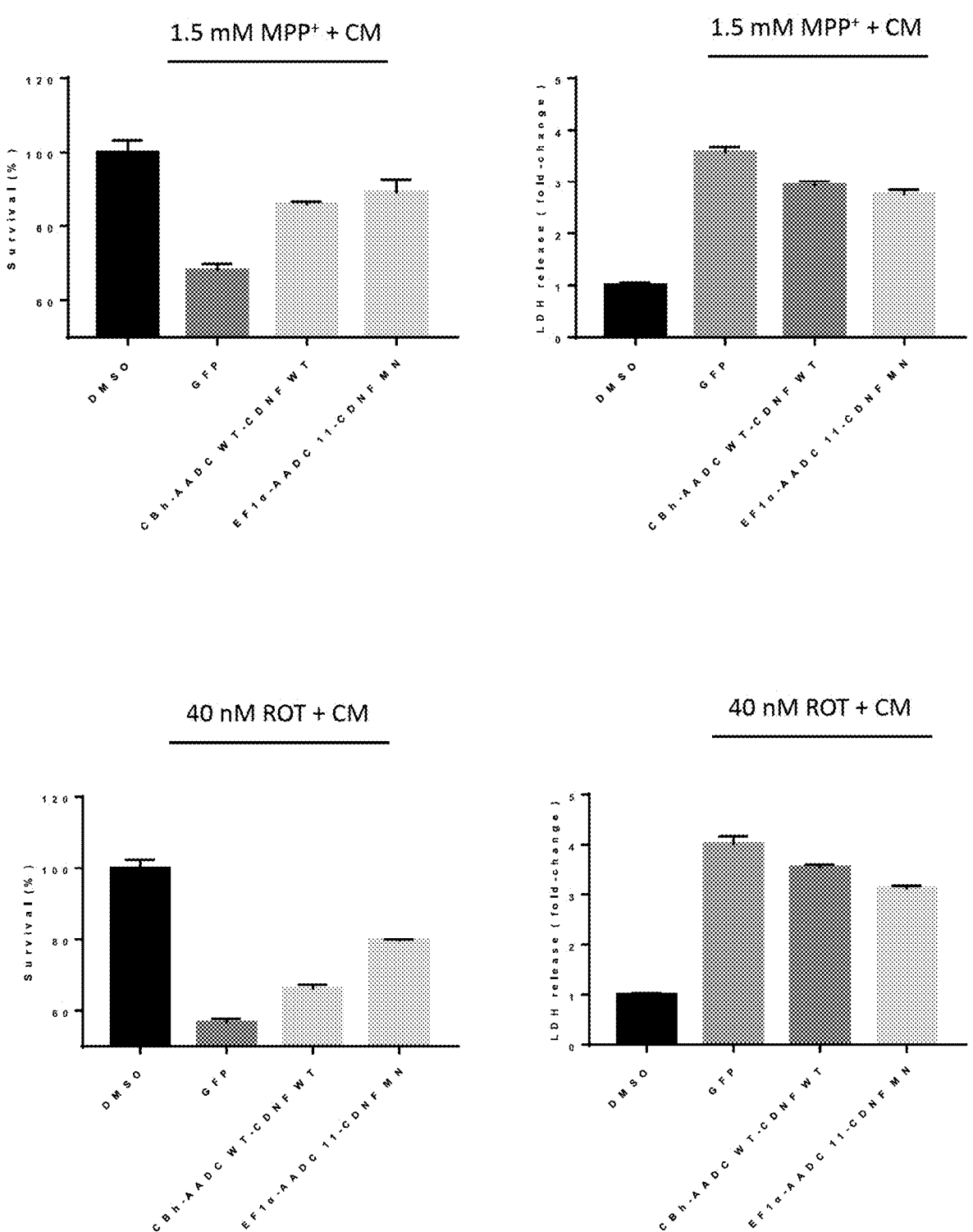
FIG. 27 shows the protective effects of CDNF in the supernatants of the HEK293 cells transfected with different candidate constructs treated with 1.5 mM MPP+ or 40 nM Rotenone, as determined by CCK-8 assay and LDH assay.
Figure 28:
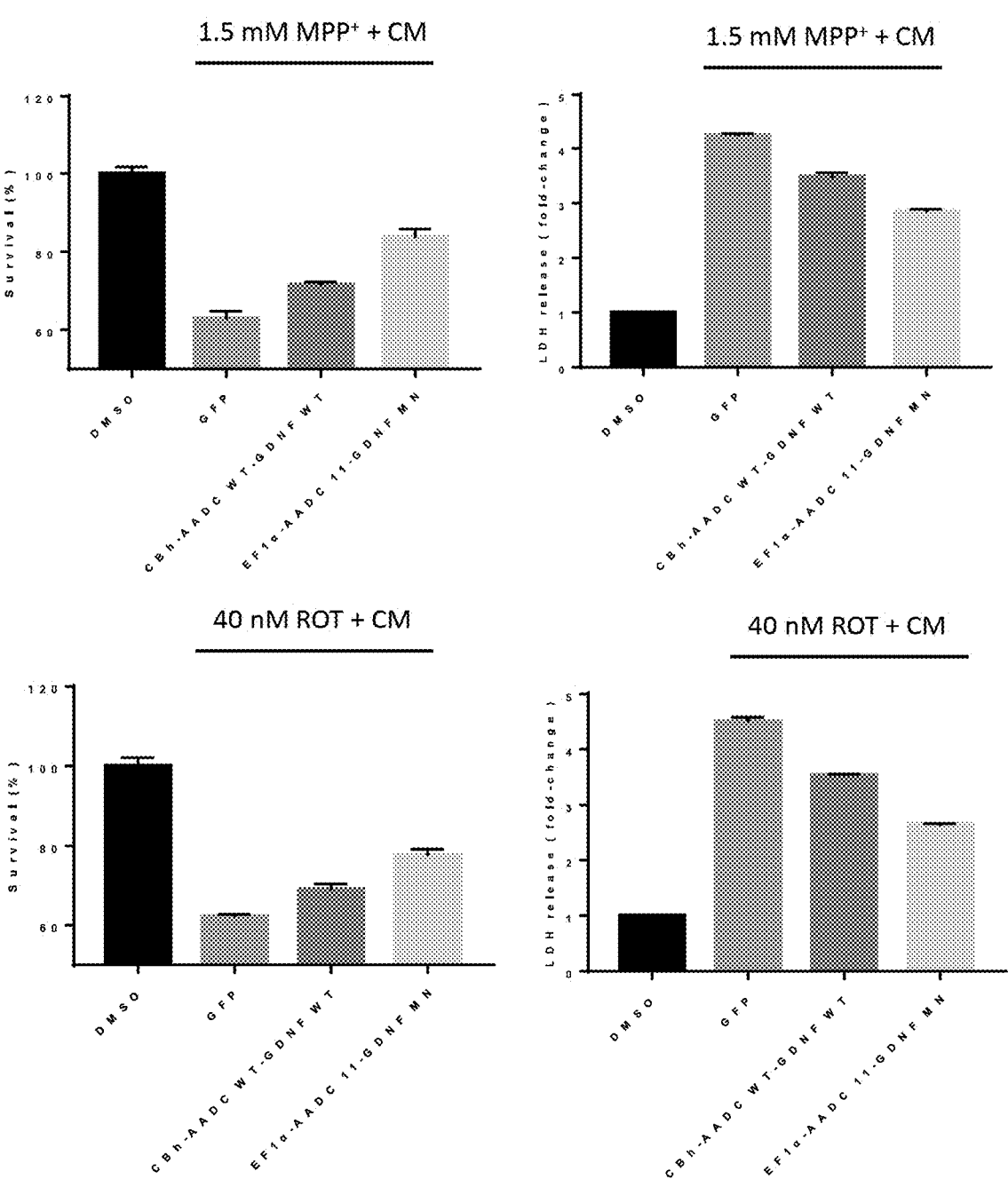
FIG. 28 shows the protective effects of GDNF protein in the supernatants of the HEK293 cells transfected with different candidate constructs treated with 1.5 mM MPP+ or 40 nM Rotenone, as determined by CCK-8 assay and LDH assay.

Example 13. Validation of the Cyto-Protective Effects of CDNF and GDNF Proteins Derived from Candidate Constructs The MPP+ and Rotenone assays as described in the previous experiment were performed to determine the cyto-protective effects of the CDNF and GDNF constructs identified in Example 12. The supernatants from cells transfected with construct EF1α-A11-CDNF MN (FIG. 27) or EF1α-A11-GDNF MN (FIG. 28) improved the viability of SH-SY5Y cells in the presence of MPP+(1.5 mM) or Rotenone (40 nM). LDH assay was also performed to confirm the cyto-protective effects of both candidate constructs.

Example 14. Evaluation of AADC and CDNF or GDNF Protein Expression of the AAV9 Packaged Combination Constructs Both EF1α-A11-CDNF MN and EF1α-A11-GDNF MN combination constructs were packaged into AAV9. The obtained AAV9-EF1α-A11-CDNF MN and AAV9-EF1α-A11-GDNF MN were added to U87-AAVR cells at MOI=1e5. At 72 hours post viral transduction, the cells were collected in the lysis buffer. Following the protocol of WB, the expressed protein levels of CDNF and AADC were determined. Meanwhile, the supernatants of all the samples were also collected and concentrated as above mentioned. The levels of secreted CDNF and GDNF proteins were also detected by WBs and the results are shown in FIG. 29.

Figure 30:
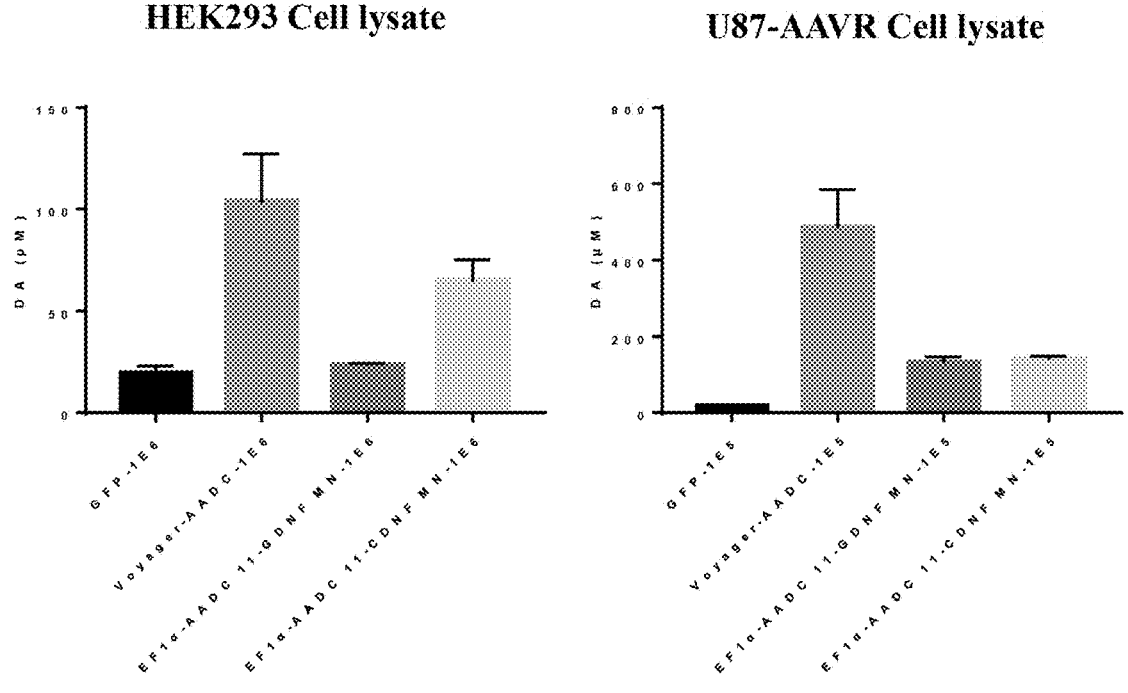
FIG. 30 shows the relative activity of the AADC protein from the HEK293 and U87-AAVR cells transduced with the indicated rAAV9 vectors.

The relative activities of the expressed AADC protein in the aforementioned cell lysates were shown in FIG. 30.

Figure 29:
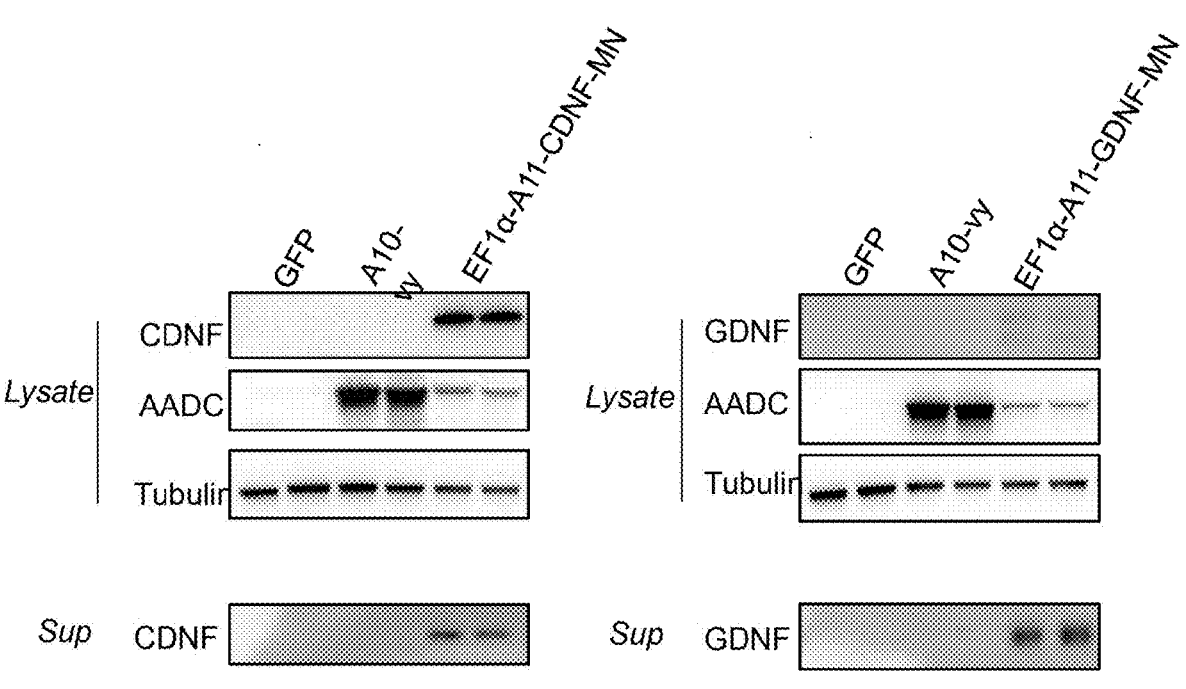
FIG. 29 shows both the AADC and NTF (CDNF or GDNF) protein expression levels in the cell lysates, and NTF levels in the supernatants of the U87-AAVR cells transduced with the indicated rAAV9 vectors.

Taken together data shown in FIGS. 29 and 30, both constructs performed as expected when packaged into AAV9 as rAAV.

Figure 31:
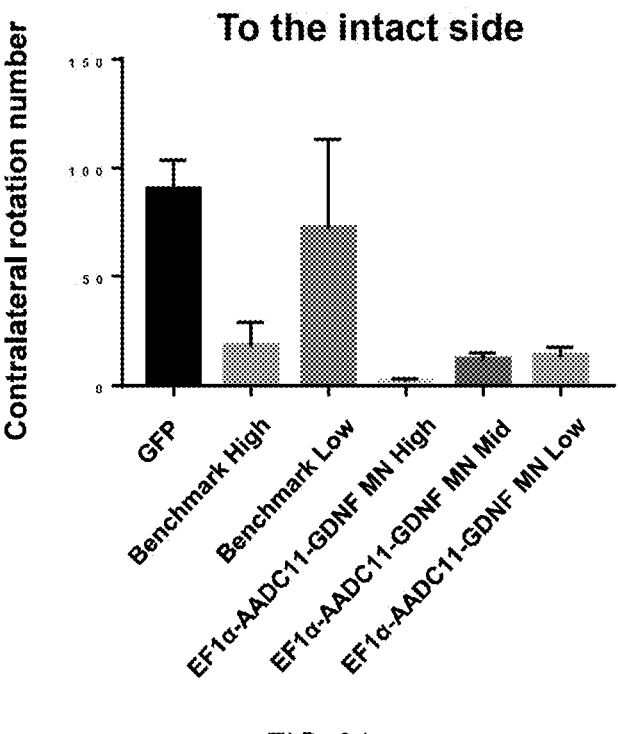
FIG. 31 shows the contralateral rotation numbers taken from study subjects of a mouse 6-OHDA induced PD model after dosing with EF1α-A11-GDNF MN and benchmark rAAV.
Figure 32:
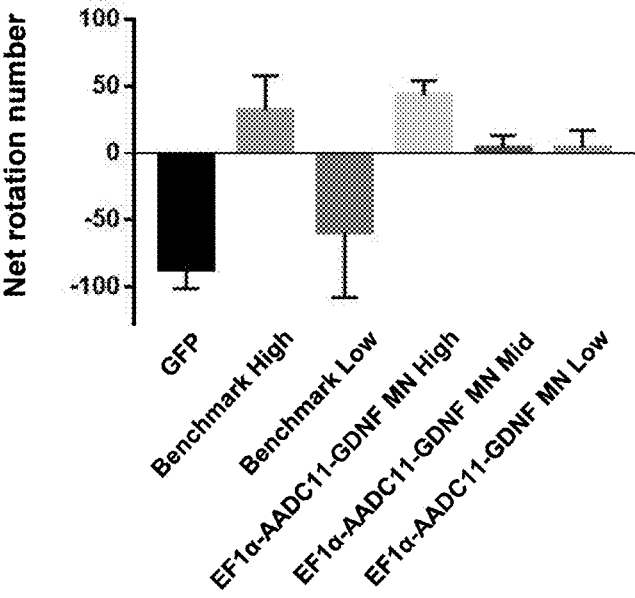
FIG. 32 shows the net rotation numbers taken from study subjects of a mouse 6-OHDA induced PD model after dosing with EF1α-A11-GDNF MN and benchmark rAAV.

Example 15. In Vivo Therapeutic Efficacy of AAV Candidates Expressing Optimized AADC in Combination with GDNF or CDNF in PD Mouse Models The therapeutic effects of AAV delivering the optimized AADC+GDNF combination construct were tested in a uni-lateral-lesioned 6-OHDA PD mouse model. Briefly, C57 mice were placed in the stereotaxic frame and anesthetized with the isoflurane mixed in oxygen. 1 μL 6-OHDA (3 mg/ml, Sigma, #162957) was injected into the right sub-stantial nigra (coordinates AP=−2.9 mm, ML=−1.1 mm, DV=−4.5 mm). One week after the lesion surgery, the mice were administrated with apomorphine (Sigma, PHMR2621-500MG) intraperitoneally, and their rotation behavior (rotat-ing to the intact side) was recorded and analyzed. Candidate rAAV vector EF1α-A11-GDNF MN was then injected into the right striatum of the subjects (coordinates AP=+0.6 mm, ML=−1.8 mm, DV=−3.2 mm) at three doses (Low: 1E+12 vg, Medium: 3.16E+12 vg, High: 1E+13 vg in mL). AAV-GFP and two doses of benchmark AAV-A10-vy (Low: 1E+12 vg, High: 1E+13 vg in mL) were also applied. 21 days post AAV injection, it was observed that the contral-ateral rotation triggered by the apomorphine was signifi-cantly decreased in all of the study groups treated with the candidate rAAV vector as compared to the control group (FIG. 31 and FIG. 32). As shown in FIG. 31, the three study groups treated with the three different doses of EF1α-A11-GDNF MN rAAV performed significantly better than the group treated with the benchmark rAAV More remarkably, the net rotation numbers (ipsilateral-contralateral) in both low and medium dose treatment groups were close to zero which indicated that these study subjects had fully recovered their balance motor behavior, while the group received the high dose of benchmark showed over-compensated ipsilat-eral rotation (an excess amount of AADC in the treated side) (FIG. 32).

In another in vivo efficacy test in PD mice (study 2), CAG-A11-GDNF MN rAAV (AAV9) was also tested in the unilateral-lesioned 6-OHDAPD mouse model. Two different doses (2.0E+09 vg and 2.0E+10 vg) of both CAG-A11-GDNF MN and EF1α-A11-GDNF MN were delivered into the PD mice via intra-striatal injection. AAV-GFP was used as untreated control and two doses of AAV2-A10-vy was used as the benchmark. 21 days post AAV injection, it was found that 2E+10 vg/animal of EF1α-A11-GDNF MN significantly decreased the ipsilateral rotation triggered by the amphetamine (i.p. 5 mg/kg), indicating a rescued motor function (FIG. 43).

The tissue samples were collected for determination of the expression of AADC and NTF proteins, and dopamine levels. Expression of the GOIs were observed in the Nigro-striatal pathway. As shown in FIG. 44, striatum tissue samples were collected from the subjects in 6-OHDA mice study 2 on day 91 post AAV injection. The protein levels of AADC and GDNF in both EF1$\alpha$ and benchmark groups were determined by WB. It was surprised to find that EF1$\alpha$ expressed more AADC in the striatum (the injection site) than A10-vy (FIG. 44A). Meanwhile, it was confirmed that EF1$\alpha$ expressed GDNF dose-dependently in vivo (FIG. 44B).

Moreover, tyrosine hydroxylase (TH) staining showed more dopaminergic terminals survived in the Nigro-striatal pathway of the EF1$\alpha$ treated animals as compared to the control animals which only received AAV9-GFP, confirming the protective effects of the candidate rAAVs (FIG. 45).

The efficacy of AAV9-EF1$\alpha$-A11-GDNF MN (EF1$\alpha$) was also tested in a unilateral-lesioned 6-OHDA PD rat model. The model was generated according to the previous study (6-OHDA Lesion Models of Parkinson's Disease in the Rat. Animal Models of Movement Disorders: volume I, Neuromethods, vol. 61, DOI 10.1007/978-1-61779-298-4_13). Briefly, 6-OHDA was injected into the right substantial nigra (coordinates AP=−4.4 mm, ML=−1.1 mm, DV=−8 mm). Two weeks after the lesion surgery, EF1$\alpha$ was then injected into two sites of the right striatum of the subjects (coordinates AP=+1.0 mm, ML=−3.0 mm, DV=−4.5 mm; AP=−0.2 mm, ML=−3.5 mm, DV=−5.0 mm) at two doses (Low: 4.0E+9 vg/animal, High: 4E+10 vg/animal). One dose of benchmark AAV2-A10-vy (4E+10 vg/animal) was also applied. 21 days post AAV injection, the spontaneous contralateral rotation behavior was recorded pre and post L-DOPA (5 mg/kg L-DOPA+2.5 mg/kg Benserazide) administration. $\Delta$rotation time per minute (Post-Pre) represented the response of subjects to L-DOPA. As shown in FIG. 46, it was found that EF1$\alpha$ significantly enhanced the response of the treated subjects to low dose L-DOPA, suggesting in the future clinical application, this candidate treatment could enhance the bioavailability of dopamine derivative like L-DOPA. In addition, EF1a showed a better result as compared to A10-vy at the same dosing level (4E+10 vg).

Figures 33A, 33B:
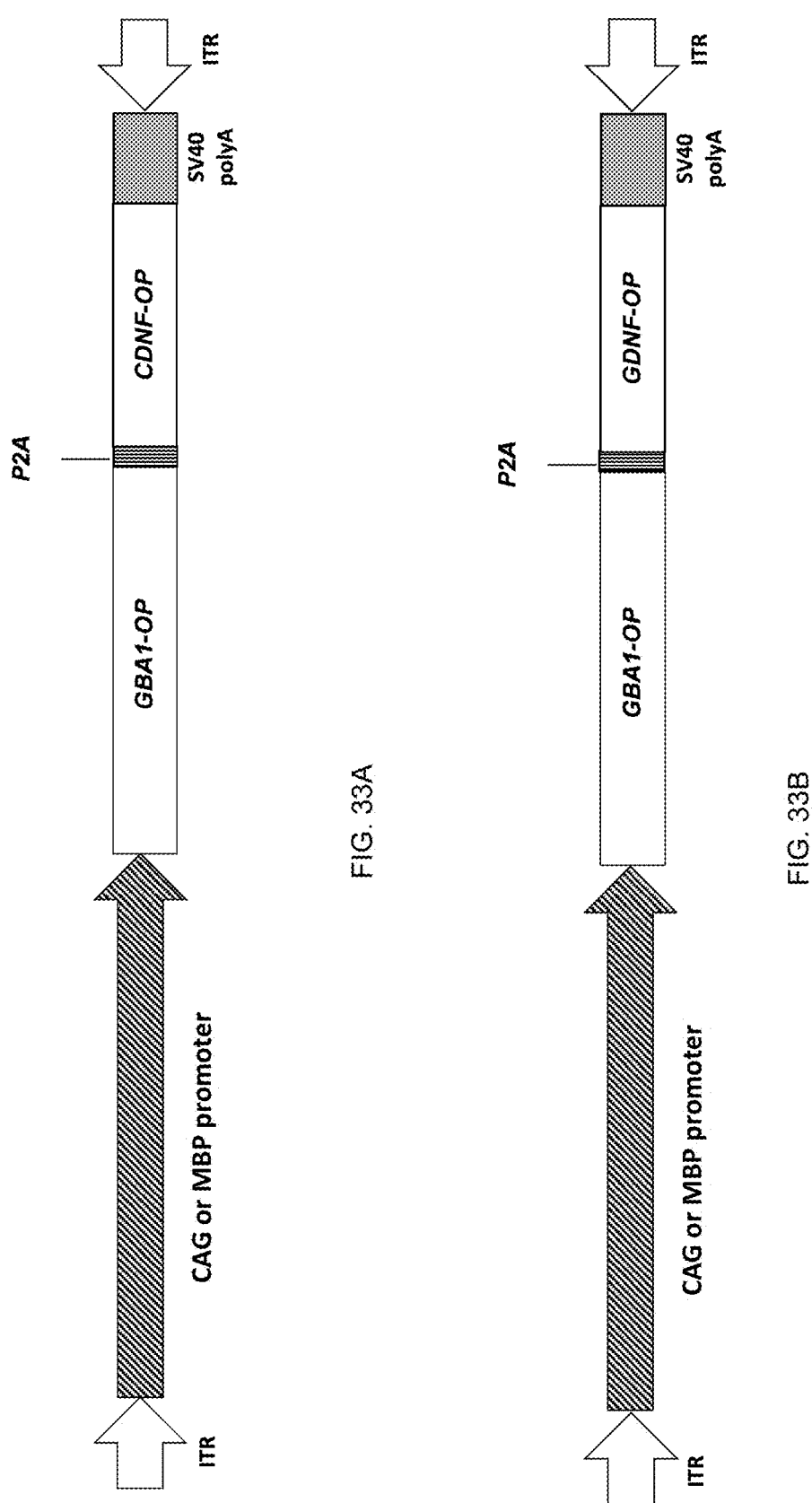
FIG. 33A and FIG. 33B show the schematic of constructs containing the optimized GBA1 linked to an optimized CDNF (FIG. 33A) or GDNF (FIG. 33B) via a P2A linker under the control of a promoter (CAG or MBP promoter). "OP" refers to optimized nucleotide sequence.

Example 16. In Vivo Therapeutic Efficacy of AAV Candidates Expressing Optimized GBA1 in Combination with CDNF or GBA1 with GDNF in the MSA Animal Models The candidate constructs with configuration as shown in FIGS. 33A and 33B were generated. These constructs contain a CAG or MBP promoter, GBA1 gene (including SEQ ID NOs: 45 and 47) in combination with CDNF (SEQ ID NOs: 23-25) or GDNF (SEQ ID NOs: 27-29).

CAG-G11-P2A-GDNF MN-SV40 polyA (CAG-G11-GDNF MN), CAG-G12-P2A-GDNF MN-SV40 polyA (CAG-G12-GDNF MN), MBP-G11-P2A-GDNF MN-bGH polyA (MBP-G11-GDNF MN), and CAG-GDNF MN-WPRE-hGH (CAG-GDNF MN) were constructed and packaged into AAVs in which serotype AAV9 was used. These candidate rAAV vectors were applied on the U-87 MG-AAVR cells (U-87 MG cells which overexpressed AAVR) and the cell lysate and supernatant samples were collected. The GCase and GDNF protein levels were determined in these samples (FIG. 47).

The efficacy of the above candidate rAAV vectors were tested in vitro in a cell model for recapitulating the pathological feature of PD and MSA, which is a stable cell line based on SH-SY5Y cell and over-expressing both AAVR and the mutated $\alpha$-synuclein (point mutation A53T) protein. The lentivirus vectors harboring AAVR sequence or mutated $\alpha$-synuclein (A53T) sequence, respectively were prepared by Azenta Life Science and applied to SH-SY5Y cells sequentially. After antibiotic- and GFP-based selection, the SH-SY5Y-AAVR-A53T stable cell line was generated. As shown in FIG. 48, it was found that candidate rAAV vectors could significantly decrease the level of $\alpha$-synuclein at high molecular weight (HMW) which was the biomarker for $\alpha$-syn aggregation in the cell model.

CAG-GDNF MN-P2A-G11-SV40 polyA (CAG-GDNF MN-G11) was constructed and transfected into HEK293 cells, together with CAG-G11-GDNF MN. 72 hours post transfection, the supernatant and cell lysate samples were collected and analyzed. It was found that CAG-GDNF MN-G11 expressed more GDNF compared to CAG-G11-GDNF MN in both supernatant and cell lysate, and surprisingly maintain the capability to express GCase (FIG. 49).

Then the therapeutic effects of AAV delivering the optimized GBA1+CDNF or GBA1+GDNF combination construct are evaluated in the mouse models of MSA. Candidate rAAV vectors after injection into the lateral ventricle (i.c.v.) rescue the motor deficiency in MSA animals. The tissue samples are collected. The expression of GBA1 and NTF proteins, and the reduced levels of $\alpha$-syn and phosphorylated $\alpha$-syn in the Nigro-striatal pathway are observed. Moreover, tyrosine hydroxylase (TH) staining shows more dopaminergic terminals survived in the striatum of the treated animals confirming the protective effects of the candidate AAVs.

Example 17. In Vivo Therapeutic Efficacy of AAV Candidates Expressing Optimized GBA1 in PD Mouse Models The therapeutic effects of the AAVs expressing optimized GBA1 are tested in PD mouse models.

The mice which are genetically engineered to overexpress mutated $\alpha$-synuclein (point mutation A53T) are used as the PD model. CAG-G11-hGH polyA (as shown in Example 8 and FIG. 38A) is packaged into AAV9 to generate rAAV vector. The candidate rAAV vector is injected into the lateral ventricle of the A53T PD mouse model to evaluate its effect. The rAAV9-CAG-G11-hGH can significantly relieve the motor deficiency in the PD mouse model and reduce the levels of $\alpha$-syn and phosphorylated $\alpha$-syn in the Nigro-striatal pathway indicating its potential in treating PD and other $\alpha$-syn proteinpathies.

SEQUENCE INFORMATION

| SEQ ID NO | TYPE | SEQUENCE | CODE NAME |
|---|---|---|---|
| 1 | DNA | ATGAACGCCAGCGAGTTTAGAAGAGGAGGCAAGGAGGATGTGGATTACATGGCCAATTATATGGAGGGCATCGAAGGCAGACAGTGTATCCTGACGTGGAACCTGGATATCGAGACCTTACTTCTTCGCCTACTTTCCCACCGCCAGCAGGTGGCCCAGCAGCTATCCCGCCATGCTGGCCAAGATGCTGCCCAAGGACGTTCTCCCAGGCGAGGGCGGCGGAGTGATTCAGGGATCCGTAGCGAAGCCCACCAGACGGCGGCGCCCGCCGCTATAGCAGCCATCAGGCCCACAGCAGCAGCGGCCGCGCGTGGAGACGAGCCGCCGGCGCAGCAACCTGCTCAGCCTGGAGTGGGAACCTCGGAGCCCCATCTGCAACAAGGAGGACATCTGGCTGCACCAGCACCTCGGCATGGCTTAACTTCAATCCCCAAGAGCTGTGGTGAATTTGACTGCAGCGCCATGTGGGTGAAGAAGAGGACCAGCCCTTCGTTCAGGGAGATCCTAGATTTGAAATCTGTGTGGAGGTGATCCTGGGCCTGGTGTTTAGACTGAAGGGAAGCAATAAAGTGAACGAAGCCTTGCTGCGAGGATCAATAGCGCCCGAGAGAATTCACCTGGTGCTGCTCGACCTGCTCGAGGAGATTCACCTGTCCACCTGACCGCCTGGAGAGCCACGACGTGCTGAGAGGGAGTGA | AADC-A1 |
| 2 | DNA | ATGAACGCCAGCGAGTTCCGGACACGGGGCAAGGAGACGATGTGGACTACATGGCCCAACTACATGGAGGGCATTGAGGGCAGACAGTGTACCCCGACGTGGAGCCCGGCTACCTGAGACCTCATCCCTGCCGCCCGGCCGGCCGCACGTGCTGGCCGCCAGTATCATTAACGACGTGGAGAAGATTATTATGCCCGGCGTGACCCACTGGCACTCCCTTACTTCTTCGCCTACTTCCCAACAGCCTCAGTACCGGCGCCGCTCCCAGCGTGCTGGGCGCAAGATGCTGCCCAAGGACGTTGGCCGGGCTGGCTGGGCTGCCCGCCGCCAGCTCTGGAGATCCTGGGCGGCGGCGTGATCCAGGGCTCGCAGGGCTCTGGAGGCGACGCCCACTTCTCGCTCATTGGCGCAGCCCCTGACGCCGGGCCATCCCTAGCGGCGCCGGCGACCAGCCTGACTGGCTGGTGCCACCATCAGCGGGCACCAGCTCCAGCGCTGGGCAGCGCAACTTGCCGACTCTTTCAACTTCAACCCACAAGTGGCTCCTGGTGAACTTGACTGCGCAGCGCCATGTGGGTGAAGAAGCGCCTTCACTGGCGGCCTTCAGGAGCCCGCGGTGCTGCTCAGACTGAAGGGAAGCACGTGACACTGGCAGATTCAACTGGGCAGGGATGTACGGCGTGAAGGGCTCTCAGGCCTACATTAGAAAGCACCTGCAGCTGTCTCACGAGTTCGAGTCTCGAGTGCGCGGCAGGATTCCTGGTGGCCTTGCCACCTGCTGTTGTGCTCAGACTTCGTGCTGCCGGTTCGCCATTTGCTCAAGGACAGTGGAGCTGCCCTGCTGCAGCGGATTAACTCTGCCAAGAGAATTCTGCCGACTCTGGCTACGCGCCATGTGGGAGTGGCGAGGAGCCTGGGGAGCTCGGGTTGTCAGAGAATTCCAGATTTGCGTGGAGGTGAATTCCGGGGAGAGCCCGAGAGCGCCGAGTGA | AADC-A2 |
| 3 | DNA | ATGAACGCCAGCGAGTTTAGAAGACGGGGCAAAGAGATGGTCGACTACATGGCCAATTACATGGAAGGCATCGAGGGCCAGGCAGGGTGTACCCTGATGTGGAACCCGGATATCTGAGACTTCTGATTTCCCGCTGAGCCTACCAGCAGTCCCTACAGCGGCCCCTATTTCCCTACAGCGCCATGCTGGCCAAGATGCTGCCCAAGGACGTTGGCGCCCTCCCCAGCGTGCTGGGCGCCAGCATCATCAACGACGTGGAGAAGATTATCATGCCCGGCGTGTGGTCCGCCATCGGCTTCAGCTGGGGCGAGGGGGGAGGAGTGATCAAGGGCTCCGGCCTTACAGCGAGGCGACCAGAGGCCTGAAAGAGATAAGGGCCGCCGACTCATCCCGTTCTTCATGGGTGGGCCACACTGGGTACAACTCTGGAAAGAAATTTGCCATGGCGGCCCCGGACTCATCCCGTTCTTCATCGGTGGGCCACACTGGGTACAACTACTACTGATCGCCAACCTGCTGAGCAATGAGGCCATCTTCAACCCCACAAGTGGCTGCTGGTGGCCTCAGCCTGATCAGCGGCTATAGCGGCCTGCAAGCCTACATTAGAAAGCACCTTCAGCTGACCACCTTTGAGGCCCAGTGTCACCCCCAGCCCGCTGTTGTGCTCAGACTTCGTGCTGCCGCTGGAATCGGGCGGAATGA | AADC-A3 |

-continued

SEQUENCE INFORMATION

| SEQ ID NO | TYPE | SEQUENCE | CODE NAME |
|---|---|---|---|
| 4 | DNA | ATGAACGCTAGCGAGTTCAGACGGAGGAGGCAAGGAGATGTGGACTACATGGCCAACTACATGGAGGGCCATCGAGGGCCAGACAAGTGTACCCCGACGTGGAGCCC GGGTACCTGAGACCCCTGATTCCTCGCTACTTCCCCACCGCTAGCAGCTACCCGCCATGCTGCCCGACATGGCTGGAGATGCTGGGCCAGAAGCTGGCGAAGGC GCCGCTAGCCCGCCTGCACCGAGCTGCACGCGCTAGCGAGCTACACTGTGGCCGCCTAGCACTGTGGCCCCTAGACTGTATCCACAGACTGCGCCTGAGCTGACC GGGGGGTGATCCAAGGCAGCGCTAGCGAGCGCTACAGCTGGTGGCCGCCTACAGCGACCAGCCCTGCAAGACCCTGAAGGCCATCCT CAAGCCGCCATCATGGAGAAGTCGTGCTGGCTACAGCAGCGACCAAGCCCACAGCAGCCTGGAGAGAGCCGCCGGCCTGATCCCCTTCTTCATGGTGGCCACCCTGGGCACC AGCGACGCGCAACTTCGCCATGAGAGCTTCGCAGCTTCGCACCATGGAGCTTCCACCACCACCACCTGTTTCTTCATGGTGGCCACCCTGGGCACC TGCCCGAGTTCAGACACCTGCTGGACAACGTTGCCGACAGCTTCAACCTCAACCCCACCAAGGTGTCGTGGTGAACTTGACTGCAGCCGCCATGTGG GTGAAGAGAGAACCGACCTGGCAGAAGATTCAGAAGCCTGAAGATGTGTTCGTGTTCTTCAGAATCAGCGCTGCCTGCACGTCCTGGTGGCCGAAGCACTGGCAG CACGAGTTCGAGAGCCTGGTGAGACAAGACCCTAGATTGCAGATCTGCCTGCCCACCTGAGGCTGTCTTCAGACTGAAGGCGCAGCAACAAGGTGAAC GAGGCCCTGCTGCCAGAGATCAACACGCCTGCAAGATCAACACTCGTGCTGCCAGAGTTCGTGCTGAGATTCGCCATCTGCCAGCAGAACCGTG GAGAGCGCCCACGTGCAGAGAGCCTGGGAGCACATCAAGGAGCTCGAGAGCGCCGAGAGAGACTGA | AADC-A4 |
| 5 | DNA | atgaatgctcagaattccgcaggaggggtaaggagatggtggactacatggccaattatatgaaggcatcgaaggtcggcaggtgtatcctgacgtggagccc ggctacttgagaccccctgattcccgcgacgccccagaaccggacacatttgaggatatcatcaatgacgctgagaagaatcatcaatgccggtgagactcat tggcactcaccgtacttttttgccctattttccgactgccctatccctgctggatggctggagaaagtgcttgagctgcccaagactgcaagactgcaactttcc gcagcatccccgccgtgaccgagctgcacgcgctggagaagatgcttgagctgcccaagcttgaatgaaaagctggcgaggggg ggcggcgtgatcccagggtctgcaagtgaagccactctggctcgaccaccagcgacaaaagttattcacagactgcaggccgcctcacctgactgacg caagcagccatcatggaaaagctgtgtggcctattcttccgaccagccacaggcgataaagctgcagtgggcttatggaggtgtgaaacttaaagctatcct tcagacgggtaatttgcatgcgccgccttcgccccctgcaggaggcctgggaacgcgcataaagctgcagtgggcttatggaggtgtgaaacttaaagctatcct actacctgttgcagcttggataaactgctggagtgggccctatttgcaaacaagaggatatctggctcgacagtgcactgcacctgactggttctgccttcatc gtgaagaaaggactgacctggcctggcgcttccggcttcggcctccggaacctcaccaagtggttgctgtgaacttcaccaagtggttgctctgacagacattggcag attcctctcggcagaagctcaggagtcctgaaaatgtggttcgtgtttcggatgacgggtgaaaggtctgcaggcctatatccgcaagcacgtgcaactttcc catgagttcgagtcctcgttcggcaggatccctgcttgagatctgtgtggaggtcattctggggctggtgcttcaggctgaaggcagcaacaaagtgaat gaggcttgcttcagaggatcaactctgccaaaagatccacttggtgccctgccatctgagggacaagctgcaggtctgaagcaagtgctattgttccagaactgtt gaaagtgcacacgtgcaacgggcgtgggagcacatcaaagaactggcgcaggcactgcccgagagggagttgcagagggagagggagTGA | AADC-A5 |
| 6 | DNA | ATGAACGCCAGCGAGTTTAGAAGGAGGAGGCAAAGGAGATGGTGGATTACATGGCTAACTACATGGAGGGGGATCGAGGGGCAGACAGGTCTTACCCTGATGTGGAGCCT GGCTACCTGAGGCCCCTGATCCCTGCCCGCCGCCTGCCCCGTGCCCCCACAGGAACCAGATACTTTTGAGGATATTATTAACGATGTCGAGAAGAATATTATTATGCGCAGGAGTGACACAC TGGCATAGCCCCTACTTCTTTGCTTATTTCCCACAGCTAGCTCTTACCCTGCCAATGTTGGCTGGAGAAATGTGCTGGCTGTGATATCGTCGCGCCATTGGCTTTAGTTGG GCTCGAGTCCTGCTGCACAGAATTGGAGACCGCCAGCACCTCAGGAGCCACCCTGAGCGACCTCGTGGCTGAAAGATCGTGAGCAAGAAGGCCGGCGAGGGG GGCGGCGTGATCCCAGGGGAGCGCCACCTGTGGCTACAGCGCCTACAGCGACCTGCCCTGGCCCCGCCACCCCAGAGCTGCGCCTGTGCCAGAGCTGACA CAGCACGGCAACTTCGCCATGAGAGCTTCGCCATGAGAGCTTCGGTGGCCTACAGCTCCGACCAGGCCAGCCGGGCCTGGTGAGGCCGTGAAGGCCATTCCC TCAGAGCGGAACTTCGCCATAGCTTCGATAACCTGCTGGAGGTGGGCAATCTGCACGTGGATGCGTCGACGTTGGATGCCGTCGACAGCTGGGCTCGGGGTCCGCCTTCATT ACCACATGCTGTCCTTCGATAACCTGCTGGAGGTGGGCAATCTGCACGTGGATGCGTCGACGTTGGATGCCGTCGACAGCTGGGCTCGGGGTCCGCCTTCATT TGCCCCGAGTTCCGGCACCTGCTGAACGGCGTGCCTTTAGGCTTCCCGATAGCTTCAACCCCACCAAGTGGTTCAACCCCACCAAGTGGTTGTGGCTGAACTTCGACTGCAGCCGCCATGTGG GTGAAGAAGGAGGACCGACCTGGCGCTTTAGGCTTCCGGAAGATGTGTTCGTGTTCTTCCGGATCAGCGGCTGCCTGACAAGCTCCAGCAGCTGGCAGCACTGGCAG ATCCCCCTCGGCCAGGCGGTTCCGGTTCCTGAAGATGTGGTTCGTGTTCCGGATCTACCGGAAGCACGTGAACGGCGTGGGGAGCCACATCAAGGGTGAAC CACGAGTTCGAGAGCCTGGTGAGACAGACCCTGGACATCTGCCTGCCCACCTGAGGCTGTCTTTCCGGCTCCAAGGTGAAC GAGGCCCTGCTGCCAGCCGATTAACCTCCGCCAAGAGAATCCACCTGGTGCTGCCCACCTGAGGGATAAGTTCGTCTGCGCACCTGAGGGATAAGTTCGTCTGCGCCATTTGCAGCAGGACAGTG GAGAGCGCCCACGTGCAGCGGGCCTGGGAGCACATTAAGGAGCTGGAGAGCGCCGAGAGGGAGTTGCAGAGGGAGTGA | AADC-A6 |

-continued

SEQUENCE INFORMATION

| SEQ ID NO | TYPE | SEQUENCE | CODE NAME |
|---|---|---|---|
| 7 | DNA | ATGAACGCCAGCGAGTTCAGACGCGAGGGGCAAGGAGATGTGGACTACACATGGCCAACTACACATGGAGGGCAGACAGTGTACCCCGACGTGGAGCCC<br>GGCTACCTCAGACCACTCATCCTCGCCCTACTTCTCCAACAGCCTCTAGCTACCCAGCCATGCTCGCCGACATGTGTGCGGCCGCCATGGCTTCTTCTTGG<br>GCCGCCTCCCCAGCCTGCACCGAGTTAGAGACAGTGCTGGGCGAAGATGCTGGGCCAAGATCGTCGAACGAGAAGGCCGGCGAGGGC<br>GGCGGCGGTGATCATGGAGAAGCTGGTGGCCTACTCTAGCGACCAGGCCCACTCTTCTGTGGAGAGAGCCGGCCGACCTGAATCCTTTCTTCATGGTGGCCACACTGGGCACC<br>CAGGCCGCCATCATGGAGAAGCTTCGCCATGAGACCGAGGCCCTGAACGGACAAGGCCGGCCGACCTGAATCCTTTCTTCATGGTGGCCACACTGGGCACC<br>TCTGACGGCAACTTCGCCATGAGAGCCGGCCGACCTGAACGGACAAGGCCGGCCGACCTGAATCCTTTCTTCATGGTGGCCACACTGGGCACC<br>ACAACATGCTGCTCTTTCGACAACCTCCTGGAGGTGGGCCCAATTTGCAACAAGGAGGACATTTGGCTCCACGTGGAACCTGCTCTGCCTTCATT<br>TGCCCTGAGTTCAGACACCTCCTGGAGGTGGAGTTCGCCGACTTCAACTTCAACCAAGTGGCTCTCGTGGAACTTGCTCTGCCTTCATT<br>GTGAAGAAGGCCACCGACCTGACCCGGCCTTCAGACTGGCATGTTGGTTCGTGTTCAGAATTGCGTGGAGGTGATTTCTCGGCCTGATAAACTGCGCCTTTATT<br>ATTCCACTGGGCAGACGGTTCCGGAGTCTTCGTTGAGACGACCCTAGGTTCGTGTTCAGAATTGCGTGGAGGTGATTTCTCGGCCTGATAAACTGCGCCTTTATT<br>CACGAGTTCGAGTCTTCTCGTTGAGACGACCCTAGGTTCGTGTTCAGAATTGCGTGGAGGTGATTTCTCGGCCTGATAAACTGCGCCTTTATT<br>GAGGCCCTCCTTCAGCGGATTAACTCTGCCAAGAGATCCACCTCTGGTCCTGCCTTTGCTGTGCTGCAAGTTCGTGCTGCGGTTCGCCATTTGCTCCCGTACAGTG<br>GAGTCTGCCCACGTGCAGCGCCTGGGAGCACATTAAGGAGAACCTCGCCGCCGACCTGCTGAGCGCGACTGA | AADC-A7 |
| 8 | DNA | ATGAACGCCAGCGAGTTCCGGAGAGGGGGAAGGAAGGAGATGTGGACTACACATGGCCAACTACACATGGAGGGGAGCAGCAGGTGTACCCCGACGTGGAGCCC<br>GGGTACCTGAGACCCCTGATTCCCGCTGCCTCGCCCTACTTCTGAGGACAACACTTCAACGACGTGGAGGACGTGGAGAAGAGAGATCATTAACGACGTGGAGGACGTGGAGAAGATCATTATGGCCAGGCGTGACCCAC<br>TGGCATAGCCCCTACTTCTTTGCCTACTTCCCCACAGCCTCCATACCCCGCTCGGCTGGGCAAGGCCTTCCTGAAGAGAAGGCCGGCGAGGGC<br>GCTGCTTCTCCGCTTGCACCGAGCTGAGAGACCGTGATGATGGACTGGCTGGGCAAGATGCTGGAGCTCCGTGGAGAGAGGCCGGCGAGGGC<br>GGAGGCGTGATCATGGAGAAGCTGGTGGCCTACTCTCCGTGGAGAGGGACCAGGGCCGGCCGTGAAACTGAAGGCCATTCCC<br>CAGGCTGCTATCATGGAGAAGCTGGTGGCCTACTCTCCGTGGAGAGGGACCAGGGCCGGCCGTGAAACTGAAGGCCATTCCC<br>TCCGACGGCAACTTCGCTATGCGGGCCAGCGCCCTGGAGGTGGGCCCCATTTGCAACAAGGAAGGACATTTGGCTGCACGTGGCTACACTGGGCACC<br>ACCACCTGCTGCTCCTTTGATAACCTGCTGGAGGTGGAGTTCGCTGACTTCCTTCAACCTCAACCCCACAAGTGGCTGGTGAACTTGCTGGTGGTGGTTGGTGGTGGTGTTCTGCCATGTGG<br>GTGAAGAAGGGACCGACCTGACCCGGGCCTTCCGGCTGAAATGTGGTTTGTTGTTCAGAATGTGGTTTGTTGTTCAGAATGTGGTTTGTTGTTCAGAATGTGGTTTGTTGTTCAGAATGTGGAGCCGAGC<br>ATCCCCCTGGGCAGAAGATTCAGAGCCTAGATTGCCTGAGACCCCAGATTTGAAATCTGCGTGGAGGTGATTTCTGAGACTGAAGGTGAAC<br>CACGAATTCGAGAGCCTGGTGAGACCAGGACCCCAGATTCAGCCAAGAGATCAACCTGGTGCCCTGTCACCTGAGAGACCAAGTTCGTGCTGAGATTCGCCATCTGCTCTAGAACAGTG<br>GAGGCCCTGCTGCAGGGGATCAACTCAGCCAAGAGATCAACCTGGTGCCCTGTCACCTGAGAGACCAAGTTCGTGCTGAGATTCGCCATCTGCTCTAGAACAGTG<br>GAGAGCGCCCACGTGCAGGAGAGCCTGGGAGCACATCAAGGAGAACCTGGCCGCCGACCTGCTGAGCGCCGAAAGAGAGTGA | AADC-A8 |
| 9 | DNA | ATGAACGCCAGCGAGTTTCGGCGAGGAGGCAAAGAAATGTGGACTACACATGGCCAACTACACATGGAAGGCATCGAGGGCCAGACAGGTGTACCCCGATGTGGAACCT<br>GGCTACCTGAGCCCTGATTCCTGCCCGCTGCTCCCCAAGAGCCTGACACCTTCGAGGACATCATCAACGACGTGGAAAAAGATCATCAACGACGTGGAAAAAGATCATCATGGCCCGCGTGACCCAC<br>TGGCACAGCCCCTACTTTTCGCCTACTTTCCCACCGCCAGCTACCCTGCTATGCTGGCTGATATGCTGTGTGGCCGCCATCGGCTTTTCTTGG<br>GCTGCTTCTCCTGCCACCGAGCTGGAAACCGTGATGATGGACTGGCTGGGCAAGATGCTGGAAGCTCCTGAAGGAAAGGTGGCGAAGGC<br>GGCGGAGTGATTCAGGGATCTGCCTCTGAAGCCAACACTGGGCCGCGATGATGGACTGGCTGGGCAAGATGCTGGAAGCTCCTGAAGGAAAGGTGGCGAAGGC<br>CAGGCCGCCATCATGGAAAAGCTGGTGGCCTACAGCAGCGATCAGGCCCACAGCTCTGTGGAAAGAGCCGGACTGAATCCCTTTTTCATGGTGGCCATTCCT<br>AGACGGCAACTTCGCCATGAGAGCCGGCCGATCTGAACGGCCAGGCCCGCTGAAAGAGAATAAGGCCGGACTGAATCCCTTTTTCATGGTGGCCATTCCT<br>ACCACCTGTTGCAGCTTGACAACCTGCTGGAAGTGGCCCTGCTGGAAGTGGAAACAAAGAGAATAAGGCCGGCTGAAAGAGAATAAGGCCGGACTGAATCCCTTTTTCATGGTGGCCATTCCT<br>TGCCCGAGTTCAGATCTGCTGAACGGCGTGGAATTCGCCGACTTCAACTTCAACCTCAACCCTCCACCAGGATAGGCGGCCTGGCTGGTCAACTTCGACTGAGCCTATGTGG<br>GTCAAGAAGCGGACCGACCTGACCGGGCCTTCAGATGGTGGTTCGTGTTCCGGAATGTGGCTGGATAGCGCCTGATCACCGACCTACACCGACCTGCAGCTGGCAG<br>ATTCCTCTGGGCAGAGATTTCGAAGATGTGGTTCGTGTTCCGGAATGTGGCTGGATAGCGCCTGATCACCGACCTGCTTTAGACTGAAGGGCCAACAAAGTGAAC<br>CACGAGTTCGAGAGCCTTGCTGCAGAGACCGTGGTGGAAGTGATCTCGGGCCTGCTTTAGACTGAAGGGCCAACAAAGTGAAC<br>GAGGCCCTGCTGCAGGGGATCAACGCGCCAAAAGATCCACCTGGTCCTGTCACCTGAGAGACAAGTTCGTGCTGAGATTCGCCATCTGCAGCCGGACAGTG<br>GAAAGCGCCCACGTGCAGGAGAGCCTGGGAGCACATCAAGGAGAACTGGCCGCCGATGTGCTGAGGGCCGAGAGAATGA | AADC-A9 |

-continued

SEQUENCE INFORMATION

| SEQ ID NO | TYPE | SEQUENCE | CODE NAME |
|---|---|---|---|
| 10 | DNA | ATGAACGCAAGTGAATTCCCGAAGGAGGAGGAGGAGATGGTGGATTACGTGGCCAACTACATGGAAGGCATTGAGGGAGCACGCCC GGGTACCTGCGGCCCGCCTACTTCTTCGGCTACTTCCCCACTGCCAGCTCGATCCGTGCTGACGCTGATGCGCCTGCTGGGTGACGGAC TGGCACAGCCCCTACTTCTTCGCCAGAGCTGAGACTGCTGGATGGACGTTGCGGACATGCTTGCGGAACTACCAAAGGCATTTTGAATGAGAAGCTGGAGAAGGG GGAGGAGTGATCTCAGGGAAGTGGCCAGTGAAGCTGGCTTACTCATCCGATGAAGCCTCAGTGGAAAGAGCTGGGTTAATTGGTGGAGTGAAATTAAAAGCCATCCCC CAGGCCGCTATCATGGACGAACTTCGCCATGGCGTGCTGTCGCCCTGGAGAGAGACAAAGCGGCTGGCCTGAATTCCTTCTTTATGGTTGCCACCCTGGGGACC TCAGATGGCAACTTCGCCATGGCTTTGACAAATCTTTAGAAGTGCGGTCCTATCTGCACAACAAGGAAGACAATATGGCTGCACGTTGATGCAGCTACGGCAGTGCATTCATC TGCCCTGAGTTCGGCACCTTCTGAATGGAGTGGAGTTTGCAGATTCAATTGGCTATTGGTGAATTTGACTGTTCTGCCATGTG GTGAAAAGAGGAACAGACTTAACGGGAGCCTTTAGCACTTTGAAAATGTGGTTGTATTTAGGATGTATGGAGCTCAAGGACTGCAGGCTTATATCCGCTAAAGGGTTCAACAAAGTGAAT CATGAGTTTGAGTCACTGGTTGCGCCTCAGGATCCCCGTTTGAAAATCCTGGCTTTGCACGTCACCTGCAGCAAGTTGTCTCCATCGTTTTGCCATCTGTTCTCCGCACGGTG GAATCTTGCCCATGTGCAGCCCATGTGCCGGAACATCAAAGAGCTGGCCCGGAGCCAGAGGACGGACTAG | AADC-A10 |
| 11 | DNA | ATGAACGCAAGTGAATTCCCGAAGGAGGAGGAGGAGATGGTGGATTACGTGGCCAACTACATGGAAGGCATTGAGGGAGCACGCCC GGGTACCTGCGGCCCGCCTACTTCTTCGGCTACTTCCCCACTGCCAGCTCGATCCGTGCTGACGCTGATGCGCCTGCTGGGTGACGCAC TGGCACAGCCCCTACTTCTTCGCCAGAGCTGAGACTGCTGGATGGACGTTGCGGACATGCTTGCGGAACTACCAAAGGCATTTTGAATGAGAAGCTGGAGAAGGG GGAGGAGTGATGATCTCAGGGAAGTGCCCAGTGAAGCTGGCTTACTCATCCGATGAAGCCTCAGTGGAAAGAGCTGGGTTAATTGGTGGAGTGAAATTAAAAGCCATCCCC CAGGCCGCTATCATGGACGAACTTCGCCATGGCGTGCTGTCGCCCTGGAGAGAGACAAAGCGGCTGGCCTGAATTCCTTCTTTATGGTTGCCACCCTGGGGACC TCAGATGGCAACTTCGCCTTGACAATCTTTAGAAGTGCGGTCCTATCTGCACAACAAGGAAGACAATATGGCTGCACGTTGATGCAGCTACGGCAGTGCATTCATC TGCCCTGAGTTCGGCACCTTCTGAATGGAGTGGAGTTTGCAGATTCATTCAACTTAATCCCCAGAGCTTAATGGCTATTGGTGAATTTGACTGTTCTGCCATGTG GTGAAAAGAGGAACAGACTTAACGGGAGCCTTTAGCACTTTGAAAATGTGGTTGTATTTAGGATGTATGGAGCTCAAGGACTGCAGGCTTATATCCGCTAAAGGGTTCAACAAAGTGAAT CATGAGTTTGAGTCACTGGTTGCGCCTCAGGATCCCCGTTTGAAAATCCTGGCTTTGCACGTCACCTGCAGCAAGTTGTCTCCATCGTTTTGCCATCTGTTCTCCGCACGGTG GAATCTTGCCCATGTGCAGCCCATGTGCCGGAACATCAAAGAGCTGGCCCGGAGCCAGAGGACGGACTAG | AADC-A0 |
| 12 | DNA | ATGGAGTTCAGCTCTCCCAGCAGAGAAGAATGTCCTAAGCCTCTGAGCAGGTGTCCATCATGGCCGGCGACTCCTGCTCCTGCAGGCCGTGAGC TGGGCCAGCGGCGCCAGGCCTTGCATTCCCAAGAGCTTCGGCTACGACGCGTGGTGCAGCGTGTGCAATCGCACAGGCTTCCTCTACCTTT CCTGCCCCTGGGGAACATTCTTCCGGGTACGGAGCAGCCCAGGAGAGCGGCCGGAGAATGGACGTGAGCATGGAACATCCTGCCCTGTCAACATCCTGCCTCTGCCCAG CTCACCCTGGAGCGAGTTCAGAAGGTGAAGGGCTTCAGAAGCCATCCGGTACACGCCTGCCGTCTGAACATCCTGGCCCTTCTGGCGATTTAGCATTAGGAACATACCTACGCC AACCTCCTGCTCAAGAGCTACTTCAGCGAGGAGGGGCATCCCATGGCCCATGGCCTACAAACATCATCAGAGTGCCCATGGCCGACTTTAGCATTAGGACATATACCTACGCC GATACACCTGATGACTTCAGCTGCATAACTTTAGCCTGCCTGAGGAGGATACCAAGCTGAAAATCCCTGATCCATCGCGCCCTGCCAGCTGGCCCAGAGACCT GTGTCCCTGGGCTGGCCAGTTGGCTATTTTGTGAAATTTGTGAATGCCAAGACGCTGAGTGTGAGATAAGGCAGCCTGGCGATATCTATCAC CAGACCTGGGCTAGGCCAGGTATTTTGTGAAATTTGTGAATGCCAAGACGCTGAGTGTGAGATGAGGAATGAACCTTCTGCGGACTGTTG AGCGGCTGCTAGTCCCTTTCAGTGTCTGGGATTCACCCTGAGCATTCACCCTGAGCAACGTGTGTCTGACCGACGCCAAGGTACGTGACCGGCATGCGCGTGCAC TGGTACCTGGAGACTTCCTGGTCTCCAAGGCCACCGGGCCGAGAACCCCATTCCTAACCATGCTGTTCCTAACCACATGGCTGTACCACCGACTGTGG TTCTGGGAGCAGTCCGTGAGGCTGGGAAGCTGGGACAATGCAGTCAGTCAACGCCACAGACCCTATCACCACGTGGTGTACCACCGACTGTGG AACCTGGCCCTGAACCTGAGCCGCCCAAACTGGGTGCGCCCAAACTGGGTGCTGCAACTTCGTGGACAGCCCTATCATCGTGACAATCAGAGTGCACATCAGCAGCCATG TTCTACCACCTGGGCACCTTCAGCAAGTTTATTCCTGAGGGCAACCGCAGCAGCAAGGACGTGCCCCTGACCATCAAGGATCCTGGGCTTCCTGGAGACCATCAGCCCTGGC CCTGATGGCAGCGCCTCGGTTGGTTCTGAAAGGTGATACAGCCAGCAAGGACGTGCCCCTGACCATCAAGGATCCTGGGCTTCCTGGAGACCATCAGCCCTGGC TACAGCATCCACACCTACCTGTGTGGGAGGACAGTGA | GBA1-G1 |

-continued

SEQUENCE INFORMATION

| SEQ ID NO | TYPE | SEQUENCE | CODE NAME |
|---|---|---|---|
| 13 | DNA | ATGGAGTTCAGCTCCCATCTAGGGAGGAGTGCCCTAAGCCACTGAGTCCGTGTCTATTATGGCCGGCTCTCCTGCTCCTGCAGGCCGTGTCTTGGGCCTGGCGCCAGACCTTGCATCCCAAAGTCTTTCGGCTACTCTAGCGTGGTGCCGTGTGCAACGCCACCATACTGCAGGCCCACCACCTTCCCCGCCTGCAGCCAGAAGTTCCAGAAGGTGAAGGCAGTGTCCATAGGACGATCCATCCGGGTGCCGTGCCCGCCGCCCTGTCCCCCACCGCCCAGAACCTGCTCAACCTGCTCTTACTTCAGCTCTTACTTCCAGCGTGCACAACTTCAGCCTTCCCGAGGAGGACACAAAGCTACACAACATCATCCGGGTGCCTATGGCCCTATGGCCCTGCTTGCGACTTCAGCATTAGAACATCACATACGCCGACACACCTGACGACTTCCAGCTGCACAACTTCAGCCTTCCCCTTGGACATCTCCAACATGGCTGAAGCCGCCGTGAACCGGCACAAACGGCCCGTGAACGACCTGTGGGGCTGGCAGGGCTCTCGAAGGGCCAGCCAGGCGACCATTTACCACGTGTCTTCGTGCCTGCCTCCCTTTGGACATCTTCGTGAAGTTCGTGACGCCCTGAGCACCTACGCCCAGGACGTTCAGTTCTGGGCTGCAGCCCTACACTCGCCAACTTCAACCACAAGTGAGACTCCTGATGTCCGACTTCCCGGCCTTCAGGCCCCTTTCCACTCATCCCACTGGGCTGGCGTTTCATTGCCGCAGAGCTTCAGGTAGTCCTACGCTGCTCTGACTGGGCCAGGTACCTCCGGTCTGCCCCTGCCACTGCTTGTGGAGGCCCATCCGTGCTCCTGGGGCGAGCATCGGGCATGCCTCATTGCGGGCCTCAGGGTGAGGCCCTTCCCTTAACCCCGATATAAGGTGCGGGGCCTCTGGTGGTGTCTGAAACAGATCTCTCAACAGTTCATCAATCCCCGAGAGAGTGCCCACTGACGCCGAAGGTGGTGTGTGCTGGGGGTCGAACAGATCTCTCAAGATTCGCTTCAATCCCCGAGAGAGTGCCCACTGACGGAGCTGAAGGTGGTGTGTGCTGGGGGTCGAACCCGCGAGGACCCCAATTATCCTGGATAGCCCTACTATACAAGCAGAGCAGACAGGAACACCTGATGCACTGACGACTTCAGCATCTGTACAACGGTCAGCAGGCTGTGTTTTACACCCTGGATCCCCTTCATCAACCGTGTTCCCAACTGGTGTTTACCCCCCCTGAACCTGGGGACACCCCCAGGGTCTCCGGGCTTCAGCTCTGGACGCGATTAGCCTTTATCTGTCCCTTCTCCTGCACTTCTCCAAGTTTATCCCTGAGGGCTCCCAGCCTGTTTACCCTGAAACAGATCTCCAAGATGTGCCCAGGTGTAGTGCCCCTGACTATCAAGAAGCGGTCAGCCAGGTTCCTGGAATTCCTGAAAACAATTCTCCAGGCTATAGCCATTCACACCTACCTGTGGCGGAGACAGTGA | GBA1-G2 |
| 14 | DNA | ATGGAGTTCAGCAGCGGGAAGAGAGTGCCCTAAGCCTCTGAGCCCAGTGTCCATCATGGCCGGTTCCTGCTGCTTCCTGCAGGCCGTGTCTTGGGCCAGCGGAGCCAGACCCTGCATCCCAAAGTCTTCGGCTACTCTCGGCGTGTCGTGCCGTGTGCAACGCCACACTGCAGGCCCACCTTCCCCTGCCTTTCAGCTACAAGATCACCGGCTTCGGCCGGGTTCCTATGGCCCTATGGCCCTGGAAAGCGCTGAACCGGCACAAAAGGGCCCGTGAACCTGCCTGAGCGAGCGGATGGGCGCCAGAGCCTTCAGCCTGGACCAGCCCTTCCTTGGACTTTCTGGACGTCCCTGCTGTGGCTTTCTTCCTGCACCTGCCTTCGCACCTTATCAACATGGCTGTGCTTCTGGACGCGGGGCCCTGGCCAGCCAGAGACCTGTGTCCCGTGGCTTTCAGCCTGACTGTCCGGAGGGCTCAAAACAAACAGGCGCCGTTGGAGATATCCATCCGGGTGTCTGGCCAGCCAGAGACCTGTGTCCCGTGGCTTTCAGCCTGACTGTGCCCCAGAAGCGGACAAACAGGCGCCGTTGGAGATATCCATCCGGGTGTCTGGCCAGCCAGAGACTGTGTGCTGTCGCCGAGCTCTCATCGCCCAGAGATCTGGCCCCTGCGCCCAGTCTTCGCCGGACTCTGCCGACTGGGCTGGCATCGCCGTTCACTGGTTACCTGGATTTTCTGGCCCCTGCAAGGCCACGCTGGGCCCTGCTGCTGGGCCACGCTGGGCCCTGGGCATGCCTCATTGTGGTGGGCTGGAGCAGACTGGTTCTGGGCACAGAGGCAATGCCTCAGATAGCCCAATACAACCTTCTATCATCACTCTATCATCATTGCCTTACTCAAGTGTTTCGCCGCCCATCACCACCAGTTGGCATCCAGACACCCCATGGGCCTCCCTTCTGCTTTCCCAGCCGGGTGGGCCTGGTTTTATCCCTGAGGGCTGCCCCAGCCCTGGACCTTCTCCAAGATTCGCTTCAATCCCTTTATCTGGACGCCTTCATCTCCTCCCAAGTTTCTGTCCCCCTCTGTGGTTATGGGCCTCTCCCACCTACAGATCTCCTGTGGTTATGGGCCTCTCCCACCTACAGATCTCCTCAAAACCTGTGTTCTGAGCTCTGAAGATCGTTCCCTGCTTCTGCACCTATGCCGACACACCTGCTGGCTCCTCCTTGGACCAGCCCTTCCTTGGACTTTCTGGACGTCCCTGCTGTGGCTTTCTTCCTGCCAGCCAACTGGTGGCCTCCTCTGGGGAGCAAATTCTGGGCTTTACCCTGAAGCTGCTGGGACGACCCCCAGGGTCCCCGACCCCCTTCATCTCTCGGGCTTTATCCCTGGATAGCCCCTGACTATCAAGAAGCTGCCCGACTATCAAGAAGCGCGTGGGATTCCTGAAAACATCAGCCCTGGC | GBA1-G3 |
| 15 | DNA | ATGGAGTTCAGCTCCCTAGCAGAGGAGTGCCCCAAGCCCCTGAGCAGAGTGTCCATTATGGCTGGCAGCGTGCTTCTGCTGCTGCAGGCCGTGAGCTGGGCTAGCGGCGTAGACCTGCATCCCCAAGAGCTTCGGCTACAGCGTGGTGCCGTGTGCAACGCCCACCCTGCAGGCCCACCTTCGACCTGCCCTGAGCGAGCAGATACCGACGCCCTGAGCGAGCAGATGGGCTTTGGGCCGGGTGTTTCAGGAGGTGAAGGCGGTCAGCATCCGGGCATGGGAGCTCGCTACAGCGTGGTGCCCCGCGTCAGAACCTGCTCCTGAGCGAGCAGATACCGACGCCCTGAGCGAGCAGATGGGCTTTGGGCCGGGTGTTTCAGGAGGTGAAGGCGGTCAGCATCCGGGCATGGGAGCAGATACCTGCTTTCAGCTACAAGATCACCGGCTTCGGCCGGGTGTTCAGCCTGACTGTGTGGCAGAAGCTGAACCGGCATGTGAAGAACCTGAAGGTGAAATATCCTGGGATAGCCCCATCAGTCAGCCAGCCAGAGACCAGCCCTGAGCGAGCAGATGGGCTTTGGGCCGGTGTTTGGGCCTGTCTGAAGATCGTTTGGGCTGTGAACATCAGCCCTGGCTGTGAACATCTTCATCGTCTAGAGAGACCTGAGAGACCTGAGCGAGCGGCTGTGGGGCTGGCAGGGCTGTGTGAGGCGCTACCCGTTTCAGTGCCGATGCTGGACCTTCTGGCCCCCTTCTGGGCCGGCCCACCTGGGCTTGTGGACGACTTCTGGCCCCCTTCTGGGCCCACCTGGGCATCAGCGAGCTGCGACCCCCTGCCCCCTGGGCGAGACCCCACAGACTGTTCCCCACAACCTGCTGGCTCCTCCTTGGACCAGCCCTTCCTTGGACTGTCCGGAGGGCCCAGCCTTCCTTGGACTTTCTGGACGTCCCTGCTGTGGCTTTCTTCCTGCCAGCCAACTGGTGGCCTCCTCTGGGGAGCAGATGGGCCATGCCTCATTGTGGTGGGCTGGAGCAGACTGGTTCTGGGAGCAGACTGGTTCTGGGAGCCAGCAGACTGCTGGGGGCTGGAGCAGACTGGTTCTGGGCACAGAGGCAATGCCTCAGATAGCCCATTATGGCCATTATGGCCATTATGGCCATTATGGCCATTATGGCTTTCCTGAGGGCTGCCCCAGCCCTGGACCTTCTGTCCCTTCATCTCTCGGGCTTTATCCCTGGATAGCCCCTGACTATCAAGAAGCGCGTGGGATTCCTGAAAACATCAGCCCTGGC | GBA1-G4 |

45

46

-continued

SEQUENCE INFORMATION

| SEQ ID NO | TYPE | SEQUENCE | CODE NAME |
|---|---|---|---|
| 16 | DNA | AACCTGGCCCCTGAACCCCGAGGGGGGCCCCAACTGGTGAGAAACTTCGTGGACAGCCCCATCATCGTGGACATCACCAAGGACACTTCTACAGCAGCCCATG TTCTACCACCTGGGCCACTTCAGCAGTTCATCCCCGAGGGCAGCCAAGGCCTGGCTAGCCAAAGAACGACCTGACGCGTGGCCTGATGCAC CCCGACGCAGCGCCGTGTCGTGCTGTGAACAGAAGCAGCAAGGACGTGCCCCTGACCATCAAGGACCCCGCCGTGGGCTTCCTGGAGACCATCAGCCCCGGC TACAGCCATCCACACACCTACCTGTGGAGAAGACAGTGA | GBA1-G5 |
| | | atggaatttagctcacctagccgggaggaatgcccaaaacccctctccccgggtgtccattatggctggacagccctctcttgcaagccgtcagc tgggcctctggggccggccatgtattccaaaatcctccggttactcatctgtggtctgtgtaatgtcaacgtactgcgactcattcgatccccccacattc ccagccctgggacgtttccccgtcacgaaagcactcggtctggcaggcggaatggaaacgtccatccaggctaaccacactggactgctg ctgacgctgcagcccgaacagaagttcagaaagttaaggggttccggcggcgccatgacatatcctggcgctgagccacctgcacag aatctgctgaaaagtcactcagtgagacaggagggatcggatacaatatcatccggacacacacagcgct gacactccagatgattccagctcataacttttctctcccgaggaggatacaaagctgaagatccatccgccatccgcctcagctggccagcgcccc gtatctcttcttgcgagccctggacaagtcctacagtctcctgatgctgatgcgtgcgccgaacacaagctgcagttctgggccgtgacggcagaaatgagcctctgctggcctgctt tctgttacacctttccagtgacctgttccaccgcagccaccagctgctggttctcatcgacatggctgaagcgcgcaagatgaagcacctcaaagtg cgccctgatgctgagtggatgaccgatcctccctcccacactgggcgaaacgcacagactacactgctaagtttgctaagtgtcttgcagttcctaag ttccgggaacagagcgtacgcctgggtcatgggacagcagggggaatcaatgtcgatattagcagcacattgctgagagcatccacactggctg aactggcctgaaccccgaggcgggggccccaactggtctggaagaaactttggaccagtccagtgacctcgagcagagcttgatgatgcggcatgtcac ccgacgcgaagtgcagttgttggtctgacctgaataggagagctcaaaggatgtccactgaccataaagacctcgggggcttcttgaaaccatttcccagggg tacagccatccacacctacctgtggcgacggcagtGA | |
| 17 | DNA | ATGGAGTTTAGCTCCCTAGCAGAGAGGAGTGCCCTAAGCCCCTGAGTAGAGTGAGCATTATGGCCGGCTCCCTGCTCCTTCTGCAGGCCGTGAGC TGGGCCAGCGGGCCCGGCCCTGCATCCTAAATCCTTCGGGTACTCCTGGTGGTTGGTGTGTGGTCAATGCTACCTACTGTGTGATTCCTTTGACCCCCCAACATTT CCCGGCCCTGGGCACCTTTAGCAGGTACGAGTCCACACGGTCCGGAGGAGGATGGAGCTTTGGCCATGGGCCCATTCAGGCCAACCACACCGGCACCTGGCTCCTG CTGACTCTGCAGCCCGAGCAGAAGTTCCGAAAGGTCCTACAAACATTATTTGGGTGCCTATGGCCAGCTTCTCCATCCGACATCACCTACGCT GATACACCCGATGACTTCCAGCTCCACAACTTTAGCCTGCCTGAGGATGCTACAAAGGGGCCCGTGAACCGGCCGTGAAGGGTCCCTGAAAGGGGCAGCCAGGCGACATCTACCAC CAGAGCCCCTCGGGCTACTTCGTGGAGTTCGTGGAATGCCTACGCCGAGCACAACCAGCTTCAGTTTTGCGGGGACTTTATTGCTCGGGACGTCCGGGACTTTAGTGCTCGGGACGTCC AGCGGGTACCCCTTCCAGTGCTGGGGTTTACACCAGAGCACGTCGGGTTCTGAACCTGTCCTAGACTGACCTGTTGCCAGCGAGGCCTGCGTGGGCTCCAAG AGGCTGCTGATGCTGGATGATCAGCGGCTCCTGCTCGCTGCCCCCACTGGGCTAAGGTGGTCCTGACTGCCGTTCCCTAACACAATGCTGTTTCCTACACGTGGTTTGGACCGACTGG TTCTGGAGCAGAGCCCGAGGGCGTGGGAGCTGGATGCCAGCCACAGCATTATCACCAGCACCTGCTTACCACAAAGGATACCTTTACAGCAGCCCATG TTCTACCACCTCGGGCACTTCTCCAAGTTCATCCCCGAGGGCTTCAAGGGCTCCAGCAAGGACGTGCCCCTGGCCCTGATGCAC CCTACGCGGAGGCGCCGTGTCGTGGTGCTGTGAACCGGCCGTCAACAATCAAGGACCCGCCGTCGGGTTCTCTGGAGACCATCAGCCCAGGC TACAGCCATTCACACATACCTGTGGGCGGCGCAGTGA | GBA1-G6 |
| 18 | DNA | ATGGAGTTCAGCTCTTCCATCTAGGGAGGAGTGCCCTAAGCCACTGTCTCTCCGTGTCTCCATCATGGCCGGCAGCCTCCTGCTCTGCGCAAGCCGTGTCT TGGGCCTCCGGCGCCAGACCTTGCATCCTAAGTCTTTCGGCTACTCTAGCGTGGTGCGTGTCAACGCCACATACTGCGACTCTTTCGACCCCCCACCAACCTTC CCCGGCCCTGGCACCTTCTCCGGGTACGAGTCTACACGGTCCGGGGCCGGCTGGTCGATGGGCCCATTCAGGCCAACCACACCGGCACCTGGCTG CTCACACTCCAACCGGAGCAGAAGTTCCGAAAGGTCCTGCAGACCATCTTCGGGTGCTACATTATCCGGGTCCTACAACATTATCCGGGTCCTATGGCCGACTTCTCTATTAGACATCACATACGCC AACCTGCTCCTGAAGTCTTACTTTCAGGAGGGCATTGGCTACAACATTATCCGGGTCCTATGGCCGACTTCTCTATTAGACATCACATACGCC GACACCCCGACGACTTCCAGCTGCACAACTTCAGCCTCCCAGAGGAGGACACAAAGCTCAAGATTCACCGGACTGTGAAGGGTCTCTGAAGGGCCAGGCCAGCATTTACCAC CAGAGCATGGGCCCGTACTTCGTGGAGTTCGTGAATTCTGCGACGCCAGCCACGGCCGAGCACAATCAGCTGCAGTTACAATTCTGGGCCGTGACGCCGAGCACAATCAGCTGCAGTTACAATTCTGGGCCGTGACGCCCTCCTG | GBA1-G7 |

-continued

SEQUENCE INFORMATION

| SEQ ID NO | TYPE | SEQUENCE | CODE NAME |
|---|---|---|---|
|  |  | TCTGGCTACCCTTTCCAGTGCCTCCGGCTTCACCCCGAGCACCAGCGGGACTTCATTGACGCGACCACCTCCGGCCAACTCTGCCCAACTCTACCCACCACAACGTG<br>AGACTGCTGATGCTCGACGACCAGAGACTGCTGCTCCCTCACTGGGCCAAGGTGGTGCTGACCAAGTGGTGCTGACCAAGCCCTGAGGCCGCCAAGTACGTGCACGGCATTGCCGTGCAC<br>TGGTATCTGGACTTCTGGCCCCAGCCAAGGCCACACTCGGCGAGACCACCAGACTGTTCCCAAACACCAATGCTGTTCGCCAGCGAGGCCTGCTGGGCCAGCAAG<br>TTCTGGGAGCAGTCTGTGAGACTCGGCTTCTTGGAGACCGCGGAATGCAGTACTCTCACTCTATCATTACAAACCTCTCTGTACCACGTGGTGGCTGGACCGACTGG<br>AACCTCGCCCTCAACCCCAGCGGGCCCTAACTGGCTGGCGGAACTTCGTGACCTCTCCTATTATTGTGGACAATCTACAAGCACACATTCTACAAGCAGCCTATG<br>TTCTACCACCTCGGCCACTTCAGCAAGTTCATCCCTGAGGGCTCTCAGAGAGTGGCCTCTGCAGAGTCGAGCAAGGTCGAGCAGGACCGTGCCACTGGCCTGATGCAC<br>CCCGACGCGGCAGCGCGTGTGGTGCTGACCAAGCAGGTCGAGCAAGGTCGAGCACCTGAACCTGAGCAATTAAGGACCCGCCGTGGGCTTCCTTGAGACAATTTCTCCAGGC<br>TACTCTATTCACACATACCTGTGGCGGAGACAGTGA |  |
| 19 | DNA | ATGGAGTTCAGCAGCCCCAGCAGGGAAGAGTGCCCCAGCCCTGAGCAGGTGAGCATCATGGCCGGAAGCCTGACCGGGCTGCTGCTGCTCGAGCCCTGAGC<br>TGGGCCAGCGGAGCTAGGCCTTGCATCCCCAAAAGCTTCGGCTACACAGCTTCCGTGTGCGTGGTGACTGAGCATGGGACTCCACCTATTGTGACTCTTTCGACCCCCCACCTTT<br>CCCGCCCTGGCCACTTTCAGCAGATATGGAGTCCACCCGAGCGGCAGAGTGGAGCCAGCGGACCTGAGCAGCCGAGGCCCTGCTG<br>CTGACCCTGCAGCTGAAACAGAAATTCCAGAAAGTGAAGGTCTTCGGCGGCGGCCGTGCGTCCCTGTCCCCCCGCCCAG<br>AACCTGCTGCTGAAGAGCTACTTCAGCGAGGAAGCATCGGCTACTACAATATCATCCGGTGCCAGCTTTCTATCAGGACCTACAACTCACCC<br>GACACCCCCGACGACTTTCAGCTGCACAACTTCAGCCTGCTGGCTGAGACCCCTGGCTGAGACCCCTGGCTGAGAGCCAACGGCGGCCGTGAACAACTGAGATCCCCATGTGAACCGGCAAAGGCAGCCTGAAAAGGCCAGCCCGGAGATATTTACCAC<br>GTGAGCCTGCTGGCCAGCCCCTGGACCATCCCCCACCTGGCTGAGACGCCTACGCCGAACGAACAAGCTGCAGTTCTGGGCCTGAACCGGACAGCAGCCGGAAATGAGCCCAGCGCTGGCCTGCTG<br>AGCGGCTACCCTTTCCAGTGCTGTGGGCTTCACCCCGACCCGACCCAACTGGGCGGCCAACTTGGCGGCCCACCTGGGCTAATAGCACCCCACAACGTG<br>AGACTGCTGATGCTGATTCTGGCCCCGCCCAAGGCCACCCTGGGCAGCTGGACGCACCGAGGCCTGCTGTTCGCCAGCGAAGCCTGCTGTGGGCCAGCAAG<br>TGGTACCTGGATTTCTGGCCTCAGCCAAGGCTCACACCTACAGCCACAGTGTTCCCAATAACCGCCACAGCATCACCAACCTGCTGTACCACGTGGTTGACAGATTGG<br>AACCTGGCCCTGAACCCCGGAGGGCCGACCCAACTGGTGGTGGACGGCTGGCCTGCTGGCTAGCCCTGACCCTGAACCATCACCAACCTGCTGTACCACGTGGTTGACAGATTGG<br>TTCTACCACCTGGGCCACTTCTCCAAGTTCATTCCCGAGGGCAGTGAACAGAAGCAGTAAGGATGTGCCCCTGACCATCAAGGATCCCGGCTGTGGGATTCCTGGGAAACCATCAGCCCTGGC<br>TACTCCATCCACACATACCTGTGGCGGAGAAGACAGTGA | GBA1-G8 |
| 20 | DNA | ATGGAATTCAGCAGCCCCAGCAGAGAGGAATGCCCCAAGCCTCTGAGCCGGTGTCAATCATGGCCGGATCTCTGACAGGACTGCTGCTTCAGGCCGTGCT<br>TGGGCTTCTGGCGCACCTTCAGCAGATACCTTGCATCCCCAAGAGCTTCGGCTACACAGAGCTTCGCGTGTGCGTGGTGCCAATGGGACTCCACCTTCCTTGTCCCACCAGGCACTGGCCTGCTG<br>CCTGCTCTGGGCACCTTCAGCAGATATGGAGGCTCACCCGAGCGGCAGAGTTCGGCAAGAGCACCGATGGAACTGAGCATGGGAGCATGGACAGAAGGCCGGCTGCTGGACGACTGG<br>AACCTGCTGCTCAAGAGCTACTTCAGCGAGGAAGCATCGGCTACTACAATCATCAGAGTGCCCATGGCCCAGCTGCAGACTTGCAGCATGGACCTACAACTACGCC<br>GACACACCCGACGATTTCCAGCTGCACAACTTCAGCCTGCTGGCTGAGGCTCCACTGGCATCTCCCACCTGGCTGAGACGCCTATGCCCGAGAGATCCCCATGGCCCAGCTGGACGCCTACGCC<br>GTGTCACTGCTGGCCTCTCCATGGACCATCCCCCACCTGGCTGAGACGCCTATGGCCGGTGAAATGGCAAAGGCGCCGTGAATGCCCAGTTTTGGGCCTGAACCGGCCAGCTGGAGCGCTGGCCTGCTG<br>AGCGGCTACCCCTTTCAGTGCTGTGGGCTTTACCCCGACCGACCTTTATCGCCAGAGATCTGGACAATCTGGACAACCGTGACCATTCACCAGCCACCACCATAATGTG<br>CGGCTGCTGATGCTGGACTTTCTGGCCCCTGCCAAGGCCACCAGACTGCTTCTGCCCCACTGGGCTAAAGTGGTGCTGACAGATCTGGACAGATCCGAGGCCTGCACGGCCGAGAATCGCCGTGCAC<br>TGGTATCTGGACTTTCTGGCCCCTGAGCCAGAATTCCAGAAAGTGAAGGTCTTCGGCGAGGAAGCCATCGGCTACTATAATCCGCCGCTCTGAATATCCTGGCCTCTGTCCCCACCAGTCAG<br>AACCTGCTGCTCAAGAGCTACTTCAGCGAGGAAGCCATCGGCTACTACAATCATCAGAGTGCCCATGGCCCAGCTGCAGACTTCAGCATCAGGACCTACAACTACGCC<br>GACACACCCGACGATTTCCAGCTGCACAACTTCCCCACCTCCCACCTGGCTGAGACGCTTCTGGACGCGCCTATGCCCGAGACAAAGGCGCCAGCTGCAGCCCAGGAAATGGCCAAGCTGGCGATATCTACCAC<br>GTGTCACTGCTGGCCTCTCCATGGACCATCCCCACCTGGCTGAGGCGCCTATGCCCGAGACAAAGGCGCCAGCTGCAGCCCAGGAAATGGCCAAGCAAGCTTCGGCCAGAGATCTGGACAATCTGGACAACCGTGACCATTCACCAGCCACCACCATAATGTG<br>AGCGGCTACCCCTTTTAGTGCTGTGGGCTTTACCCCGACCGGACTTTATCGCCAGAGATCTGGACAATCTGGACAACCGTGACCATTCACCAGCCACCACCATAATGTG<br>CGGCTGCTGATGCTGGACTTTCTGGACCGCCCTGCCAAGGCCACCAGACTGCTTCTGCCCCACTGGGCTAAAGTGGTGCTGACAGATCTGGACAGATCCGAGGCCTGCACGGCCGAGAATCGCCGTGCAC<br>TTTTGGGAACAGAGCCTGTGAATCTGGAGGCGGCGCCTAACTGGCTGGGGCGGAACTTCGTGACACGCCTCAGCATCATGGACAGTGCCCCTGACCATCAAGGACAACCTTCTACAAGCAGCCCATG<br>AATCTGGCCCTGAACCCCGGAGGGCCCGACCAACTGGTGGTGGACGGCTGGCCCCTGCTGGCTAGCCCTGACCCTGAACCATCACCAACCTGCTGTACCACGTGGGTGACAGATTGG<br>TTCTACCACCTGGGACACTTCAGCAAGTTCATCCCCGAGGGCTCTCAGCAGAAGCAGGTCGGCATGTGCCCCTGACCATCAAGGATCCCGGCTGTGGGATTCCTGGGAAACCATCAGCCCTGGC<br>TACTCCATCCACACATACCTGTGGCGGAGAAGACAGTGA | GBA1-G9 |
| 21 | DNA | atggaattcagcagccccagcagagaggaatgccccaagcctctgagccggtgtcaatcatggccggatctctgacaggactgctgcttcaggccgtgctt<br>tgggcttctggcgcaccttcagcagatacctttggctacacagagcttcggctacacagagcttcgcgtgtgtggtgtaatgggaccatccacactgcccatg<br>cctgctctgggcaccttcagcagatacctttggctacacagagcttcggctacacagagcttcgcgtgtgtggtgtaatgggaccatccacactgcccatg<br>ctgacactgctggcctctccatggaccatcccccacctggctgagacgcctatgcccgagacaaaggtgaaaggctcggcggcggagccatgacgagcatcctggctcttcctgccaccagctcag | GBA1-G10 |

-continued

SEQUENCE INFORMATION

| SEQ ID NO | TYPE | SEQUENCE | CODE NAME |
|---|---|---|---|
| | | aacctgctgctcaagagctacttcagcgaggaagtcatggtgctacaacatcatcagagtgcccatggcagcatcagcatcaggacctacacctacgcc gacacaccgacgatttccagctgcgacacacttcagcctgcctgaagatgcaccaagctgatccacagagccctgaaagccgtcagctggcacaaagacc gtgtcactgctgccgctcctccatggacatctccacctggctgaaaacaaatggcgctgtagaaggcagcctgaaaggccaaactggcgacatctaccac cagacctgggccagatacttcagtgcctttgagtgccagaccaccagcgggacttcatcgccgtgatcttacgccgtgatctttgggccgagacgaacctct ctgtggactgctg aggcgctgatgctggacgacagaagactgctctgcccaccagcggacttctatcgccgcttatcgccgtgatctggaacccacgccaatagcaccaccataatgtg cggctgctgatgctggacgacagaagactgctctgcccccgaccggagcgggccaaatacgaacgaggatgccgtgcac tggtatctggactttctggccccctgccaagggcaacactggaggacacacagactgtttcccaacaccatcgttccggagcctgtgggccgaggctgtgggaccaag tttgggaacagacagcgtgcggcgtgcggctccagctggggatagaggcatgcagctacgaggacctgtaaccacgtgtcggctggaccgactgg aatctggccctgaatcctgaaggctccaactctggggacctccaactctcccagagcagtccaagcagcaacaatcagccctggc ttctcacacctgggaccctcatcctccagccgggcagctcttccccagcaagacgatctggaccgccgtggcgctctgtatycac cctgatgatcgtgctgctggtggtcctgaacccagcagcaagaaaatgtgccctgaccgacagagcaacaatcagccctggc tactccatccacaccacctgtggcgtagacagtGA |  |
| 22 | DNA | ATGGAGTTTTCAAGTCCTTCCAGACAGACAGAATGTCCCAAGCCTTTGAGTAGGGTAAGCATCATGGCTGGCAGCCTCACACAGATTGCTTCTACTTCAGGCAGTGTCG TGGGCATCAGGTGCCCGCCCCTGCATCCCTAAAAGCTTCCGCTACAGCTTCGGTGTGTTCAATGCCACCATACTGTGACTCCTTTGACCCCCCGACCTTT CCTGCCCCTTGGTACCTTGTGACCGCGTATGAGAGTACACGCAGTGGGCGACGGATGGGCCATCAGACAGATGGGAGGGCCATGACAGATGCATCCTTCTCAACATCCTTGCCCTGTCACCCCCTGCCCAA CTGACCCCTGCAGCCAGAACAGAGTTCCAGAAAGTGAAGGGAGTTTGGAGGGCCATGACAGATGCATCCTTCTCAACATCCTTGCCCTGTCACCCCCTGCCCAA AATTTGCTACTTAAATCGTACTTCTCTGAAGAAGGAATCGGATATAAACATCACTATCCGGGTACCCATGGCCAGCTGTGAGTTCTCATCCGCACCTACACCTATGCA GACACCCCTGATGATTTCCAGCCCCTGGACATCACCCCACTTGGCTCAAGACCACTTGGCTCAAGACCACTGGACATCACCCCACTTGGCTCAAGACC GTTTCACTCCTTGCCAGCCCCTGGACATACTTTGTGAAGTTCCTGGAAGTCCTGGAAGTGCTCATGGCTGGAATCCATGCTGAGCAAGTTACAGTTCTGGGCAGTGACAGCTGAAAATGAGCCTTCTGCTGGGCTGTTG AGTGGATACCCCTTCCAGTGCCTGGGCTTCACCCTGAGCCTTCATTGCCCGTGACCTAGTCCTGCAACATCAGCGAGACTTCAGTGCCTGGACCTACCTCACCCTGAGCCTTCATTGCCCGACCTAGTCCTGCAACAGTACTCCACCAATGTC CGCCTACTACTTGGACTTTTCTGGCTCCAGCCAAAGCCACCCTAGGGGAGACCACCCGTGCGCCCTGGGCTGTGTGGGCTCCAAG TGGTTACCTGGACTTTTCTGGCTCCAGCCAAAGCCACCCTAGGGGGAGACCACCCGTGTCGAGGATCGGGGTCGAGGATGGGGGGCTAACTTTGTGTACTAGACAGACATCAGACCCGTGTTCGCAGGGGGATGGGGGGCTAACTTTGTGTACTAGACAGACATCAGACTTTTACAAACAGCCCATG TTCTACCACCTTGGCACTTCAGCAAGTTCATTCCTGAGGCTCCTGAGGCTCCAAGGGACCTGAGGATCGGGGGGGTCTTTACCATCCAGGGACACTCGCAGGGCACTCGCAGCAGTGCACTGATGCAT CCCGATGGCTCTGCTGTTGTGGTGCTGCTAAACCGCTCCTCTAAGGGAGGTGCCTCTTACCATCCAGGATGTCCATCCATCCAAGGATCCTGCTGGGCTTCCTGGGACAATCTCACCTGGC TACTCCATTCACACTGCGCTGTGGCGTCGCCAGTGA |  |
| 23 | DNA | ATGTGGTGCGCGCGAGCCCAGTTGCTCTGGTGGCCTTTTGCGCCGGGCTTTTGCGCCCGGGCTTTTGCGCCCGGGCTCTCTCACCCGGTGCTGACGCAAGGCCGGCGGCGGAAGGACCTGGTGCT GATTGCGAGGTGTGCAAGGAATTCCTGAACCCGTTTTATAAGTCCCTGATCGACAGAGGCGTGAACTTCAGCTTGGATACCATCGAGAGAAGAACTCATCTCCTTC TGCCTGGACACCAAGGCAGGAAAACCGGCTGTGCTACTACCTGGGCGGCCACAAAGATCCTGAGCGAGGTGACCAGACCAATGAGCGTG CACATGCCTCCCCATGAAAATCTGTCAAAAACTGAAAAAGCTGGACAGCCCAGATCTGCCGAGTACGAGGACCCTGGATCTGGCTTCTGTCGACCTGAGA AAGATGCCGGGTGGCCGAACTGGCAGACGTGGGGCGAGGAATGTGGGGCGAGGAATGTAGAGCCTGCGCCGAGAGAGACCGACTACGTGAATCTGATTCAGGAGCTGGCC CCTAAGTACGCCGCCACCCCACCCCGCCACCCCACCCCAAGACAGAGCTGTGA |  |
| 24 | DNA | ATGTGGTGCGCGCGAGCCCAGTTGCTGTGTGGTGGCCTTTTGCGCCCGGGCTTTTGCGCCCGGGCCCCGGGCCCCAGGAGGCCCGGGGGGCCCCGGGGCC GACTGCGAGGTGTGTAAGGAGTTTCTGAACCGGTTCTACAAGTCCCTGATCGATGGGGCGTCAACTTCAGCCTGGATACTATCGAGAGGAGCTGATCAGCTTC TGCCTGGATACAAAGGGAGGAGAACCGGCTGTGCTACTACCTGGGGGCCCACAAGACGACCCCCCACAGATCTGTCCGAGGTGACCAGGATACGAGAAAACACTGGACCTGGGGGCCCACAAGACGACCCCCCACAGATCTGTCCGAGGTGACCAGGATACGAGAAAACACTGGACCTGCGAGCTGAAGTACGAGGACCCTGGAGCTGTCGACCTGAGG AAGATGAGGGTGGCCGAGCTGGAAGCAGATTCTGCACAGCTGGGGGAGGAGAATGCAGGGCCTGCGCCGAGAGAGATGCAGGGCCTGCGCCGAGAGAGACTGATTACGTCAACCTGATCCAGGAGCTGGCC CCAAAGTACGCTGCCACACCACCCCCCAAGACAGAGCTGTGA |  |
| 25 | DNA | ATGTGGTGCGCGCGAGCCCAGTTGCTGTGTGGTGGCCTTTTGCGCCGGGCTTTTGGTCTCTCACCCGGTGCTGACGCAGGGCCAGGAGGCTGGCGCT GACTGCGAGGTGTGCAAGGAGTTGCCTGAACCAGGTTCTACAAGAGCCTGATCGACAGGGGAGTGAACTTCAGCCTGGACACCATTGAGAAGAGGACTCATCAGCTTC TGCCTGGACACCAAGGGCAAGAGGAGGAGGAGAACCAGGCTGTTGCTACTACCTGGGAGGCCACAAGGACGACGCTGCCCAAGATCCTGTCCGAGGTGACCAGACCCATGAGCGTG |  |

-continued

SEQUENCE INFORMATION

| SEQ ID NO | TYPE | SEQUENCE | CODE NAME |
|---|---|---|---|
| | | CATATGCCTGCCATGAAGATCTGTGAGAAGCTGAAGAAGCTGGCAGCCAGATCTGTGAGCTGAAGTATGAGAGACCCTGGACCTGAGG AAGATGAGAGTGGCCGAGCTGAAGCAGATCCTGCACAGCTGGGGAGGAGGAGTGCAGGAGCCTACGTGAACCTGACTCGCGACCTGGCT CCTAAGTACGCCGGCCACCCATCCCAAGACCGAGCTGTGA | |
| 26 | DNA | ATGTTGGTGCCGCGAGCCCAGTTGCGTGGTGGCCTTTTGGCCCGGGCTTTTGGTCTCTCACCCGTGCTGACGCAGGGCCAGGAGGCCGGGGGCCAGGGGGCC GACTGTGAAGTATGTAAAGAATTCTTGAACCGATTCTACAAGTCACTGACAGAGGAGTTAACTTTCGCTGGACACTATAGAGAAGAAATTGATCAGTTTT TGCTTGGACACCAAGAGAAAGAAACCGCCTGTGCTATTATCTGGAGAGCCACAAAGAGATCCTAAGTGAAGTCACTCGCCCCAATGAGTGTG CATATGCCTGCAATGAAGATTTGTGAGAAGCTGAAGAAGTTGGATAGCCCAGATCTGTGAGCTGAAGTCGTGAGCTGCATCAGTTGACCTGCCG AAGATGAGAGTGGCAGAGCTGAAGCAGATCCTGCATAGCTGGGGAGGGAGGAGTGCAGGAGCCTGTGCCAGAAAAAAACTGACTATGTGAATCTCATTCAAGAGCTGGCC CCCAAGTATGCCAGCGACCACACCCCAAAAACAGAGCTCTGA | CDNF-WT |
| 27 | DNA | ATGAAGTTATGGGATGTCGTGGCTGTCTGCCTGGTTCTGTGCCTCCACACCGCGTCCGCTTCCACTGCCTGCCGGCAAGGGCCCCTGCTGAAGAT AGAAGCCTGGGCAGACGGGCGGGCCCCTTTCGCCCGTGTCTTAGCGACAGCCAACATGCCTGAGGACTAACCCGATCAGTTGACTTCATCCAGGCT ACAATCAAGAGACTGAAGCGGAGCCCTGACAAACAGATGCCGTGCTGCCAAGCGCGAGAGAAATAGACAGGCCGCCTGCTAATCTGAGACACAGCAGAGGC AAAGGCAGAAGGGCAGAGAGGCAAGAACAGAGGATGTGTCTGACCGCGCCATTCACCTGACAGACCTGGATGGATATGAGACCAAGGAAGAGCTG ATCTTCAGATACTGCAGCGGCTCTTGCGACGCCGCCGAACACCACTACAGACAAGATCCTGAAAAACCTCTCCAGAAACCGGCGGCTGTGTCCGATAAGGTGGGC CAAGCCTGTTGCAGACCTTTGACGATGATCTGAGCTTTCCTGGATGCAAACCTGGTCTTACCACATCCTGAGAAGACAACCTGGTCTACCATCCTGAGATAACCTGGTCTACCATCCTGAGATAACCTGGTCTTACCACATCCTGAGAAGACAACCTGGTCTACCATCC ATCTTGA | GDNFGS |
| 28 | DNA | ATGAAGTTATGGGATGTCGTGGCTGTCTGCCTGGTTCTGTGCCTCCACACCGCGTCCGCTTCCCGCTGCCTGCCGGCAAGGGCCCCGCCGAAGAC CGCTCCCTGGCCCGCCGCCGTGTCCCGCCCTTTCGCGTTAGCAGTGACTCAAATATGCCAGAGGATTATCTGATCAGTTCCAGATGAGTTTTATTCAAGCC ACCATTAAAAGACTGAAGCGGTCTCCCGATAAGGCAGATGGCCGTGTTGCCCGCGGCGAGCGGGAAGCAGGCAGGGGCGCCCGACCCCGAGAACAGCAGAGGGGG AAGGGCAGGCAGGGCGGGGGCAGCCAAGAACAGGGGCGTGCGTGCTGCCGAGACCAGCTACACCGTGAACGTGACCAGAGACAGTCTGGGGGTACGAGACACAAGGAGGAGCTG ATCTTCAGGTACTGCAGCGGGGAGCTGCGACGCCTGCCGAGACCAATACAGATCGCATAAGATCCTGGTGTACCATATCCGGCACCATTACCTGGTGTACCATATTCTGGTGATAACCTGGT CAGGCCTGTTGCAGCCCCATTGCCTTTGATGATGATCTGAGCTTTCCTGGTATGCATAACCTGGT ATTTGA | GDNFSA |
| 29 | DNA | ATGAAGTTATGGGATGTCGTGGCTGTCTGCCTGGTTCTGTGCCTCCACACCGCGTCCGCTTCCCTCTGCTGCCGGCAAGAGGCCTTCCCGGAGGCTTCTGCCGAGGAC AGAAGCCTGGCAGAGGAGGAGCTCCTTTTGCCCTGAGCAGCGACAGCAACATGCCTGAGGACTACCCCGACCAGTTTGATGACGTGACTTCATCCAGGCC ACCATCAAAAGACTGAAAAGGTCACCTGACAAGGAAGGCGATGGCCGAGGGGAGGGCCGAGAGGCAGGGGCGCCCTGCCAATCCTGAGAAATAGCAGAGGC AAAGGCAGGCAGGAGGGCAGAGAGGCAAGAACAGGGGCCGTGTGTGCTGAGACCAGCTGGGACTACAAGGAGGAGCTGATATGGGACTATGAACCAAGAAGAGCTGACCAAGGAGGAGCTG ATCTTTAGATACTGCTCTGGCCAGCTGTGATGCCGCTGCCGCTGCGACCGACCAGAAGATCCTGAAAGAACCTGAGCAGAAACAGGAGACCTGGTGAGCGACAAGGTGGGC CAGGCCTGTTGCAGCCCCATCGCCTTTGACGACGACCTGAGCTTCCTGGACGCGCAACCTGGTTACCACATCCTGGTTACCACATCCTGGTTTTACCATATTCTGGTGTACCATATTCTGGTGTACCATATTCTGGTGATGATAA ATCTGA | GDNFMN |
| 30 | DNA | ATGAAGTTATGGGATGTCGTGGCTGTCTGCCTGGTTCTGTGCCTCTCCACACCGCGTCCGCTTCCCCGCTGCCTGCCGGTCAAGAGGCCTTCCCGGAGGCGCCCGCCGAAGAC CGCTCCCTGGCCCGCCGCCGCCCCTTTCGCGTTAGCGGTGAGCAGTGACTCAAATATGCCAGAGGATTATCTGATCAGTTCCAGATGAGTTTTATTCAAGCC ACCATTAAAAGACTGAAAAGGTCACCAGATAAACAAATGCCGTTCCTAGAAGAGAGCGGAATCGGCAGCGCTGCCAACCCAGAGATTCCAGAGA AAAGGTCGGACAGGCAGAGGGCAGAAACCGGTTGTTGTCTTAACTGCAATACATTTAAATGTCAATACATTTAAATGTCAATACATTTAAATGTCAATACATTGGTGGTTTGGGTCTGGTGTATGAAACCAAGGAGGAACTG ATTTTTAGGTACTGCAGCGGCTCTTGCGATGCCGCTGCGGACCGACGACAAACCTATCCAGAAAATAGGAAGGCTGGTGAGTGACAAACTAGGG CAGGCATGTTGCAGACCCCATCGCCTTTGATGATGACCTGTGTTTTACCATATTCTAAGAAGACATTCCCCTAAAAGGTGTGGATGT ATCTGA | GDNF-WT |

-continued

SEQUENCE INFORMATION

| SEQ ID NO | TYPE | SEQUENCE | CODE NAME |
|---|---|---|---|
| 31 | PRT | MNASERRRGKEMVDYMANVMEGIEGRQVVPDVEPGYLRPLIPAAAPQEPDTFEDIINDVEKIIMPGVTHWHSPYFFAYFPTASSYPAMLADMLCGAIGCIGESW AASPACTELETVMMDWLGKMLELPKAFLNEKAGEGGGVIQGSASEATLVALLAARTKVIHRLQAASPELTQAAIMEKLVAYSSDQAHSSVERAGLIGGVKLKAIP SDGNFAMRASALQFALERDKAAGLIPFFMVATILGTTTCCSFDNLLEVGPICNKEDIWLHVDAAYAGSAFICPEFRHLINGVEFADSENENPHKWLLVNEDCSAMW VKKRTDLTGAFRLDPTYLKHSHQDSGLITDYRHWQIPLGRRERSLKMWFVERMYGVKGLQAYIRKEVQLSHEFESLVRQDPRFEICVEVILGLVCFRLKGSNKVN EALLQRINSAKKIHLVPCHLRDKFVLRFAICSRTVESAHVQRAWEHIKELAADVLRAERE | AADC |
| 32 | PRT | MEFSSPSREECPKPLSRVSIMAGSLTGLLLLQAVSKASGARPCIPKSEGYSSVVCVNATYCDSFDPPTFPALGIFSRYESTRSGRRMELSMGPIQANHTGTLL LTLQPEQKFQKVKGBEGGAMTDAAALNILALSPPAQNLLLKSYFSEEGIGYNIIRVPMASCDESIRTYTYADTEDDEQLHNESLPEEDTKLKIPLIHRALQLAQRP VSLLASPWTSPTWLKINGAVNGKGSLKGQPGDIYHQTWARYEVKELDAYAEHKLQFWAVTAENEPSAGLLSGYPFQCLGETPEHQRDETARDLGETLANSTHANV RLLMLDDQRLLLPHWAKVVLTDPEAAKYVHGIAVAWYLDELAPAKATLGETHRLFPNTMLEASEACVGSKEWEQSVRLGSWDRGMQYSHSIITNLLYHVVGWTDW NLALNPEGGPNWVRNFVDSPIIVDITKDTFYKQPMFYHIGHFSKFIPEGSQRVGLVASQKNDLDAVALMHPDGSAVVVLNRSSKDVPLTIKDPAVGFLETISPG YSIHTYLWRRQ | GBA1 |
| 33 | PRT | MWCASPVAVVAFCAGLLVSHPVLTQGQEAGGRPGADCEVCKEFLNRFYKSLIDRGVNESLDTIEKELISFCLDTKGKENRLCYYLGATKDAATKILSEVTRPMSV HMPAMKICEKLKKLDSQICELKYEKTLDLASVDLRKMRVAELKQILHSWGEECRACAEKTDYVNLICELAPKYAATHPKTEL | CDNF |
| 34 | PRT | MKLWDVVAVCLVLLHTASAFPLPAGKRPPEAPAEDRSLGRRRAPPFALSSDSNMPEDYPDQFDDVMDFIQATIKRLKRSPDKQMAVLPRRERNRQAAANPENSRG KGRRQRGKNRGCVLTAIHINVIDLGLGYETKEELIFRYCSGSCDAAETTYDKILKNLSRNRRLVSDKVGQACCRPIAFDDDLSELDDNLVYHILRKASAKRCGC I | GDNF |
| 35 | DNA | GGAAGCGGACAGTGTACTAATTATGTCTCTCTTGAAATTGGCTGAGATGTTGAGAGCAACCCTGGACCT | E2A |
| 36 | PRT | GSGQCTNYALLKLAGDVESNPGP | E2A |
| 37 | DNA | GGAAGCGGAGTGAAACAGACTTTGAATTTTGACCTTCTCAAGTTGGCGGAGACCTGGAGTCCAACCCTGGACCT | F2A |
| 38 | PRT | GSGVKQTINEDLLKLAGDVESNPGP | F2A |
| 39 | DNA | GGAAGCGGAGAGGGCGAGAGAAGTCTGCTAACATGCGGTGACGTCGAGGAGAATCCTGGACCT | T2A |
| 40 | PRT | GSGEGRGSLLTCGDVEENPGP | T2A |
| 41 | DNA | GGAAGCGGAGCTACTAACTTCAGCCTGCTGAAGCAGGCTGGAGACGTGAGGAGGAACCCTGGACCT | P2A |
| 42 | PRT | GSGATNFSLLKQAGDVEENPGP | P2A |
| 43 | DNA | TTTATAAATTCTTCTTCCAGAA | min iIRES |
| 44 | DNA | ACGTTACTGGCCGAAGCCGCTTGGAATAAGGCCGGTGTGCGTTTGTCTATATATGTTATTTTCCACCATATTGCCGTCTTTTGGCAATGTGAGGGCCCGGAAACCTG GCCCTGTCTTCTTGACGAGCATTCCTAGGGGTCTTTCCCCTCTCGCCAAAGGAATGCAAGGTCTGTTGAATGTCGTGAAGGAAGCAGTTCCTCTGGAAGCTTCTT GAAGACAAACAAGCTGTGTAGCGACCCTTTGCAGGCCAGCGGAACCCCCCACCTGGCGACAGGTGCCTCTGCGGCCAAAGCCACGTGTATAAGATACACCTGCAA AGGCGGCACAACCCCAGTGCCACGTTGTGAGTTGGATAGTTGTGGAAAGAGTCAAATGGCTCTCCTCAAGCGTATTCAACAAGGGCTGAAGGATGCCCAGAAGG TACCCCATTGTATGGGATCTGATCTGGGGCCTCGGTGCACATGCTTTACGTGTTTAGTCGAGGTTAAAAAAACGTCTAGGCCCCCCGAACCACGGGGACGTGG TTTTCCTTTGAAAAACACGATGATAATA | EMCV IRES |

-continued

SEQUENCE INFORMATION

| SEQ ID NO | TYPE | SEQUENCE | CODE NAME |
|---|---|---|---|
| 45 | DNA | ATGGAGTTCAGCTCTCCCAGCAGGAAGAATGTCCTAAGCCTCTTGAGCCAGGGTGTCCATCATGGCTGGCAGCCTGACACGGGGACTCCTGCTCCTGCGAGCGTGTGAGCTGGGCCTCTGGGAACATTCAGCAGATATGAGAGCACCCAGGACGCGCCGGAGAATGGAGCTGAGCATGGAGCTGAGCATGCAGATGCTGCCGTCTGCCTGCCTGGAGGAGCCATGACAGATGCTTCAGGAAGGTGAAGGCTTCAGAAATCCCTGAACCATCCTGGCCCTGAGCCCTCTGCCCAGAACCCCTGCTGCAGCCTGAGCGAGCTACTTCAGCGAGAAGAAGAATCGGCTACCAACATCACAGAGTCCCCATGACCCCATGACCGCCCTCAGCGACGTGTCCCGCTGGCCCAGCTTGGCCCAGCTACTTTGTGGAAGTTCTGGGATTCACCCGTGGAGTGCTGTGACCGCCAGTTCCCGCAAGCGGCTATCCCTTTCAGTGTCTGGGGATTCACCCTGGCCTGCTGATGCTGACGATCAGGACTTCCTGCCCAGCGGCCCACCCTGGGCGAGACCTCCTGCCAAGGCCACCCTGGGAAGCTGGCAGGGCCCAAACTGGGTGCCGAGTTTATTCCTGGAGGCAGCCAGCAGCAAGGACGTGCCCCTGACCGAGATCCTGCCCATCAACTGGAACAGCCGCAATGAAGTGCTGCTGCCTGGACCCCATGACGGTGGTGCTGCTGACCGACTGGAACCTGGCCCTGACGTTCGTGGACACCCTGACGTCTGACTGCAGGTCTGATGCATTCTTACCACCTGGGCCACTTCAGCAAGTTTATTCTGCCTTCTGGACGCAGCCAAAGGGTGGCAGCCTGACGTCTGATGCATCCTGATGGCAGCGCCGTCGTTGCCTGTGTCCTGACCCGCAGCAGCGCCCAAGGCACGTGCCCCTGGACCATCAGCCCTGGCTACAGGCATCCACACACTACCTGTGGAGGAGCAGTGA | GBA1-G11 |
| 46 | DNA | ATGAATGCCAGCAGCGAGTTTAGAAGAAGGGGCAAAGAGATGGTTGACTACATGGCCAATTACATGGAGGCATCGAGGGCAGGGCAGGTGTACCTGATGTGGAACCTGGATATCTGAGACCTCTGATTCCTCTGCTCCTGGCCACTCTCCTTATTTCTTTGCCTATTCCTACCACCTCATTCCTCAGGAGCCCTCTACCAGCCAGCAGCAGAATGCTGGCGAAACAGTGATGATTGAGGCCGGGAAGATGGTCCAGAACAGCAGCAAATCGGCAGGCCCTTTCAGAGGTCGGCAAGTGCATCAGGGTCGGCTGTCGCGCCCAAGCCCAGCTCGCCTGGTTGGCTGGCTTACAGCTCTGAAGAGCCCATTGCCGACTCTGAAGAGCTGTGGGCAGATATCCCTCAGGCAGCCATCATGAGAAAGTGGCCTGGCCTGCTCGCCTGGGTCTCTGGGATGGCAACCTGCTGGCAAGCTGTTGGCAACATGGTGGGTGGCCTATCTGCCACATGCTGCTCGTTCAACCTCAACCCTGCCTGCAGCTTTGACTGCTGCTTCAACTTGACTGCTCTGTATGTCGGTGAAGAGAGAATTCCTGGCACGGTCAGGGCAGATCAACGAACCGCCACCACCAGATTCTGGCCTGATCACCAGATTACAGACACTGGCAGGAGGCTCTGCTGCAGGATCAACAGCCGCCAAGAGAATCAACCTGGTCCTTCGTGCTGCTTCACCTGATCTGTGGAGGTGAATCGGTGGAGTTTGTGCTGAGATTTGCTATTTGTGAGCAGAACCGTGGAAAGGCCCCACGTGCAGAGAGCCTGGGCAAGGATCAACAGGCAGGTGCCCAAGAACCTGGGAGCCACACTGGCCTGGGACAGATCAACTGCCTCTGCTCAGGAGGCCTGGGATGCTGCACATCAAGAGAACCTGGCCGCTGATTGCTGAGAGCGCAGCGGAATGA | AADC A11 |
| 47 | DNA | ATGGAGTTTTCAAGTCCTTCCAGGAGGAAGTGTCCAAGCCTTTGAGTAGGGTAAGCATCATGGCTGGCAGCCTCACCACGGTAAGCATCATGGCTGGCAGCCTCACCTACTGGACACGGGGACTCCTGCTCCTGCGAGCGTGTCGGCCTCTGTCGCTGAGCCTCTGCAACGCCCACACCACCAGCCTCTCTGGGGGAACATTCAGCAGATATGAGAGCACCCAGGTTCGGCCGGAGAATGGAGCTTCGGAGGAGCCATGACAGATGCTTCAGGAAGGTGAAGGCTTCAGAAATCCCTGAACCATCCTGGCCCTGAGCCCTCTGCCCAGAACCCCTGCTGCAGCCTGAGCGAGCTACTTCAGCGAGAAGAAGAATCGGCTACCAACATCATCAGAGTCCCCATGACCCTGGCAGCCCTGGACAAGCCCTACATGCCTCGCAGCATGGTCAAGGCAAGTGCATCAGGGTCGGCTGTCGCGCCCAAGCCCAGCTACTTTGTGGAAGTTCTGGGATTCACCCTGGCCTGCTGATGCTGACGATCAGGACTTCCTGCCCAGCGGCCCACCCTGGGCGAGACCTCCTGCCAAGGCCACCCTGGGAAGCTGGCAGGGCCCAAACTGGGTGCCGAGTTCATTCCTGGAGGCAGCCAGCAGCAAGGACGTGCCCCTGACCGAGATCCTGCCCATCAACTGGAACAGCCGCAATGAAGTGCTGCTGCCTGGACCCCATGACGGTGGTGCTGCTGACCGACTGGAACCTGGCCCTGACGTTCGTGGACACCCTGACGTCTGACTGCAGGTCTGATGCATTCTTACCACCTGGGCCACTTCAGCAAGTTTATTCTGCCTTCTGGACGCAGCCAAAGGGTGGCAGCCTGACGTCTGATGCATCCTGATGGCAGCGCCGTCGTTGCCTGTGTCCTGACCCGCAGCAGCGCCCAAGGCACGTGCCCCTGGACCATCAGCCCTGGCTACAGGCATCATTGTGGACATCACCAAACCTTCGTGGACATCACCAAACCTTCTACCAAGGACACCTTCTACAAGCAACCATGG | GBA1-G12 |

-continued

SEQUENCE INFORMATION

| SEQ ID NO | TYPE | SEQUENCE | CODE NAME |
|---|---|---|---|
| | | TTCTACCACCTGGCCACTTCAGCAAGTTTATTCTGAGGGCAGCCAAAGGGTGGGACTGGTCGGCCAGCCAGAAAAATGACCTTCGAGCGCCGTGGCTCTGATGCAT<br>CCTGATGGCTCTGCTGTGGTGGTTGTCCTGAACAGAAGCAGCAAGGATGTGCCACTGACCATCAAGGATCCTGCTGTGGGCTTCCTGGAGACCATCAGCCCTGGC<br>TACAGCATCCACACCTACCTGTGGAGGAGACAGTGA | |
| 48 | DNA | cgttacataacttacggtacgtacggtggccgcctggctggcacgaccccgccacgaccccgccagttgactgcttcaataatgacgtacgttccaatagtaacgccaataggac<br>tttccattgacgtacgggttggatattacggtaaacgccccacttggccactggcatcaagtgatcatcaagctattaccatggtgatcgttt<br>taaatggccccgcctcgcattatgccagtacatcatgacctttatqggactttcctacttggccagtacatctaccgtacactaCgtattagtcatcgctattaccatggtatgcggtt<br>ttggcagtacatcaatggcgtggatagcggtttgactcacgggatctccacccattgacgtcaatggagttgttttggcaccaaaatcaacg<br>ggactttccaaaatgtcgtaacaactccgccccattgacgcaaatgggcggtaggcgtgtacggtgggaggtctatataagcagagctcgtttagtgaaccgtca<br>gatccgctggagacgccaagtcctgcagttcccatagaagcaggcgcgatccccggcggaacggcgacggtcattggaa<br>cgcggatcccccgtgccaagagtgacgtaagtaccgcgctatagagctcataggcccacaaaaatgctttcttcttcttaataactttttgtttatcttattc<br>taatacttttcctaatctctttctttcaggcaataatgataccatgtctttcgaccattctaaagaataacagtgataattttcgggttaagca<br>atattcagtattcctaat<br>atttatggttggttggataaggctaagctggccttttgtcaatcatgtcataccatcctcttatcctctccacagtcctccggcaacgtg<br>ctggtctgtgtgctcgtgctggcacatttggcaaagaattggatttcgaaacatcgattcgaacatcgattgaacatcctgagaagggagg<br>gaaggagagatggtggattacggttacggtggccaactacatgaagcattgaagggacgcagcaggttcccgctgaacactgtcccccgcccctgatcctcgcgc<br>tgccctgccagcgtcgtcgtaccccggcccatgctcgtggacatgtgtcgggacgccatgacggcagatgaagaatcatcgctgtcgggggcaagctgatccagagctgga<br>gactgatgatgagcttgtccggaaagtcgtcggacacaaagtgatctggaacttccaaagcattctgagcgagcgccgtcggagctacatcggcagggsaagtggtggc<br>ttactcatcgatcaggcacactcctcagtggaaagagctgggtaattggacggaaataaaagctcatcgctgtccttgacaatcttcctt<br>tgccctgccaggagaagcctgagacaggacacatatggcggcctgattcctttatgtgtcacgtgatgcagcctacggggcagtgatccatcctgccttggcctcctttgacacttctgaatg<br>agtggagtttgcagattcattcaactttaatcccacacaaatgctattggtgaatttgacttgccatctgtctctgccatgggtgaaaaagagaaacagacttaacgggagc<br>cttagacctgaccccactacctgaagccagtgtagaactcaaagactcaggccttatatccgcaagatgaagcattgagtct<br>gaaaatgtcatcccccttgaaatctgtggaaagtaatcatccatatattatggggcttgtcgttctcggctcggactttggctgtgtgccagga<br>tccccgcttgaaaatcttctcatctgtggaagtcatctcgggcttggtttggtatggagcaagggcaagttgggaagacaaccgtaggggctcattggga<br>accaagctgagtgcagtgcagtaccttggctcactgcacaatctgttcctgccgcttgcctacctctccagcctccgagttgttgggattccaggc<br>atgatgaccaggctcagcaatttcttgttttttggtagagacgggtttcaccatattggtcaggctggtctcgaacctcctgaccctcaggtgatcctacccacc<br>ttggcctccaaaattgctgggattacaggcgtgaaccactgcgcccggcctcctttcctgtccctt | A10-vy |
| 49 | DNA | acggtgacgtctccacatgtgaagcttgatctgaatctggtacccagttastaatagtaatcaattacgggtcattagttcatagcccatatggagttc<br>cgcttacataacttacggtaaatggccccgcctggctgaccccgccactggcagtaaactgccacttggccagtacatcaagtgtacatcaagatgccctattgacgtcaatgac<br>acttccattgacgtcaatggtgactattacggtaaactcgccccattggcagtacatcaatgggcgtggatagcggtttgactcacggggatttccaagtctccaccccattgacgtcaatggga<br>ggtaaatggcccgcctggcattatgcccagtacatgaccttatgggactttcctacttggcagtacatctacgtattagtcatcgctattaccatggtgatgcggttttggcagtacatcaatgggcgtggatagcggtttgactcacggggatttccaagtctccaccccattggcagttttgtcaggctggcatgggccggggggcgtggggg<br>cctttatgcgcgaggcgccgcgcgccgccggcgccggcggccggctgactgaccgctactccacaggtgagcgcggggggggaagtcgcggcgccgctccgacccccgctccgccgc<br>cgcctcgaggcgccgcccgccggcttgactgaccgcgctgaaagcctggggggtaattgtttaatg<br>acggctgttctctggcgcgtgaaagcctgaggggctgaaagcctggggggtacttttcatcatttgcaaagaatggctggggcaggaacctcaggcaagaggaatgcccaagctctgagccggtgcaatatttccacaaccggt<br>acgtgcggttattgtgcgtctcatcatttgcaaagaatggccacaactgttcatgcctctacatgttcagatccggatccttcctacacgtcctggcagatatcaccggt<br>tgagccaccatggaattcagcagcccagcagaggatgcccaagctctgagccggtgcaatatttccacaaccggtgagaactctgagccggtgcaatatttccacaaccggt<br>gccgtgcttgggctctggcctagacctgacccaagctgcatcccccaagagctttggctcacgtagagaagcagagcttcggctcacactactggcgacttcgaccctt | G10-p |

-continued

SEQUENCE INFORMATION

| SEQ ID NO | TYPE | SEQUENCE | CODE NAME |
|---|---|---|---|
| | | cctacctttcctgctctgggcaccttcagcagatacgagagcaccagatccggcagacagatcggaactgagcagatggaccgatccatccaggccaatcacacaggcact<br>ggcctgctgcactgcacctgctagcaggactactccagaaggcttcggcggagcaagatgtaaaggcttcggcggagccatgacagatgccgcgccctctgaatatcctggctctgtctcca<br>ccagctcagaacctgctgctcaagagctcactcagctgcacctcagctgcacaatcatcagagtgccatggccatccccagatcccacagagccctgagcgtgccagctggca<br>acctacgccgacacaccgacgattccagctgcacctcagctccaccaactgcctgctgaagaggacaccaaggcgccgtgaatggcaaggcagcctgaaaggccaacctggcgac<br>caaagaccgtgctactggctggcctctccatggcacatcucccacctggctgaaaacaaatggcgccgtgaatggcaaggcagcctgaaaggccaacctggcgac<br>atctaccaccaccagacgacccgggcagacagattggggagtcctgagaagtgtgttttggggcacgacagatggggccagagagaacgaaccttctgct<br>ggactgctgagcggctacccccttcagtgcctgggcttacacccgacaaccagggggacttcatcgccgtggacctcgggaacccacactggccaatagcaccac<br>cataatgtgcggctgctgatgctggacgaccagagactgcttctgcccactgggtcaaggtggctgcacaatcctgaggccgccaaatacgtgcacggaatc<br>gccgtgcactggtattctggactttctggccccctgccaagcacaccagactgtcccccaacaccatgctgttcccgcagggaagcctgtgtg<br>ggcagcaagtttcggaacagcttggctaggaaccagagactgcttctgtcagcactcaccagctcagctgctg<br>acgactggaatctggcccaccgtgaatcctgaggcggccctaactggtccgaaacttcgtggacagccccatcatcgtggacaatcaccaaggacacctctacaag<br>cagccatgtctccaacctgggacacttcagcaagttcatcccgagggctctcagccgtggacggtgctccagaagaacgatctgacgccgtggct<br>ctgatgcacctgcatggatctgctggtggtgggctgacgaaccgacagcagaaagatgtgcctggaaagatgtcacggaatc<br>agcctgcactccaccaccaccacctgtcgcgctcagctgtggcactgacagctaccctgctgctgaataagtttaaacctgagggccccaagctatcaaccctga<br>ttacaaaattgtgaaggatgacaagatgctctgtgcactccacgctgctcttgatacgctgctttaatgctcatgctctttgatatcatgctcattgctccg<br>tatggctttcatttctcctcctgtataaactctggtgctgcttccagggagttcgcggcctttcggctccaccggcccctgtcggtgctgcttgc<br>tgacgcaaccccactggtgggggcattgcccacctgtccagctcagtcctttccgggactttcggttcggggaaatcatcgtctttcctgcgctg<br>cctgccccgctgctgaacagaggcctttcctcctccccttgtgctggcactgaactgcttccgggaatcagcgacctccttccagccctgcgtgcgtgtgccac<br>ctggattctcgcgggacgtccctctgctacgtcccttcggccgccgcctccctcccggacctccttccgtccgtccgtcct<br>tcgccttcgccctcagacgagtcggattcccctcccccgtgcctcctgacccggaaggtgccactcccactgttgccttcctaataaatgaggaaattgcaccgcattgtctg<br>agtagtgtctattctattctcggggtatggcgcctagaacagctggggaggaagcagcaaggggaggattggggaagacaatagcaggcatgctgggagagatcccacgataacaaac<br>agctttttgggtgaacatattgact | |
| 50 | DNA | TCTAGAGTGCCCGTCAGTGGGCAGAGCGCACATCGCCCCACAGTCCCCGAGAAGTTGGGGGGAGGGGTCGGCAATTGAACCGGTGCCTAGAGAAGGTGGCGCGGGG<br>TAAACTGGGAAAGTGATGTCGTGTACTGGCTCCGCCTTTTCCCGAGGGTGGGGGAGAACCGTATATAAGTGCAGTAAGTCGCCGTGAACGTTCTTTTCGCAACG<br>GGTTTGCCGCAGAACACAGTAAGTGCCCAGCTTCGGGTTCGGGTTGGAAGTGGGTGGGAGAGTTCGAGGGCCTTGCGCTTAAGGAGCCCCTTCGCCTCGTGCTTCGCCTCGTGCTTGAGGAGCCCTGGCA<br>AGTACGTGATTCTTGATCCCGAGCTTCGGGTTGGAAGTGGGTGGGAGAGTTCGAGGGCCTTGCGCTTAAGGAGCCCCTTCGCCTCGTGCTTCGCTCTCTGATAAGTCTCTAGCCATTTAAAATTTTTGATGACCTGCTGCGA<br>CGCTTTTTTTCTGGCAAGATAGTCTTGTAAATGCGGGCCAAGATCTGCACACTGGTATTTCGGTTTTTCGGTTTTGGGCGCCCGGCGGGCCCGGCGGGCCCTGCGTCCCAGC<br>GTCGGCACCCAGTTCGTGAGCGGAAAGATGGCCGCTTCCCGGCCGCTTCCGGCTGCTTCATGTGACTCCCACACTGAGTGGGTGGAGACCAGCTTGGCACTTGATGTAATTCTC<br>CACACAAGGAAAAGGGCCTTTCCGCTCCCAGCCCTCATGTGACTCCCACACTGAGTGGGTGGAGACCAGCTTGGCACTTGATGTAATTCTC<br>CTTGGAATTTGCCCTTTTGAGTTTGGATCTTGGTTCATTTCTCCATTTCAGGTGTCGTGAACGCGT | EFS It1 |
| 51 | DNA | TCTAGAGTGCCCGTCAGTGGGCAGAGCGCACATCGCCCCACAGTCCCCGAGAAGTTGGGGGGAGGGGTCGGCAATTGAACCGGTGCCTAGAGAAGGTGGCGCGGGG<br>TAAACTGGGAAAGTGATGTCGTGTACTGGCTCCGCCTTTTCCCGAGGGTGGGGGAGAACCGTATATAAGTGCAGTAAGTCGCCGTGAACGTTCTTTTCGCAACG<br>GGTTTGCCGCAGAACACAGTAAGTGCCCAGCTTCGGGTTGGAAGTGGGTGGGAGAGTTCGAGGGCCTTGCGCTTAAGGAGCCCCTTCGCCTCGTGCTTGAGGAGCCCTGGC<br>AGTACGTGATTCTTGATCCCGAGCTTCGGGTTGGAAGTGGGTGGGAGAGTTCGAGGGCCTTGCGCTTAAGGAGCCCCTTCGCCTCGTGCTTGAGGAGCCCTGGC<br>CTGGGCGCTCGGGGCCGCCGTGCGAATCTGGTGCACCTGGTATTTCGGTTTTTCGGTTTTGGGCGCCCGGCGGGCCCTGCGTCCCAGC<br>CGCTTTTTTTCTGGCAAGATAGTCTTGTAAATGCGGGCCAAGATCTGCACACTGG<br>CAGGGAGCTCAAAATGGGAGGACGCGCGGCGGGCCGGTGGAGGGCCGGCGGGCCTTTGCGTCCTTCAGCCGTCGCTTCATGTGACT<br>CCACGGAAGTACCGGGGCCTCTCAGGCACCTCGATTAGTTCTCGGAGCTTTTGGAGTTTATGCGGTTTATGCGGATGAGTTCCCC<br>ACACTGAGTGGGTGGAGACTGAAGTTAGGCCAGCTTGGCACTTGATGTAATTCTCCTTGAATTTGCCCTTTTGAGTTTGGATCTTGGTTCATTTCTCAAGCCTC<br>AGACAGTGGTTCAAAGTTTTTTTCTTCCATTTCAGGTGTCGTGAACGCGT | EFS It2 |

-continued

SEQUENCE INFORMATION

| SEQ ID NO | TYPE | SEQUENCE | CODE NAME |
|---|---|---|---|
| 52 | DNA | TCTAGAGTGCCCGTCAGTGGGCAGAGCGCACATCGCCCACAGTCCCGAGAAGTTGGGGGGAGGGGTCGGCAATTGAACCGGTGCCGCGGGG TAAACTGGGAAAGTGATGTCGTGTACTGGCCTCCGCCTTTTCCCGAGGGTGGGGGGAGAACCGTATATAAGTGCAGTAGTGCCCGTGAACGTTCTTTTCGCAACG GGTTTGCCGCCAGAACACAGGTAAGTGCCGTGTGGTTCCCGCGGGCCTGGCCTCTTTACGGGTTATGCCCCTTGCGCTGCCTTGAATTACTTCCACCTGGCTGC AGTACGTGATTCTTGATCCCGAGCTTCGGGTTGGGAGAGTGGGAGAGTGGGAGAGTGGGAGTGCTTGAGCGTTCGCGTCTTCGCTGCTTTCGCTGCTTTAAAATTTTTGATGACCTGCTGCGA CTGGGCGGCTGGGCCGCCGGCGGCGAATCTGGTGCGCACCTTCGGTGGGAGTGTGGCACCTTCGCGTCTTCGCTGCGTCTCGGCTT TCACCCACACAAAGGAAAAGGGCCTTTCCGTCCTGCTTCATGTGACTCACGGAGTACCGGGCGCCGTCCAGGCACCTCGATTAGTTCTCGAGCTTT TGGAGTACGTCGTCTTTAGGTGGGGGGAGGGGTTTATGCGAGTGATGGAGTTTCCCCACACTGAGTTAGGCCAGCTTGACACTTGATGTAA TTCTCCTTGGAATTTGCCCTTTTGAGTTTGGATCTTGGTCATTCTCAAGCCTCAGACAGTGGTTCAAGTTTTTTTCTTCCATTTCAGGTGTCGTGAACGCGT | EFS It3 |
| 53 | DNA | TCTAGAGTGCCCGTCAGTGGGCAGAGCGCACATCGCCCACAGTCCCGAGAAGTTGGGGGGAGGGGTCGGCAATTGAACCGGTGCCGCGGGG TAAACTGGGAAAGTGATGTCGTGTACTGGCCTCCGCCTTTTCCCGAGGGTGGGGGGAGAACCGTATATAAGTGCAGTAGTGCCCGTGAACGTTCTTTTCGCAACG GGTTTGCCGCCAGAACACAGGTAAGTGCCGTGTGGTTCCCGCGGGCCTGGCCTCTTTACGGGTTATGCCCCTTAAGGAGCCCTTGCGCTGCCTTGAATTACTTCCACCTGGCTGC AGTACGTGATTCTTGATCCCGAGCTTCGGGTTGGGAGAGTGGGAGAGTGGGAGTGCCTTGAGCGTTCGCGTCTTCGCTGCTT CTGGGCGCGTGGGGCCGCCGGCGGCGAATCTGGTGCGCACCTTCGGTGGGAGTGTGGCACCTTCGCGTCTTCGCTGCGTCTCTGCTT TGACTCCACGGAGTACCGGGCACCTCGATTAGTTCTCGAGCTTTGGAGTACGTCGTCTTTGGAGTTGGGTGGGGGAGGGGTTTATGCGATGGAGTT TCCCCACACTGAGTTAGGCCAGCTTGACACTTGATGTAATTCTCCTTGGAATTTGCCCTTTTGAGTTTGGATCTTGGTCATTCTCAA GCCTCAGACAGTGGTTCAAGTTTTTTTCTTCCATTTCAGGTGTCGTGAACGCGT | EFS It4 |
| 54 | DNA | TCTAGAGTGCCCGTCAGTGGGCAGAGCGCACATCGCCCACAGTCCCGAGAAGTTGGGGGGAGGGGTCGGCAATTGAACCGGTGCCGCGGGG TAAACTGGGAAAGTGATGTCGTGTACTGGCCTCCGCCTTTTCCCGAGGGTGGGGGGAGAACCGTATATAAGTGCAGTAGTGCCCGTGAACGTTCTTTTCGCAACG GGTTTGCCGCCAGAACACAGGTAAGTGCCGTGTGGTTCCCGCGGGCCTGGCCTCTTTACGGGTTATGCCCCTTAAGGAGCCCTTGCGCTGCCTTGAATTACTTCCACCTGGCTGC AGTACGTGATTCTTGATCCCGAGCTTCGGGTTGGGAGAGTGGGAGTGGAGTTCCCCACACTGAGTGGGTGGAGACTGAAGTTAGGCCAGCTTGACACTTGA CTGGGCGGCTG GCTTTTGGAGTACGTCGTCTTTAGGTTGGGGGGAGGGGTTTATGCGATGGAGTTCATTCTGGTTGCATTCTCAAGCCTCAGACAGTGGTTCAAGTTTTTTTCTTCCATTTCAGGTGTCGTGAA TGTAATTCTCCTTGGAATTTGCCCTTTTGAGTTTGGATCTTGGTCATTCTGGAATTTGCCCTTTTGAGTTTGGATCTTGGTCATTCTCAAGCCTCAGACAGTGGTTCAAGTTTTTTTCTTCCATTTCAGGTGTCGTGAA CGCGT | EFS It5 |
| 55 | DNA | TCTAGAGTGCCCGTCAGTGGGCAGAGCGCACATCGCCCACAGTCCCGAGAAGTTGGGGGGAGGGGTCGGCAATTGAACCGGTGCCGCGGGG TAAACTGGGAAAGTGATGTCGTGTACTGGCCTCCGCCTTTTCCCGAGGGTGGGGGGAGAACCGTATATAAGTGCAGTAGTGCCCGTGAACGTTCTTTTCGCAACG GGTTTGCCGCCAGAACACAGGTAAGTGCCGTGTGGTTCCCGCGGGCCTGGCCTCTTTACGGGTTATGCCCCTTAAGGAGCCCTTGCGCTGCCTTGAATTACTTCCACCTGGCTGC AGTACGTGATTCTTGATCCCGAGCTTCGGGTTGGGAGAGTGGGAGAGTGGGAGTGCTTGAGCGTTCGCGTCTTCGCTGCT GAGTTCCCCACACTGAGTTAGGCCAGCTTGACACTTGATGTAATTCTCCTTGGAATTTGCCCTTTTGAGTTTGGATCTTGGTTCATT CTCAAGCCTCAGACAGTGGTTCAAGTTTTTTTCTTCCATTTCAGGTGTCGTGAACGCGT | EFS It6 |
| 56 | DNA | TCTAGAGTGCCCGTCAGTGGGCAGAGCGCACATCGCCCACAGTCCCGAGAAGTTGGGGGGAGGGGTCGGCAATTGAACCGGTGCCGCGGGG TAAACTGGGAAAGTGATGTCGTGTACTGGCCTCCGCCTTTTCCCGAGGGTGGGGGGAGAACCGTATATAAGTGCAGTAGTGCCCGTGAACGTTCTTTTCGCAACG GGTTTGCCGCCAGAACACAGGTAAGTGCCGTGTGGTTCCCGCGGGCCTGGCCTCTTTACGGGTTATGCCCCTTAAGGAGCCCTTGCGCTGCCTTGAATTACTTCCACCTGGCTGC AGTACGTGATTCTTG CTTGATGTAATTCTCCTTGGAATTTGCCCTTTTGAGTTTGGATCTTGGTCATTCTGGTTCATTCTCAAGCCTCAGACAGTGGTTTTTTTTTCTTCCATTTCAGGTGTC GTGAACGCGT | EFS It7 |
| 57 | DNA | TCTAGAGTGCCCGTCAGTGGGCAGAGCGCACATCGCCCACAGTCCCGAGAAGTTGGGGGGAGGGGTCGGCAATTGAACCGGTGCCGCGGGG TAAACTGGGAAAGTGATGTCGTGTACTGGCCTCCGCCTTTTCCCGAGGGTGGGGGGAGAACCGTATATAAGTGCAGTAGTGCCCGTGAACGTTCTTTTCGCAACG GGTTTGCCGCCAGAACACAGGTAAGTGCCGTGTGGTTCCCGCGGGCCTGGCCTCTTTACGGGTTATGCCCCTTAAGGAGCCCTTGCGCTGCCTTGAATTACTTCCACCTGGCTGC AGTACGTGATTCTTGATCCCGAGCTTCGGGTTGGGAGAGTGGGAGAGTGGGAGTGCCTTGAGCGTTCGCGTCTTCGCTGC | EF1α |

-continued

SEQUENCE INFORMATION

| SEQ ID NO | TYPE | SEQUENCE | CODE NAME |
|---|---|---|---|

CTGGGCGCTGGGGCCGCCGCGTGCCAATCTGGTGCACCTTCGCCGCCTGTCTCCGCTGCTTCCGCTGCTTCGATAAGTCTCTAGCCATTTAAAATTTTGATGACCTGCTGCGA
CGCTTTTTTCTGGCAAGATAGTCTTGTAAATGCGGGCCAAGATCTGCACACTGGTATTTCGGTTTTCGGGTCCCCGGGGGGCGACGGGGGCCCGTCCGGCCGGGCGTCCCAGC
GCACATGTTCGGCGAGGCGGGGCCTGCGAGCGCGGCCGCCGAGAATCGACGGGGGTAGTCTCAAGCTGGCCGCGCTTCGTGCCTCGCGCCTCCGCCGCGCCGT
GTATCGCCCCGCCCTTGGGCGGCCAAGGCTGGCCCGTCGGCGCACCCAGTTGCCGTGAGCGGAAAGATGCCGCTTCCCGCCCTGCTGCAGGGAGCTCAAAATGGAGGA
CGCGGCGCTGGCGGGGCGCGGTGACGCTTCGAGCTTTGGAGTACGTGCGTCTTAGGTTGGGCGGAGGGGTTTATGCGATGGAGGGTTTCCCACACTGAGTGGGTGGGGACTG
AAGTTAGGCCAGCTTGGCACTTGATGTAATTCTCCTTGGAATTTGCCCTTTTTGAGTTTGGAGTCTTGGATCTTGGTTCATTCTCAAGCCTCAGACAGTGTGTTCAAAGTTTTT
TTCTTCCATTTCAGTGTCGTGAACGCGT

| 58 | DNA | | CAG | gacattgattactagttattaatagtaatcaattacggggtcattagttcatagcccatatagtgagttccgcgttacataacttacggtaaatggcccgc
ctggctgaccgcccaacgacccccgcccataatgacgtcaataatgacgtatgttcccatagtaacgccaatagggactttccattgacgtcaatgggtggactatt
tacggtaaactgcccacttggcagtacatcaagtgtatcaatgggcgtggatagcggtttgactcacggggatttccaagtctccaccccattgacgtcaatgggagtttgttttggcaccaaaatcaacgggactttccaaaatgtcgtaacaactccgccccattgacgcaaaatgggcggtaggcgtg
acatgacctttatggagcttcctactggcagtacatctacgtattagtcatcgctattaccatggtgatgcggttttggcagtacatcaatgggcgtggatagcggtttgactcacggggatttccaagtctccaccccattgacgtcaatgggagtttgttttggcaccaaaatcaacgggactttccaaaatgtcgtaacaactccgccccattgacgcaaaatgggcggtaggcgtg
tcccccccccccaatttgattattttattattttgtgcagcgatgggggcgggggggggggggcgcgcgccaggcggggcggggcgagggcggcggcggcgggccc
ggcgaggggcgggggcggagcggaggtcggccggcagcaatcagagcgccgctccgaaagttccttttatggcgaggcggcgggccgcggcgggccc
tataaaaagcgaagcgcgcggcgggcgggacggcccttctccctccccggcgtgcgccccgctcggcctggttaatgacggcttcctttctctgtggctgcgtgaaagctt
aaagggctccggaggggcccttgtgcgggggctttgtgcgctcgcgcgctgtgtgcgcgggggagccgccgggccgggcggtggggggcgcgcgcaggcggggcg
tgtgagcgcgcgggcgcgcgggcttgtgcgtctgcgctcgcggggggtgagcaggggagccgggcggtgcggcaggggcggcggtgcggggaa
caaaggctcgtgcgtgcgggtgtgcgtggggggtgagcaggggcgtgcggcaggggcggcggtgcggggtgaaccccccccgaccccctccccgagttgctgagc
acgcccggctccggtcgggggctcgggggtccgcacgggcgtggcgggggtccgcacgggcgtggcgggccagtggggtcgcgggccggggcgc
ctcgggcggggggggctcctttgtccgggggtcccggggctgcgggggggctcctttgtccccaaatctgggaggcgccgaaatcggggagccgaaatctgggagcgccggcggtgccgggccgcaggggccggtgccgggccgcaggggccggtgccgggcgtccggggggacccgctcgggg
gcaggaaggaagaatggcgggggggggcgggggctcgtcctcgtccgcgggtccggggctcctcggcgcctgtgggggacccgctcgggg
gggacggggcagggcgggtcgcttcgggcttcgggcttcgtccatcattttggcaaa

| 59 | DNA | | MBP | aagctttgagagaagaaaggagaccagatcttattcctcaccgtggcttaacacttagagaaaatgcatccctctaatcaataagtcatcgacagtgggtagatgg
aggaacggcagtgcgtagtgagatgcgtctaagcatagctccgtgcatgggtcatagctcgtggcccaggtgcatagctcgtggcccaggtggcatggtaagaagtgggta
gatgattgatgttaggtaaatatcactgggtggacagatgggtgtagtggatggttagaatagtcagaaagtgcagaatcaagggcagatggattgataagtgaacagatga
taaatgacggtgatagacttggaaggtgtcaaaagaggatggcagcgtatttctaaggtcagtaatagagtggggaagaggttaagttac
atccatttaaacctcacacgaagctgagtggaatggacttgctgcctgtggtggaggaaagcgttgcattttccgtggtcgttggtgtggaagtgctcaggtccc
acatgaagcagtcaggttacctggcgcttacagaggagccagatccaaatgccccgagtaagtaagcgcacgtccccagcgaacactaaaagcacctttgtcaaacgaccgcttca
catcggggtgccctgcctttcctggactggtaagctgctaagctgaagtctccactgagaaacctggggagtctcctgctacactctcggctgagcagtggcaacctcaggaaatgctcttgg
cttgattgctgtgggctccaggccatcgctccctgatctctccctcggaggtggtgcttcttaatgagaaacctgaattggcccgcgtcagcatgtataccaaagctcaatccag
gttagctcccctcggttggggcaagctaacgtgctcctggcgcttacagctctctccattgttgttgcaggggaggcagatcgatccaagaatggaacccaggacggacggc
ggtgacagacagcacagcacagagcaccagaagaataactggctccattccgtggggaggtgatccaggaaccgacccccactctgatccgcccctctccccgaga
tgcccgggagggagggacaacacctccaagacagacaggccctcaagacaggccctcagagtcccgacgagcttcagacaccatccaagagagaccccacagacccccactct
g -continued

SEQUENCE INFORMATION

| SEQ ID NO | TYPE | SEQUENCE | CODE NAME |
|---|---|---|---|
| 60 | DNA | cgttacataacttacggtaaatggcccgcctggctgaccgcccaacgacccccgccattgacgtcaataatgacgtatgttcccatagtaacgccaatagggac ttccattgacgtcaatgggtggagtattacggtaaactggcccacttggcagtacatcaagtgtatcatatgccaagtacgccccctattgacgtcaatgacgg taaatggcccgcctggcattatgcccagtacatgaccttatgggactttcctacttggcagtacatctacgtattagtcatcgctattaccatggtcgaggtgag ccccacgttctgcttcactctccccatctcccccccctccccacccccaattttgtatttatttattttttaattattttgtgcagcgatgggggcggggggg gggggggcgcgcgccaggcggggcggggcgggggcgaggggcggggcggggcgaggcggagaggtgcggcggcagccaatcagagcggcgcgctccgaaagtttcc tttatggcgaggcggcggcggcggcggccctataaaaagcgaagcgcgcggcgggcgggagtcgctgcgacgctgccttcgccccgtgccccgctccgccgccg cctcgcgccgcccgccccgctctgactgaccgcgttactcccacaggtgagcgggcgggacggcccttctcctccgggctgtaattagcgcttggtttaatgacgg ggtttaaggggatggttggttgggttaatgtcttaatgtttaattacctggagcacctgcctgaaatcactttttttcag | CBh |

The invention claimed is:

1. An isolated nucleic acid molecule, comprising a first nucleotide sequence encoding a first protein operatively linked to a second nucleotide sequence encoding a second protein, wherein the first protein and the second protein are selected from the following combination (a) or (b):

(a) the first protein is human aromatic L-amino acid decarboxylase (AADC), and the second protein is human glial cell derived neurotrophic factor (GDNF); or (b) the first protein is human GDNF, and the second protein is human AADC, wherein the first nucleotide sequence is located upstream of the second nucleotide sequence;

wherein the human AADC is encoded by the nucleotide sequence comprising or consisting of any one of SEQ ID NOs: 3, 5, 6, 8, 9 or 46.

2. The isolated nucleic acid molecule of claim 1, wherein:

the polypeptide sequence of AADC comprises or is the amino acid sequence as shown in SEQ ID NO: 31; and/or the polypeptide sequence of GDNF comprises or is the amino acid sequence as shown in SEQ ID NO: 34.

3. The isolated nucleic acid molecule of claim 1, wherein the first protein is human AADC.

4. The isolated nucleic acid molecule of claim 1, when the second protein is human GDNF, wherein the second nucleotide sequence comprises or is a nucleotide sequence selected from a group consisting of the nucleotide sequence as shown in any one of SEQ ID NOs: 27-30.

5. The isolated nucleic acid molecule of claim 1, wherein the nucleotide sequence encoding human GDNF is a codon-optimized coding sequence of GDNF, and the codon-optimized coding sequence differs from the wild-type coding sequence of GDNF as shown in SEQ ID NO: 30 in nucleo-
tides not present in the region coding for the signal peptide
or pre-peptide of GDNF.

6. The isolated nucleic acid molecule of claim 5, wherein
the nucleotide sequence encoding human GDNF is a codon-
optimized coding sequence of GDNF and has reduced CpG
sites or has no CpG islands as compared to the wild-type
coding sequence of GDNF as shown in SEQ ID NO: 30.

7. The isolated nucleic acid molecule of claim 1, wherein
the first nucleotide sequence and the second nucleotide
sequence are linked in frame and are operatively linked to a
promoter located at the 5' upstream to both the first and the
second nucleotide sequences.

8. The isolated nucleic acid molecule of claim 7, wherein
the promoter is selected from a CBh promoter, an EFla
promoter, a CAG promoter, a MBP promoter or a variant
thereof.

9. The isolated nucleic acid molecule of claim 8, wherein
the promoter is a truncated variant of EFla promoter having
the nucleotide sequence of any one of SEQ ID NOs: 50-56.

10. A codon-optimized sequence of AADC, having a
nucleotide as shown in any one of SEQ ID NOs: 3, 5, 6, 8,
9 or 46.

11. A recombinant adeno-associated viral (rAAV) vector,
comprising the isolated nucleic acid molecule of claim 1.

12. A viral particle comprising the rAAV vector of claim
11.

13. The viral particle of claim 12, which comprises a
capsid protein of AAV1, AAV2, AAV5, AAV8 or AAV9.

14. A pharmaceutical composition, comprising the viral
particle of claim 12, and a pharmaceutically acceptable
excipient.

* * * * *